(12) United States Patent
Chen et al.

(10) Patent No.: US 9,062,045 B2
(45) Date of Patent: Jun. 23, 2015

(54) TRIAZOLOPYRIDINE COMPOUNDS

(75) Inventors: Chao Chen, Shanghai (CN); Haibing Deng, Shanghai (CN); Haibing Guo, Shanghai (CN); Feng He, Shanghai (CN); Lei Jiang, Shanghai (CN); Fang Liang, Lanzhou (CN); Yuan Mi, Shanghai (CN); Huixin Wan, Shanghai (CN); Yao-Chang Xu, Shanghai (CN); Hongping Yu, Shanghai (CN); Ji Yue (Jeff) Zhang, Shanghai (CN)

(73) Assignee: Novartis AG, Basel (CH)

( * ) Notice: Subject to any disclaimer, the term of this patent is extended or adjusted under 35 U.S.C. 154(b) by 320 days.

(21) Appl. No.: 13/613,291

(22) Filed: Sep. 13, 2012

(65) Prior Publication Data

US 2013/0245002 A1    Sep. 19, 2013

(51) Int. Cl.
A61K 31/397    (2006.01)
C07D 471/04    (2006.01)
C07D 519/00    (2006.01)
A61K 31/437    (2006.01)
A61K 31/496    (2006.01)
A61K 31/5377   (2006.01)
A61K 31/5513   (2006.01)
A61K 45/06     (2006.01)
C07D 491/107   (2006.01)

(52) U.S. Cl.
CPC ............ *C07D 471/04* (2013.01); *C07D 519/00* (2013.01); *A61K 31/437* (2013.01); *A61K 31/496* (2013.01); *A61K 31/5377* (2013.01); *A61K 31/5513* (2013.01); *A61K 45/06* (2013.01); *C07D 491/107* (2013.01)

(58) Field of Classification Search
CPC .. C07D 471/04; C07D 401/12; C07D 401/06; C07D 487/04; C07D 403/04
USPC ............ 514/210.21, 253.04, 303, 218, 233.2, 514/278; 546/119, 15; 540/575; 544/362, 544/127
See application file for complete search history.

(56) References Cited

U.S. PATENT DOCUMENTS

| 4,358,453 | A  | 11/1982 | Bristol et al. |
| 4,886,805 | A  | 12/1989 | Bru-Magniez et al. |
| 5,608,041 | A  | 3/1997  | Schefczik et al. |
| 6,043,369 | A  | 3/2000  | Schefczik |
| 6,303,625 | B1 | 10/2001 | Hoekstra et al. |
| 7,713,973 | B2 | 5/2010  | Dong et al. |
| 7,767,675 | B2 | 8/2010  | Zhuo et al. |
| 8,389,526 | B2 | 3/2013  | Furet et al. |
| 8,410,264 | B2 | 4/2013  | Dai et al. |
| 8,420,645 | B2 | 4/2013  | Weng et al. |
| 8,461,330 | B2 | 6/2013  | Zhuo et al. |
| 8,497,368 | B2 | 7/2013  | He et al. |
| 8,507,676 | B2 | 8/2013  | Dai et al. |
| 8,546,393 | B2 | 10/2013 | Albert et al. |
| 8,822,468 | B2 | 9/2014  | Furet et al. |
| 2005/0009871 | A1 | 1/2005 | Ramesh et al. |
| 2005/0272736 | A1 | 12/2005 | Altenbach et al. |
| 2006/0030610 | A1 | 2/2006 | Koch et al. |
| 2006/0148801 | A1 | 7/2006 | Hsieh et al. |
| 2006/0281750 | A1 | 12/2006 | Li et al. |
| 2006/0287324 | A1 | 12/2006 | Sun et al. |
| 2009/0093516 | A1 | 4/2009 | Li et al. |
| 2011/0021521 | A1 | 1/2011 | Corkey et al. |
| 2011/0263594 | A1 | 10/2011 | Bacque et al. |
| 2011/0313003 | A1 | 12/2011 | Shi et al. |
| 2012/0040987 | A1 | 2/2012 | Bacque et al. |
| 2012/0100157 | A1 | 4/2012 | Vande Woude et al. |

(Continued)

FOREIGN PATENT DOCUMENTS

DE    10038019 A1    2/2002
EP    2425830 A1     9/2010

(Continued)

OTHER PUBLICATIONS

Davis, Mindy I. et al., "Comprehensive analysis of kinase inhibitor selectivity", Nature Biotechnology, Oct. 30, 2011, vol. 29, No. 11, Nature America, Inc., pp. 1046-1051.

(Continued)

*Primary Examiner* — Jason Sims
*Assistant Examiner* — Ibrahim D Bori
(74) *Attorney, Agent, or Firm* — Qian Zhang; Jing G. Sun

(57) ABSTRACT

The invention relates to compounds of formula (I) and salts thereof:

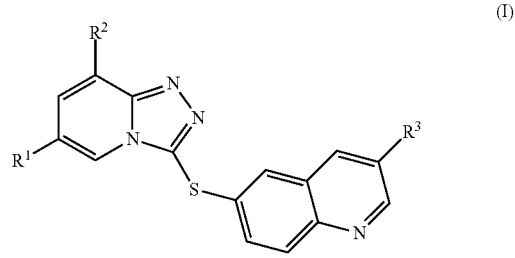

(I)

wherein the substituents are as defined in the specification; a compound of formula (I) for use in the treatment of the human or animal body, in particular with regard to c-Met tyrosine kinase mediated diseases or conditions; the use of a compound of formula (I) for manufacturing a medicament for the treatment of such diseases; pharmaceutical compositions comprising a compound of the formula (I), optionally in the presence of a combination partner, and processes for the preparation of a compound of formula (I).

15 Claims, No Drawings

(56) References Cited

U.S. PATENT DOCUMENTS

| | | |
|---|---|---|
| 2012/0165326 A1 | 6/2012 | Nemecek et al. |
| 2013/0289036 A1 | 10/2013 | Weng et al. |
| 2013/0324515 A1 | 12/2013 | Zhuo et al. |
| 2013/0324526 A1 | 12/2013 | He et al. |

FOREIGN PATENT DOCUMENTS

| | | |
|---|---|---|
| WO | 01/07046 A1 | 2/2001 |
| WO | 2004/020438 A2 | 3/2004 |
| WO | 2005/113536 A2 | 12/2005 |
| WO | 2006/018727 A2 | 2/2006 |
| WO | 2006/091897 A2 | 8/2006 |
| WO | 2007/075567 A1 | 7/2007 |
| WO | 2007/132308 | 11/2007 |
| WO | 2007/138472 | 12/2007 |
| WO | 2008/008539 A2 | 1/2008 |
| WO | 2008/051805 A2 | 5/2008 |
| WO | 2008/051808 A2 | 5/2008 |
| WO | 2008/155378 | 12/2008 |
| WO | 2009/026717 A1 | 3/2009 |
| WO | 2009/068955 | 6/2009 |
| WO | 2009/073777 A1 | 6/2009 |
| WO | 2009/091374 | 7/2009 |
| WO | 2010/019899 A1 | 2/2010 |
| WO | 2010/089506 | 8/2010 |
| WO | 2010/089507 | 8/2010 |
| WO | 2010/130424 A1 | 11/2010 |
| WO | 2011/017561 A1 | 2/2011 |
| WO | 2011/020861 A1 | 2/2011 |
| WO | 2011/090738 A2 | 7/2011 |
| WO | 2011/100607 A1 | 8/2011 |
| WO | 2012/044577 A1 | 4/2012 |
| WO | 2012/107500 A1 | 8/2012 |

OTHER PUBLICATIONS

Zhang, Yu-Wen et al., "MET Kinase Inhibitor SGX523 Synergizes with Epidermal Growth Factor Receptor Inhibitor Erlotinib in a Hepatocyte Growth Factor-Dependent Fashion to Suppress Carcinoma Growth", Cancer Research 2010, vol. 70, Issue 17, pp. 6880-6890.

Zhang, YW et al. "Correction: MET Kinase Inhibitor SGX523 Synergizes with Epidermal Growth Factor Receptor Inhibitor Erlotinib in a Hepatocyte Growth Factor-Dependent Fashion to Suppress Carcinoma Growth", Cancer Res; Apr. 1, 2011, vol. 71, Issue 7, p. 2804.

TRIAZOLOPYRIDINE COMPOUNDS

The invention relates to bicyclic compounds of formula (I) and salts thereof, the uses of such compounds to treat the human or animal body, in particular with regard to a proliferative disease, pharmaceutical compositions comprising such compounds, combinations comprising a compound of formula (I), and processes for the preparation of such compounds.

INTRODUCTION

The Hepatocyte Growth Factor Receptor, herein referred to as c-Met, is a receptor tyrosine kinase that has been shown to be over-expressed and/or genetically altered in a variety of malignancies, specifically, gene amplification and a number of c-Met mutations are found in various solid tumors, see e.g. WO 2007/126799. Further, the receptor tyrosine kinase c-Met is involved in the processes of migration, invasion and morphogenesis that accompany embryogenesis and tissue regeneration. C-Met is also involved in the process of metastasis. Several lines of evidence have indicated that c-Met plays a role in tumor pathogenesis. Gain of function germ line mutations in c-Met is associated with development of hereditary papillary renal cell carcinoma (PRCC). Amplification or mutations in c-Met have also been reported in sporadic forms of PRCC, in head and neck squamous cell carcinoma, in gastric carcinoma, in pancreatic carcinoma and in lung cancer. Such alterations have been shown in selected instances to confer dependence of the tumor on c-Met and/or resistance to other targeted therapies. Elevated levels of c-Met, together with its unique ligand HGF/SF, are observed at high frequency in multiple clinically relevant tumors. A correlation between increased expression and disease progression, metastases and patient mortality has been reported in several cancers, including bladder, breast, squamous cell carcinoma and gastric carcinoma as well as leiomyosarcoma and glioblastoma.

c-Met inhibitors have been described in the prior art. For example, WO 2008/008539, WO 2009/091374, WO 2010/019899 and WO 2010/007316 disclose certain triazolopyridine derivatives which are useful in the treatment of c-Met related diseases. WO 2008/051808, WO 2010/019899, WO 2010/007316, WO 2009/056692, WO 2010/089506, WO 2010/089507, WO 2010/089508, and WO 2010/089509 disclose a variety of fused heterocyclic compounds with different kinds of 9-10 membered heteroaryl moieties linked via an S— linker, which compounds are indicated for the treatment of c-Met mediated diseases. Furthermore, international patent applications WO 2011/018454 and WO 2011/020861 disclose certain substituted triazolopyridazine derivatives with an oxime or hydrazone moiety linked to a potentially substituted quinoline moiety which are useful in the treatment of c-Met mediated disorders.

SUMMARY OF THE INVENTION

It is an aim of the present invention to provide further compounds that modulate, and in particular inhibit, c-Met. It has now been found that the compounds of the formula (I) described herein are inhibitors of c-Met and have a number of therapeutic applications. For example, the compounds of formula (I) are suitable for use in the treatment of diseases dependent on c-Met activity, especially solid tumors or metastasis derived therefrom. Through the inhibition of c-Met, compounds of the invention also have utility as anti-inflammatory agents, for example for the treatment of an inflammatory condition which is due to an infection.

Preferably, the compounds of the invention are metabolically stable, are non-toxic and demonstrate few side-effects. In addition, preferred compounds of the invention exist in a physical form that is stable, non-hygroscopic and easily formulated. One aspect of the invention is directed to compounds of formula (I) having an activity that is at least similar, better superior to the activity of compounds of the prior art, or other similar compounds. Another aspect of the invention is directed to compounds of formula (I) having a good kinase selectivity. In particular, preferred compounds should have high affinity to the c-Met receptor and show functional antagonistic activity, while having little affinity for other kinase receptors or for targets known to be associated with adverse effects. In one aspect of the invention, preferred compounds demonstrate comparably low antagonistic activity against human PDE3 than related derivatives. Furthermore, the compounds of the invention are metabolically stable, in particular with regard to degradation by aldehyde oxidase enzymatic activities. Preferred compounds of the invention posses favourable pharmacokinetic properties, such as good in-vivo exposure and/or solubility and especially good metabolic stability, and/or do not form metabolites with unfavourable pharmacological properties. Particularly preferred compounds of the invention have favourable characteristics in more than one of the assays described herein.

The present invention relates to a compound of the formula (I)

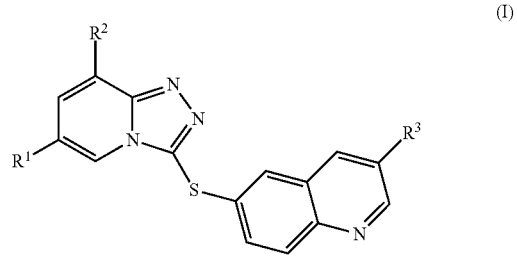

wherein $R^1$ is selected from:

(i) pyrazolyl, optionally substituted by $(C_1$-$C_4)$alkyl, said $(C_1$-$C_4)$alkyl being optionally substituted by one OH group, and (ii) —$CR^9$=N—O—$R^{10}$, wherein $R^9$ is hydrogen or $(C_1$-$C_4)$alkyl; and, $R^{10}$ is hydrogen or $(C_1$-$C_4)$alkyl, said $(C_1$-$C_4)$alkyl being optionally substituted by one OH group;

$R^2$ is selected from hydrogen and halo; and $R^3$ is selected from (i) optionally substituted —$(C_0$-$C_2)$alkyl-heterocyclyl$^1$, and (ii) —$NHR^4$, wherein $R^4$ is selected from hydrogen, optionally substituted —$(C_0$-$C_2)$alkyl-heterocyclyl$^3$ and $(C_1$-$C_4)$alkyl, said $(C_1$-$C_4)$alkyl being optionally substituted by one, two or three substituents independently selected from OH and halo;

or a pharmaceutically acceptable salt thereof.

The present invention relates to a compound of the formula (I), wherein
R$^1$ is selected from:
(i) pyrazolyl, optionally substituted by (C$_1$-C$_4$)alkyl, said (C$_1$-C$_4$)alkyl being optionally substituted by one OH group, and
(ii) —CR$^9$=N—O—R$^{10}$, wherein
R$^9$ is hydrogen or (C$_1$-C$_4$)alkyl; and,
R$^{10}$ is hydrogen or (C$_1$-C$_4$)alkyl, said (C$_1$-C$_4$)alkyl being optionally substituted by one OH group;
R$^2$ is selected from hydrogen and halo; and
R$^3$ is optionally substituted —(C$_0$-C$_2$)alkyl-heterocyclyl$^1$, wherein heterocyclyl$^1$ has the meaning as defined herein,
or a pharmaceutically acceptable salt thereof.

The present invention in particular relates to a compound of formula (I)

wherein
R$^1$ is selected from
(i) pyrazolyl, optionally substituted by (C$_1$-C$_4$)alkyl, said (C$_1$-C$_4$)alkyl being optionally substituted by one OH group, and
(ii) —CR$^9$=N—O—R$^{10}$, wherein
R$^9$ is hydrogen or (C$_1$-C$_4$)alkyl; and,
R$^{10}$ is hydrogen or (C$_1$-C$_4$)alkyl, said (C$_1$-C$_4$)alkyl being optionally substituted by one OH group;
R$^2$ is selected from hydrogen and halo; and
R$^3$ is —(C$_0$-C$_2$)alkyl-heterocyclyl$^1$,
wherein heterocyclyl$^1$ is a 4, 5, 6, 7 or 8 membered saturated or partially unsaturated N-heterocyclic ring which is attached via the N-atom and optionally comprises additional 1 or 2 ring heteroatoms independently selected from N, O and S in a position or positions other than adjacent to the linking N atom, wherein the total number of ring S-atoms does not exceed 1, and the total number of ring O-atoms does not exceed 1,
wherein the N-heterocyclic ring is optionally substituted
(i) by one, two or three substituents independently selected from —OH, halo, —CONH$_2$, —CONH(C$_1$-C$_4$)alkyl, —CON((C$_1$-C$_4$)alkyl)$_2$, —COO(C$_1$-C$_4$)alkyl, —NH$_2$, —NH—COO(C$_1$-C$_4$)alkyl, —NH(C$_1$-C$_3$)alkyl, —N((C$_1$-C$_3$)alkyl)$_2$, —O(C$_1$-C$_4$)alkyl, heterocyclyl$^1$, —(C$_3$-C$_8$)cycloalkyl, phenyl and (C$_1$-C$_4$)alkyl, said (C$_1$-C$_4$)alkyl being optionally substituted by one, two or three substituents independently selected from OH and halo; wherein heterocyclyl$^1$ is a 5 or 6-membered saturated or partially unsaturated monocyclic group comprising 1 or 2 ring heteroatoms independently selected from N and O, wherein the total number of ring O atoms does not exceed 1, and which is optionally substituted by one or two substituents independently selected from OH and (C$_1$-C$_4$)alkyl; or
(ii) by two groups which are attached to the same carbon atom and are combined into a cyclic 4, 5, 6, or 7 membered saturated or partially unsaturated ring system optionally comprising 1 or 2 ring heteroatoms independently selected from N, O and S, wherein the total number of ring S atoms does not exceed 1, which cyclic ring system is optionally substituted by —OH or (C$_1$-C$_4$)alkyl;
and wherein the substituted N-heterocyclic ring is optionally substituted by one or two additional (C$_1$-C$_4$)alkyl groups;
or a pharmaceutically acceptable salt thereof.

In one embodiment, R$^3$ is selected from
(i) optionally substituted —(C$_1$-C$_2$)alkyl-heterocyclyl$^1$, under the proviso that R$^1$ is optionally substituted pyrazole, and
(ii) optionally substituted heterocyclyl$^1$, wherein heterocyclyl$^1$ has the meaning as defined herein.

The meaning of "optionally substituted —(C$_1$-C$_2$)alkyl-heterocyclyl$^1$, under the proviso that R$^1$ is optionally substituted pyrazole" is equivalent to "optionally substituted —(C$_1$-C$_2$)alkyl-heterocyclyl$^1$, wherein R$^1$ is optionally substituted pyrazole".

In one embodiment, the present invention relates to a compound of the formula (I), wherein
R$^1$ is selected from:
(i) pyrazolyl, optionally substituted by (C$_1$-C$_4$)alkyl, said (C$_1$-C$_4$)alkyl being optionally substituted by one OH group, and
(ii) —CR$^9$=N—O—R$^{10}$, wherein
R$^9$ is hydrogen or (C$_1$-C$_4$)alkyl; and,
R$^{10}$ is hydrogen or (C$_1$-C$_4$)alkyl, said (C$_1$-C$_4$)alkyl being optionally substituted by one OH group;
R$^2$ is selected from hydrogen and halo; and
R$^3$ is selected from
(i) optionally substituted —(C$_1$-C$_2$)alkyl-heterocyclyl$^1$, under the proviso that R$^1$ is optionally substituted pyrazole, and
(ii) optionally substituted heterocyclyl$^1$,
wherein heterocyclyl$^1$ has the meaning as defined herein.

In one embodiment, the present invention relates to a compound of the formula (I), wherein
R$^1$ is pyrazolyl, optionally substituted by (C$_1$-C$_4$)alkyl, said (C$_1$-C$_4$)alkyl being optionally substituted by one OH group;
R$^2$ is selected from hydrogen and halo; and
R$^3$ is optionally substituted —(C$_0$-C$_2$)alkyl-heterocyclyl$^1$, wherein heterocyclyl$^1$ has the meaning as defined herein,
or a pharmaceutically acceptable salt or solvate thereof.

In an alternative embodiment, the present invention relates to a compound of the formula (I), wherein
R$^1$ is —CR$^9$=N—O—R$^{10}$, wherein
R$^9$ is hydrogen or (C$_1$-C$_4$)alkyl; and,
R$^{10}$ is hydrogen or (C$_1$-C$_4$)alkyl, said (C$_1$-C$_4$)alkyl being optionally substituted by one OH group;
R$^2$ is selected from hydrogen and halo; and
R$^3$ is optionally substituted-heterocyclyl$^1$, wherein heterocyclyl$^1$ has the meaning as defined herein,
or a pharmaceutically acceptable salt or solvate thereof.

One embodiment of the present invention relates to a compound of formula (I), wherein
$R^1$ is selected from 1-methyl-1H-pyrazol-4-yl, 1-yl-ethanone oxime, and 1-yl ethanone O-(2-hydroxyethyl)-oxime, preferably $R^1$ is 1-methyl-1H-pyrazol-4-yl,
$R^2$ is hydrogen or fluoro, and
$R^3$ is optionally substituted heterocyclyl$^1$, wherein heterocyclyl$^1$ has the meaning as defined herein,
or a pharmaceutically acceptable salt or solvate thereof.

In an alternative embodiment, the present invention relates to a compound of the formula (I), wherein
$R^1$ is pyrazolyl, optionally substituted by $(C_1-C_4)$alkyl, said $(C_1-C_4)$alkyl being optionally substituted by one OH group;
$R^2$ is selected from hydrogen and halo; and
$R^3$ is —NHR$^4$, wherein $R^4$ is hydrogen or $(C_1-C_4)$alkyl, said $(C_1-C_4)$alkyl being optionally substituted by one, two or three substituents independently selected from OH and halo;
or a pharmaceutically acceptable salt or solvate thereof.

In an alternative embodiment, the present invention relates to a compound of the formula (I), wherein
$R^1$ is selected from:
(i) pyrazolyl, optionally substituted by $(C_1-C_4)$alkyl, said $(C_1-C_4)$alkyl being optionally substituted by one OH group, and
(ii) —CR$^9$=N—O—R$^{10}$, wherein
  $R^9$ is hydrogen or $(C_1-C_4)$alkyl; and,
  $R^{10}$ is hydrogen or $(C_1-C_4)$alkyl, said $(C_1-C_4)$alkyl being optionally substituted by one OH group;
$R^2$ is selected from hydrogen and halo; and
$R^3$ is —NHR$^4$, wherein $R^4$ is optionally substituted —(C$_0$-C$_2$)alkyl-heterocyclyl$^3$; wherein heterocyclyl$^3$ has the meaning as defined herein,
or a pharmaceutically acceptable salt or solvate thereof.

DEFINITIONS

The following general definitions shall apply in this specification, unless otherwise specified:

Unless specified otherwise, the term "compound of the invention", or "compounds of the invention", or "a compound of the present invention" or "compounds of the present invention" refer to compounds of Formula (I) and subformulae thereof, prodrugs thereof, salts of the compounds and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

As used herein, the terms "including", "containing" and "comprising" are used herein in their open, non-limiting sense.

Where the plural form (e.g. compounds, salts) is used, this includes the singular (e.g. a single compound, a single salt). "A compound" does not exclude that (e.g. in a pharmaceutical formulation) more than one compound of the formula (I) (or a salt thereof) is present.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

As used herein, the term "halo" means fluoro, chloro, bromo or iodo. In a particular embodiment of the invention, halo is fluoro or chloro. Preferably, halo is fluoro.

As used herein, the term "heteroatoms" refers to nitrogen (N), oxygen (O) or sulfur (S) atoms, in particular nitrogen or oxygen.

Any non-cyclic carbon containing group or moiety with more than 1 carbon atom can be straight-chain or branched.

As used herein, the term "alkyl" refers to a straight-chain or branched-chain alkyl group. For example, $(C_1-C_4)$alkyl includes methyl, ethyl, n- or iso-propyl, and n-, iso-, sec- or tert-butyl.

As used herein, the term "cycloalkyl" refers to a saturated or partially unsaturated monocyclic hydrocarbon groups having 3, 4, 5, 6, 7 or 8 ring carbon atoms, preferably from 3 up to and including 6 ring carbon atoms. Exemplary monocyclic hydrocarbon groups include, but are not limited to, cyclopropyl, cyclobutyl, cyclopentyl, cyclopentenyl, cyclohexyl and cyclohexenyl and the like.

In the context of R$^3$ herein "optionally substituted —(C$_0$-C$_2$)alkyl-heterocyclyl$^1$" means the substitution is present on the heterocyclyl$^1$ of —(C$_0$-C$_2$)alkyl-heterocyclyl$^1$.

As used herein, the term "heterocyclyl$^1$" used as "heterocyclyl$^1$" alone as well as a part of "—(C$_0$-C$_2$)alkyl-heterocyclyl$^1$" or "—(C$_1$-C$_2$)alkyl-heterocyclyl$^1$" or "-methyl-heterocyclyl$^1$" refers to a 4, 5, 6, 7 or 8 membered saturated or partially unsaturated N-heterocyclic ring which is attached via the N-atom and optionally comprises additional 1 or 2 ring heteroatoms independently selected from N, O and S in a position or positions other than adjacent to the linking N atom, wherein the total number of ring S-atoms does not exceed 1, and the total number of ring O-atoms does not exceed 1. Specific examples of heterocyclyl$^1$ include, but are not limited to azetidinyl, pyrrolidinyl, 2,3-dihydro-1H-pyrrolyl, 2,5-dihydro-1H-pyrrolyl, imidazolidinyl, 4,5-dihydro-1H-imidazolyl, 2,5-dihydro-1H-imidazolyl, 2,3-dihydro-1H-imidazolyl, 1,2-dihydropyridinyl, 1,2,3,4-tetrahydropyridinyl, 1,2,3,6-tetrahydropyridinyl, morpholinyl, thiomorpholinyl, piperidinyl, piperazinyl, quinuclidinyl, oxazolidinyl, 2,3-dihydrooxazolyl, thiazolidinyl, 2,3-dihydrothiazolyl, hexahydropyrimidinyl, 1,2,5,6-tetrahydropyrimidinyl, 1,4,5,6-tetrahydropyrimidinyl, 1,2,3,4-tetrahydropyrazinyl, 1,2,3,6-tetrahydropyrazinyl, [1,3,5]triazinanyl, [1,3]oxazinanyl, 3,4-dihydro-2H-[1,4]oxazinyl, 3,4-dihydro-2H-[1,3]oxazinyl, 3,6-dihydro-2H-[1,3]oxazinyl, [1,3]thiazinanyl, 3,6-dihydro-2H-[1,3]thiazinyl, 3,4-dihydro-2H-[1,3]thiazinyl, 3,4-dihydro-2H-[1,4]thiazinyl, azepanyl, diazepanyl, oxazepanyl, and thiazepanyl.

In one embodiment, the term "heterocyclyl$^1$" refers to a 4, 5, 6, or 7 membered saturated N-heterocyclic ring which is attached via the N-atom and optionally comprises one additional ring heteroatom independently selected from N and O in a position other than adjacent to the linking N atom. Specific examples of such heterocyclyl$^1$ include, but are not limited to azetidinyl, pyrrolidinyl, 2,3-dihydro-1H-pyrrolyl, 2,5-dihydro-1H-pyrrolyl, imidazolidinyl, 4,5-dihydro-1H-imidazolyl, 2,5-dihydro-1H-imidazolyl, 2,3-dihydro-1H-imidazolyl, 1,2-dihydropyridinyl, 1,2,3,4-tetrahydropyridinyl, 1,2,3,6-tetrahydropyridinyl, morpholinyl, piperidinyl, piperazinyl, quinuclidinyl, oxazolidinyl, 2,3-dihydrooxazolyl, 2,3-hexahydropyrimidinyl, 1,2,5,6-tetrahydropyrimidinyl, 1,4,5,6-tetrahydropyrimidinyl, 1,2,3,4-tetrahydropyrazinyl, 1,2,3,6-tetrahydropyrazinyl, [1,3]oxazinanyl, 3,4-dihydro-2H-[1,4]oxazinyl, 3,4-dihydro-2H-[1,3]oxazinyl, 3,6-dihydro-2H-[1,3]oxazinyl, azepanyl, diazepanyl, and oxazepanyl. Preferred examples of such heterocyclyl$^1$ include, but are not limited to piperidin-1-yl, pyrrolidin-1-yl, piperazin-1-yl, morpholin-4-yl, azetidin-1-yl, and 1,4-diazepan-1-yl.

In another embodiment, the term "heterocyclyl$^1$" refers to a 5 or 6 membered saturated N-heterocyclic ring which is attached via the N-atom and optionally comprises one additional ring heteroatoms independently selected from N and O in a position other than adjacent to the linking N atom. Preferred examples of such heterocyclyl$^1$ include, but are not limited to piperidin-1-yl, pyrrolidin-1-yl, piperazin-1-yl, and morpholin-4-yl, preferably piperazin-1-yl and morpholin-4-yl.

Within the context of the present invention, a heterocyclyl$^1$ group of the present invention (being an N-heterocyclic ring as defined above) can be optionally substituted (i) by one, two or three substituents independently selected from —OH, halo, —CONH$_2$, —CONH(C$_1$-C$_4$)alkyl, —CON((C$_1$-C$_4$)alkyl)$_2$, —COO(C$_1$-C$_4$)alkyl, —NH$_2$, —NH—COO(C$_1$-C$_4$)alkyl, —NH(C$_1$-C$_3$)alkyl, —N((C$_1$-C$_3$)alkyl)$_2$, —O(C$_1$-C$_4$)alkyl, heterocyclyl$^2$, —(C$_3$-C$_8$)cycloalkyl, phenyl and (C$_1$-C$_4$)alkyl, said (C$_1$-C$_4$)alkyl being optionally substituted by one, two or three substituents independently selected from OH and halo; or (ii) by two groups which are attached to the same carbon atom and are combined into a cyclic 4, 5, 6, or 7 membered saturated or partially unsaturated ring system optionally comprising 1 or 2 ring heteroatoms independently selected from N, O and S, wherein the total number of ring S atoms does not exceed 1, which cyclic ring system is optionally substituted by —OH or (C$_1$-C$_4$)alkyl. Additionally, heterocyclyl$^1$ can be substituted with one or two further (C$_1$-C$_4$) alkyl groups.

In one embodiment, a heterocyclyl$^1$ group can be optionally substituted (i) by one, two or three substituents independently selected from —OH, halo, —COO(C$_1$-C$_4$)alkyl, —NH$_2$, —NH—COO(C$_1$-C$_4$)alkyl, —NH(C$_1$-C$_3$)alkyl, —N((C$_1$-C$_3$)alkyl)$_2$, —O(C$_1$-C$_4$)alkyl, heterocyclyl$^2$, —(C$_3$-C$_8$)cycloalkyl, phenyl and (C$_1$-C$_4$)alkyl, said (C$_1$-C$_4$)alkyl being optionally substituted by one, two or three substituents independently selected from OH and halo; or (ii) by two groups which are attached to the same carbon atom and are combined into a cyclic 4, 5, or 6 membered saturated ring system optionally comprising 1 ring heteroatom independently selected from N and O.

In one embodiment of the present invention, a heterocyclyl$^1$ group as defined above comprising an additional ring N-atom is substituted at such additional ring N-atom with a substituent selected from cyclohexyl, phenyl and (C$_1$-C$_4$) alkyl, preferably a (C$_1$-C$_2$)alkyl group, optionally substituted by one, two or three substituents independently selected from OH and halo.

In a further embodiment, a heterocyclyl$^1$ group as defined above can be optionally substituted
(i) at one or two ring C-atoms by overall one or two substituents independently selected from —OH, halo, —NH$_2$, —NH—COO(C$_1$-C$_4$)alkyl, —NH(C$_1$-C$_3$)alkyl, —N((C$_1$-C$_3$)alkyl)$_2$, —O(C$_1$-C$_4$)alkyl, heterocyclyl$^2$, and (C$_1$-C$_4$) alkyl;
(ii) at the optionally present additional ring N-atom by one substituent selected from —COO(C$_1$-C$_4$)alkyl, —(C$_5$-C$_6$) cycloalkyl, phenyl and (C$_1$-C$_4$)alkyl, said (C$_1$-C$_4$)alkyl being optionally substituted by one, two or three substituents independently selected from OH and halo; or
(iii) by two groups which are attached to the same carbon atom and are combined into a cyclic 4, 5, or 6 membered saturated ring system comprising 1 ring O-atom.

In another embodiment, a heterocyclyl$^1$ group as defined above can be optionally substituted
(i) at one or two ring C-atoms by overall one or two substituents independently selected from —OH, halo, —NH$_2$, —NH(C$_1$-C$_3$)alkyl, —N((C$_1$-C$_3$)alkyl)$_2$, —O(C$_1$-C$_4$) alkyl, heterocyclyl$^2$, and (C$_1$-C$_4$)alkyl;
(ii) at the optionally present additional ring N-atom by one substituent selected from —(C$_5$-C$_6$)cycloalkyl, phenyl and (C$_1$-C$_2$)alkyl, said (C$_1$-C$_2$)alkyl being optionally substituted by one, two or three substituents independently selected from OH and halo; or
(iii) by two groups which are attached to the same carbon atom and are combined into a cyclic 4 or 6 membered saturated ring system comprising 1 ring O-atom.

In a further embodiment, a heterocyclyl$^1$ group as defined above can be optionally substituted
(i) at one or two ring C-atoms by overall one or two substituents independently selected from —OH, halo, —NH$_2$, —N(methyl)$_2$, —O-methyl, heterocyclyl$^2$, and methyl;
(ii) at the optionally present additional ring N-atom by one substituent selected from cyclohexyl, phenyl and methyl; or
(iii) by two groups which are attached to the same carbon atom and are combined into a cyclic 4 or 6 membered saturated ring system comprising 1 ring O-atom.

In another preferred embodiment, a heterocyclyl$^1$ group as defined above can be optionally substituted
(i) at one or two ring C-atoms by overall one or two substituents independently selected from —OH, halo, —NH$_2$, —N(methyl)$_2$, —O-methyl, piperidin-1-yl, pyrrolidin-1-yl, and methyl;
(ii) at the optionally present additional ring N-atom by one substituent selected from cyclohexyl and methyl; or
(iii) by two groups which are attached to the same carbon atom and are combined into a cyclic 4 or 6 membered saturated ring system comprising 1 ring O-atom.

In one embodiment of the present invention, the term "optionally substituted heterocyclyl$^1$" refers to a group selected from piperidin-1-yl, pyrrolidin-1-yl, piperazin-1-yl, morpholin-4-yl, azetidin-1-yl, 1,4-diazepan-1-yl, 3-aminopyrrolidin-1-yl, 3-N,N-dimethylaminopyrrolidin-1-yl, 3-aminopiperidin-1-yl, 4-aminopiperidin-1-yl, 4-(pyrrolidin-1-yl)piperidin-1-yl, 1,4'-bipiperidin-1'-yl, 4-methoxypiperidin-1-yl, 4-hydroxypiperidin-1-yl, 4,4-difluoro-piperidin-1-yl, 2,2,2-trifluoroethylpiperazin-1-yl, 4-cyclohexylpiperazin-1-yl, 4-phenylpiperazin-1-yl, 3,5-dimethylpiperazin-1-yl, 2-methylpiperazin-1-yl, 4-methylpiperazin-1-yl, 2-methylmorpholin-4-yl, 2,6-dimethylmorpholin-4-yl, 3-methylmorpholin-4-yl, 4-methyl-1,4-diazepan-1-yl, 4-(2-hydroxyethyl)-1,4-diazepan-1-yl, 2-oxa-6-azaspiro[3.3]heptan-6-yl, and 8-oxa-2-azaspiro[4.5] decan-2-yl. Preferably, optionally substituted "heterocyclyl$^1$" refers to a group selected from piperazin-1-yl, morpholin-4-yl, 4-methoxypiperidin-1-yl, 4-hydroxypiperidin-1-yl, 3,5-dimethylpiperazin-1-yl, 3-N,N-dimethylaminopyrrolidin-1-yl, 3-amino-piperidin-1-yl, 3-aminopyrrolidin-1-yl and 4-methyl-piperazin-1-yl.

In another embodiment of the present invention, the term "heterocyclyl$^1$" refers to
a) a 4, 5 or 6 membered saturated N-heterocyclic ring attached via the N-atom and substituted
(i) at one or two ring C-atoms by overall one or two substituents selected from —OH, fluoro, —N(methyl)$_2$, methoxy, pyrrolidin-1-yl, and methyl; or
(ii) by two groups which are attached to the same carbon atom and are combined into a cyclic 4 or 6 membered saturated ring system comprising 1 ring O-atom;

b) a 6 membered saturated N-heterocyclic ring attached via the N-atom and comprising one additional ring O-atom in a position other than adjacent to the linking N atom, wherein the N-heterocyclic ring is optionally substituted by one or two methyl groups; or c) a 6 or 7 membered saturated N-heterocyclic ring attached via the N-atom and comprising one additional ring N-atom in a position other than adjacent to the linking N atom, wherein the N-heterocyclic ring is optionally substituted (i) at the additional ring N-atom with a substituent selected from cyclohexyl, phenyl and ($C_1$-$C_2$)alkyl, said ($C_1$-$C_2$) alkyl being optionally substituted by one, two or three substituents independently selected from OH and halo; or (ii) at one or two ring C-atoms adjacent to the additional ring N-atom by one or two methyl groups.

In a further preferred embodiment of the present invention, the term "heterocyclyl$^1$" refers to a) a 4, 5 or 6 membered saturated N-heterocyclic ring attached via the N-atom and substituted (i) at one ring C-atom by —OH, difluoro, —N(methyl)$_2$, methoxy, piperidin-1-yl, or pyrrolidin-1-yl; or (ii) by two groups which are attached to the same carbon atom and are combined into a cyclic 4 or 6 membered saturated ring system comprising 1 ring O-atom;

b) a 6 membered saturated N-heterocyclic ring attached via the N-atom and comprising one additional ring O-atom in a position other than adjacent to the linking N atom, wherein the N-heterocyclic ring is optionally substituted by one or two methyl groups; or c) a 6 or 7 membered saturated N-heterocyclic ring attached via the N-atom and comprising one additional ring N-atom in a position other than adjacent to the linking N atom, wherein the N-heterocyclic ring is substituted (i) at the additional ring N-atom with a methyl group; or (ii) at one or two ring C-atoms adjacent to the additional ring N-atom by one or two methyl groups.

Preferably, the term "heterocyclyl$^1$" refers to a group selected from piperazin-1-yl, morpholin-4-yl, 4-methoxypiperidin-1-yl, 4-hydroxypiperidin-1-yl, 3,5-dimethylpiperazin-1-yl, 3-N,N-dimethylaminopyrrolidin-1-yl, and 4-methyl-piperazin-1-yl; in particular piperazin-1-yl, morpholin-4-yl, 4-methoxypiperidin-1-yl, 4-hydroxypiperidin-1-yl, 3,5-dimethylpiperazin-1-yl, and 4-methyl-piperazin-1-yl.

As used herein, the term "heterocyclyl$^2$" refers to a 5 or 6-membered saturated or partially unsaturated monocyclic group comprising 1 or 2 ring heteroatoms independently selected from N and O, wherein the total number of ring O atoms does not exceed 1, and which is optionally substituted by one or two substituents independently selected from OH and ($C_1$-$C_4$)alkyl.

In one embodiment, "heterocyclyl$^2$" refers to a 5 or 6-membered saturated monocyclic group comprising 1 ring heteroatom independently selected from N and O.

In another preferred embodiment, wherein "heterocyclyl$^2$" refers to a 5 or 6-membered saturated N-heterocyclic ring which is attached via the N-atom.

Specific examples of heterocyclyl$^2$ include, but are not limited to, tetrahydrofuranyl, tetrahydrothiophenyl, 3,6-dihydro-2H-pyridinyl, 1,2,3,4-tetrahydropyridinyl, 1,2,5,6-tetrahydropyridinyl, pyrrolidinyl, morpholinyl, piperidinyl, piperazinyl, oxazolinyl, oxazolidinyl, 3,4-dihydro-2H-pyranyl, 5,6-dihydro-2H-pyranyl, 2H-pyranyl, tetrahydropyranyl, and dihydro-1H-pyrrolyl. In one embodiment, heterocyclyl$^2$ includes piperidinyl and pyrrolidinyl, in particular piperidin-1-yl and pyrrolidin-1-yl. Heterocyclyl$^2$ is optionally substituted by —OH or ($C_1$-$C_3$)alkyl, preferably methyl. In a preferred embodiment, heterocyclyl$^2$ is not substituted.

As used herein, the term "heterocyclyl$^3$" refers to a 4, 5, 6, 7 or 8-membered saturated or partially unsaturated heterocyclic ring which is attached via a ring C-atom and comprises 1 ring heteroatom selected from N, O and S in a position other than adjacent to the linking C atom. Specific examples of such heterocyclyl$^3$ include, but are not limited to azetidinyl, oxetanyl, pyrrolidinyl, 2,3-dihydro-1H-pyrrolyl, 2,5-dihydro-1H-pyrrolyl, tetrahydrofuryl, tetrahydrothiophenyl, piperidinyl, 1,2-dihydropyridinyl, 3,6-dihydro-2H-pyridinyl, 1,2,3,4-tetrahydropyridinyl, 1,2,3,6-tetrahydropyridinyl, quinuclidinyl, tetrahydropyranyl, 3,4-dihydro-2H-pyranyl, 5,6-dihydro-2H-pyranyl, tetrahydrothiopyranyl, oxepanyl and azepanyl.

In one embodiment, the term "heterocyclyl$^3$" refers to a 4, 5, 6 or 7-membered saturated heterocyclic ring which is attached via a ring C-atom and comprises 1 ring heteroatom selected from N and O in a position other than adjacent to the linking C atom. Specific examples of such heterocyclyl$^1$ include, but are not limited to, azetidinyl, oxetanyl, pyrrolidinyl, tetrahydrofuryl, piperidinyl, tetrahydropyranyl, oxepanyl and azepanyl. Preferred examples of such heterocyclyl$^3$ include, but are not limited to oxetanyl, pyrrolidinyl, tetrahydrofuryl, piperidinyl, and tetrahydropyranyl; in particular oxetan-3-yl, pyrrolidin-3-yl, tetrahydrofuran-3-yl, piperidin-4-yl, and tetrahydropyran-4-yl.

Within the context of the present invention, a heterocyclyl$^3$ group of the present invention (being an heterocyclic ring attached via a ring C-atom as defined above) can be optionally substituted by one or two substituents independently selected from —OH, halo, —COO($C_1$-$C_4$)alkyl, —O($C_1$-$C_4$)alkyl, and ($C_1$-$C_4$)alkyl, said ($C_1$-$C_4$)alkyl being optionally substituted by one, two or three substituents independently selected from OH and halo. Additionally, heterocyclyl$^3$ can be substituted by one or two further ($C_1$-$C_4$)alkyl groups.

In one embodiment of the present invention, a heterocyclyl$^3$ group as defined above comprising a ring N-atom is substituted (i) at such ring N-atom with a substituent selected from —COO($C_1$-$C_4$)alkyl and ($C_1$-$C_4$)alkyl, preferably a ($C_1$-$C_2$)alkyl group, optionally substituted by one, two or three substituents independently selected from OH and halo, or (ii) at one or both ring C-atoms next to the ring N-atom by up to four ($C_1$-$C_2$)alkyl groups.

In one embodiment of the present invention, the term "optionally substituted heterocyclyl$^3$" refers to a group selected from oxetan-3-yl, pyrrolidin-3-yl, 1-methylpyrrolidin-3-yl, tetrahydrofuran-3-yl, piperidin-4-yl, 2,2,6,6-tetramethylpiperidin-4-yl, 1-methyl-piperidin-4-yl, and tetrahydropyran-4-yl. Preferably, "optionally substituted heterocyclyl$^3$" refers to a group selected from oxetan-3-yl, 1-methyl-pyrrolidin-3-yl, tetrahydro-furan-3-yl, 2,2,6,6-tetramethylpiperidin-4-yl, 1-methyl-piperidin-4-yl, and tetrahydropyran-4-yl.

EMBODIMENTS

In one embodiment, the invention provides a compound of formula (I) or a salt or solvate thereof, wherein $R^1$ is pyrazolyl, optionally substituted by ($C_1$-$C_4$)alkyl, said ($C_1$-$C_4$) alkyl being optionally substituted by one OH group. In particular, $R^1$ is 1H-pyrazol-4-yl, optionally substituted by methyl or 2-hydroxy-ethyl. In a preferred embodiment of the invention, $R^1$ is selected from 1-methyl-1H-pyrazol-4-yl, 1H-pyrazol-4-yl, and 1-(2-hydroxy-ethyl)-1H-pyrazol-4-yl. In particular, $R^1$ is 1-methyl-1H-pyrazol-4-yl.

In an alternative embodiment, the invention provides a compound of formula (I) or a salt or solvate thereof, wherein $R^1$ is —$CR^9$=N—O—$R^{10}$, wherein $R^9$ is hydrogen or ($C_1$-$C_4$)alkyl; and $R^{10}$ is hydrogen or ($C_1$-$C_4$)alkyl, said ($C_1$-$C_4$)alkyl being optionally substituted by one OH group. In one embodiment, $R^1$ is —$CR^9$=N—O—$R^{10}$, wherein $R^9$ is ($C_1$-$C_2$)alkyl; and, $R^{10}$ is hydrogen or ($C_1$-$C_2$)alkyl, said ($C_1$-$C_2$)alkyl being optionally substituted by one OH group. In a preferred embodiment of the invention, $R^1$ is —$CR^9$=N—O—$R^{10}$, wherein $R^9$ is methyl; and $R^{10}$ is hydrogen or 2-hydroxy-ethyl. In particular, $R^1$ is selected from 1-yl-ethanone oxime and 1-yl ethanone O-(2-hydroxy-ethyl)-oxime. Preferably, when $R^1$ is —$CR^9$=N—O—$R^{10}$, then $R^3$ is optionally substituted heterocyclyl$^1$ as defined herein.

In one embodiment, the invention provides a compound of formula (I) or a salt or solvate thereof, wherein $R^2$ is selected from hydrogen and fluoro. In one embodiment, $R^2$ is hydrogen. In another embodiment, $R^2$ is fluoro. Preferably, $R^2$ is hydrogen.

In another embodiment, the invention provides a compound of formula (I) or a salt or solvate thereof, wherein $R^3$ is —($C_0$-$C_1$)alkyl-heterocyclyl$^1$. In another embodiment, $R^3$ is —$CH_2$-heterocyclyl$^1$. In another preferred embodiment, $R^3$ is heterocyclyl$^1$. The heterocyclyl$^1$ group has a meaning and can be optionally substituted as defined herein.

In a preferred embodiment of the invention, $R^3$ is —$CH_2$-heterocyclyl$^1$ or heterocyclyl$^1$, wherein heterocyclyl$^1$ is a 4, 5, 6, or 7 membered saturated N-heterocyclic ring which is attached via the N-atom and optionally comprises one additional ring heteroatom independently selected from N and O in a position other than adjacent to the linking N atom, wherein the N-heterocyclic ring is optionally substituted
(i) by one, two or three substituents independently selected from —OH, halo, —COO($C_1$-$C_4$)alkyl, —$NH_2$, —NH—COO($C_1$-$C_4$)alkyl, —NH($C_1$-$C_3$)alkyl, —N(($C_1$-$C_3$)alkyl)$_2$, —O($C_1$-$C_4$)alkyl, heterocyclyl$^2$, —($C_3$-$C_8$)cycloalkyl, phenyl and ($C_1$-$C_4$)alkyl, said ($C_1$-$C_4$)alkyl being optionally substituted by one, two or three substituents independently selected from OH and halo;
wherein heterocyclyl$^1$ is a 5 or 6-membered saturated monocyclic group comprising 1 ring heteroatom independently selected from N and O; or
(ii) by two groups which are attached to the same carbon atom and are combined into a cyclic 4, 5, or 6 membered saturated ring system optionally comprising 1 ring heteroatom independently selected from N and O In another embodiment of the invention, $R^3$ is —$CH_2$-heterocyclyl$^1$, wherein heterocyclyl$^1$ is a 5 or 6 membered saturated N-heterocyclic ring which is attached via the N-atom and optionally comprises one additional ring heteroatom selected from N and O in a position other than adjacent to the linking N atom, wherein any additional ring N-atom is substituted with an ($C_1$-$C_4$)alkyl group. Preferably, $R^3$ is 4-methyl-piperazin-1-ylmethyl or morpholin-4-ylmethyl. In embodiments when $R^3$ is such —$CH_2$-heterocyclyl$^1$, then $R^1$ is preferably optionally substituted pyrazole.

In a preferred embodiment of the invention, $R^3$ is heterocyclyl$^1$ being a 4, 5, 6, or 7 membered saturated N-heterocyclic ring which is attached via the N-atom and optionally comprises one additional ring heteroatom independently selected from N and O in a position other than adjacent to the linking N atom, wherein the N-heterocyclic ring is optionally substituted
(i) at one or two ring C-atoms by overall one or two substituents independently selected from —OH, halo, —$NH_2$, —NH—COO($C_1$-$C_4$)alkyl, —NH($C_1$-$C_3$)alkyl, —N(($C_1$-$C_3$)alkyl)$_2$, —O($C_1$-$C_4$)alkyl, heterocyclyl$^2$, and ($C_1$-$C_4$)alkyl;
preferably selected from —OH, halo, —$NH_2$, —NH($C_1$-$C_3$)alkyl, —N(($C_1$-$C_3$)alkyl)$_2$, —O($C_1$-$C_4$)alkyl, heterocyclyl$^2$, and ($C_1$-$C_4$)alkyl,
more preferably from —OH, halo, —N(methyl)$_2$, —O-methyl, heterocyclyl$^2$, and methyl;
wherein heterocyclyl$^2$ is a 5 or 6-membered saturated N-heterocyclic ring which is attached via the N-atom;
(ii) at the optionally present additional ring N-atom by one substituent selected from —COO($C_1$-$C_4$)alkyl, —($C_5$-$C_6$)cycloalkyl, phenyl and ($C_1$-$C_4$)alkyl, said ($C_1$-$C_4$)alkyl being optionally substituted by one, two or three substituents independently selected from OH and halo;
preferably selected from —($C_5$-$C_6$)cycloalkyl, phenyl and ($C_1$-$C_2$)alkyl, said ($C_1$-$C_2$)alkyl being optionally substituted by one, two or three substituents independently selected from OH and halo;
more preferably by one substituent selected from cyclohexyl, phenyl and methyl; or
(iii) by two groups which are attached to the same carbon atom and are combined into a cyclic 4, 5, or 6 membered saturated ring system comprising 1 ring O-atom, preferably by two groups which are attached to the same carbon atom and are combined into a cyclic 4 or 6 membered saturated ring system comprising 1 ring O-atom.

In a preferred embodiment of the invention, $R^3$ is heterocyclyl$^1$ being a 4, 5, 6, or 7 membered saturated N-heterocyclic ring which is attached via the N-atom and optionally comprises one additional ring heteroatom independently selected from N and O in a position other than adjacent to the linking N atom, wherein the N-heterocyclic ring is optionally substituted
(i) at one or two ring C-atoms by overall one or two substituents independently selected from —OH, halo, —$NH_2$, —N(methyl)$_2$, —O-methyl, heterocyclyl$^2$, and methyl;
wherein heterocyclyl$^2$ is a 5 or 6-membered saturated N-heterocyclic ring which is attached via the N-atom;
(ii) at the optionally present additional ring N-atom by one substituent selected from cyclohexyl, phenyl and methyl; or
(iii) by two groups which are attached to the same carbon atom and are combined into a cyclic 4 or 6 membered saturated ring system comprising 1 ring O-atom.

In a preferred embodiment of the invention, $R^3$ is heterocyclyl$^1$ being selected from piperidin-1-yl, pyrrolidin-1-yl, piperazin-1-yl, morpholin-4-yl, azetidin-1-yl, and 1,4-diazepan-1-yl, wherein heterocyclyl$^1$ is optionally substituted
(i) at one or two ring C-atoms by overall one or two substituents independently selected from —OH, halo, —$NH_2$, —N(methyl)$_2$, —O-methyl, piperidin-1-yl, pyrrolidin-1-yl, and methyl;
(ii) at the optionally present additional ring N-atom by one substituent selected from cyclohexyl and methyl; or
(iii) by two groups which are attached to the same carbon atom and are combined into a cyclic 4 or 6 membered saturated ring system comprising 1 ring O-atom.

In another embodiment, the invention provides a compound of formula (I) or a salt or solvate thereof, wherein $R^3$ is heterocyclyl$^1$ being selected from piperidin-1-yl, pyrrolidin-1-yl, piperazin-1-yl, morpholin-4-yl, azetidin-1-yl, and 1,4-diazepan-1-yl, 3-aminopyrrolidin-1-yl, 3-N,N-dimethylaminopyrrolidin-1-yl, 3-aminopiperidin-1-yl, 4-aminopiperidin-1-yl, 4-(pyrrolidin-1-yl)piperidin-1-yl, 1,4'-bipiperidin-1'-yl, 4-methoxypiperidin-1-yl, 4-hydroxypiperidin-1-yl, 4,4-difluoro-piperidin-1-yl, 2,2,2-trifluoroethylpiperazin-1-yl, 4-cyclohexylpiperazin-1-yl, 4-phenylpiperazin-1-yl, 3,5-dimethylpiperazin-1-yl, 2-methylpiperazin-1-yl, 4-methylpiperazin-1-yl, 2-methylmorpholin-4-yl, 2,6-dimethylmorpholin-4-yl, 3-methylmorpholin-4-yl, 4-methyl-1,4-diazepan-1-yl, 4-(2-hydroxyethyl)-1,4-diazepan-1-yl, 2-oxa-6-azaspiro[3.3]heptan-6-yl, and 8-oxa-2-azaspiro[4.5]decan-2-yl. Preferably, $R^3$ is heterocyclyl$^1$ being selected from 4,4-difluoro-piperidin-1-yl, 3-N,N-dimethylaminopyrrolidin-1-yl, 4-methoxypiperidin-1-yl, 1,4'-bipiperidin-1'-yl, 4-(pyrrolidin-1-yl)piperidin-1-yl, 2-oxa-6-azaspiro[3.3]heptan-6-yl, 4-hydroxypiperidin-1-yl, 8-oxa-2-azaspiro[4.5]decan-2-yl, 3,5-dimethylpiperazin-1-yl, 4-methyl-piperazin-1-yl, 4-methyl-1,4-diazepan-1-yl, piperazin-1-yl, morpholin-4-yl, 2-methylmorpholin-4-yl, and 2,6-dimethylmorpholin-4-yl.

In particular, $R^3$ is heterocyclyl$^1$ being selected from piperazin-1-yl, morpholin-4-yl, 4-methoxypiperidin-1-yl, 4-hydroxypiperidin-1-yl, 3,5-dimethylpiperazin-1-yl, 3-N,N-dimethylaminopyrrolidin-1-yl, 3-amino-piperidin-1-yl, 3-amino-pyrrolidin-1-yl and 4-methyl-piperazin-1-yl. In a further embodiment thereof, $R^3$ is heterocyclyl$^1$ being selected from piperazin-1-yl, morpholin-4-yl, 4-methoxypiperidin-1-yl, 4-hydroxypiperidin-1-yl, 3,5-dimethylpiperazin-1-yl, and 4-methyl-piperazin-1-yl.

In another embodiment, the invention provides a compound of formula (I) or a salt or solvate thereof, wherein
$R^1$ is selected from 1-methyl-1H-pyrazol-4-yl, 1-yl-ethanone oxime, and 1-yl ethanone O-(2-hydroxyethyl)-oxime, preferably 1-methyl-1H-pyrazol-4-yl,
$R^2$ is hydrogen or fluoro,
$R^3$ is heterocyclyl$^1$, wherein heterocyclyl$^1$ is selected from
a) a 4, 5 or 6 membered saturated N-heterocyclic ring attached via the N-atom and substituted
  (i) at one or two ring C-atom or atoms by overall one or two substituents selected from —OH, fluoro, —NH$_2$, —N(methyl)$_2$, methoxy, piperidin-1-yl, pyrrolidin-1-yl, and methyl; or
  (ii) by two groups which are attached to the same carbon atom and are combined into a cyclic 4 or 6 membered saturated ring system comprising 1 ring O-atom;
b) a 6 membered saturated N-heterocyclic ring attached via the N-atom and comprising one ring O-atom in a position other than adjacent to the linking N atom, wherein the N-heterocyclic ring is optionally substituted by one or two methyl groups; and
c) a 6 or 7 membered saturated N-heterocyclic ring attached via the N-atom and comprising one additional ring N-atom in a position other than adjacent to the linking N atom, wherein the N-heterocyclic ring is optionally substituted
  (i) at the additional ring N-atom by a substituent selected from cyclohexyl, phenyl and (C$_1$-C$_2$)alkyl, said (C$_1$-C$_2$) alkyl being optionally substituted by one, two or three substituents independently selected from OH and halo; or
  (ii) at one or two ring C-atoms by one or two methyl groups.

In this embodiment, $R^3$ is preferably heterocyclyl$^1$, wherein heterocyclyl$^1$ is selected from
a) a 4, 5 or 6 membered saturated N-heterocyclic ring attached via the N-atom and substituted
  (i) at one ring C-atom by —OH, difluoro, —NH$_2$, —N(methyl)$_2$, methoxy, piperidin-1-yl, and pyrrolidin-1-yl; or
  (ii) by two groups which are attached to the same carbon atom and are combined into a cyclic 4 or 6 membered saturated ring system comprising 1 ring O-atom;
b) a 6 membered saturated N-heterocyclic ring attached via the N-atom and comprising one ring O-atom in a position other than adjacent to the linking N atom, wherein the N-heterocyclic ring is optionally substituted by one or two methyl groups; and
c) a 6 or 7 membered saturated N-heterocyclic ring attached via the N-atom and comprising one additional ring N-atom in a position other than adjacent to the linking N atom, wherein the N-heterocyclic ring is optionally substituted
  (i) at the additional ring N-atom by a substituent selected from cyclohexyl and methyl; or
  (ii) at one or two ring C-atoms adjacent to the additional ring N-atom by one or two methyl groups.

In a preferred embodiment, the invention provides a compound of formula (I) or a pharmaceutically acceptable salt or solvate thereof, wherein
$R^1$ is selected from 1-methyl-1H-pyrazol-4-yl, 1-yl-ethanone oxime, and 1-yl ethanone O-(2-hydroxyethyl)-oxime, preferably 1-methyl-1H-pyrazol-4-yl,
$R^2$ is hydrogen or fluoro, and
$R^3$ is heterocyclyl$^1$, wherein heterocyclyl$^1$ is selected from piperazin-1-yl, morpholin-4-yl, 4-methoxypiperidin-1-yl, 4-hydroxypiperidin-1-yl, 3,5-dimethylpiperazin-1-yl, 3-N,N-dimethylaminopyrrolidin-1-yl, 3-amino-piperidin-1-yl, 3-amino-pyrrolidin-1-yl and 4-methyl-piperazin-1-yl.

In another embodiment thereof, the invention provides a compound of formula (I) or a pharmaceutically acceptable salt or solvate thereof, wherein
$R^1$ is selected from 1-methyl-1H-pyrazol-4-yl,
$R^2$ is hydrogen or fluoro, and
$R^3$ is heterocyclyl$^1$, wherein heterocyclyl$^1$ is selected from piperazin-1-yl, morpholin-4-yl, 4-methoxypiperidin-1-yl, 4-hydroxypiperidin-1-yl, 3,5-dimethylpiperazin-1-yl, and 4-methyl-piperazin-1-yl.

In an alternative embodiment, the present invention relates to a compound of the formula (I), wherein
$R^1$ is selected from 1-methyl-1H-pyrazol-4-yl, 1-yl-ethanone oxime, and 1-yl ethanone O-(2-hydroxyethyl)-oxime, preferably 1-methyl-1H-pyrazol-4-yl;
$R^2$ is hydrogen or fluoro; and
$R^3$ is —NHR$^4$, wherein R$^4$ is —(C$_0$-C$_1$)alkyl-heterocyclyl$^3$; wherein heterocyclyl$^3$ refers to a 4, 5 or 6-membered saturated heterocyclic ring which is attached via a ring C-atom and comprises 1 ring heteroatom selected from N and O in a position other than adjacent to the linking C atom, wherein a heterocyclyl$^3$ group comprising a ring N-atom is substituted
  (i) at such ring N-atom with a substituent selected from —COO(C$_1$-C$_4$)alkyl and (C$_1$-C$_4$)alkyl, preferably a (C$_1$-C$_2$)alkyl group, optionally substituted by one, two or three substituents independently selected from OH and halo, or
  (ii) at one or both ring C-atoms next to the ring N-atom by up to four (C$_1$-C$_2$)alkyl groups,
or a pharmaceutically acceptable salt or solvate thereof.

In a preferred embodiment thereof, $R^3$ is —NHR$^4$, wherein R$^4$ is —(C$_0$-C$_1$)alkyl-heterocyclyl$^3$; wherein heterocyclyl$^3$ is selected from azetidinyl, oxetanyl, pyrrolidinyl, tetrahydrofuryl, piperidinyl, tetrahydropyranyl, oxepanyl and azepanyl.

In a further preferred embodiment thereof, $R^3$ is —NHR$^4$, wherein R$^4$ is selected from oxetan-3-yl, 1-methyl-pyrrolidin-3-yl, tetrahydrofuran-3-yl, (tetrahydrofuran-3-yl)-methyl, 2,2,6,6-tetramethylpiperidin-4-yl, 1-methyl-piperidin-4-yl, and tetrahydropyran-4-yl.

In a further aspect, the present invention relates to a compound of the formula (I), wherein
$R^1$ is —CR$^9$=N—O—R$^{10}$, wherein
  $R^9$ is methyl; and
  $R^{10}$ is hydrogen or 2-hydroxy-ethyl;
$R^2$ is hydrogen or fluoro, and
$R^3$ is optionally substituted-heterocyclyl$^1$ as defined herein;
or a pharmaceutically acceptable salt or solvate thereof.

In a preferred embodiment thereof, $R^3$ is heterocyclyl[1] which is a 5 or 6-membered saturated N-heterocyclic ring attached via the N-atom and optionally comprises one additional ring heteroatom independently selected from N and O in a position other than adjacent to the linking N atom, and optionally substituted with a substituent selected from —OH, —N(methyl)$_2$, methoxy and methyl. Preferably, $R^3$ is heterocyclyl[1], wherein heterocyclyl[1] is selected from morpholin-4-yl, 4-methoxypiperidin-1-yl, 4-hydroxypiperidin-1-yl, N,N-dimethylamino-pyrrolidin-1-yl, 4-methyl-piperazin-1-yl and 3,5-dimethylpiperazin-1-yl.

Various embodiments of the invention are described herein. It will be recognized that features specified in each embodiment may be combined with other specified features to provide further embodiments.

In a particular embodiment, the invention provides one or more individual compounds as those listed in the Examples section below, or a pharmaceutically acceptable salt or solvate thereof.

In another embodiment the invention provides a compound of the formula (I), which is selected from the following compounds:

No. 1 tert-Butyl 1-(6-(6-(1-methyl-1H-pyrazol-4-yl)-[1,2,4]triazolo[4,3-a]pyridin-3-ylthio)quinolin-3-yl)pyrrolidin-3-ylcarbamate No. 2 1-(6-(6-(1-Methyl-1H-pyrazol-4-yl)-[1,2,4]triazolo[4,3-a]pyridin-3-ylthio)quinolin-3-yl)pyrrolidin-3-amine No. 3 (S)—N,N-Dimethyl-1-(6-(6-(1-methyl-1H-pyrazol-3-yl)-[1,2,4]triazolo[4,3-a]pyridin-3-ylthio)quinolin-3-yl)pyrrolidin-3-amine No. 4 (S)-tert-Butyl 3-(6-(6-(1-methyl-1H-pyrazol-4-yl)-[1,2,4]triazolo[4,3-a]pyridin-3-ylthio)quinolin-3-ylamino)pyrrolidine-1-carboxylate No. 5 (S)-6-(6-(1-Methyl-1H-pyrazol-4-yl)-[1,2,4]triazolo[4,3-a]pyridin-3-ylthio)-N-(pyrrolidin-3-yl)quinolin-3-amine No. 6 6-(6-(1-Methyl-1H-pyrazol-4-yl)-[1,2,4]triazolo[4,3-a]pyridin-3-ylthio)-3-((4-methylpiperazin-1-yl)methyl)quinoline No. 7 6-(8-Fluoro-6-(1-methyl-1H-pyrazol-4-yl)-[1,2,4]triazolo[4,3-a]pyridin-3-ylthio)-N-(2,2,6,6-tetramethylpiperidin-4-yl)quinolin-3-amine No. 8 {6-[8-Fluoro-6-(1-methyl-1H-pyrazol-4-yl)-[1,2,4]triazolo[4,3-a]pyridin-3-ylsulfanyl]-quinolin-3-yl}-(1-methyl-piperidin-4-yl)-amine No. 9 tert-Butyl 1-(6-(6-(1-methyl-1H-pyrazol-4-yl)-[1,2,4]triazolo[4,3-a]pyridin-3-ylthio)quinolin-3-yl)piperidin-3-ylcarbamate No. 10 1-(6-(6-(1-Methyl-1H-pyrazol-4-yl)-[1,2,4]triazolo[4,3-a]pyridin-3-ylthio)quinolin-3-yl)piperidin-3-amine No. 11 6-(6-(1-Methyl-1H-pyrazol-4-yl)-[1,2,4]triazolo[4,3-a]pyridin-3-ylthio)-N-((tetrahydrofuran-3-yl)methyl)quinolin-3-amine No. 12 6-(6-(6-(1-Methyl-1H-pyrazol-4-yl)-[1,2,4]triazolo[4,3-a]pyridin-3-ylthio)quinolin-3-yl)-2-oxa-6-azaspiro[3.3]heptane No. 13 (S)-1-(6-(8-Fluoro-6-(1-methyl-1H-pyrazol-4-yl)-[1,2,4]triazolo[4,3-a]pyridin-3-ylthio)quinolin-3-yl)-N,N-dimethylpyrrolidin-3-amine No. 14 6-(8-Fluoro-6-(1-methyl-1H-pyrazol-4-yl)-[1,2,4]triazolo[4,3-a]pyridin-3-ylthio)-3-(4-(pyrrolidin-1-yl)piperidin-1-yl)quinoline No. 15 (1-Methyl-piperidin-4-yl)-{6-[6-(1-methyl-1H-pyrazol-4-yl)-[1,2,4]triazolo[4,3-a]pyridin-3-ylsulfanyl]-quinolin-3-yl}-amine No. 17 3-(4-Methyl-1,4-diazepan-1-yl)-6-(6-(1-methyl-1H-pyrazol-4-yl)-[1,2,4]triazolo[4,3-a]pyridin-3-ylthio)quinoline No. 18 tert-Butyl 4-(6-(6-(1-methyl-1H-pyrazol-4-yl)-[1,2,4]triazolo[4,3-a]pyridin-3-ylthio)quinolin-3-yl)-1,4-diazepane-1-carboxylate No. 19 3-(1,4-Diazepan-1-yl)-6-(6-(1-methyl-1H-pyrazol-4-yl)-[1,2,4]triazolo[4,3-a]pyridin-3-ylthio)quinoline No. 20 tert-Butyl 1-(6-(6-(1-methyl-1H-pyrazol-4-yl)-[1,2,4]triazolo[4,3-a]pyridin-3-ylthio)quinolin-3-yl)piperidin-4-ylcarbamate No. 21 1-(6-(6-(1-Methyl-1H-pyrazol-4-yl)-[1,2,4]triazolo[4,3-a]pyridin-3-ylthio)quinolin-3-yl)piperidin-4-amine No. 22 tert-Butyl 4-(6-(6-(1-methyl-1H-pyrazol-4-yl)-[1,2,4]triazolo[4,3-a]pyridin-3-ylthio)quinolin-3-ylamino)piperidine-1-carboxylate No. 23 6-(6-(1-Methyl-1H-pyrazol-4-yl)-[1,2,4]triazolo[4,3-a]pyridin-3-ylthio)-N-(piperidin-4-yl)quinolin-3-amine No. 24 6-[8-Fluoro-6-(1-methyl-1H-pyrazol-4-yl)-[1,2,4]triazolo[4,3-a]pyridin-3-ylsulfanyl]-3-(4-methyl-piperazin-1-yl)-quinoline No. 25 {6-[8-Fluoro-6-(1-methyl-1H-pyrazol-4-yl)-[1,2,4]triazolo[4,3-a]pyridin-3-ylsulfanyl]-quinolin-3-yl}-(tetrahydro-pyran-4-yl)-amine No. 26 tert-Butyl 4-(6-(6-(1-methyl-1H-pyrazol-4-yl)-[1,2,4]triazolo[4,3-a]pyridin-3-ylthio)quinolin-3-yl)piperazine-1-carboxylate No. 27 6-(6-(1-Methyl-1H-pyrazol-4-yl)-[1,2,4]triazolo[4,3-a]pyridin-3-ylthio)-3-(piperazin-1-yl)quinoline No. 28 6-(6-(1-Methyl-1H-pyrazol-4-yl)-[1,2,4]triazolo[4,3-a]pyridin-3-ylthio)-3-(4-(2,2,2-trifluoroethyl)piperazin-1-yl)quinoline No. 29 2-(4-(6-(6-(1-Methyl-1H-pyrazol-4-yl)-[1,2,4]triazolo[4,3-a]pyridin-3-ylthio)quinolin-3-yl)-1,4-diazepan-1-yl)ethanol No. 30 3-(1,4'-Bipiperidin-1'-yl)-6-(6-(1-methyl-1H-pyrazol-4-yl)-[1,2,4]triazolo[4,3-a]pyridin-3-ylthio)quinoline No. 31 3-(1,4'-Bipiperidin-1'-yl)-6-(8-fluoro-6-(1-methyl-1H-pyrazol-4-yl)-[1,2,4]triazolo[4,3-a]pyridin-3-ylthio)quinoline No. 32 3-(4-Cyclohexylpiperazin-1-yl)-6-(6-(1-methyl-1H-pyrazol-4-yl)-[1,2,4]triazolo[4,3-a]pyridin-3-ylthio)quinoline No. 33 6-(6-(1-Methyl-1H-pyrazol-4-yl)-[1,2,4]triazolo[4,3-a]pyridin-3-ylthio)-3-(4-(pyrrolidin-1-yl)piperidin-1-yl)quinoline No. 34 6-(6-(1-Methyl-1H-pyrazol-4-yl)-[1,2,4]triazolo[4,3-a]pyridin-3-ylthio)-3-(4-phenylpiperazin-1-yl)quinoline No. 35 2-Methyl-4-(6-(6-(1-methyl-1H-pyrazol-4-yl)-[1,2,4]triazolo[4,3-a]pyridin-3-ylthio)quinolin-3-yl)morpholine No. 35A (S)-2-Methyl-4-(6-(6-(1-methyl-1H-pyrazol-4-yl)-[1,2,4]triazolo[4,3-a]pyridin-3-ylthio)quinolin-3-yl)morpholine No. 35B (R)-2-Methyl-4-(6-(6-(1-methyl-1H-pyrazol-4-yl)-[1,2,4]triazolo[4,3-a]pyridin-3-ylthio)quinolin-3-yl)morpholine No. 36 4-(6-(8-Fluoro-6-(1-methyl-1H-pyrazol-4-yl)-[1,2,4]triazolo[4,3-a]pyridin-3-ylthio)quinolin-3-yl)-2-methylmorpholine No. 37 2,6-Dimethyl-4-(6-(6-(1-methyl-1H-pyrazol-4-yl)-[1,2,4]triazolo[4,3-a]pyridin-3-ylthio)quinolin-3-yl)morpholine No. 38 4-(6-(8-Fluoro-6-(1-methyl-1H-pyrazol-4-yl)-[1,2,4]triazolo[4,3-a]pyridin-3-ylthio) quinolin-3-yl)-2,6-dimethylmorpholine No. 39 (2S,6R)-tert-Butyl 4-(6-(8-fluoro-6-(1-methyl-1H-pyrazol-4-yl)-[1,2,4]triazolo[4,3-a]pyridin-3-ylthio)quinolin-3-yl)-2,6-dimethylpiperazine-1-carboxylate No. 40 3-((3S,5R)-3,5-Dimethylpiperazin-1-yl)-6-(8-fluoro-6-(1-methyl-1H-pyrazol-4-yl)-[1,2,4]triazolo[4,3-a]pyridin-3-ylthio)quinoline No. 41 (2S,6R)-tert-Butyl 2,6-dimethyl-4-(6-(6-(1-methyl-1H-pyrazol-4-yl)-[1,2,4]triazolo[4,3-a]pyridin-3-ylthio)quinolin-3-yl)piperazine-1-carboxylate No. 42 3-((3S,5R)-3,5-Dimethylpiperazin-1-yl)-6-(6-(1-methyl-1H-pyrazol-4-yl)-[1,2,4]triazolo[4,3-a]pyridin-3-ylthio)quinoline No. 43 3-(4-Methoxypiperidin-1-yl)-6-(6-(1-methyl-1H-pyrazol-4-yl)-[1,2,4]triazolo[4,3-a]pyridin-3-ylthio)quinoline No. 44 6-(8-Fluoro-6-(1-methyl-1H-pyrazol-4-yl)-[1,2,4]triazolo[4,3-a]pyridin-3-ylthio)-3-(4-methoxypiperidin-1-yl)quinoline No. 45 (S)-tert-Butyl 4-(6-(8-fluoro-6-(1-methyl-1H-pyrazol-4-yl)-[1,2,4]triazolo[4,3-a]pyridin-3-ylthio)quinolin-3-yl)-3-methylpiperazine-1-carboxylate No. 46 (S)-6-(8-Fluoro-6-(1-methyl-1H-pyrazol-4-yl)-[1,2,4]triazolo[4,3-a]pyridin-3-ylthio)-3-(2-methylpiperazin-1-yl)quinoline No. 47 2-(6-((6-(1-Methyl-1H-pyrazol-4-yl)-[1,2,4]triazolo[4,3-a]pyridin-3-yl)thio)quinolin-3-yl)-8-oxa-2-azaspiro[4.5]decane No. 48 2-(6-(8-Fluoro-6-(1-methyl-1H-pyrazol-4-yl)-[1,2,4]triazolo[4,3-a]pyridin-3-ylthio)quinolin-3-yl)-8-oxa-2-azaspiro[4.5]decane No. 49 1-(6-((6-(1-Methyl-1H-pyrazol-4-yl)-[1,2,4]triazolo[4,3-a]pyridin-3-yl)thio)quinolin-3-yl)piperidin-4-ol No. 50 1-(6-((8-Fluoro-6-(1-methyl-1H-pyrazol-4-yl)-[1,2,4]triazolo[4,3-a]pyridin-3-yl)thio)quinolin-3-yl)piperidin-4-ol No. 51 6-[6-(1-Methyl-1H-pyrazol-3-yl)-[1,2,4]triazolo[4,3-a]pyridin-3-ylsulfanyl]-quinolin-3-yl}-(tetrahydro-furan-3-yl)-amine No. 52 {6-[8-Fluoro-6-(1-methyl-1H-pyrazol-3-yl)-[1,2,4]triazolo[4,3-a]pyridin-3-ylsulfanyl]-quinolin-3-yl}-(tetrahydro-furan-3-yl)-amine No. 53 2-(6-(6-(1-methyl-1H-pyrazol-4-yl)-[1,2,4]triazolo[4,3-a]pyridin-3-ylthio)quinolin-3-ylamino)ethanol No. 54 2-(6-(8-Fluoro-6-(1-methyl-1H-pyrazol-4-yl)-[1,2,4]triazolo[4,3-a]pyridin-3-ylthio)quinolin-3-ylamino)ethanol No. 55 6-(8-Fluoro-6-(1-methyl-1H-pyrazol-4-yl)-[1,2,4]triazolo[4,3-a]pyridin-3-ylthio)quinolin-3-amine hydrochloride No. 56 6-(6-(1-Methyl-1H-pyrazol-4-yl)-[1,2,4]triazolo[4,3-a]pyridin-3-ylthio)quinolin-3-amine hydrochloride No. 57 4-(6-(6-(1H-pyrazol-4-yl)-[1,2,4]triazolo[4,3-a]pyridin-3-ylthio)quinolin-3-yl)morpholine No. 58 4-(6-(8-Fluoro-6-(1H-pyrazol-4-yl)-[1,2,4]triazolo[4,3-a]pyridin-3-ylthio)quinolin-3-yl)morpholine No. 59 3-Methyl-4-(6-(6-(1-methyl-1H-pyrazol-4-yl)-[1,2,4]triazolo[4,3-a]pyridin-3-ylthio)quinolin-3-yl)-morpholine No. 60 4-(6-(8-Fluoro-6-(1-methyl-1H-pyrazol-4-yl)-[1,2,4]triazolo[4,3-a]pyridin-3-ylthio)quinolin-3-yl)-3-methylmorpholine No. 61 3-(4,4-Difluoro-piperidin-1-yl)-6-[6-(1-methyl-1H-pyrazol-4-yl)-[1,2,4]triazolo[4,3-a]pyridin-3-ylsulfanyl]-quinoline No. 62 6-(6-(1-Methyl-1H-pyrazol-4-yl)-[1,2,4]triazolo[4,3-a]pyridin-3-ylthio)-N-(2,2,6,6-tetramethyl piperidin-4-yl)quinolin-3-amine No. 64 6-(8-Fluoro-6-(1-methyl-1H-pyrazol-4-yl)-[1,2,4]triazolo[4,3-a]pyridin-3-ylthio)-N-(oxetan-3-yl) quinolin-3-amine No. 67 3-(4,4-Difluoro-piperidin-1-yl)-6-[8-fluoro-6-(1-methyl-1H-pyrazol-4-yl)[1,2,4]triazolo[4,3-a]pyridin-3-ylsulfanyl]-quinoline No. 68 {6-[6-(1-Methyl-1H-pyrazol-4-yl)-[1,2,4]triazolo[4,3-a]pyridin-3-ylsulfanyl]-quinolin-3-yl}-(tetrahydro-pyran-4-yl)-amine No. 69 4-(6-(6-(1-Methyl-1H-pyrazol-4-yl)-[1,2,4]triazolo[4,3-a]pyridin-3-ylthio)quinolin-3-yl)morpholine No. 70 4-(6-(8-Fluoro-6-(1-methyl-1H-pyrazol-4-yl)-[1,2,4]triazolo[4,3-a]pyridin-3-ylthio)quinolin-3-yl)morpholine No. 71 6-(6-(1-Methyl-1H-pyrazol-4-yl)-[1,2,4]triazolo[4,3-a]pyridin-3-ylthio)-N-(oxetan-3-yl)quinolin-3-amine No. 72 2-(4-(3-(3-Morpholin-4-yl-quinolin-6-ylthio)-[1,2,4]triazolo[4,3-a]pyridin-6-yl)-1H-pyrazol-1-yl)ethanol No. 74 3-(4-Methyl-piperazin-1-yl)-6-[6-(1-methyl-1H-pyrazol-4-yl)-[1,2,4]triazolo[4,3-a]pyridin-3-ylsulfanyl]-quinoline No. 75 4-((6-(6-(1-Methyl-1H-pyrazol-4-yl)-[1,2,4]triazolo[4,3-a]pyridin-3-ylthio)quinolin-3-yl)methyl)-morpholine No. 76 (E)-1-(3-((3-(4-Hydroxypiperidin-1-yl)quinolin-6-yl)thio)-[1,2,4]triazolo[4,3-a]pyridin-6-yl)-ethanone O-(2-hydroxyethyl)oxime No. 77 (E)-1-(3-((3-Morpholin-4-yl-quinolin-6-yl)thio)-[1,2,4]triazolo[4,3-a]pyridin-6-yl)ethanone oxime No. 78 (E)-1-(3-((3-Morpholin-4-yl-quinolin-6-yl)thio)-[1,2,4]triazolo[4,3-a]pyridin-6-yl)ethanone O-(2-hydroxyethyl)oxime No. 79 (E)-1-(3-(3-(Morpholin-4-yl-methyl)quinolin-6-ylthio)-[1,2,4]triazolo[4,3-a]pyridin-6-yl)ethanone oxime No. 80 (E)-1-(3-((3-(Morpholin-4-yl-methyl)quinolin-6-yl)thio)-[1,2,4]triazolo[4,3-a]pyridin-6-yl)ethanone O-(2-hydroxyethyl)oxime No. 81 (S,E)-1-(3-(3-(3-(Dimethylamino)pyrrolidin-1-yl)quinolin-6-ylthio)-[1,2,4]triazolo[4,3-a]pyridin-6-yl)ethanone O-2-hydroxyethyl oxime No. 82 (S,E)-1-(3-(3-(3-(Dimethylamino)pyrrolidin-1-yl)quinolin-6-ylthio)-[1,2,4]triazolo[4,3-a]pyridin-6-yl)ethanone oxime No. 83 (E)-1-(3-(3-(Tetrahydro-2H-pyran-4-ylamino)quinolin-6-ylthio)-[1,2,4]triazolo[4,3-a]pyridin-6-yl)ethanone O-2-hydroxyethyl oxime No. 84 (E)-1-(3-(3-(Tetrahydro-2H-pyran-4-ylamino)quinolin-6-ylthio)-[1,2,4]triazolo[4,3-a]pyridin-6-yl)ethanone oxime No. 85 (S,E)-1-{3-[3-(3-dimethylamino-pyrrolidin-1-yl)-quinolin-6-ylthio]-8-fluoro-[1,2,4]triazolo[4,3-a]pyridin-6-yl}ethanone O-(2-hydroxy-ethyl)-oxime No. 86 (S,E)-1-(3-(3-(4-Methylpiperazin-1-yl)quinolin-6-ylthio)-[1,2,4]triazolo[4,3-a]pyridin-6-yl)ethanone O-2-hydroxyethyl oxime In a further embodiment, the invention provides a compound of the formula (I), which is selected from No. 1 tert-Butyl 1-(6-(6-(1-methyl-1H-pyrazol-4-yl)-[1,2,4]triazolo[4,3-a]pyridin-3-ylthio)quinolin-3-yl)pyrrolidin-3-ylcarbamate No. 2 1-(6-(6-(1-Methyl-1H-pyrazol-4-yl)-[1,2,4]triazolo[4,3-a]pyridin-3-ylthio)quinolin-3-yl)pyrrolidin-3-amine No. 3 N,N-Dimethyl-1-(6-(6-(1-methyl-1H-pyrazol-3-yl)-[1,2,4]triazolo[4,3-a]pyridin-3-ylthio)quinolin-3-yl)pyrrolidin-3-amine No. 4 tert-Butyl 3-(6-(6-(1-methyl-1H-pyrazol-4-yl)-[1,2,4]triazolo[4,3-a]pyridin-3-ylthio)quinolin-3-ylamino)pyrrolidine-1-carboxylate No. 5 6-(6-(1-Methyl-1H-pyrazol-4-yl)-[1,2,4]triazolo[4,3-a]pyridin-3-ylthio)-N-(pyrrolidin-3-yl)quinolin-3-amine No. 6 6-(6-(1-Methyl-1H-pyrazol-4-yl)-[1,2,4]triazolo[4,3-a]pyridin-3-ylthio)-3-((4-methylpiperazin-1-yl)methyl)quinoline No. 7 6-(8-Fluoro-6-(1-methyl-1H-pyrazol-4-yl)-[1,2,4]triazolo[4,3-a]pyridin-3-ylthio)-N-(2,2,6,6-tetramethylpiperidin-4-yl)quinolin-3-amine No. 8 {6-[8-Fluoro-6-(1-methyl-1H-pyrazol-4-yl)-[1,2,4]triazolo[4,3-a]pyridin-3-ylsulfanyl]-quinolin-3-yl}-(1-methyl-piperidin-4-yl)-amine No. 9 tert-Butyl 1-(6-(6-(1-methyl-1H-pyrazol-4-yl)-[1,2,4]triazolo[4,3-a]pyridin-3-ylthio)quinolin-3-yl)piperidin-3-ylcarbamate No. 10 1-(6-(6-(1-Methyl-1H-pyrazol-4-yl)-[1,2,4]triazolo[4,3-a]pyridin-3-ylthio)quinolin-3-yl)piperidin-3-amine No. 11 6-(6-(1-Methyl-1H-pyrazol-4-yl)-[1,2,4]triazolo[4,3-a]pyridin-3-ylthio)-N-((tetrahydrofuran-3-yl)methyl)quinolin-3-amine No. 12 6-(6-(6-(1-Methyl-1H-pyrazol-4-yl)-[1,2,4]triazolo[4,3-a]pyridin-3-ylthio)quinolin-3-yl)-2-oxa-6-azaspiro[3.3]heptane No. 13 1-(6-(8-Fluoro-6-(1-methyl-1H-pyrazol-4-yl)-[1,2,4]triazolo[4,3-a]pyridin-3-ylthio)quinolin-3-yl)-N,N-dimethylpyrrolidin-3-amine No. 14 6-(8-Fluoro-6-(1-methyl-1H-pyrazol-4-yl)-[1,2,4]triazolo[4,3-a]pyridin-3-ylthio)-3-(4-(pyrrolidin-1-yl)piperidin-1-yl)quinoline No. 15 (1-Methyl-piperidin-4-yl)-{6-[6-(1-methyl-1H-pyrazol-4-yl)-[1,2,4]triazolo[4,3-a]pyridin-3-ylsulfanyl]-quinolin-3-yl}amine No. 17 3-(4-Methyl-1,4-diazepan-1-yl)-6-(6-(1-methyl-1H-pyrazol-4-yl)-[1,2,4]triazolo[4,3-a]pyridin-3-ylthio)quinoline No. 18 tert-Butyl 4-(6-(6-(1-methyl-1H-pyrazol-4-yl)-[1,2,4]triazolo[4,3-a]pyridin-3-ylthio)quinolin-3-yl)-1,4-diazepane-1-carboxylate No. 19 3-(1,4-Diazepan-1-yl)-6-(6-(1-methyl-1H-pyrazol-4-yl)-[1,2,4]triazolo[4,3-a]pyridin-3-ylthio)quinoline No. 20 tert-Butyl 1-(6-(6-(1-methyl-1H-pyrazol-4-yl)-[1,2,4]triazolo[4,3-a]pyridin-3-ylthio)quinolin-3-yl)piperidin-4-ylcarbamate No. 21 1-(6-(6-(1-Methyl-1H-pyrazol-4-yl)-[1,2,4]triazolo[4,3-a]pyridin-3-ylthio)quinolin-3-yl)piperidin-4-amine No. 22 tert-Butyl 4-(6-(6-(1-methyl-1H-pyrazol-4-yl)-[1,2,4]triazolo[4,3-a]pyridin-3-ylthio)quinolin-3-ylamino)piperidine-1-carboxylate No. 23 6-(6-(1-Methyl-1H-pyrazol-4-yl)-[1,2,4]triazolo[4,3-a]pyridin-3-ylthio)-N-(piperidin-4-yl)quinolin-3-amine No. 24 6-[8-Fluoro-6-(1-methyl-1H-pyrazol-4-yl)-[1,2,4]triazolo[4,3-a]pyridin-3-ylsulfanyl]-3-(4-methyl-piperazin-1-yl)-quinoline No. 25 {6-[8-Fluoro-6-(1-methyl-1H-pyrazol-4-yl)-[1,2,4]triazolo[4,3-a]pyridin-3-ylsulfanyl]-quinolin-3-yl}-(tetrahydro-pyran-4-yl)-amine No. 26 tert-Butyl 4-(6-(6-(1-methyl-1H-pyrazol-4-yl)-[1,2,4]triazolo[4,3-a]pyridin-3-ylthio)quinolin-3-yl)piperazine-1-carboxylate No. 27 6-(6-(1-Methyl-1H-pyrazol-4-yl)-[1,2,4]triazolo[4,3-a]pyridin-3-ylthio)-3-(piperazin-1-yl)quinoline No. 28 6-(6-(1-Methyl-1H-pyrazol-4-yl)-[1,2,4]triazolo[4,3-a]pyridin-3-ylthio)-3-(4-(2,2,2-trifluoroethyl)piperazin-1-yl)quinoline No. 29 2-(4-(6-(6-(1-Methyl-1H-pyrazol-4-yl)-[1,2,4]triazolo[4,3-a]pyridin-3-ylthio)quinolin-3-yl)-1,4-diazepan-1-yl)ethanol No. 30 3-(1,4'-Bipiperidin-1'-yl)-6-(6-(1-methyl-1H-pyrazol-4-yl)-[1,2,4]triazolo[4,3-a]pyridin-3-ylthio)quinoline No. 31 3-(1,4'-Bipiperidin-1'-yl)-6-(8-fluoro-6-(1-methyl-1H-pyrazol-4-yl)-[1,2,4]triazolo[4,3-a]pyridin-3-ylthio)quinoline No. 32 3-(4-Cyclohexylpiperazin-1-yl)-6-(6-(1-methyl-1H-pyrazol-4-yl)-[1,2,4]triazolo[4,3-a]pyridin-3-ylthio)quinoline No. 33 6-(6-(1-Methyl-1H-pyrazol-4-yl)-[1,2,4]triazolo[4,3-a]pyridin-3-ylthio)-3-(4-(pyrrolidin-1-yl)piperidin-1-yl)quinoline No. 34 6-(6-(1-Methyl-1H-pyrazol-4-yl)-[1,2,4]triazolo[4,3-a]pyridin-3-ylthio)-3-(4-phenylpiperazin-1-yl)quinoline No. 35 2-Methyl-4-(6-(6-(1-methyl-1H-pyrazol-4-yl)-[1,2,4]triazolo[4,3-a]pyridin-3-ylthio)quinolin-3-yl)morpholine No. 36 4-(6-(8-Fluoro-6-(1-methyl-1H-pyrazol-4-yl)-[1,2,4]triazolo[4,3-a]pyridin-3-ylthio)quinolin-3-yl)-2-methylmorpholine No. 37 2,6-Dimethyl-4-(6-(6-(1-methyl-1H-pyrazol-4-yl)-[1,2,4]triazolo[4,3-a]pyridin-3-ylthio)quinolin-3-yl)morpholine No. 38 4-(6-(8-Fluoro-6-(1-methyl-1H-pyrazol-4-yl)-[1,2,4]triazolo[4,3-a]pyridin-3-ylthio)quinolin-3-yl)-2,6-dimethylmorpholine No. 39 tert-Butyl 4-(6-(8-fluoro-6-(1-methyl-1H-pyrazol-4-yl)-[1,2,4]triazolo[4,3-a]pyridin-3-ylthio)quinolin-3-yl)-2,6-dimethylpiperazine-1-carboxylate No. 40 3-(3,5-Dimethylpiperazin-1-yl)-6-(8-fluoro-6-(1-methyl-1H-pyrazol-4-yl)-[1,2,4]triazolo[4,3-a]pyridin-3-ylthio)quinoline No. 41 tert-Butyl 2,6-dimethyl-4-(6-(6-(1-methyl-1H-pyrazol-4-yl)-[1,2,4]triazolo[4,3-a]pyridin-3-ylthio)quinolin-3-yl)piperazine-1-carboxylate No. 42 3-(3,5-Dimethylpiperazin-1-yl)-6-(6-(1-methyl-1H-pyrazol-4-yl)-[1,2,4]triazolo[4,3-a]pyridin-3-ylthio)quinoline No. 43 3-(4-Methoxypiperidin-1-yl)-6-(6-(1-methyl-1H-pyrazol-4-yl)-[1,2,4]triazolo[4,3-a]pyridin-3-ylthio)quinoline No. 44 6-(8-Fluoro-6-(1-methyl-1H-pyrazol-4-yl)-[1,2,4]triazolo[4,3-a]pyridin-3-ylthio)-3-(4-methoxypiperidin-1-yl)quinoline No. 45 tert-Butyl 4-(6-(8-fluoro-6-(1-methyl-1H-pyrazol-4-yl)-[1,2,4]triazolo[4,3-a]pyridin-3-ylthio)quinolin-3-yl)-3-methylpiperazine-1-carboxylate No. 46 6-(8-Fluoro-6-(1-methyl-1H-pyrazol-4-yl)-[1,2,4]triazolo[4,3-a]pyridin-3-ylthio)-3-(2-methylpiperazin-1-yl)quinoline No. 47 2-(6-((6-(1-Methyl-1H-pyrazol-4-yl)-[1,2,4]triazolo[4,3-a]pyridin-3-yl)thio)quinolin-3-yl)-8-oxa-2-azaspiro[4.5]decane No. 48 2-(6-(8-Fluoro-6-(1-methyl-1H-pyrazol-4-yl)-[1,2,4]triazolo[4,3-a]pyridin-3-ylthio)quinolin-3-yl)-8-oxa-2-azaspiro[4.5]decane No. 49 1-(6-((6-(1-Methyl-1H-pyrazol-4-yl)-[1,2,4]triazolo[4,3-a]pyridin-3-yl)thio)quinolin-3-yl)piperidin-4-ol No. 50 1-(6-((8-Fluoro-6-(1-methyl-1H-pyrazol-4-yl)-[1,2,4]triazolo[4,3-a]pyridin-3-yl)thio)quinolin-3-yl)piperidin-4-ol No. 51 6-[6-(1-Methyl-1H-pyrazol-3-yl)-[1,2,4]triazolo[4,3-a]pyridin-3-ylsulfanyl]-quinolin-3-yl}-(tetrahydro-furan-3-yl)-amine No. 52 {6-[8-Fluoro-6-(1-methyl-1H-pyrazol-3-yl)-[1,2,4]triazolo[4,3-a]pyridin-3-ylsulfanyl]-quinolin-3-yl}-(tetrahydro-furan-3-yl)-amine No. 53 2-(6-(6-(1-methyl-1H-pyrazol-4-yl)-[1,2,4]triazolo[4,3-a]pyridin-3-ylthio)quinolin-3-ylamino)ethanol No. 54 2-(6-(8-Fluoro-6-(1-methyl-1H-pyrazol-4-yl)-[1,2,4]triazolo[4,3-a]pyridin-3-ylthio)quinolin-3-ylamino)ethanol No. 55 6-(8-Fluoro-6-(1-methyl-1H-pyrazol-4-yl)-[1,2,4]triazolo[4,3-a]pyridin-3-ylthio)quinolin-3-amine hydrochloride No. 56 6-(6-(1-Methyl-1H-pyrazol-4-yl)-[1,2,4]triazolo[4,3-a]pyridin-3-ylthio)quinolin-3-amine hydrochloride No. 57 4-(6-(6-(1H-pyrazol-4-yl)-[1,2,4]triazolo[4,3-a]pyridin-3-ylthio)quinolin-3-yl)morpholine No. 58 4-(6-(8-Fluoro-6-(1H-pyrazol-4-yl)-[1,2,4]triazolo[4,3-a]pyridin-3-ylthio)quinolin-3-yl)morpholine No. 59 3-Methyl-4-(6-(6-(1-methyl-1H-pyrazol-4-yl)-[1,2,4]triazolo[4,3-a]pyridin-3-ylthio)quinolin-3-yl)-morpholine No. 60 4-(6-(8-Fluoro-6-(1-methyl-1H-pyrazol-4-yl)-[1,2,4]triazolo[4,3-a]pyridin-3-ylthio)quinolin-3-yl)-3-methylmorpholine No. 61 3-(4,4-Difluoro-piperidin-1-yl)-6-[6-(1-methyl-1H-pyrazol-4-yl)-[1,2,4]triazolo[4,3-a]pyridin-3-ylsulfanyl]-quinoline No. 62 6-(6-(1-Methyl-1H-pyrazol-4-yl)-[1,2,4]triazolo[4,3-a]pyridin-3-ylthio)-N-(2,2,6,6-tetramethyl piperidin-4-yl)quinolin-3-amine No. 64 6-(8-Fluoro-6-(1-methyl-1H-pyrazol-4-yl)-[1,2,4]triazolo[4,3-a]pyridin-3-ylthio)-N-(oxetan-3-yl) quinolin-3-amine No. 67 3-(4,4-Difluoro-piperidin-1-yl)-6-[8-fluoro-6-(1-methyl-1H-pyrazol-4-yl)[1,2,4]triazolo[4,3-a]pyridin-3-ylsulfanyl]-quinoline No. 68 {6-[6-(1-Methyl-1H-pyrazol-4-yl)-[1,2,4]triazolo[4,3-a]pyridin-3-ylsulfanyl]-quinolin-3-yl}-(tetrahydro-pyran-4-yl)-amine No. 69 4-(6-(6-(1-Methyl-1H-pyrazol-4-yl)-[1,2,4]triazolo[4,3-a]pyridin-3-ylthio)quinolin-3-yl)morpholine No. 70 4-(6-(8-Fluoro-6-(1-methyl-1H-pyrazol-4-yl)-[1,2,4]triazolo[4,3-a]pyridin-3-ylthio)quinolin-3-yl)morpholine No. 71 6-(6-(1-Methyl-1H-pyrazol-4-yl)-[1,2,4]triazolo[4,3-a]pyridin-3-ylthio)-N-(oxetan-3-yl)quinolin-3-amine No. 72 2-(4-(3-(3-Morpholin-4-yl-quinolin-6-ylthio)-[1,2,4]triazolo[4,3-a]pyridin-6-yl)-1H-pyrazol-1-yl)ethanol No. 74 3-(4-Methyl-piperazin-1-yl)-6-[6-(1-methyl-1H-pyrazol-4-yl)-[1,2,4]triazolo[4,3-a]pyridin-3-ylsulfanyl]-quinoline No. 75 4-((6-(6-(1-Methyl-1H-pyrazol-4-yl)-[1,2,4]triazolo[4,3-a]pyridin-3-ylthio)quinolin-3-yl)methyl)-morpholine No. 76 1-(3-((3-(4-Hydroxypiperidin-1-yl)quinolin-6-yl)thio)-[1,2,4]triazolo[4,3-a]pyridin-6-yl)-ethanone O-(2-hydroxyethyl)oxime No. 77 1-(3-((3-Morpholin-4-yl-quinolin-6-yl)thio)-[1,2,4]triazolo[4,3-a]pyridin-6-yl)ethanone oxime No. 78 1-(3-((3-Morpholin-4-yl-quinolin-6-yl)thio)-[1,2,4]triazolo[4,3-a]pyridin-6-yl)ethanone O-(2-hydroxyethyl)oxime No. 79 1-(3-(3-(Morpholin-4-yl-methyl)quinolin-6-ylthio)-[1,2,4]triazolo[4,3-a]pyridin-6-yl)ethanone oxime No. 80 1-(3-((3-(Morpholin-4-yl-methyl)quinolin-6-yl)thio)-[1,2,4]triazolo[4,3-a]pyridin-6-yl)ethanone O-(2-hydroxyethyl)oxime No. 81 1-(3-(3-(Dimethylamino)pyrrolidin-1-yl)quinolin-6-ylthio)-[1,2,4]triazolo[4,3-a]pyridin-6-yl)ethanone O-2-hydroxyethyl oxime No. 82 1-(3-(3-(3-(Dimethylamino)pyrrolidin-1-yl)quinolin-6-ylthio)-[1,2,4]triazolo[4,3-a]pyridin-6-yl)ethanone oxime No. 83 1-(3-(3-(Tetrahydro-2H-pyran-4-ylamino)quinolin-6-ylthio)-[1,2,4]triazolo[4,3-a]pyridin-6-yl)ethanone O-2-hydroxyethyl oxime No. 84 1-(3-(3-(Tetrahydro-2H-pyran-4-ylamino)quinolin-6-ylthio)-[1,2,4]triazolo[4,3-a]pyridin-6-yl)ethanone oxime No. 85 1-{3-[3-(3-dimethylamino-pyrrolidin-1-yl)-quinolin-6-ylthio]-8-fluoro-[1,2,4]triazolo[4,3-a]pyridin-6-yl}-ethanone O-(2-hydroxy-ethyl)-oxime No. 86 1-(3-(3-(4-Methylpiperazin-1-yl)quinolin-6-ylthio)-[1,2,4]triazolo[4,3-a]pyridin-6-yl)ethanone O-2-hydroxyethyl oxime In a further embodiment, the invention provides a compound of the formula (I), which is selected from No. 2 1-(6-(6-(1-Methyl-1H-pyrazol-4-yl)-[1,2,4]triazolo[4,3-a]pyridin-3-ylthio)quinolin-3-yl)pyrrolidin-3-amine No. 3 (S)—N,N-Dimethyl-1-(6-(6-(1-methyl-1H-pyrazol-3-yl)-[1,2,4]triazolo[4,3-a]pyridin-3-ylthio)quinolin-3-yl)pyrrolidin-3-amine No. 6 6-(6-(1-Methyl-1H-pyrazol-4-yl)-[1,2,4]triazolo[4,3-a]pyridin-3-ylthio)-3-((4-methylpiperazin-1-yl)methyl)quinoline No. 10 1-(6-(6-(1-Methyl-1H-pyrazol-4-yl)-[1,2,4]triazolo[4,3-a]pyridin-3-ylthio)quinolin-3-yl)piperidin-3-amine No. 12 6-(6-(6-(1-Methyl-1H-pyrazol-4-yl)-[1,2,4]triazolo[4,3-a]pyridin-3-ylthio)quinolin-3-yl)-2-oxa-6-azaspiro[3.3]heptane No. 13 (S)-1-(6-(8-Fluoro-6-(1-methyl-1H-pyrazol-4-yl)-[1,2,4]triazolo[4,3-a]pyridin-3-ylthio)quinolin-3-yl)-N,N-dimethylpyrrolidin-3-amine No. 14 6-(8-Fluoro-6-(1-methyl-1H-pyrazol-4-yl)-[1,2,4]triazolo[4,3-a]pyridin-3-ylthio)-3-(4-(pyrrolidin-1-yl)piperidin-1-yl)quinoline No. 17 3-(4-Methyl-1,4-diazepan-1-yl)-6-(6-(1-methyl-1H-pyrazol-4-yl)-[1,2,4]triazolo[4,3-a]pyridin-3-ylthio)quinoline No. 19 3-(1,4-Diazepan-1-yl)-6-(6-(1-methyl-1H-pyrazol-4-yl)-[1,2,4]triazolo[4,3-a]pyridin-3-ylthio)quinoline No. 21 1-(6-(6-(1-Methyl-1H-pyrazol-4-yl)-[1,2,4]triazolo[4,3-a]pyridin-3-ylthio)quinolin-3-yl)piperidin-4-amine No. 24 6-[8-Fluoro-6-(1-methyl-1H-pyrazol-4-yl)-[1,2,4]triazolo[4,3-a]pyridin-3-ylsulfanyl]-3-(4-methyl-piperazin-1-yl)-quinoline No. 27 6-(6-(1-Methyl-1H-pyrazol-4-yl)-[1,2,4]triazolo[4,3-a]pyridin-3-ylthio)-3-(piperazin-1-yl)quinoline No. 28 6-(6-(1-Methyl-1H-pyrazol-4-yl)-[1,2,4]triazolo[4,3-a]pyridin-3-ylthio)-3-(4-(2,2,2-trifluoroethyl)piperazin-1-yl)quinoline No. 29 2-(4-(6-(6-(1-Methyl-1H-pyrazol-4-yl)-[1,2,4]triazolo[4,3-a]pyridin-3-ylthio)quinolin-3-yl)-1,4-diazepan-1-yl)ethanol No. 30 3-(1,4'-Bipiperidin-1'-yl)-6-(6-(1-methyl-1H-pyrazol-4-yl)-[1,2,4]triazolo[4,3-a]pyridin-3-ylthio)quinoline No. 31 3-(1,4'-Bipiperidin-1'-yl)-6-(8-fluoro-6-(1-methyl-1H-pyrazol-4-yl)-[1,2,4]triazolo[4,3-a]pyridin-3-ylthio)quinoline No. 32 3-(4-Cyclohexylpiperazin-1-yl)-6-(6-(1-methyl-1H-pyrazol-4-yl)-[1,2,4]triazolo[4,3-a]pyridin-3-ylthio)quinoline No. 33 6-(6-(1-Methyl-1H-pyrazol-4-yl)-[1,2,4]triazolo[4,3-a]pyridin-3-ylthio)-3-(4-(pyrrolidin-1-yl)piperidin-1-yl)quinoline No. 34 6-(6-(1-Methyl-1H-pyrazol-4-yl)-[1,2,4]triazolo[4,3-a]pyridin-3-ylthio)-3-(4-phenylpiperazin-1-yl)quinoline No. 35 2-Methyl-4-(6-(6-(1-methyl-1H-pyrazol-4-yl)-[1,2,4]triazolo[4,3-a]pyridin-3-ylthio)quinolin-3-yl)morpholine No. 35A (S)-2-Methyl-4-(6-(6-(1-methyl-1H-pyrazol-4-yl)-[1,2,4]triazolo[4,3-a]pyridin-3-ylthio)quinolin-3-yl)morpholine No. 35B (R)-2-Methyl-4-(6-(6-(1-methyl-1H-pyrazol-4-yl)-[1,2,4]triazolo[4,3-a]pyridin-3-ylthio)quinolin-3-yl)morpholine No. 36 4-(6-(8-Fluoro-6-(1-methyl-1H-pyrazol-4-yl)-[1,2,4]triazolo[4,3-a]pyridin-3-ylthio)quinolin-3-yl)-2-methylmorpholine No. 37 2,6-Dimethyl-4-(6-(6-(1-methyl-1H-pyrazol-4-yl)-[1,2,4]triazolo[4,3-a]pyridin-3-ylthio)quinolin-3-yl)morpholine No. 38 4-(6-(8-Fluoro-6-(1-methyl-1H-pyrazol-4-yl)-[1,2,4]triazolo[4,3-a]pyridin-3-ylthio) quinolin-3-yl)-2,6-dimethylmorpholine No. 40 3-((3S,5R)-3,5-Dimethylpiperazin-1-yl)-6-(8-fluoro-6-(1-methyl-1H-pyrazol-4-yl)-[1,2,4]triazolo[4,3-a]pyridin-3-ylthio)quinoline No. 42 3-((3S,5R)-3,5-Dimethylpiperazin-1-yl)-6-(6-(1-methyl-1H-pyrazol-4-yl)-[1,2,4]triazolo[4,3-a]pyridin-3-ylthio)quinoline No. 43 3-(4-Methoxypiperidin-1-yl)-6-(6-(1-methyl-1H-pyrazol-4-yl)-[1,2,4]triazolo[4,3-a]pyridin-3-ylthio) quinoline No. 44 6-(8-Fluoro-6-(1-methyl-1H-pyrazol-4-yl)-[1,2,4]triazolo[4,3-a]pyridin-3-ylthio)-3-(4-methoxypiperidin-1-yl)quinoline No. 46 (S)-6-(8-Fluoro-6-(1-methyl-1H-pyrazol-4-yl)-[1,2,4]triazolo[4,3-a]pyridin-3-ylthio)-3-(2-methylpiperazin-1-yl)quinoline No. 47 2-(6-((6-(1-Methyl-1H-pyrazol-4-yl)-[1,2,4]triazolo[4,3-a]pyridin-3-yl)thio)quinolin-3-yl)-8-oxa-2-azaspiro[4.5]decane No. 48 2-(6-(8-Fluoro-6-(1-methyl-1H-pyrazol-4-yl)-[1,2,4]triazolo[4,3-a]pyridin-3-ylthio)quinolin-3-yl)-8-oxa-2-azaspiro[4.5]decane No. 49 1-(6-((6-(1-Methyl-1H-pyrazol-4-yl)-[1,2,4]triazolo[4,3-a]pyridin-3-yl)thio)quinolin-3-yl)piperidin-4-ol No. 50 1-(6-((8-Fluoro-6-(1-methyl-1H-pyrazol-4-yl)-[1,2,4]triazolo[4,3-a]pyridin-3-yl)thio)quinolin-3-yl)piperidin-4-ol No. 57 4-(6-(6-(1H-pyrazol-4-yl)-[1,2,4]triazolo[4,3-a]pyridin-3-ylthio)quinolin-3-yl)morpholine No. 58 4-(6-(8-Fluoro-6-(1H-pyrazol-4-yl)-[1,2,4]triazolo[4,3-a]pyridin-3-ylthio)quinolin-3-yl)morpholine No. 59 3-Methyl-4-(6-(6-(1-methyl-1H-pyrazol-4-yl)-[1,2,4]triazolo[4,3-a]pyridin-3-ylthio)quinolin-3-yl)-morpholine No. 60 4-(6-(8-Fluoro-6-(1-methyl-1H-pyrazol-4-yl)-[1,2,4]triazolo[4,3-a]pyridin-3-ylthio)quinolin-3-yl)-3-methylmorpholine No. 61 3-(4,4-Difluoro-piperidin-1-yl)-6-[6-(1-methyl-1H-pyrazol-4-yl)-[1,2,4]triazolo[4,3-a]pyridin-3-ylsulfanyl]-quinoline No. 67 3-(4,4-Difluoro-piperidin-1-yl)-6-[8-fluoro-6-(1-methyl-1H-pyrazol-4-yl)[1,2,4]triazolo[4,3-a]pyridin-3-ylsulfanyl]-quinoline No. 69 4-(6-(6-(1-Methyl-1H-pyrazol-4-yl)-[1,2,4]triazolo[4,3-a]pyridin-3-ylthio)quinolin-3-yl)morpholine No. 70 4-(6-(8-Fluoro-6-(1-methyl-1H-pyrazol-4-yl)-[1,2,4]triazolo[4,3-a]pyridin-3-ylthio)quinolin-3-yl)morpholine No. 72 2-(4-(3-(3-Morpholin-4-yl-quinolin-6-ylthio)-[1,2,4]triazolo[4,3-a]pyridin-6-yl)-1H-pyrazol-1-yl)ethanol No. 74 3-(4-Methyl-piperazin-1-yl)-6-[6-(1-methyl-1H-pyrazol-4-yl)-[1,2,4]triazolo[4,3-a]pyridin-3-ylsulfanyl]-quinoline No. 75 4-((6-(6-(1-Methyl-1H-pyrazol-4-yl)-[1,2,4]triazolo[4,3-a]pyridin-3-ylthio)quinolin-3-yl)methyl)-morpholine In a further embodiment, the invention provides a compound of the formula (I), which is selected from No. 76 (E)-1-(3-((3-(4-Hydroxypiperidin-1-yl)quinolin-6-yl)thio)-[1,2,4]triazolo[4,3-a]pyridin-6-yl)-ethanone O-(2-hydroxyethyl)oxime No. 77 (E)-1-(3-((3-Morpholin-4-yl-quinolin-6-yl)thio)-[1,2,4]triazolo[4,3-a]pyridin-6-yl)ethanone oxime No. 78 (E)-1-(3-((3-Morpholin-4-yl-quinolin-6-yl)thio)-[1,2,4]triazolo[4,3-a]pyridin-6-yl)ethanone O-(2-hydroxyethyl)oxime No. 81 (S,E)-1-(3-(3-(3-(Dimethylamino)pyrrolidin-1-yl)quinolin-6-ylthio)-[1,2,4]triazolo[4,3-a]pyridin-6-yl)ethanone O-2-hydroxyethyl oxime No. 82 (S,E)-1-(3-(3-(3-(Dimethylamino)pyrrolidin-1-yl)quinolin-6-ylthio)-[1,2,4]triazolo[4,3-a]pyridin-6-yl)ethanone oxime No. 85 (S,E)-1-{3-[3-(3-dimethylamino-pyrrolidin-1-yl)-quinolin-6-ylthio]-8-fluoro-[1,2,4]triazolo[4,3-a]pyridin-6-yl}-ethanone O-(2-hydroxy-ethyl)-oxime No. 86 (S,E)-1-(3-(3-(4-Methylpiperazin-1-yl)quinolin-6-ylthio)-[1,2,4]triazolo[4,3-a]pyridin-6-yl)ethanone O-2-hydroxyethyl oxime In a further embodiment, the invention provides a compound of the formula (I), which is selected from No. 53 2-(6-(6-(1-methyl-1H-pyrazol-4-yl)-[1,2,4]triazolo[4,3-a]pyridin-3-ylthio)quinolin-3-ylamino)ethanol No. 54 2-(6-(8-Fluoro-6-(1-methyl-1H-pyrazol-4-yl)-[1,2,4]triazolo[4,3-a]pyridin-3-ylthio)quinolin-3-ylamino)ethanol No. 55 6-(8-Fluoro-6-(1-methyl-1H-pyrazol-4-yl)-[1,2,4]triazolo[4,3-a]pyridin-3-ylthio)quinolin-3-amine hydrochloride No. 56 6-(6-(1-Methyl-1H-pyrazol-4-yl)-[1,2,4]triazolo[4,3-a]pyridin-3-ylthio)quinolin-3-amine hydrochloride In a further embodiment, the invention provides a compound of the formula (I), which is selected from No. 5 (S)-6-(6-(1-Methyl-1H-pyrazol-4-yl)-[1,2,4]triazolo[4,3-a]pyridin-3-ylthio)-N-(pyrrolidin-3-yl)quinolin-3-amine No. 7 6-(8-Fluoro-6-(1-methyl-1H-pyrazol-4-yl)-[1,2,4]triazolo[4,3-a]pyridin-3-ylthio)-N-(2,2,6,6-tetramethylpiperidin-4-yl)quinolin-3-amine No. 8 {6-[8-Fluoro-6-(1-methyl-1H-pyrazol-4-yl)-[1,2,4]triazolo[4,3-a]pyridin-3-ylsulfanyl]-quinolin-3-yl}-(1-methyl-piperidin-4-yl)-amine No. 11 6-(6-(1-Methyl-1H-pyrazol-4-yl)-[1,2,4]triazolo[4,3-a]pyridin-3-ylthio)-N-((tetrahydrofuran-3-yl)methyl)quinolin-3-amine No. 15 (1-Methyl-piperidin-4-yl)-{6-[6-(1-methyl-1H-pyrazol-4-yl)-[1,2,4]triazolo[4,3-a]pyridin-3-ylsulfanyl]-quinolin-3-yl}-amine No. 23 6-(6-(1-Methyl-1H-pyrazol-4-yl)-[1,2,4]triazolo[4,3-a]pyridin-3-ylthio)-N-(piperidin-4-yl)quinolin-3-amine No. 25 {6-[8-Fluoro-6-(1-methyl-1H-pyrazol-4-yl)-[1,2,4]triazolo[4,3-a]pyridin-3-ylsulfanyl]-quinolin-3-yl}-(tetrahydro-pyran-4-yl)-amine No. 51 6-[6-(1-Methyl-1H-pyrazol-3-yl)-[1,2,4]triazolo[4,3-a]pyridin-3-ylsulfanyl]-quinolin-3-yl)-(tetrahydro-furan-3-yl)-amine No. 52 {6-[8-Fluoro-6-(1-methyl-1H-pyrazol-3-yl)-[1,2,4]triazolo[4,3-a]pyridin-3-ylsulfanyl]-quinolin-3-yl}-(tetrahydro-furan-3-yl)-amine No. 62 6-(6-(1-Methyl-1H-pyrazol-4-yl)-[1,2,4]triazolo[4,3-a]pyridin-3-ylthio)-N-(2,2,6,6-tetramethyl piperidin-4-yl) quinolin-3-amine No. 64 6-(8-Fluoro-6-(1-methyl-1H-pyrazol-4-yl)-[1,2,4]triazolo[4,3-a]pyridin-3-ylthio)-N-(oxetan-3-yl) quinolin-3-amine No. 68 {6-[6-(1-Methyl-1H-pyrazol-4-yl)-[1,2,4]triazolo[4,3-a]pyridin-3-ylsulfanyl]-quinolin-3-yl}-(tetrahydro-pyran-4-yl)-amine No. 71 6-(6-(1-Methyl-1H-pyrazol-4-yl)-[1,2,4]triazolo[4,3-a]pyridin-3-ylthio)-N-(oxetan-3-yl)quinolin-3-amine No. 83 (E)-1-(3-(3-(Tetrahydro-2H-pyran-4-ylamino)quinolin-6-ylthio)-[1,2,4]triazolo[4,3-a]pyridin-6-yl)ethanone O-2-hydroxyethyl oxime No. 84 (E)-1-(3-(3-(Tetrahydro-2H-pyran-4-ylamino)quinolin-6-ylthio)-[1,2,4]triazolo[4,3-a]pyridin-6-yl)ethanone oxime In a further embodiment, the invention provides a compound of the formula (I), which is selected from No. 27 6-(6-(1-Methyl-1H-pyrazol-4-yl)-[1,2,4]triazolo[4,3-a]pyridin-3-ylthio)-3-(piperazin-1-yl)quinoline No. 40 3-((3S,5R)-3,5-Dimethylpiperazin-1-yl)-6-(8-fluoro-6-(1-methyl-1H-pyrazol-4-yl)-[1,2,4]triazolo[4,3-a]pyridin-3-ylthio)quinoline No. 43 3-(4-Methoxypiperidin-1-yl)-6-(6-(1-methyl-1H-pyrazol-4-yl)-[1,2,4]triazolo[4,3-a]pyridin-3-ylthio) quinoline No. 44 6-(8-Fluoro-6-(1-methyl-1H-pyrazol-4-yl)-[1,2,4]triazolo[4,3-a]pyridin-3-ylthio)-3-(4-methoxypiperidin-1-yl)quinoline No. 49 1-(6-((6-(1-Methyl-1H-pyrazol-4-yl)-[1,2,4]triazolo[4,3-a]pyridin-3-yl)thio)quinolin-3-yl)piperidin-4-ol No. 50 1-(6-((8-Fluoro-6-(1-methyl-1H-pyrazol-4-yl)-[1,2,4]triazolo[4,3-a]pyridin-3-yl)thio)quinolin-3-yl)piperidin-4-ol No. 69 4-(6-(6-(1-methyl-1H-pyrazol-4-yl)-[1,2,4]triazolo[4,3-a]pyridin-3-ylthio)quinolin-3-yl)morpholine No. 70 4-(6-(8-fluoro-6-(1-methyl-1H-pyrazol-4-yl)-[1,2,4]triazolo[4,3-a]pyridin-3-ylthio)quinolin-3-yl)morpholine No. 74 3-(4-Methyl-piperazin-1-yl)-6-[6-(1-methyl-1H-pyrazol-4-yl)-[1,2,4]triazolo[4,3-a]pyridin-3-ylsulfanyl]-quinoline In a further embodiment, the invention provides a compound of the formula (I), which is selected from No. 76 (E)-1-(3-((3-(4-hydroxypiperidin-1-yl)quinolin-6-yl)thio)-[1,2,4]triazolo[4,3-a]pyridin-6-yl)-ethanone O-(2-hydroxyethyl)oxime No. 77 (E)-1-(3-((3-morpholin-4-yl-quinolin-6-yl)thio)-[1,2,4]triazolo[4,3-a]pyridin-6-yl)ethanone oxime No. 78 (E)-1-(3-((3-morpholin-4-yl-quinolin-6-yl)thio)-[1,2,4]triazolo[4,3-a]pyridin-6-yl)ethanone O-(2-hydroxyethyl)oxime No. 82 (S,E)-1-(3-(3-(3-(dimethylamino)pyrrolidin-1-yl)quinolin-6-ylthio)-[1,2,4]triazolo[4,3-a]pyridin-6-yl)ethanone oxime, and No. 86 (E)-1-(3-(3-(4-methylpiperazin-1-yl)quinolin-6-ylthio)-[1,2,4]triazolo[4,3-a]pyridin-6-yl)ethanone O-2-hydroxyethyl oxime In a further embodiment, the invention provides a compound of formula (I), which is selected from No. 8 {6-[8-Fluoro-6-(1-methyl-1H-pyrazol-4-yl)-[1,2,4]triazolo[4,3-a]pyridin-3-ylsulfanyl]-quinolin-3-yl}-(1-methyl-piperidin-4-yl)-amine, and No. 15 (1-Methyl-piperidin-4-yl)-{6-[6-(1-methyl-1H-pyrazol-4-yl)-[1,2,4]triazolo[4,3-a]pyridin-3-ylsulfanyl]-quinolin-3-yl}-amine.

Further Definitions

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastreriomeric mixtures and optically pure forms. Optically active (R)- and (S)-isomers may be prepared using chiral synthons or chiral reagents, or resolved using conventional techniques. If the compound contains a disubstituted cycloalkyl, the cycloalkyl substituent may have a cis- or trans-configuration. All tautomeric forms are also intended to be included.

Substituents at atoms with unsaturated bonds may, if possible, be present in cis-(Z)- or trans-(E)-form. Preferably, the oximes of the present invention have the trans-(E)-form.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g. acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Pharmaceutically acceptable solvates in accordance with the invention include those wherein the solvent of crystallization may be isotopically substituted, e.g. $D_2O$, $d_6$-acetone, $d_6$-DMSO.

The compounds of the present invention, including salts, hydrates and solvates thereof, may inherently or by design form polymorphs.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by c-Met or (ii) associated with c-Met activity, or (iii) characterized by activity (normal or abnormal) of c-Met; or (2) reducing or inhibiting the activity of c-Met; or (3) reducing or inhibiting the expression of c-Met. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of c-Met; or at least partially reducing or inhibiting the expression of c-Met.

As used herein, the term "subject" refers to an animal. Typically the animal is a mammal. A subject also refers to for example, primates (e.g., humans, male or female), monkeys, cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

"Disease" as used herein includes a disorder or condition.

In the context of the present invention, "c-Met tyrosine kinase mediated diseases" are especially such disorders that respond in a beneficial way (e.g. amelioration of one or more symptoms, delay of the onset of a disease, up to temporary or complete cure from a disease) to the inhibition of a protein tyrosine kinase, especially inhibition of a c-Met kinase. These disorders include proliferative diseases such as tumor diseases and cancer. These disorders further include inflammatory conditions, such as inflammatory conditions due to an infection. In particular, c-Met inhibitors are intended to treat (solid) tumors driven by high c-Met pathway activity. Met activating kinase mutations, focal amplification of the Met gene, and high expression of its cognate ligand, HGF, can all lead to high c-Met pathway activation, which leads to tumor transformation.

Indications

The compounds of formula (I) in free form or in salt form, exhibit valuable pharmacological properties, e.g. c-Met kinase inhibiting properties, e.g. as indicated in in vitro and in vivo tests as provided herewithin and are therefore indicated for therapy.

Therefore, in one embodiment, the invention relates to a compound of formula (I) or a pharmaceutically acceptable salt thereof, for use in medicine.

In a further embodiment, the invention relates to a compound of formula (I) or a pharmaceutically acceptable salt thereof, for use in the treatment of one or more c-Met tyrosine kinase mediated disorders or diseases, preferably for use in the treatment of a proliferative disease or an inflammatory condition.

In a further embodiment, the invention relates to the use of a compound of formula (I) or a pharmaceutically acceptable salt thereof, in the manufacture of a medicament for the treatment of one or more c-Met tyrosine kinase mediated disorders or diseases, preferably for use in the treatment of a proliferative disease or an inflammatory condition.

In another embodiment, the invention relates to a method of treating a c-Met related disorder or disease in a subject wherein the method comprises administering to the subject in need thereof a therapeutically effective amount of a compound of formula (I) or a pharmaceutically acceptable salt thereof. The disorder or condition to be treated is preferably a proliferative disease such as a cancer or an inflammatory condition.

In a further related embodiment to several of the above methods, following administration to the subject, these methods can further involve observing amelioration or retardation of development or metastasis of the cancer.

In one embodiment of the invention, subjects to be treated with a compound of the invention are preselected via biomarker analysis to identify patients having tumors driven by high c-Met pathway activity as indicated above.

In a further embodiment of the present invention, compounds of the present invention are useful for treating tumors resistant to existing chemotherapies.

Compounds of formula (I) are further useful for treating diseases associated with a c-Met-related condition.

As stated above, c-Met tyrosine kinase mediated or related disorders or diseases in particular refer to a proliferative disease or an inflammatory condition. Proliferative diseases and inflammatory conditions are defined in more detail below.

A: Proliferative Diseases

Proliferative diseases comprise cancer indications wherein the cancer is selected from the group consisting of brain cancer, stomach cancer, genital cancer, urinary cancer, prostate cancer, bladder cancer (superficial and muscle invasive), breast cancer, cervical cancer, colon cancer, colorectal cancer, glioma (including glioblastoma, anaplastic astrocytoma, oligoastrocytoma, oligodendroglioma), esophageal cancer, gastric and/or gastroesophageal cancer (GC), gastrointestinal cancer, liver cancer, hepatocellular carcinoma (HCC) including childhood HCC, head and neck cancer (including head and neck squamous-cell carcinoma, nasopharyngeal carcinoma (NPC)), Hurthle cell carcinoma, epithelial cancer, skin cancer, melanoma (including malignant melanoma), mesothelioma, lymphoma, myeloma (including multiple myeloma), leukemias, lung cancer (including non-small cell lung cancer (NSCLC) (including all histological subtypes: adenocarcinoma, squamous cell carcinoma, bronchoalveolar carcinoma, large-cell carcinoma, and adenosquamous mixed type), small-cell lung cancer), ovarian cancer, pancreatic cancer, prostate cancer, kidney cancer (including but not limited to papillary renal cell carcinoma (PRCC)), intestine cancer, renal cell cancer (including hereditary and sporadic papillary renal cell cancer, Type I and Type II, and clear cell renal cell cancer); sarcomas, in particular osteosarcomas, clear cell sarcomas, and soft tissue sarcomas (including alveolar and embryonal rhabdomyosarcomas, alveolar soft part sarcomas); thyroid carcinoma (papillary and other subtypes).

In one embodiment, cancer is selected from the group consisting of stomach cancer, colon cancer, liver cancer, genital cancer, urinary cancer, melanoma, or prostate cancer. In a particular embodiment, the cancer is liver or esophageal cancer.

In one embodiment, cancer refers in particular to solid tumors and metastasis derived thereof, e.g. hereditary papillary renal cell carcinoma (PRCC), sporadic forms of PRCC, head and neck cancer, squamous cell carcinoma, gastric carcinoma, pancreatic carcinoma, lung cancer, bladder cancer, breast cancer, leiomyosarcoma, glioblastoma, melanoma, and alveolar soft part sarcoma.

Furthermore, compounds of formula (I) are particularly useful for the treatment of colon cancer, including metastases, e.g. in the liver, and of non-small-cell lung carcinoma.

Compounds of formula (I) may also be used in the treatment of hereditary papillary renal carcinoma (Schmidt, L. et al. Nat. Genet. 16, 68-73, 1997) and other proliferative diseases in which c-Met is overexpressed or constitutively activated by mutations (Jeffers and Vande Woude. Oncogene 18, 5120-5125, 1999; and reference cited therein) or chromosomal rearrange-ments (e.g. TPR-MET; Cooper et al. Nature 311, 29-33, 1984; Park. et al. Cell 45, 895-904, 1986).

B: Inflammatory Conditions:

Inflammatory conditions in the context of the present invention comprise inflammatory condition being due to an infection. In one embodiment, the method of treatment would be to block pathogen infection. In a particular embodiment, the infection is a bacterial infection, e.g., a *Listeria* infection. See, e.g., Shen et al. Cell 103: 501-10, (2000) whereby a bacterial surface protein activates c-Met kinase through binding to the extracellular domain of the receptor, thereby mimicking the effect of the cognate ligand HGF/SF. Compounds of formula (I) are further useful in the treatment of additional inflammatory disorders and conditions as provided herein or known in the art.

Pharmaceutical Formulations

In another aspect, the present invention provides a pharmaceutical composition comprising a compound of formula (I) and/or a pharmaceutically acceptable salt thereof, as active ingredient in association with at least one pharmaceutically acceptable carrier and/or diluent. In particular, the present invention provides a pharmaceutical composition comprising a therapeutically effective amount of a compound of formula (I) or a pharmaceutically acceptable salt thereof, and one or more pharmaceutically acceptable carriers.

In a further embodiment, the invention relates to a pharmaceutical composition for treatment of a disease, e.g. of a proliferative disease or an inflammatory condition, e.g. of a solid tumor in warm-blooded animals, including humans, comprising a dose effective in the treatment of said disease of a compound of the formula (I) as described above or a pharmaceutically acceptable salt of such a compound together with a pharmaceutically acceptable carrier.

Such pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques. Tablets may be either film coated or enteric coated according to methods known in the art. Tablets may be coated or formulated in a particular way to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Dosages

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated, the route of administration; the renal and hepatic function of the patient; and the particular compound employed. A physician, clinician or veterinarian of ordinary skill can readily determine the effective amount of each of the active ingredients necessary to prevent, treat or inhibit the progress of the disorder or disease. Optimal precision in achieving concentration of drug within the range that yields efficacy without toxicity requires a regimen based on the kinetics of the drug's availability to target sites. This involves a consideration of the distribution, equilibrium, and elimination of a drug.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

Combinations

The compound of the present invention may be used in combination therapy, i.e. administered either simultaneously with, or before or after, one or more other therapeutic agents. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by c-Met tyrosine kinase. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

Accordingly, in one embodiment, the present invention relates to a combination comprising a therapeutically effective amount of a compound of formula (I) or a pharmaceutically acceptable salt thereof as defined in the present invention, and one or more additional therapeutically active agents.

In one embodiment, the invention provides a pharmaceutical composition comprising a compound of formula (I) and another therapeutic agent(s). Optionally, the pharmaceutical composition may comprise a pharmaceutically acceptable excipient, as described above. In particular, the present invention refers to a pharmaceutical composition comprising (i) a therapeutically effective amount of a compound of formula (I) or a pharmaceutically acceptable salt thereof as defined herein, (ii) one or more pharmaceutically acceptable carriers, and (iii) one or more additional therapeutically active agents.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

A compound of formula (I) can besides or in addition be administered especially for tumor therapy in combination with chemotherapy, radiotherapy, immunotherapy, photodynamic therapy, surgical intervention, implants, e.g. with corticosteroids or hormones, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

More general, a compound of the formula (I) may be used in combination with other antiproliferative compounds. Such antiproliferative compounds include, but are not limited to aromatase inhibitors; antiestrogens; anti-androgens; gonadorelin agonists; topoisomerase I inhibitors; topoisomerase II inhibitors; microtubule active compounds; alkylating compounds; histone deacetylase inhibitors; antineoplastic antimetabolites; platin compounds; compounds targeting/decreasing a protein or lipid kinase activity; compounds targeting/decreasing/inhibiting a protein or lipid phosphatase activity; further anti-angiogenic compounds; compounds which induce cell differentiation processes; compounds targeting VEGF and/or VEGFR; cyclooxygenase inhibitors; bisphosphonates; mTOR inhibitors; heparanase inhibitors; biological response modifiers; telomerase inhibitors; inhibitors of Ras oncogenic isoforms; methionine aminopeptidase inhibitors; proteasome inhibitors; matrix metalloproteinase (MMP) inhibitors; compounds used in the treatment of hematologic malignancies; compounds which target, decrease or inhibit the activity of FMS-like tyrosine kinase receptors (Flt-3R); Hsp90 inhibitors; kinesin spindle protein inhibitors; MEK inhibitors; EDG binders; antileukemia compounds; ribonucleotide reductase inhibitors; antiproliferative antibodies; S-adenosylmethionine decarboxylase inhibitors; angiostatic steroids; somatostatin receptor antagonists; corticosteroids; other chemotherapeutic compounds (as defined below); and photosensitizing compounds.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g. in the form as it is marketed, e.g. under the trademark VINBLASTIN. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA). Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g. in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; as used herein includes, but is not limited to, other serine and/or threonine kinase inhibitors or lipid kinase inhibitors, in particular also other c-Met tyrosine kinase inhibitors, e.g.

a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin kinase family inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, e.g. imatinib;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

j) compounds targeting, decreasing or inhibiting the activity of members of the protein kinase C(PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a PI-3K inhibitor) or BEZ235 (a PI-3K inhibitor) or AT7519 (CDK inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the 5-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™) Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d] pyrimidine derivatives which are disclosed in WO 03/013541; and m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF; and n) compounds targeting, decreasing or inhibiting the activity of the Ron receptor tyrosine kinase.

The term "protein or lipid phosphatase activity" as used herein includes, but is not limited to inhibitors of phosphatase 1, phosphatase 2A, or CDC25, e.g. okadaic acid or a derivative thereof.

The term "further anti-angiogenic compounds" as used herein includes, but is not limited to compounds having another mechanism for their activity, e.g. unrelated to protein or lipid kinase inhibition e.g. thalidomide (THALOMID) and TNP-470.

The term "Compounds which induce cell differentiation processes" includes, but is not limited to e.g. retinoic acid, α- γ- or δ-tocopherol or α- γ- or δ-tocotrienol.

"Compounds targeting VEGF and/or VEGFR" include, but are not limited to, compounds, proteins or monoclonal antibodies targeting VEGF/VEGFR such as disclosed in WO 98/35958, e.g. 1-(4-chloroanilino)-4-(4-pyridylmethyl)phthalazine or a pharmaceutically acceptable salt thereof, e.g. the succinate (also named PTK787/ZK 222584), or in WO 00/09495, WO 00/27820, WO 00/59509, WO 98/11223, WO 00/27819 and EP 0 769 947; those as described by Prewett et al, Cancer Res, Vol. 59, pp. 5209-5218 (1999); Yuan et al., Proc Natl Acad Sci USA, Vol. 93, pp. 14765-14770 (1996); Zhu et al., Cancer Res, Vol. 58, pp. 3209-3214 (1998); and Mordenti et al., Toxicol Pathol, Vol. 27, No. 1, pp. 14-21 (1999); in WO 00/37502 and WO 94/10202; ANGIOSTATIN, described by O'Reilly et al., Cell, Vol. 79, pp. 315-328 (1994); ENDOSTATIN, described by O'Reilly et al., Cell, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™)

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

The term "Compounds which target, decrease or inhibit the activity of FMS-like tyrosine kinase receptors (Flt-3R)" are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG, 17-DMAG), a geldanamycin derivative; other geldanamycin related compounds; radicicol and HDAC inhibitors; IPI-504, CNF1010, CNF2024, CNF1010 from Conforma Therapeutics; temozolomide (TEMODAL®), AUY922 from Novartis.

The term "kinesin spindle protein inhibitors" is known in the field and includes SB715992 or SB743921 from GlaxoSmithKline and pentamidine/chlorpromazine from CombinatoRx;

The term "MEK inhibitors" is known in the field and includes ARRY142886 from Array PioPharma, AZD6244 from AstraZeneca, PD181461 from Pfizer, leucovorin.

The term "EDG binders" as used herein refers a class of immunosuppressants that modulates lymphocyte recirculation, such as Fingolimod (FTY720).

The term "antileukemia compounds" includes, for example, Ara-C, a pyrimidine analog, which is the 2"-alpha-hydroxy ribose (arabinoside) derivative of deoxycytidine. Also included is the purine analog of hypoxanthine, 6-mercaptopurine (6-MP) and fludarabine phosphate. For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g. farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "ribonucleotide reductase inhibitors" includes, but is not limited to to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "antiproliferative antibodies" as used herein includes, but is not limited to, trastuzumab (Herceptin™), Trastuzumab-DM1, erbitux, bevacizumab (Avastin™) rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

The term "S-adenosylmethionine decarboxylase inhibitors" as used herein includes, but is not limited to the compounds disclosed in U.S. Pat. No. 5,461,076.

"Angiostatic steroids" as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

"Somatostatin receptor antagonists" as used herein refers to compounds which target, treat or inhibit the somatostatin receptor such as octreotide, and SOM230.

"Corticosteroids" as used herein includes, but is not limited to compounds, such as e.g. fluocinolone, dexamethasone; in particular in the form of implants.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

"Photosensitizing compounds" are used in the context of "photodynamic therapy" referring to a therapy which uses certain chemicals, i.e. photosensitizing compounds, to treat or prevent cancers. Examples of photodynamic therapy include treatment with compounds, such as e.g. VISUDYNE and porfimer sodium.

"Tumor cell damaging approaches" refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., $4^{th}$ Edition, Vol. 1, pp. 248-275 (1993).

In certain preferred embodiments, the compounds of the present invention are co-administered with a chemotherapeutic agent, in particular an anti-cancer agent which is a pathway specific inhibitor. The pathway specific inhibitor may be a chemotherapeutic agent or may be a biologic agent, e.g., such as an antibody. Preferred pathway specific inhibitors include, but are not limited to, inhibitors of EGFR, Her-2, Her-3, VEGFR, PDGFR, Ron, IGF-IR, PI-3K, mTOR, and Raf, such as defined above.

Some combinations might be particularly useful for the treatment of certain types of proliferative diseases. The following non-exhaustive list indicates some preferred combinations and the respective diseases:

a compound of the present invention in combination with an inhibitor of EGFR (e.g. Iressa™), in particular for the treatment of NSCLC;

a compound of the present invention in combination with an inhibitor of PI-3K, such as BEZ235 (CAS No. 915019-65-7) from Novartis, in particular for the treatment of Nasopharyngeal carcinoma (NPC) and some other cancers;

a compound of the present invention in combination with an inhibitor of mTOR;

a compound of the present invention in combination with a tyrosine protein kinase and/or Raf inhibitor such as Sorafenib, in particular for the treatment of primary kidney cancer (advanced renal cell carcinoma) and advanced primary liver cancer (hepatocellular carcinoma);

a compound of the present invention in combination with an VEGFR inhibitor such as PTK787 or an antibody against the ligand VEGF such as Avastin®;

a compound of the present invention in combination with an PDGFR inhibitor, e.g. imatinib (STI571 or Glivec®);

a compound of the present invention in combination with an mTOR inhibitors, such as rapamycin and everolimus (RAD001).

In another embodiment, a compound of formula (I) may also be used in combination with one or more further drug substances selected from the group of anti-inflammatory drug substances; antagonists of chemokine receptors; antihistamine drug substances; bronchodilatatory drug substances, and nonsteroidal anti-inflammatory drugs (NSAIDs).

The compounds of the invention are also useful as co-therapeutic compounds for use in combination with such further drug substances, particularly in the treatment of inflammatory diseases such as those mentioned hereinbefore, for example as potentiators of therapeutic activity of such drugs or as a means of reducing required dosaging or potential side effects of such drugs. A compound of the invention may be mixed with such other drug substance in a fixed pharmaceutical composition or it may be administered separately (i.e. before, simultaneously with or after the other drug substance). Accordingly, the invention includes a combination of a compound of formula (I) with one or more further drug substance selected from the group of anti-inflammatory drug substances; antihistamine drug substances; bronchodilatatory drug substances, NSAID and antagonists of chemokine receptors; said compound of the formula (I) and said drug substance being in the same or different pharmaceutical composition.

Suitable anti-inflammatory drug substances include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

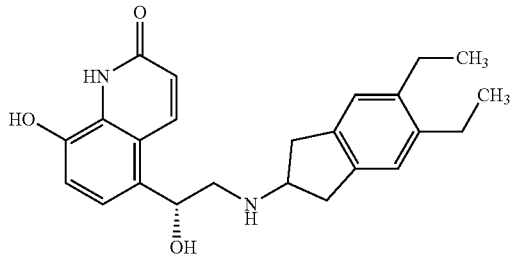 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of WO 04/033412.

Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable chemokine receptor antagonists include but are not limited to antagonists against CCR-1, CCR-2, CCR-3, CCR-4, CCR-5, CCR-6, CCR-7, CCR-8, CCR-9 and CCR10, CXCR1, CXCR2, CXCR3, CXCR4, and CXCR5. In particular CCR-5 antagonists such as Schering-Plough antagonists SC-351125, SCH-55700 and SCH-D, Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The above-mentioned compounds, which can be used in combination with a compound of the formula (I), can be prepared and administered as described in the art, such as in the documents cited above.

Accordingly, the invention provides the use of a compound of formula (I) for treating a disease or condition mediated by c-Met tyrosine kinase, wherein the medicament is prepared for administration with another therapeutic agent as exemplified above. The invention also provides the use of another therapeutic agent for treating a disease or condition mediated by c-Met tyrosine kinase, wherein the medicament is administered with a compound of formula (I).

The invention also provides a compound of formula (I) for use in a method of treating a disease or condition mediated by c-Met tyrosine kinase, wherein the compound of formula (I) is prepared for administration with another therapeutic agent. The invention also provides another therapeutic agent for use in a method of treating a disease or condition mediated by c-Met tyrosine kinase, wherein the other therapeutic agent is prepared for administration with a compound of formula (I). The invention also provides a compound of formula (I) for use in a method of treating a disease or condition mediated by c-Met tyrosine kinase, wherein the compound of formula (I) is administered with another therapeutic agent. The invention also provides another therapeutic agent for use in a method of treating a disease or condition mediated by c-Met tyrosine kinase, wherein the other therapeutic agent is administered with a compound of formula (I).

The invention also provides the use of a compound of formula (I) for treating a disease or condition mediated by c-Met tyrosine kinase, wherein the patient has previously (e.g. within 24 hours) been treated with another therapeutic agent. The invention also provides the use of another therapeutic agent for treating a disease or condition mediated by c-Met tyrosine kinase, wherein the patient has previously (e.g. within 24 hours) been treated with a compound of formula (I).

In one embodiment, the other therapeutic agent is selected from:

an EGFR inhibitor such as Iressa™
Raf inhibitor such as Sorafenib,
PI-3K inhibitor such as BEZ235 (CAS No. 915019-65-7)
VEGFR inhibitor such as PTK787
VEGF antibody such as Avastin®,
PDGFR inhibitor such as STI571 (Glivec®),
mTOR inhibitors such as rapamycin and everolimus
aromatase inhibitor such as letrozole (Femara®) or anastrozole,
microtubule active compound such as paclitaxel or an epothilone,
antineoplastic antimetabolite such as gemcitabine or capecitabine,
platin compounds such as carboplatin or cis-platin,
bisphosphonates such as AREDIA® or ZOMETA®,
HER2 antibodies such as trastuzumab.

Preparation of the Compounds

In another embodiment of the invention, there is provided a method of manufacturing a compound of formula (I) and intermediates thereof. A compound of the formula (I) may be prepared by processes that, though not applied hitherto for the new compounds of the present invention where they thus form new processes, are known per se. The schemes provide a general overview of synthetic strategies to obtain a compound of formula (I).

Thus, the invention relates in a further aspect to a manufacturing process (a method for manufacturing) a compound of formula (I) comprising at least one reaction step as disclosed herein, and intermediates thereof.

The compounds of the present invention may be prepared by use of known chemical reactions and procedures. Nevertheless, the following general preparative methods are presented to aid the reader in synthesizing the compounds of formula (I), with specific details provided below in the experimental section to illustrate working examples. The desired specific compounds can be prepared by selecting the appropriate starting materials, reactants and reaction conditions.

All variable groups of these methods are as described in the generic description if they are not specifically defined below.

It is recognized that compounds of the invention with each claimed optional functional group may not be prepared by each of the below-listed methods. Within the scope of each method, optional substituents may appear on reagents or intermediates which may act as protecting or otherwise non-participating groups. Utilizing methods well known to those skilled in the art, these groups are introduced and/or removed during the course of the synthetic schemes which provide the compounds of the present invention.

Typically, the compounds of formula (I) can be prepared according to the Schemes provided infra Scheme 1 provides details for a synthetic strategy to obtain preferred compounds of formula (I-A) wherein $R^1$ is optionally substituted pyrazolyl, starting from compounds of formula (II.1).

$R^3$ is as defined herein for compounds of the present invention.

Depending on the nature of $Z^1$ and $R^{3a}$, the reaction carried out in Step a might require slightly different reaction conditions. The reaction product of step A, a compound of formula (I.1) either already represents a compound of formula (I) or requires further modifications of substituents $R^{3a}$ to $R^3$ and/or $R^{8a}$ to $R^8$ to deliver a compound of formula (I-A). Such modifications like the removal of protection groups are well known to a person skilled in the art.

Scheme 2 provides details for a synthetic strategy to obtain preferred compounds of formula (I-B) wherein $R^1$ is an optionally substituted oxime group $-CR^9=N-O-R^{10}$, starting from compounds of formula (II.2).

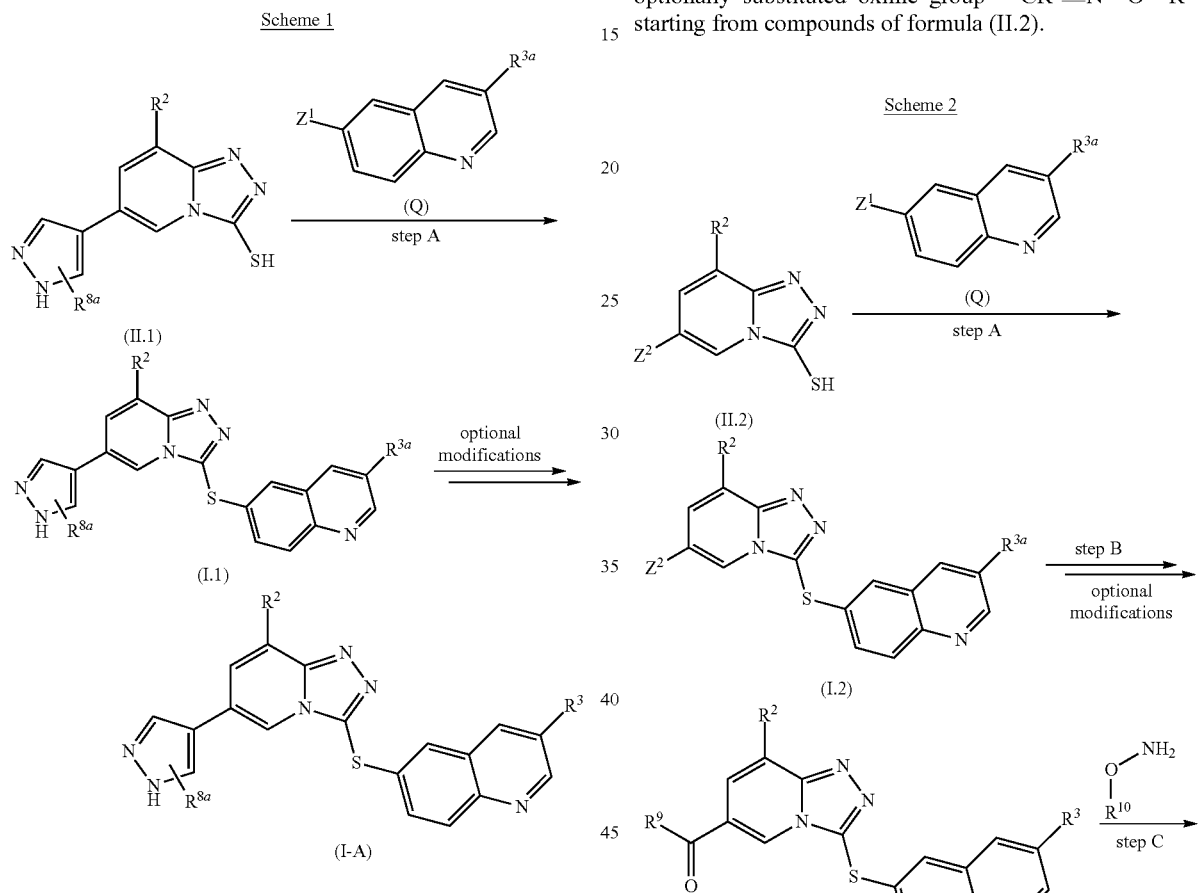

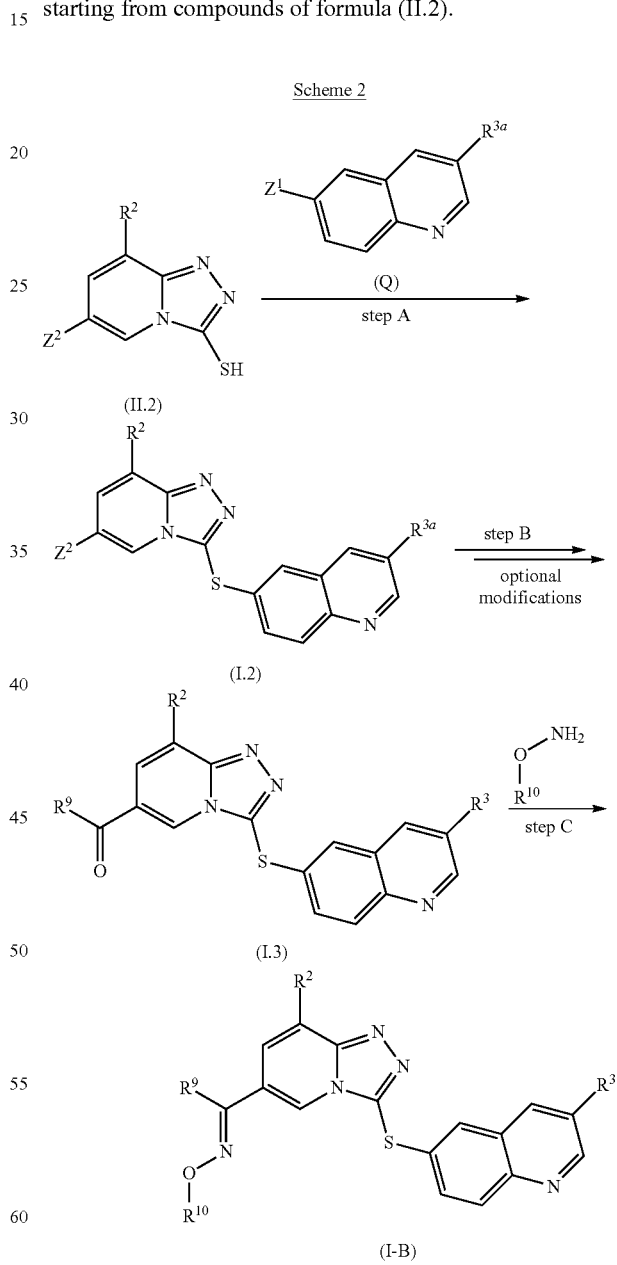

Wherein
$R^{8a}$ is hydrogen or $(C_1-C_4)$alkyl, said $(C_1-C_4)$alkyl being optionally substituted by a protected OH group;
$R^8$ is hydrogen or $(C_1-C_4)$alkyl, said $(C_1-C_4)$alkyl being optionally substituted by one OH group;
$R^2$ is selected from hydrogen and halo;
$Z^1$ is a leaving group such as Br, I, or triflate ($CF_3-SO_2-O-$ or TfO—) or any other suitable leaving group; and
$R^{3a}$ is selected from
(i) optionally substituted $-(C_0-C_2)$alkyl-heterocyclyl$^1$, wherein free —OH and —NH$_2$ groups are adequately protected if necessary,
(ii) —NHR$^{4a}$, wherein $R^{4a}$ is a protection group such as t-BOC(N-tert-butoxycarbonyl) or $(C_1-C_4)$alkyl, said $(C_1-C_4)$alkyl being optionally substituted by one, two or three substituents independently selected from protected OH and halo,
or wherein $R^{4a}$ is optionally substituted $-(C_0-C_2)$alkyl-heterocyclyl$^3$, wherein free —OH and —NH$_2$ groups are adequately protected if necessary; and wherein
$Z^2$ is a leaving group such as Cl, Br, or I or any other suitable leaving group;
$R^2$ is selected from hydrogen and halo;

$Z^1$ is leaving group such as Br, I, or triflate (CF$_3$—SO$_2$—O— or TfO—) or any other suitable leaving group; and $R^{3a}$ is selected from
(i) optionally substituted —(C$_0$-C$_2$)alkyl-heterocyclyl$^1$, wherein free OH and NH$_2$ groups are adequately protected if necessary,
(ii) —NHR$^{4a}$, wherein R$^{4a}$ is a protection group such as t-BOC(N-tert-butoxycarbonyl) or (C$_1$-C$_4$)alkyl, said (C$_1$-C$_4$)alkyl being optionally substituted by one, two or three substituents independently selected from protected OH and halo,
   or wherein R$^{4a}$ is optionally substituted —(C$_0$-C$_2$)alkyl-heterocyclyl$^3$, wherein free —OH and —NH$_2$ groups are adequately protected if necessary; and $R^3$ is as defined herein for compounds of the present invention.

Depending on the nature of $Z^1$ and $R^{3a}$, the reaction carried out in step A might require slightly different reaction conditions. The reaction product of step A, a compound of formula (I.2) will then be transformed in the desired oxime derivate (1-B) by steps B and C. Substituent $R^{3a}$ either already represents the desired residue $R^3$ or requires further modifications such as the removal of protection groups which are well known to a person skilled in the art. Such modifications are preferably carried out before reaction step C.

Scheme 3 provides details for a synthetic strategy to obtain the building blocks (II.1) and (II.2) used in the aforementioned Schemes A and B.

Scheme 3

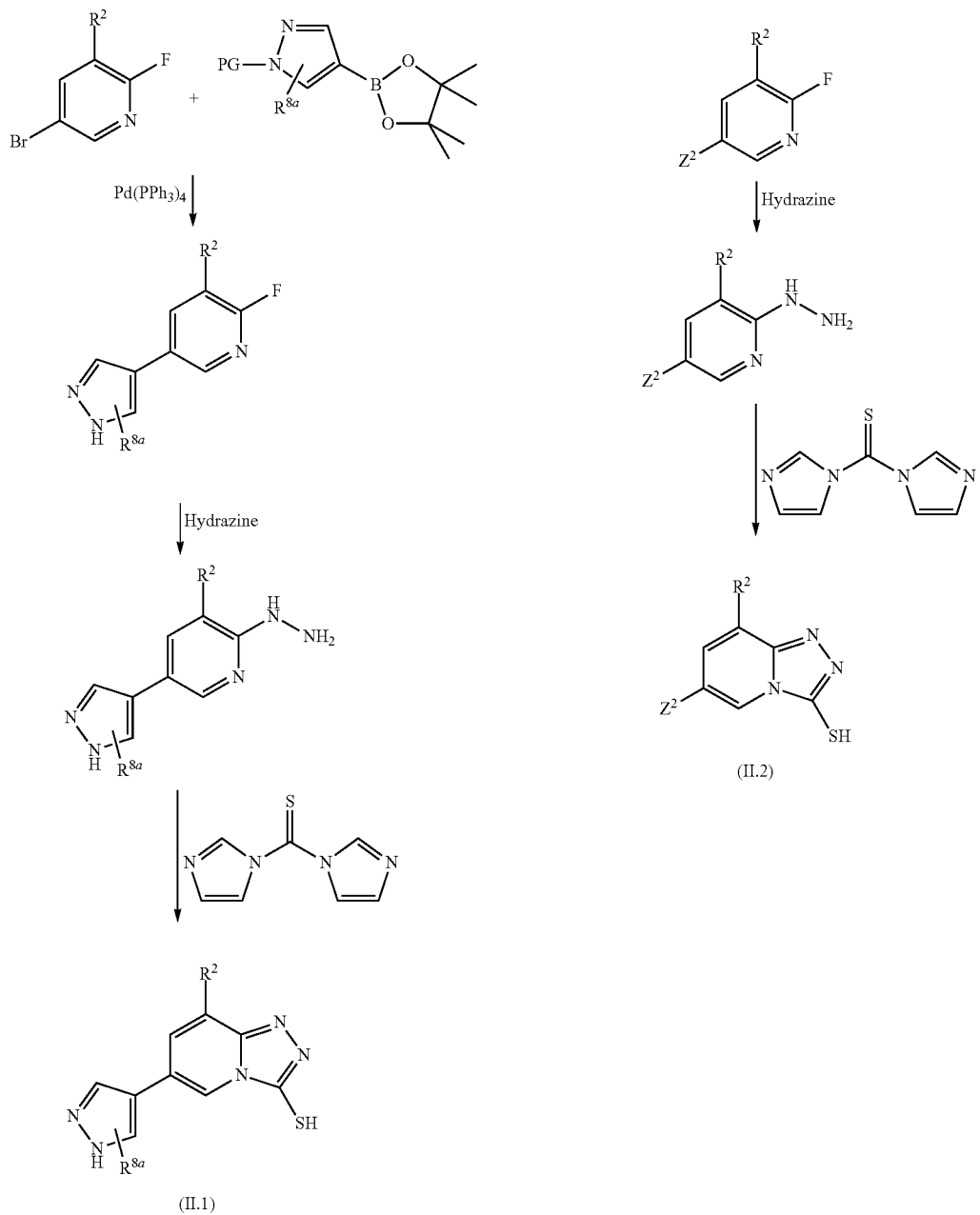

wherein $R^2$ is selected from hydrogen and halo;

$Z^2$ is a leaving group such as Cl, Br, or I or any other suitable leaving group;

$R^{8a}$ is hydrogen or $(C_1-C_4)$alkyl, said $(C_1-C_4)$alkyl being optionally substituted by a protected OH group; and PG is hydrogen or a suitable protection group.

Scheme 4 provides details for a synthetic strategy to obtain the quinoline building blocks (Q) used in the aforementioned Schemes A and B.

Scheme 4

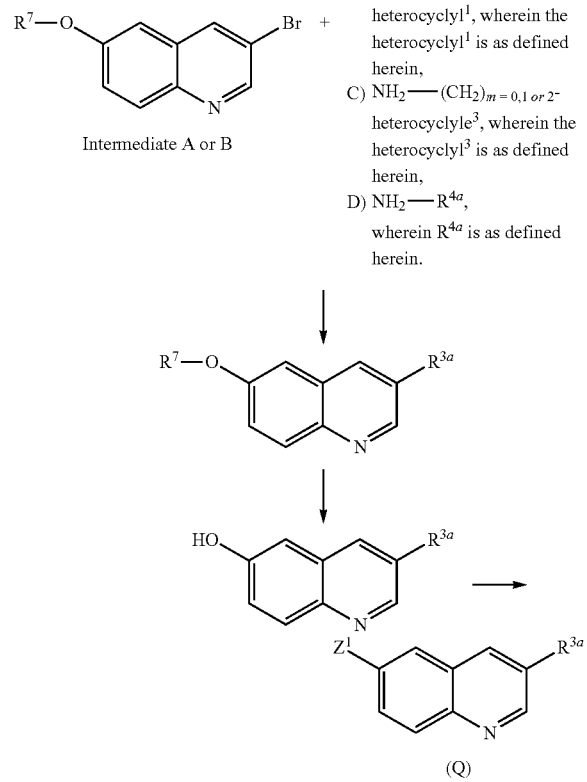

Wherein $R^7$ is a group such as benzyl or acetyl or any other suitable protection group;

$Z^1$ is a leaving group such as Br, I, or triflate ($CF_3$—$SO_2$—O— or TfO—) or any other suitable leaving group; and $R^{3a}$ is selected from (i) optionally substituted —$(C_0-C_2)$alkyl-heterocyclyl$^1$, wherein free —OH and —$NH_2$ groups are adequately protected if necessary, (ii) —$NHR^{4a}$, wherein $R^{4a}$ is a protection group such as t-BOC(N-tert-butoxycarbonyl) or $(C_1-C_4)$alkyl, said $(C_1-C_4)$alkyl being optionally substituted by one, two or three substituents independently selected from protected OH and halo, or wherein $R^{4a}$ is optionally substituted —$(C_0-C_2)$alkyl-heterocyclyl$^3$, wherein free —OH and —$NH_2$ groups are adequately protected if necessary.

The starting materials and reagents in the above scheme are all either available commercially or can be prepared following literature precedents.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Accordingly, the present invention relates to a process of manufacturing a compound of formula (I)

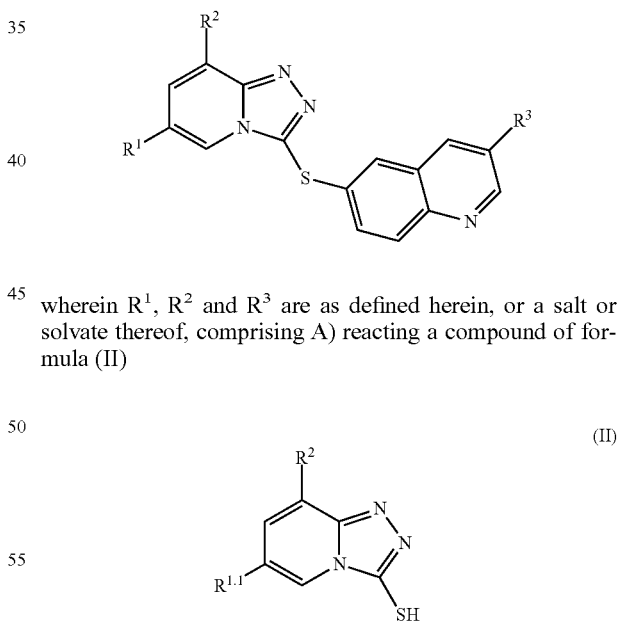

wherein $R^1$, $R^2$ and $R^3$ are as defined herein, or a salt or solvate thereof, comprising A) reacting a compound of formula (II)

(II)

wherein $R^{1.1}$ is selected from (i) pyrazolyl, optionally substituted by $(C_1-C_4)$alkyl, said $(C_1-C_4)$alkyl being optionally substituted by a protected OH group, and (ii) $Z^2$ which is a suitable leaving group;

and $R^2$ is selected from hydrogen and halo;

with a compound of formula (III)

(Q)

wherein $Z^1$ is a suitable leaving group, and
$R^{3a}$ is selected from
(i) optionally substituted —$(C_0-C_2)$alkyl-heterocyclyl$^1$, wherein any free —OH and —NH$_2$ groups are adequately protected if necessary,
(ii) —NHR$^{4a}$, wherein R$^{4a}$ is a suitable protection group or $(C_1-C_4)$alkyl, said $(C_1-C_4)$alkyl being optionally substituted by one, two or three substituents independently selected from protected OH and halo,
or wherein R$^{4a}$ is optionally substituted —$(C_0-C_2)$alkyl-heterocyclyl$^3$, wherein any free —OH and —NH$_2$ groups are adequately protected if necessary;
in a palladium coupling reaction in the presence of a bidentate ligand and a base in a polar aprotic solvent at a temperature from about 80° C. to 120° C. under protective atmosphere, to deliver a compound of formula (I.0)

(I.0)

B) optional further reaction steps to convert substituent $R^{3a}$ into $R^3$ if necessary, and
C) optional further reaction steps to convert substituent $R^{1.2}$ into $R^1$.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). Unless otherwise indicated, the reactions take place at room temperature (rt). The structure of final products, intermediates and starting materials is confirmed by standard analytical methods, e.g., microanalysis and spectroscopic characteristics, e.g., MS, IR, NMR.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21).

Further, if not indicated otherwise, the analytical and preparative HPLC conditions are as follows:
Method A:
The flow is 0.5 mL/min of methanol and water (with 0.5% acetic acid)
0-4.0 min: 10% to 90% of methanol
4.0-6.0 min: 90% of methanol
Column: GP C18 3 µm 4.6×30 mm from Sepax.
Oven temperature: 30° C.
Method B:
The flow is 1.2 mL/min of methanol and water (with 0.5% acetic acid)
0-2.0 min: 10% to 90% of methanol
2.0-3.0 min 90% of methanol
Column: GP C18 3 µm 4.6×30 mm from Sepax.
Oven temperature: 30° C.
Method C:
The flow is 0.5 mL/min of methanol and water (with 0.5% acetic acid)
0-3.0 min: 60% to 90% of methanol
3.0-5.0 min: 90% of methanol
Column: GP C18 3 µm 4.6×30 mm from Sepax.
Oven temperature: 30° C.
Method D:
The flow is 0.5 mL/min of methanol and water (with 0.5% acetic acid)
0-3.0 min: 10% to 50% of methanol
3.0-4.0 min: 50% of methanol
Column: GP C18 3 µm 4.6×30 mm from Sepax.
Oven temperature: 30° C.
Method E:
The flow is 0.5 mL/min of methanol and water (with 0.5% acetic acid)
0-4.0 min: 10% to 90% of methanol
4.0-8.0 min: 90% of methanol
Column: GP C18 3 µm 4.6×30 mm from Sepax.
Oven temperature: 30° C.
Method F:
The flow is 1 mL/min of Hexane/Ethanol/Diethyleamine 80/20/0.1, v/v/v
Column: AD-H
Oven temperature: 25° C.
Method G:
The flow is 1 mL/min of Hexane/Ethanol/Diethyleamine 70/30/0.1, v/v/v
Column: AD-H
Oven temperature: 25° C.
Method H:
The flow is 1 mL/min of Hexane/Isopropanol/Diethylamine 70/30/0.1, v/v/v
Column: CHIRALPAK OD-H
Oven temperature: 25° C.
Method I:
SFC equipment: Thar SFC Prep 80
The flow is 45 g/min of Methanol/CO$_2$ 70/30
Column: CHIRALPAK OD-H, 2.0×25 cm
Wave length: UV 254 nm
Oven temperature: 35° C.
Method J:
The flow is 1.2 mL/min of methanol and water (with 0.5% acetic acid)
0-3.0 min: 60% to 90% of methanol
Column: GP C18 3 µm 4.6×30 mm from Sepax.
Oven temperature: 30° C.

Method K
The flow is 1 mL/min of Hexane/Ethanol/Diethyleamine 80/20/0.1, v/v/v
Column: OJ-H
Oven temperature: 25° C.
Method L
SFC equipment: Thar SFC Prep 80
The flow is 45 g/min of Methanol/CO$_2$ 75/25
Column: CHIRALPAK AD-H, 2.0×25 cm
Wave length: UV 254 nm
Oven temperature: 35° C.
Method M:
The flow is 0.5 mL/min of methanol and water (with 0.5% formic acid)
0-4.0 min: 10% to 90% of methanol
4.0-6.0 min: 90% of methanol
Column: GP C18 3 μm 4.6×30 mm from Sepax.
Oven temperature: 30° C.
Method N:
The flow is 1.5 mL/min of methanol and water (with 0.5% formic acid)
0-2.0 min: 10% to 90% of methanol
2.0-3.0 min 90% of methanol
Column: GP C18 3 μm 4.6×30 mm from Sepax.
Oven temperature: 30° C.
Method O:
The flow is 1.8 mL/min of methanol and water (with 0.5% formic acid)
0-4.0 min: 10% to 95% of methanol
4.0-5.0 min 95% of methanol
Column: GP C18 3 μm 4.6×30 mm from Sepax.
Oven temperature: 30° C.
Method P:
The flow is 1.8 mL/min of acetonitrile (with 0.01% TFA) and water (with 0.01% TFA)
0-0.2 min: 5% of acetonitrile
0.2-1.4 min: 5% to 95% of acetonitrile
1.4-3.0 min: 95% of acetonitrile
Column: Xbridge, 3.5 μm, 4.6×50 mm
Oven temperature: 50° C.
Method Q:
SFC equipment: Thar SFC Prep 80
The flow is 45 g/min of Methanol/CO$_2$ 25/75
Column: CHIRALPAK AS-D, 2.0×25 cm
Wave length: UV 254 nm
Oven temperature: 35° C.

Abbreviations used are those conventional in the art. In particular, in the following examples, the abbreviations given below are used:
AcOH acetic acid
aq. aqueous
Ar Argon
atm. atmosphere
BINAP 2,2'-bis-diphenylphosphanyl-[1,1']binaphthalenyl
Bn benzyl
Boc tert-butoxycarbonyl
DCC dicyclohexylcarbodiimide
DCM dichloromethane
DME 1,2-dimethoxyethane or dimethyl ethylene glycol ether
DMF N,N-dimethylformamide
DMSO dimethyl sulfoxide
eq. equivalent(s)
Et$_2$O diethyl ether
EtOAc or EA ethyl acetate
EtOH ethanol
h hour(s)
HATU 2-(1H-7-Azabenzotriazol-1-yl)-1,1,3,3-tetramethyluronium hexafluorophosphate
Hex Hexane
HPLC High Performance Liquid Chromatography
HV high vacuum
IBX 2-iodoxybenzoic acid
Isolute Isolute® HM-N by International Solvent Technology Ltd., U.K.
KO$^t$Bu potassium 2-methylpropan-2-olate (Potassium tert-butoxide)
LAH lithium aluminium hydride
LCMS liquid chromatography coupled with mass spectrometry
LDA lithium diisopropylamide
MeOH methanol
min minute(s)
mL milliliter(s)
mmol millimol
MPLC Medium Pressure Liquid Chromatography
MS-ES electrospray mass spectrometry
MW microwave
NBS N-bromosuccinimide
n-BuLi n-butyllithium
NMP N-methylpyrrolidinone
Pd$_2$(dba)$_3$ tris(dibenzylideneacetone)dipalladium (0)
PdCl$_2$(dppf) 1,1-bis(diphenylphosphino)ferrocenedichloropalladium (II)
PdCl$_2$(Ph$_3$)$_2$ dichlorobis(triphenylphosphine)palladium (II)
R$_f$ ratio of fronts in TLC
rt room temperature
TBAF tetrabutylammonium fluoride
TBME methyl tert-butyl ether
TFA trifluoroacetic acid
THF tetrahydrofuran
TLC thin layer chromatography
t$_R$ retention time
UV Ultraviolet
Xantphos 4,5-Bis(diphenylphosphino)-9,9-dimethylxanthene The compounds of the present invention can be produced by organic synthesis methods known to one of ordinary skill in the art as shown in the following examples.

Syntheses of Intermediates

Intermediate A & Intermediate B 3-bromoquinolin-6-yl acetate (intermediate A)

6-(benzyloxy)-3-bromoquinoline (intermediate B)

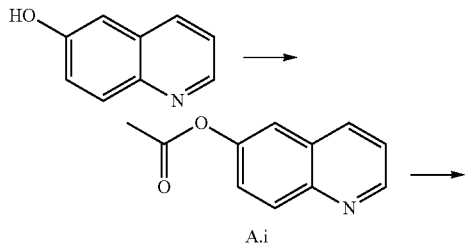

A.i

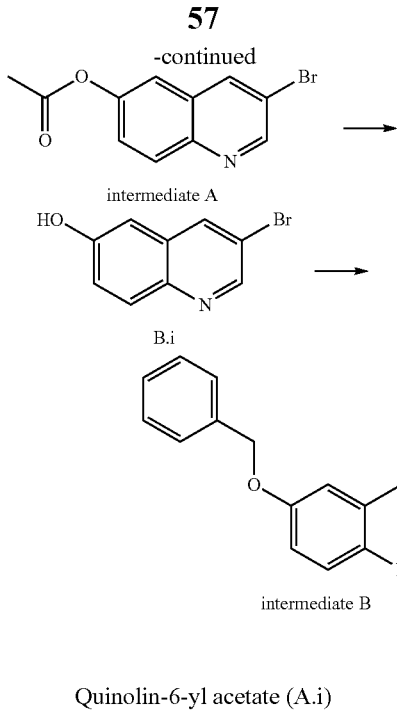

intermediate A

B.i intermediate B

Quinolin-6-yl acetate (A.i)

To a solution of quinolin-6-ol (4.5 g, 31.0 mmol) and pyridine (3.01 ml, 37.2 mmol) in DCM (50 ml) was added acetyl chloride (2.65 ml, 37.2 mmol) at 0° C. The mixture was then stirred at rt for 8 h. The reaction was quenched with saturated NaHCO$_3$ and the mixture was extracted with DCM (30 ml) three times. The combined organic phase was washed with brine and dried over anhydrous MgSO$_4$, filtered and concentrated to give the title compound (5.0 g, 68.9% yield), which was used directly in next step. LCMS (method B): [M+H]$^+$=188, $t_R$=1.64 min.

3-Bromoquinolin-6-yl acetate (Intermediate A)

To a solution of A.i (5 g, 26.7 mmol) and pyridine (6.48 ml, 80 mmol) in CCl$_4$ (100 ml) was added Br$_2$ (4.13 ml, 80 mmol) at 0° C. The resultant brown suspension was then heated at 90° C. for 3 h. After being cooled to rt, the mixture was diluted with DCM and water. The organic phase was separated and washed with water and brine, dried over anhydrous MgSO$_4$, filtered and concentrated. The residue was purified by silica gel chromatography with Hex/EA (from 100% to 90%) to afford the title compound as white solid (3.2 g, 40.5% yield). $^1$H-NMR (400 MHz, DMSO-d$_6$) δ ppm 8.95 (s, 1H), 8.73 (s, 1H), 8.08 (d, 1H), 7.74 (d, 1H), 7.62 (dd, 1H), 2.34 (s, 3H). LCMS (method B): [M+H]$^+$=267, $t_R$=2.29 min.

3-Bromoquinolin-6-ol (B.i)

A solution of Intermediate A (1 g, 3.76 mmol) and K$_2$CO$_3$ (1.04 g, 7.52 mmol) in MeOH/H$_2$O (5 mL/3 mL) was stirred at rt for 2 hours. The reaction mixture was concentrated under reduced pressure to afford a crude solid which was further purified by washing with water, dried under vacuum to give the title compound as white solid (760 mg, yield 86%). LCMS (method N): [M+H]$^+$=224, $t_R$=2.29 min.

6-(Benzyloxy)-3-bromoquinoline (intermediate B)

A solution of B.i (760 mg, 3.39 mmol), benzyl bromide (0.44 mL, 3.73 mmol) and K$_2$CO$_3$ (563 mg, 4.07 mmol) in acetone (20 mL) was stirred at rt overnight. The reaction mixture was concentrated under reduced pressure. The crude product was purified by chromatography (eluting with 20% EtOAc in haxane) to give the title compound as white solid (970 mg, yield 89%). LCMS (method N): [M+H]$^+$=314, $t_R$=2.91 min. $^1$H-NMR (400 MHz, DMSO-d$_6$) δ ppm 8.76 (d, 1H), 8.23 (d, 1H), 8.05 (d, 1H), 7.49-7.34 (m, 6H), 7.08 (d, 1H), 5.20 (s, 2H).

Building Blocks of Formula (II.1)

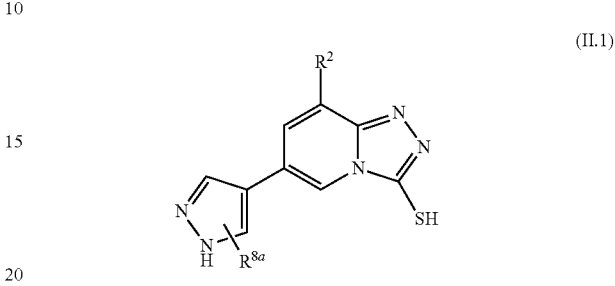

(II.1)

Building blocks of formula (II.1) comprising Intermediates C, D, E, F and G were synthesized according to general Scheme 3, left side.

Intermediate C 6-(1H-pyrazol-4-yl)-[1,2,4]triazolo[4,3-a]pyridine-3-thiol

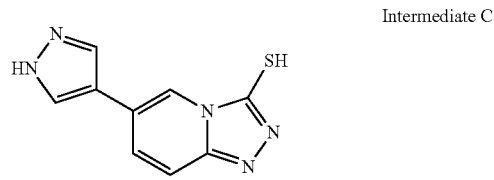 [SMILES: Sc1nnc2ccc(-c3cn[nH]c3)cn12]

Intermediate C 2-fluoro-5-(1H-pyrazol-4-yl)pyridine (C.i)

To a solution of 5-bromo-2-fluoropyridine (1.0 g, 5.68 mmol) in dioxane (30 ml) was added tert-butyl 4-(4,4,5,5-tetramethyl-1,3,2-dioxaborolan-2-yl)-1H-pyrazole-1-carboxylate (1.671 g, 5.68 mmol), Na$_2$CO$_3$ (1.205 g, 11.36 mmol) and Pd(Ph$_3$P)$_4$ (0.657 g, 0.568 mmol). The reaction mixture was stirred at 100° C. under Ar atmosphere for overnight. The reaction was cooled and concentrated under reduced pressure. The residue was purified by silica gel chromatography (DCM/MeOH=30/1) to afford the title compound as white solid (0.5 g, 44.2% yield). $^1$H-NMR (400 MHz, DMSO-d$_6$) δ ppm 13.0 (s, 1H), 8.29 (s, 1H), 8.2 (d, 1H), 8.18 (d, 1H), 7.99 (s, 1H), 7.18 (dd, 1H). LCMS (method B): [M+H]$^+$=164, $t_R$=1.73 min.

2-hydrazinyl-5-(1H-pyrazol-4-yl)pyridine (C.ii)

To a solution of C.i (0.5 g, 3.06 mmol) in dioxane (10 ml), hydrazine monohydrate (0.385 ml, 12.26 mmol) was added, and the mixture was refluxed for overnight. The reaction was then cooled and concentrated under reduced pressure. The residue was recrystallized from DCM/MeOH (10/1) to afford the title compound as white solid (0.4 g, 44.0% yield). LCMS (method B): [M+H]$^+$=176, $t_R$=0.5 min.

6-(1H-pyrazol-4-yl)-[1,2,4]triazolo[4,3-a]pyridine-3-thiol (Intermediate C)

C.ii (0.4 g, 2.283 mmol) and di(1H-imidazol-1-yl)methanethione (0.407 g, 2.283 mmol) were dissolved in DMF (10 ml). The reaction mixture was stirred at 90° C. for 3 h. The solvent was removed under reduced pressure to afford the crude product, which was recrystallized from DCM/MeOH (10/1) to afford the title compound as pale yellow solid (0.3 g, 52.6% yield). LCMS (method B): [M+H]$^+$=218, $t_R$=1.66 min.

Intermediate D 8-fluoro-6-(1H-pyrazol-4-yl)-[1,2,4]triazolo[4,3-a]pyridine-3-thiol

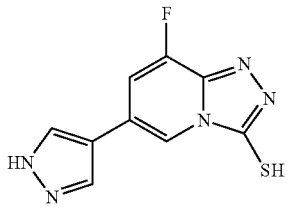

Intermediate D

2,3-difluoro-5-(1H-pyrazol-4-yl)pyridine (D.i)

5-bromo-2,3-difluoropyridine (2.0 g, 10.31 mmol), tert-butyl 4-(4,4,5,5-tetramethyl-1,3,2-dioxaborolan-2-yl)-1H-pyrazole-1-carboxylate (3.03 g, 10.31 mmol), Na$_2$CO$_3$ (2.186 g, 20.62 mmol) and Pd(Ph$_3$P)$_4$ (1.191 g, 1.031 mmol) were dissolved in dioxane (20 ml). The mixture was bubbled with Ar for 10 min. The reaction was stirred at 100° C. for overnight, cooled and concentrated under reduced pressure. The residue was purified by silica gel chromatography (DCM/MeOH=30/1) to afford the title compound as white solid (1.0 g, 53.5% yield). LCMS (method B): [M+H]$^+$=182, $t_R$=1.98 min.

3-fluoro-2-hydrazinyl-5-(1H-pyrazol-4-yl)pyridine (D.ii)

To a solution of D.i (500 mg, 2.76 mmol) in dioxane (10 ml), hydrazine monohydrate (0.347 ml, 11.04 mmol) was added. The reaction mixture was heated at reflux for overnight, cooled and concentrated under reduced pressure. The residue was recrystallized from DCM/MeOH (10/1) to afford the title compound (500 mg, 68.1% yield) as white solid. LCMS (method B): [M+H]$^+$=194, $t_R$=0.5 min.

8-fluoro-6-(1H-pyrazol-4-yl)-[1,2,4]triazolo[4,3-a]pyridine-3-thiol (Intermediate D)

D.ii (0.4 g, 2.071 mmol) and di(1H-imidazol-1-yl)methanethione (0.369 g, 2.071 mmol) were dissolved in DMF (10 ml). The resulting solution was stirred at 90° C. for 3 h, cooled and concentrated under reduced pressure. The residue was recrystallized from DCM/MeOH (10/1) to afford the title compound as pale green solid (0.2 g, 28.7% yield). LCMS (method B): [M+H]$^+$=236, $t_R$=1.78 min.

Intermediate E 6-(1-methyl-1H-pyrazol-4-yl)-[1,2,4]triazolo[4,3-a]pyridine-3-thiol

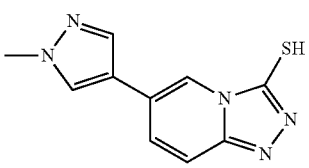

Intermediate E

2-fluoro-5-(1-methyl-1H-pyrazol-4-yl)pyridine (E.i)

A mixture of 5-bromo-2-fluoropyridine (1.75 g, 9.94 mmol), 1-methyl-4-(4,4,5,5-tetramethyl-1,3,2-dioxaborolan-2-yl)-1H-pyrazole (2.069 g, 9.94 mmol), Pd(PPh$_3$)$_4$ (1.149 g, 0.994 mmol) and K$_2$CO$_3$ (2.75 g, 19.89 mmol) in 1,4-dioxane (20 ml) was bubbled with argon for 10 min. The suspension was then stirred at 90° C. for 8 h. The mixture was filtered and the filtrate was diluted with EA, washed with water and brine. The organic phase was dried over anhydrous MgSO$_4$, filtered and concentrated. The residue was recrystallized from MeOH to give the title compound as white solid (1.2 g, 61.3% yield). $^1$H-NMR (400 MHz, DMSO-d$_6$) δ ppm 8.46 (s, 1H), 8.22 (s, 1H), 8.15 (dd, 1H), 7.93 (s, 1H), 7.18 (dd, 1H). LCMS (method B): [M+H]$^+$=178, $t_R$=1.80 min.

2-hydrazinyl-5-(1-methyl-1H-pyrazol-4-yl)pyridine (E.ii)

To a solution of E.i (1.0 g, 5.64 mmol) in MeOH (20 ml) was added hydrazine monohydrate (0.531 ml, 16.93 mmol). The reaction was heated at reflux for 24 h. The solution was concentrated and the precipitate produced was collected by filtration, washed with EA and dried to afford the title compound as white solid. (0.9 g, 76% yield). $^1$H-NMR (400 MHz, DMSO-d$_6$) δ ppm 8.21 (s, 1H), 7.96 (s, 1H), 7.72 (s, 1H), 7.63 (dd, 1H), 7.32 (s, 1H), 6.70 (d, 1H), 4.12 (s, 2H), 3.82 (s, 3H). LCMS (method B): [M+H]$^+$=190, $t_R$=0.30 min.

6-(1-methyl-1H-pyrazol-4-yl)-[1,2,4]triazolo[4,3-a]pyridine-3-thiol (Intermediate E)

To a suspension of E.ii (1 g, 5.28 mmol) in DMF (15 ml) was added di(1H-imidazol-1-yl)methanethione (0.942 g, 5.28 mmol) and the mixture was stirred at 80° C. for 5 h. The mixture was cooled to rt and the precipitate produced was collected, washed with DCM and dried to afford the title compound as yellow solid (0.78 g, 57.4% yield). $^1$H-NMR (400 MHz, DMSO-d$_6$) δ ppm 14.4 (s, 1H), 8.35 (d, 2H), 8.00

(s, 1H), 7.76 (d, 1H), 7.69 (d, 1H), 3.82 (s, 3H). LCMS (method B): [M+H]⁺=232, $t_R$=1.75 min.

Intermediate F 8-fluoro-6-(1-methyl-1H-pyrazol-4-yl)-[1,2,4]tria-zolo[4,3-a]pyridine-3-thiol Intermediate F

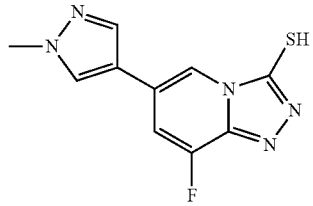

2,3-difluoro-5-(1-methyl-1H-pyrazol-4-yl)pyridine (F.i)

A mixture of 5-bromo-2,3-difluoropyridine (1.9 g, 9.79 mmol) and 1-methyl-4-(4,4,5,5-tetramethyl-1,3,2-diox-aborolan-2-yl)-1H-pyrazole (2.038 g, 9.79 mmol), Na₂CO₃ (2.076 g, 19.59 mmol) and Pd(PPh₃)₄ (1.131 g, 0.979 mmol) in DMF (8 ml) was bubbled with N₂ for 10 min and was then heated to 80° C. for 10 h. After being cooled to rt, the mixture was filtered and the filtrate was diluted with EA, washed with water and brine, dried over anhydrous MgSO₄. Filtered and concentrated. The residue was purified by silica gel chromatography eluted with Hex/EA (from 100% to 20%) to afford the title compound as a white solid (1.5 g, 57.4% yield). ¹H-NMR (400 MHz, DMSO-d₆) δ ppm 8.29 (d, 3H), 7.99 (d, 1H), 3.87 (s, 3H). LCMS (method B): [M+H]⁺=196, $t_R$=1.91 min.

3-fluoro-2-hydrazinyl-5-(1-methyl-1H-pyrazol-4-yl) pyridine (F.ii)

To a solution of F.i (1.6 g, 8.20 mmol) in MeOH (25 ml) was added hydrazine monohydrate (1.029 ml, 32.8 mmol) and the mixture was heated at 60° C. for 10 h. The reaction was then cooled to rt and the precipitate produced was collected by filtration and washed with cooled EtOH to afford the title compound (1.2 g, 63.6% yield). LCMS (method B): [M+H]⁺=208, $t_R$=0.27 min.

8-fluoro-6-(1-methyl-1H-pyrazol-4-yl)-[1,2,4]tria-zolo[4,3-a]pyridine-3-thiol (Intermediate F)

To a suspension of F.ii (0.8 g, 3.86 mmol) in CHCl₃ (8 ml) was added di(1H-imidazol-1-yl)methanethione (0.688 g, 3.86 mmol), and the mixture was stirred at 90° C. for 5 h. The reaction was then cooled to rt and the precipitate produced was collected, washed with cool DCM and dried to afford the title compound (0.502 g, 46.9% yield). The product was used in the next step without further purification. LCMS (method B): [M+H]⁺=250, $t_R$=1.80 min.

Intermediate G 6-(1-(2-(tetrahydro-2H-pyran-2-yloxy)ethyl)-1H-pyrazol-4-yl)-[1,2,4]triazolo[4,3-a]pyridine-3-thiol Intermediate G

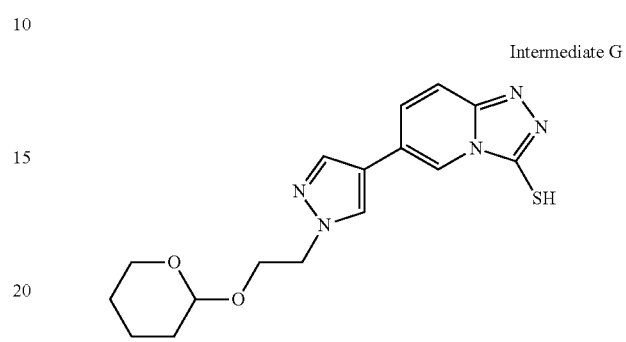

2-fluoro-5-(1-(2-(tetrahydro-2H-pyran-2-yloxy) ethyl)-1H-pyrazol-4-yl)pyridine (G.i)

A mixture of 5-bromo-2-fluoropyridine (176 mg, 1.00 mmol), 1-(2-(tetrahydro-2H-pyran-2-yloxy)ethyl)-4-(4,4,5, 5-tetramethyl-1,3,2-dioxaborolan-2-yl)-1H-pyrazole (322 mg, 1.00 mmol), Pd(PPh₃)₄ (115 mg, 0.100 mmol) and Na₂CO₃ (212 mg, 2.00 mmol) in 1,4-dioxane (5 ml) was bubbled with N₂ for 10 min and then stirred at 85° C. for 6 h. After being cooled to rt, the reaction mixture was filtered through celite and the filtrate was diluted with EA. The organic phase was washed with water, brine and dried over anhydrous MgSO₄. Filtered and concentrated to afford the title compound (0.206 g, yield 63.6%), which was used in next step without further purification. ¹H-NMR (400 MHz, DMSO-d₆) δ ppm 8.48 (s, 1H), 8.27 (s, 1H), 8.17 (dd, 1H), 7.98 (s, 1H), 7.19 (d, 1H), 4.53 (s, 1H), 4.30 (t, 2H), 3.95 (m, 1H), 3.75 (m, 1H), 3.53 (m, 1H), 3.35 (t, 1H), 1.65 (m, 1H), 1.57 (m, 1H), 1.40 (m, 4H). LCMS (method B): [M+H]⁺=292, $t_R$=2.16 min.

2-hydrazinyl-5-(1-(2-(tetrahydro-2H-pyran-2-yloxy) ethyl)-1H-pyrazol-4-yl)pyridine (G.ii)

To a solution of G.i (800 mg, 2.75 mmol) in MeOH (5 ml) was added hydrazine monohydrate (0.673 ml, 10.98 mmol) and the mixture was stirred at 70° C. for 8 h. The solvent was removed to afford the title compound (500 mg, 60.2% yield). LCMS (method B): [M+H]⁺=304, $t_R$=0.26 min.

6-(1-(2-(tetrahydro-2H-pyran-2-yloxy)ethyl)-1H-pyrazol-4-yl)-[1,2,4]triazolo[4,3-a]pyridine-3-thiol (Intermediate G)

To a solution of G.ii (180 mg, 0.593 mmol) in DMF (5 ml) was added di(1H-imidazol-1-yl)methanethione (106 mg, 0.593 mmol) and the mixture was heated at 50° C. for 5 h. The resultant suspension was diluted with water and extracted with DCM. The extract was washed with water, brine and dried over anhydrous MgSO₄. Filtered and concentrated. The residue was purified by silica gel chromatography (DCM/MeOH: 100% to 95%) to afford a yellow solid. (0.12 g, 25.7% yield). LCMS (method B): [M+H]⁺=346, $t_R$=2.10 min.

Building Blocks of Formula (II.2)

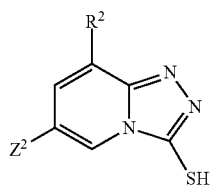

(II.2)

Building blocks of formulate (II.2) comprising Intermediates H and I were synthesized according to general Scheme 3, right side.

Intermediate H

6-Bromo-8-fluoro-[1,2,4]triazolo[4,3-a]pyridine-3-thiol

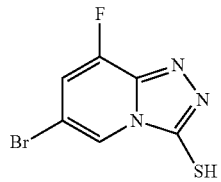

Intermediate H

5-Bromo-3-fluoro-2-hydrazinylpyridine (H.i)

To a solution of 5-bromo-2,3-difluoropyridine (15 g, 77 mmol)) in EtOH (250 ml) was added hydrazine hydrate (19.36 g, 387 mmol), the mixture was heated to reflux and stirred overnight (16 hr). The solvent of the reaction mixture was evaporated about half under reduced pressure, then cooling in an ice bath there precipitation was occurred, filtered and washed the product with a minimum of EtOH and water, dried in vacuum to obtain pure desired product as white powder (15 g, yield 94%). LCMS (method A): [M+H]$^+$=206.0, 208.0, $t_R$=1.01 min.

6-Bromo-8-fluoro-[1,2,4]triazolo[4,3-a]pyridine-3-thiol (Intermediate H)

To a solution of H.i (15 g, 72.8 mmol) in anhydrous DMF (150 ml) was added di(1H-imidazol-1-yl)methanethione (12.98 g, 72.8 mmol) by portions at 0° C., after the addition was completed, the mixture was heated to 85° C. and stirred for about 3 hr. The solvent was evaporated under reduced pressure and the residue was recrystallized from DCM/MeOH (5:1) to give pure desired product as yellow solid (3.5 g, yield 19.3%). LCMS (method A): [M–H]$^-$=246, 248, $t_R$=2.10 min. $^1$H-NMR (400 MHz, DMSO-d$_6$) δ ppm 14.98 (s, 1H), 8.24 (s, 1H), 7.75 (d, 1H).

Intermediate I

6-Bromo-[1,2,4]triazolo[4,3-a]pyridine-3-thiol

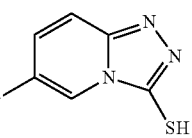

Intermediate I

5-bromo-2-hydrazinylpyridine (I.i)

To a solution of 5-bromo-2-fluoropyridine (10 g, 56.8 mmol) in EtOH (120 ml) was added hydrazine hydrate (14.22 g, 284 mmol), the mixture was heated to reflux and stirred overnight (16 hr). The solvent of the reaction mixture was evaporated about half under reduced pressure, then cooling in an ice bath there precipitation was occurred, filtered and washed the product with a minimum of EtOH and water, dried in vacuum to obtain pure desired product as white powder (10.2 g, yield 91%). LCMS (method A): [M+H]$^+$=188.1, 190.1, $t_R$=0.62 min.

6-Bromo-[1,2,4]triazolo[4,3-a]pyridine-3-thiol (Intermediate I)

To a solution of I.i (10.2 g, 54.2 mmol) in anhydrous DMF (150 ml) was added di(1H-imidazol-1-yl)methanethione (9.67 g, 54.2 mmol) by portions at 0° C., after the addition was completed, the mixture was heated to 85° C. and stirred for about 3 hr. The solvent was evaporated under reduced pressure and the residue was recrystallized from DCM/MeOH (5:1) to give pure desired product as yellow solid (7.3 g, yield 55.6%). LCMS (method A): [M–H]$^-$=227.9, 230, $t_R$=2.03 min. $^1$H-NMR (400 MHz, DMSO-d$_6$) δ ppm 14.69 (s, 1H), 8.38 (s, 1H), 7.67 (d, 1H), 7.41 (d, 1H).

Building Blocks of Formula (Q)

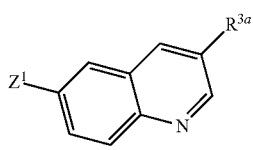

(Q)

Building blocks of formulate (Q) comprising Intermediates Q1 to Q36 are synthesized according to general Scheme 4 starting from Intermediates A or B.

Intermediate Q1

3-(3-(tert-butoxycarbonylamino)pyrrolidin-1-yl)quinolin-6-yl trifluoromethanesulfonate

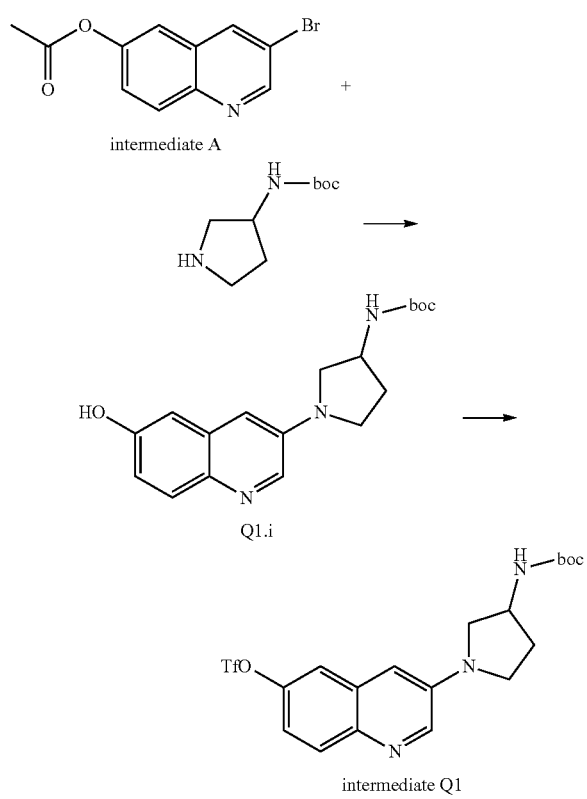

tert-butyl 1-(6-hydroxyquinolin-3-yl)pyrrolidin-3-ylcarbamate (Q1.i)

A mixture of Intermediate A (1.50 g, 5.07 mmol), tert-butyl pyrrolidin-3-ylcarbamate (1.13 g, 6.09 mmol), Pd$_2$(dba)$_3$ (0.232 g, 0.254 mmol), Xantphos (0.294 g, 0.507 mmol) and KO$^t$Bu (1.14 g, 10.2 mmol) in DMF (15 mL) was bubbled with argon for 20 min. The result mixture was heated at 110° C. overnight. The solution was cooled to rt and the solvent was removed under reduced pressure. The residue was diluted with water, extracted with DCM three times. The combined organic phase was dried over anhydrous Na$_2$SO$_4$, filtered and concentrated. The crude product was purified by chromatography (eluting with 5% MeOH in DCM) to give the title compound as yellow solid (0.2 g, yield 11%). LCMS (method N): [M+H]$^+$=330, t$_R$=1.93 min.

3-(3-(tert-butoxycarbonylamino)pyrrolidin-1-yl)quinolin-6-yl trifluoromethanesulfonate (intermediate Q1)

To a suspension of Q1.i (200 mg, 0.546 mmol) in pyridine (1.5 mL) was added Tf$_2$O (0.11 mL, 0.656 mmol) dropwise under ice-bath. The reaction was stirred at rt overnight, then quenched by saturated NaHCO$_3$ and concentrated under reduced pressure. The residue was diluted with water, extracted with DCM three times. The combined organic phase was washed with brine, dried over anhydrous Na$_2$SO$_4$, filtered and concentrated. The crude product was purified by chromatography (eluting with 5% MeOH in DCM) to give the title compound as yellow solid (130 mg, yield 46%). LCMS (method N): [M+H]$^+$=462, t$_R$=2.78 min. $^1$H-NMR (400 MHz, DMSO-d$_6$) δ ppm 8.62 (d, 1H), 7.97 (d, 1H), 7.87 (s, 1H), 7.37 (dd, 1H), 7.27 (d, 1H), 7.23 (s, 1H), 4.20 (broad, 1H), 3.67-3.63 (m, 1H), 3.56~3.54 (m, 1H), 3.45~3.43 (m, 1H), 3.26~3.22 (m, 1H), 2.24~2.16 (m, 1H), 1.99~1.94 (m, 1H), 1.40 (s, 9H).

Intermediate Q2

(S)-3-(3-(dimethylamino)pyrrolidin-1-yl)quinolin-6-yl trifluoromethanesulfonate

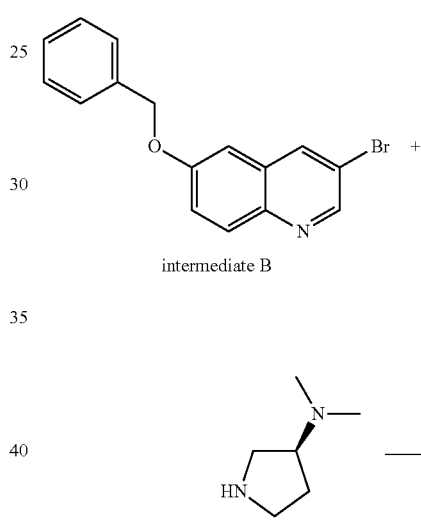

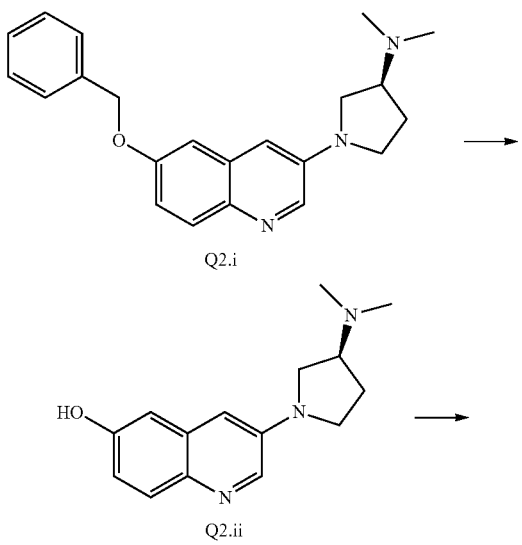

-continued

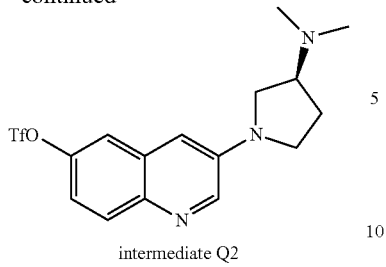

intermediate Q2

(S)-1-(6-(benzyloxy)quinolin-3-yl)-N,N-dimethylpyrrolidin-3-amine (Q2.i)

A mixture of Intermediate B (450 mg, 1.43 mmol), (S)—N,N-dimethylpyrrolidin-3-amine (196 mg, 1.72 mmol), Pd$_2$(dba)$_3$ (65.6 mg, 0.072 mmol), Xantphos (83 mg, 0.143 mmol) and KO$^t$Bu (241 mg, 2.15 mmol) in toluene (4.5 mL) was bubbled with argon for 20 min. The resulting mixture was heated at 110° C. overnight. The solution was cooled to rt and the solvent was removed under reduced pressure. The residue was diluted with water, extracted with DCM three times. The combined organic phase was dried over anhydrous Na$_2$SO$_4$, filtered and concentrated. The crude product was purified by chromatography (eluting with 5% MeOH in DCM) to give the title compound as yellow solid (435 mg, yield 83%). LCMS (method N): [M+H]$^+$=348, t$_R$=1.72 min.

(S)-3-(3-(dimethylamino)pyrrolidin-1-yl)quinolin-6-ol (Q2.ii)

To a solution of Q2.i (435 mg, 1.43 mmol) in MeOH (10 mL) was added 10% Pd/C (133 mg, 0.125 mmol). The mixture was reacted under hydrogen atmosphere overnight. The result mixture was filtrated. The filtrate was concentrated under reduced pressure, dried in vacuum to give the title compound as yellow solid (280 mg, yield 78%). $^1$H-NMR (400 MHz, DMSO-d$_6$) δ ppm 9.68 (s, 1H), 8.29 (d, 1H), 7.63 (d, 1H), 6.90~6.87 (m, 3H), 3.61~3.57 (m, 1H), 3.53~3.49 (m, 1H), 3.38~3.32 (m, 1H), 3.16-3.12 (m, 1H), 2.83-2.79 (m, 1H), 2.22-2.16 (m, 7H), 1.85~1.80 (m, 1H).

(S)-3-(3-(dimethylamino)pyrrolidin-1-yl)quinolin-6-yl trifluoromethanesulfonate (intermediate Q2)

To a suspension of Q2.ii (280 mg, 0.979 mmol) and pyridine (0.2 mL, 2.45 mmol) in DCM (5 mL) was added Tf$_2$O (0.15 mL, 1.96 mmol) dropwise under ice-bath. The reaction was stirred at rt overnight, then quenched by saturated NaHCO$_3$ and concentrated under reduced pressure. The residue was diluted with water, extracted with DCM three times. The combined organic phase was washed with brine, dried over anhydrous Na$_2$SO$_4$, filtered and concentrated. The crude product was purified by chromatography (eluting with 5% MeOH in DCM) to give the title compound as yellow solid (130 mg, yield 46%). LCMS (method N): [M+H]$^+$=390, t$_R$=2.75 min. $^1$H-NMR (400 MHz, DMSO-d$_6$) δ ppm 8.65 (d, 1H), 7.97 (d, 1H), 7.83 (s, 1H), 7.37 (d, 1H), 7.24 (s, 1H), 4.09~4.06 (m, 2H), 3.66 (t, 1H), 3.59 (t, 1H), 3.44~3.38 (m, 1H), 3.24~3.20 (m, 1H), 2.90 (broad, 1H), 2.26 (s, 6H), 1.93~1.83 (m, 1H).

Intermediate Q3

(S)-tert-butyl 3-(6-(trifluoromethylsulfonyloxy)quinolin-3-ylamino)pyrrolidine-1-carboxylate

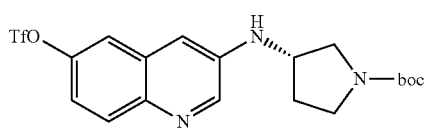

intermediate Q3

(S)-tert-butyl 3-(6-(benzyloxy)quinolin-3-ylamino)pyrrolidine-1-carboxylate (Q3.i) was prepared using the same procedure as described for Intermediate Q2.i, by using Intermediate B and the equivalent amount of (S)-tert-butyl 3-aminopyrrolidine-1-carboxylate instead of the (S)—N,N-dimethylpyrrolidin-3-amine. LCMS (method P): [M+H]$^+$=420, t$_R$=1.71 min.

(S)-tert-butyl 3-(6-hydroxyquinolin-3-ylamino)pyrrolidine-1-carboxylate (Q3.ii) was prepared from Q3.i using the same procedure as described for intermediate Q2.ii. LCMS (method P): [M+H]$^+$=330, t$_R$=1.64 min.

(S)-tert-butyl 3-(6-(trifluoromethylsulfonyloxy)quinolin-3-ylamino)pyrrolidine-1-carboxylate (Intermediate Q3) was prepared using from Q3.ii the same procedure as described for intermediate Q2. LCMS (method P): [M+H]$^+$=406, t$_R$=1.76 min. $^1$H-NMR (400 MHz, MeOH-d$_4$) δ ppm 8.51 (d, 1H), 7.94 (d, 1H), 7.73 (s, 1H), 7.33 (dd, 1H), 7.25 (d, 1H), 4.17 (broad, 1H), 3.77~3.71 (m, 1H), 3.56~3.49 (m, 2H), 3.37~3.34 (m, 1H), 2.34~2.27 (m, 1H), 2.03~2.00 (m, 1H), 1.48 (d, 6H).

Intermediate Q4

3-((4-methylpiperazin-1-yl)methyl)quinolin-6-yl trifluoromethanesulfonate

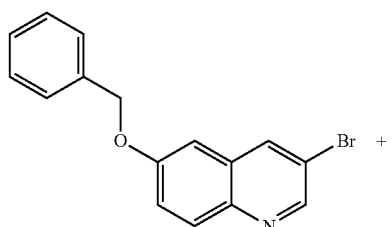

intermediate B

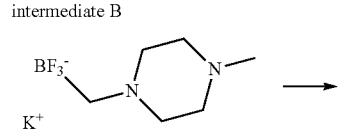

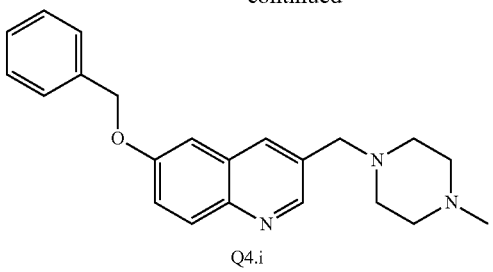

Q4.i

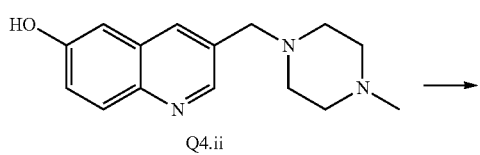

Q4.ii

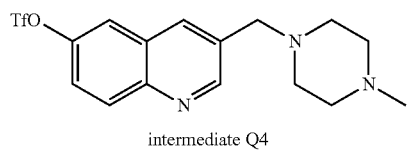

intermediate Q4

1-((6-(benzyloxy)naphthalen-2-yl)methyl)-4-methylpiperazine (Q4.i)

A mixture of Intermediate B (500 mg, 1.60 mmol), potassium trifluoro[(4-methylpiperazin-1-yl)methyl]borate (351 mg, 1.60 mmol), dibromobis(tri-tert-butylphosphine)dipalladium(I) (124 mg, 0.16 mmol), and caesium carbonate (1.56 g, 4.79 mmol) in THF (5 mL)/H$_2$O (0.5 mL) was bubbled with argon for 20 min. The result mixture was kept at 80° C. and stirred overnight. Then the reaction mixture was cooled to rt, water was added and the product was then extracted with DCM three times. The combined organic phase was dried over anhydrous Na$_2$SO$_4$, filtered and concentrated. The crude product was purified by chromatography (eluting with 5% MeOH in DCM) to give the title compound as yellow solid (180 mg, yield 33%). $^1$H-NMR (400 MHz, CDCl$_3$) δ ppm 8.74 (s, 1H), 8.00 (d, 1H), 7.93 (s, 1H), 7.49~7.35 (m, 5H), 7.13 (s, 1H), 5.19 (s, 2H), 3.67 (s, 2H), 3.49 (s, 1H), 2.75~2.40 (broad, 7H), 2.32 (s, 3H).

3-((4-methylpiperazin-1-yl)methyl)quinolin-6-ol (Q4.ii) was prepared from Q4.i using the same procedure as described for intermediate Q2.ii. LCMS (method N): [M+H]$^+$=258, t$_R$=0.29 min.

3-((4-methylpiperazin-1-yl)methyl)quinolin-6-yl trifluoromethanesulfonate (intermediate Q4) was prepared from Q4.ii using the same procedure as described for intermediate Q2. $^1$H-NMR (400 MHz, MeOH-d$_4$) δ ppm 8.92 (s, 1H), 8.33 (d, 1H), 8.13 (dd, 1H), 7.96 (d, 1H), 7.68 (dd, 1H), 3.77 (s, 2H), 2.87~2.71 (broad, 4H), 2.70~2.55 (broad, 4H), 2.50 (s, 3H).

Intermediate Q5

3-(3-(tert-butoxycarbonylamino)piperidin-1-yl)quinolin-6-yl trifluoromethanesulfonate intermediate Q5

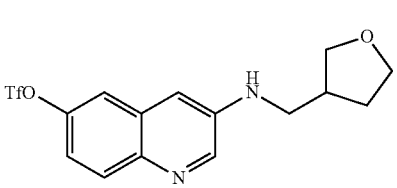

tert-butyl 1-(6-(benzyloxy)quinolin-3-yl)piperidin-3-ylcarbamate (Q5.i) was prepared from Intermediate B using the same procedure as described for intermediate Q2.i, by using the equivalent amount of tert-butyl piperidin-3-ylcarbamate instead of the (S)—N,N-dimethylpyrrolidin-3-amine. LCMS (method P): [M+H]$^+$=434, t$_R$=1.61 min.

tert-butyl 1-(6-hydroxyquinolin-3-yl)piperidin-3-ylcarbamate (Q5.ii) was prepared from Q5.i using the same procedure as described for intermediate Q2.ii. LCMS (method P): [M+H]$^+$=344, t$_R$=1.33 min.

3-(3-(tert-butoxycarbonylamino)piperidin-1-yl)quinolin-6-yl trifluoromethanesulfonate (intermediate Q5) was prepared from Q5.ii using the same procedure as described for intermediate Q2. LCMS (method P): [M+H]$^+$=476, t$_R$=1.80 min. $^1$H-NMR (400 MHz, MeOH-d$_4$) δ ppm 8.82 (d, 1H), 7.95 (d, 1H), 7.76 (d, 1H), 7.57 (d, 1H), 7.40 (dd, 1H), 3.85~3.82 (m, 1H), 3.70~3.67 (m, 2H), 3.02~2.96 (m, 1H), 2.88~2.82 (m, 1H), 1.99~1.87 (m, 2H), 1.75~1.71 (m, 1H), 1.51~1.49 (m, 1H), 1.46 (s, 9H).

Intermediate Q6

3-((tetrahydrofuran-3-yl)methylamino)quinolin-6-yl trifluoromethanesulfonate intermediate Q6

6-(benzyloxy)-N-((tetrahydrofuran-3-yl)methyl)quinolin-3-amine (Q6.i) was prepared from Intermediate B using the same procedure as described for intermediate Q2.i, by using the equivalent amount of (tetrahydrofuran-3-yl)methanamine instead of the (S)—N,N-dimethylpyrrolidin-3-amine. LCMS (method N): [M+H]$^+$=335, t$_R$=2.32 min.

3-((tetrahydrofuran-3-yl)methylamino)quinolin-6-ol (Q6.ii) was prepared from Q6.i using the same procedure as described for intermediate Q2.ii. LCMS (method N): [M+H]$^+$= 245, t$_R$=1.40 min.

3-((tetrahydrofuran-3-yl)methylamino)quinolin-6-yl trifluoromethanesulfonate (intermediate Q6) was prepared from Q6.ii using the same procedure as described for intermediate Q2. LCMS (method N): [M+H]⁺=377, $t_R$=6.01 min. ¹H-NMR (400 MHz, CDCl₃) δ ppm 8.48 (s, 1H), 8.01 (d, 1H), 7.53 (s, 1H), 7.27 (d, 1H), 6.99 (s, 1H), 4.36 (broad, 1H), 4.02~3.97 (m, 1H), 3.93~3.89 (m, 1H), 3.84~3.78 (m, 1H), 3.73~3.70 (m, 1H), 3.26 (d, 2H), 2.67 (broad, 1H), 2.23~2.15 (m, 1H), 1.80~1.72 (m, 1H).

Intermediate Q7

3-(2-oxa-6-azaspiro[3.3]heptan-6-yl)quinolin-6-yl trifluoromethanesulfonate

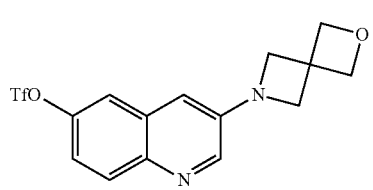

intermediate Q7

6-(6-(benzyloxy)quinolin-3-yl)-2-oxa-6-azaspiro[3.3]heptane (Q7.i) was prepared from Intermediate B using the same procedure as described for intermediate Q2.i, by using the equivalent amount of 2-oxa-6-azaspiro[3.3]heptane instead of the (S)—N,N-dimethylpyrrolidin-3-amine. LCMS (method N): [M+H]⁺=333, $t_R$=5.62 min.

3-(2-oxa-6-azaspiro[3.3]heptan-6-yl)quinolin-6-ol (Q7.ii) was prepared from Q7.i using the same procedure as described for intermediate Q2.ii. LCMS (method N): [M+H]⁺=242, $t_R$=1.03 min.

3-(2-oxa-6-azaspiro[3.3]heptan-6-yl)quinolin-6-yl trifluoromethanesulfonate (intermediate Q7) was prepared from Q7.ii using the same procedure as described for intermediate Q2. LCMS (method N): [M+H]⁺=375, $t_R$=5.92 min.

Intermediate Q8

Trifluoro-methanesulfonic acid 3-(4,4-difluoro-piperidin-1-yl)-quinolin-6-yl ester

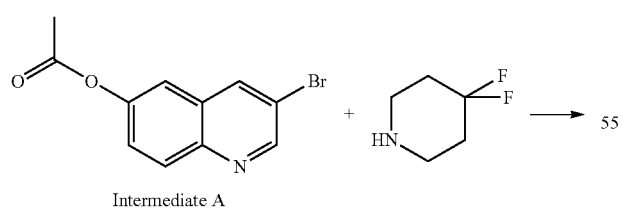

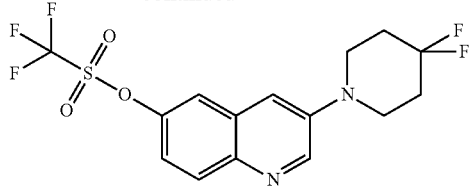

Intermediate Q8

3-(4,4-difluoropiperidin-1-yl)quinolin-6-ol (Q8.i)

A mixture of Intermediate B (879 mg, 3.30 mmol), 4,4-difluoropiperidine (400 mg, 3.30 mmol), Pd₂(dba)₃ (302 mg, 0.330 mmol), xantphos (382 mg, 0.660 mmol) and KOᵗBu (748 mg, 6.60 mmol) in toluene (10 ml) was bubbled with argon for 10 min. The mixture was then heated at 100° C. for overnight. The reaction was quenched with 60% NaHCO₃ aqueous solution. The aqueous phase was extracted with DCM/IPA (20 ml×3, V/V=3/1). The combined organic phase was dried over anhydrous MgSO₄. Filtered and concentrated. The residue was purified by silica gel chromatography (eluted with 2% MeOH in DCM) to give the title compound as yellow solid (270 mg, 31% yield). LCMS (method B): [M+H]⁺=265, $t_R$=1.79 min.

Trifluoro-methanesulfonic acid 3-(4,4-difluoro-piperidin-1-yl)-quinolin-6-yl ester (intermediate Q8)

To a solution of Q8.i (270 mg, 1.022 mmol) in THF (5 ml) was added NaH (60%, 36.8 mg, 1.533 mmol) and the solution was stirred at rt for 10 min. Then 1,1,1-trifluoro-N-phenyl-N-(trifluoromethylsulfonyl)methanesulfonamide (438 mg, 1.226 mmol) was added and the reaction mixture was stirred for another 1 h. The reaction was quenched with saturated aqueous NaHCO₃ solution. The aqueous phase was extracted with DCM/IPA (20 ml×3, v/v=3:1). The combined extract was dried over anhydrous MgSO₄, filtered and concentrated. The residue was purified by silica gel chromatography (eluted with 2% MeOH in DCM) to give the title compound as yellow solid (320 mg, 79% yield). LCMS (method B): [M+H]⁺=397, $t_R$=2.68 min.

Intermediate Q9

Trifluoro-methanesulfonic acid 3-(tetrahydro-pyran-4-ylamino)-quinolin-6-yl ester

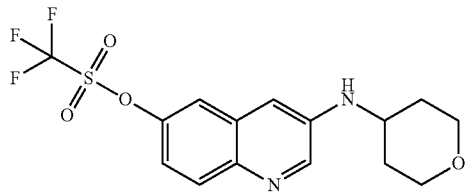

Intermediate Q9

Intermediate Q9 was synthesized from Intermediate A with similar procedure as intermediate 8. LCMS (method B): [M+H]$^+$=377, $t_R$=2.61 min.

Intermediate Q10

3-(4-Methyl-1,4-diazepan-1-yl)quinolin-6-yl trifluoromethanesulfonate

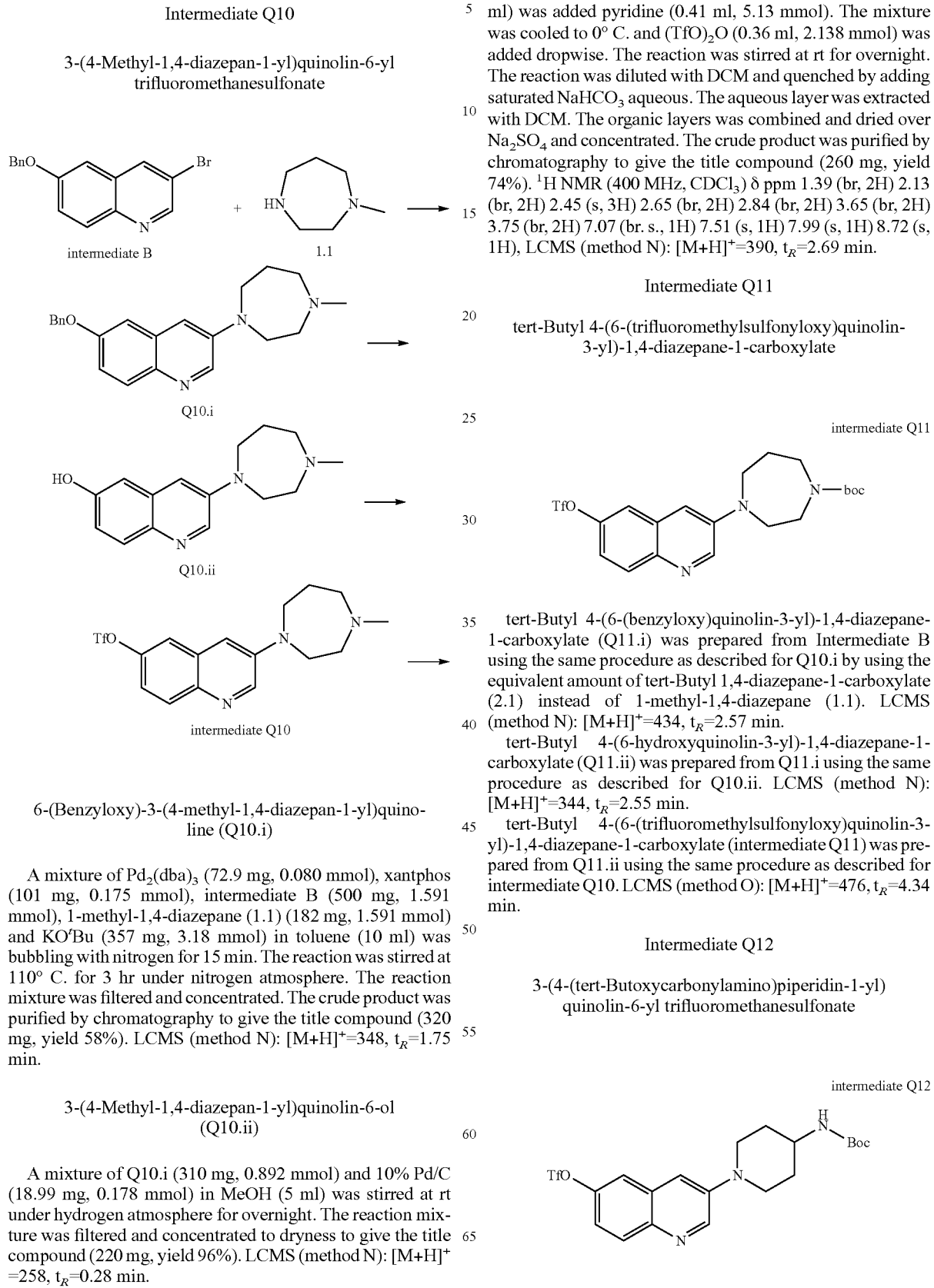

6-(Benzyloxy)-3-(4-methyl-1,4-diazepan-1-yl)quinoline (Q10.i)

A mixture of Pd$_2$(dba)$_3$ (72.9 mg, 0.080 mmol), xantphos (101 mg, 0.175 mmol), intermediate B (500 mg, 1.591 mmol), 1-methyl-1,4-diazepane (1.1) (182 mg, 1.591 mmol) and KO$^t$Bu (357 mg, 3.18 mmol) in toluene (10 ml) was bubbling with nitrogen for 15 min. The reaction was stirred at 110° C. for 3 hr under nitrogen atmosphere. The reaction mixture was filtered and concentrated. The crude product was purified by chromatography to give the title compound (320 mg, yield 58%). LCMS (method N): [M+H]$^+$=348, $t_R$=1.75 min.

3-(4-Methyl-1,4-diazepan-1-yl)quinolin-6-ol (Q10.ii)

A mixture of Q10.i (310 mg, 0.892 mmol) and 10% Pd/C (18.99 mg, 0.178 mmol) in MeOH (5 ml) was stirred at rt under hydrogen atmosphere for overnight. The reaction mixture was filtered and concentrated to dryness to give the title compound (220 mg, yield 96%). LCMS (method N): [M+H]$^+$=258, $t_R$=0.28 min.

3-(4-Methyl-1,4-diazepan-1-yl)quinolin-6-yl trifluoromethanesulfonate (intermediate Q10)

To a solution of Q10.ii (220 mg, 0.855 mmol) in DCM (3 ml) was added pyridine (0.41 ml, 5.13 mmol). The mixture was cooled to 0° C. and (TfO)$_2$O (0.36 ml, 2.138 mmol) was added dropwise. The reaction was stirred at rt for overnight. The reaction was diluted with DCM and quenched by adding saturated NaHCO$_3$ aqueous. The aqueous layer was extracted with DCM. The organic layers was combined and dried over Na$_2$SO$_4$ and concentrated. The crude product was purified by chromatography to give the title compound (260 mg, yield 74%). $^1$H NMR (400 MHz, CDCl$_3$) δ ppm 1.39 (br, 2H) 2.13 (br, 2H) 2.45 (s, 3H) 2.65 (br, 2H) 2.84 (br, 2H) 3.65 (br, 2H) 3.75 (br, 2H) 7.07 (br. s., 1H) 7.51 (s, 1H) 7.99 (s, 1H) 8.72 (s, 1H), LCMS (method N): [M+H]$^+$=390, $t_R$=2.69 min.

Intermediate Q11 tert-Butyl 4-(6-(trifluoromethylsulfonyloxy)quinolin-3-yl)-1,4-diazepane-1-carboxylate tert-Butyl 4-(6-(benzyloxy)quinolin-3-yl)-1,4-diazepane-1-carboxylate (Q11.i) was prepared from Intermediate B using the same procedure as described for Q10.i by using the equivalent amount of tert-Butyl 1,4-diazepane-1-carboxylate (2.1) instead of 1-methyl-1,4-diazepane (1.1). LCMS (method N): [M+H]$^+$=434, $t_R$=2.57 min.

tert-Butyl 4-(6-hydroxyquinolin-3-yl)-1,4-diazepane-1-carboxylate (Q11.ii) was prepared from Q11.i using the same procedure as described for Q10.ii. LCMS (method N): [M+H]$^+$=344, $t_R$=2.55 min.

tert-Butyl 4-(6-(trifluoromethylsulfonyloxy)quinolin-3-yl)-1,4-diazepane-1-carboxylate (intermediate Q11) was prepared from Q11.ii using the same procedure as described for intermediate Q10. LCMS (method O): [M+H]$^+$=476, $t_R$=4.34 min.

Intermediate Q12

3-(4-(tert-Butoxycarbonylamino)piperidin-1-yl)quinolin-6-yl trifluoromethanesulfonate tert-Butyl 1-(6-(benzyloxy)quinolin-3-yl)piperidin-4-yl-carbamate(Q12.i) was prepared from Intermediate B using the same procedure as described for Q10.i by using the equivalent amount of tert-Butyl 1-piperidin-4-ylcarbamate (3.1) instead of 1-methyl-1,4-diazepane (1.1). LCMS (method O): [M+H]$^+$=434, $t_R$=4.17 min.

tert-Butyl 1-(6-hydroxyquinolin-3-yl)piperidin-4-ylcarbamate (Q12.ii) was prepared from Q12.i using the same procedure as described for Q10.ii. LCMS (method N): [M+H]$^+$=344, $t_R$=1.99 min.

3-(4-(tert-Butoxycarbonylamino)piperidin-1-yl)quinolin-6-yl trifluoromethanesulfonate (intermediate Q12) was prepared from Q12.ii using the same procedure as described for intermediate Q10. $^1$H NMR (400 MHz, CDCl$_3$) δ ppm 1.48 (s, 9H) 1.60-1.66 (m, 3H) 2.16 (d, 2H) 3.04 (t, 2H) 3.80 (d, 2H) 7.30-7.42 (m, 2H) 7.58 (s, 1H) 8.10 (d, 1H) 8.84 (s, 1H), LCMS (method O): [M+H]$^+$=476, $t_R$=4.38 min.

Intermediate Q13 tert-Butyl 4-(6-(trifluoromethylsulfonyloxy)quinolin-3-ylamino)piperidine-1-carboxylate intermediate Q13

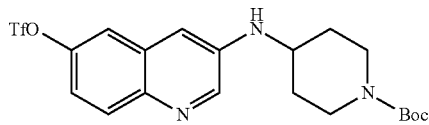

tert-Butyl 4-(6-(benzyloxy)quinolin-3-ylamino)piperidine-1-carboxylate (Q13.i) was prepared from Intermediate B using the same procedure as described for Q10.i by using the equivalent amount of tert-Butyl 4-aminopiperidine-1-carboxylate (4.1) instead of 1-methyl-1,4-diazepane (1.1). LCMS (method P): [M+H]$^+$=434, $t_R$=1.88 min.

tert-Butyl 4-(6-hydroxyquinolin-3-ylamino)piperidine-1-carboxylate (Q13.ii) was prepared from Q13.i using the same procedure as described for Q13.ii. LCMS (method P): [M+H]$^+$=344, $t_R$=1.36 min.

tert-Butyl 4-(6-(trifluoromethylsulfonyloxy)quinolin-3-ylamino)piperidine-1-carboxylate (intermediate Q13) was prepared from Q13.i using the same procedure as described for intermediate Q10. $^1$H-NMR (400 MHz, MeOH-d$_4$) δ ppm 1.29-1.45 (m, 2H) 1.48 (s, 9H) 2.07 (t, 2H) 3.05-3.07 (m, 2H) 3.60-3.65 (m, 1H) 4.08 (t, 2H) 7.25-7.32 (m, 2H) 7.69 (d, 1H) 7.91 (d, 1H) 8.47 (d, 1H). LCMS (method P): [M+H]$^+$=476, $t_R$=1.78 min.

Intermediate Q14

3-(4-methylpiperazin-1-yl)quinolin-6-yl trifluoromethanesulfonate intermediate Q14

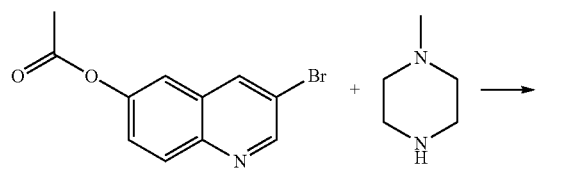

-continued

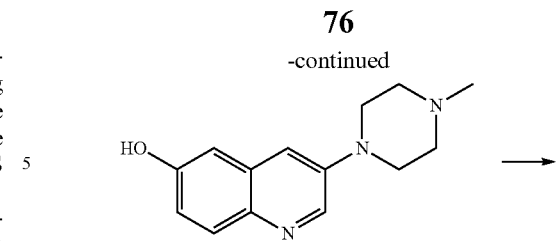

Intermediate Q14 was synthesized from intermediate A and 1-methyl-piperazine with similar procedure as intermediate 8. LCMS (method B): [M+H]$^+$=376, $t_R$=1.90 min.

Intermediate Q15 tert-Butyl 4-(6-(trifluoromethylsulfonyloxy)quinolin-3-yl)piperazine-1-carboxylate intermediate Q15

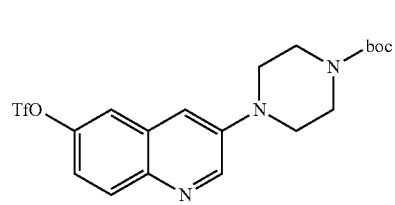

tert-Butyl 4-(6-(benzyloxy)quinolin-3-yl)piperazine-1-carboxylate (Q15.i) was prepared from Intermediate B using the same procedure as described for Q10.i by using the equivalent amount of tert-Butyl 4-piperazine-1-carboxylate (6.1) instead of 1-methyl-1,4-diazepane (1.1). LCMS (method P): [M+H]$^+$=420, $t_R$=1.88 min.

tert-Butyl 4-(6-hydroxyquinolin-3-yl)piperazine-1-carboxylate (Q15.ii) was prepared from Q15.i using the same procedure as described for Q10.ii. LCMS (method P): [M+H]$^+$=330, $t_R$=1.57 min.

tert-Butyl 4-(6-(trifluoromethylsulfonyloxy)quinolin-3-yl)piperazine-1-carboxylate (intermediate Q15) was prepared from Q15.ii using the same procedure as described for intermediate Q10. $^1$H NMR (400 MHz, MeOH-d$_4$) δ ppm 1.47 (s, 9H) 3.31-3.39 (m, 4H) 3.66 (br, 4H) 7.48 (d, 1H) 7.67

(s, 1H) 7.83 (s, 1H) 8.02 (s, 1H) 8.90 (s, 1H). LCMS (method P): [M+H]$^+$=462, $t_R$=1.82 min.

Intermediate Q16

3-(1,4'-Bipiperidin-1'-yl)quinolin-6-yl trifluoromethanesulfonate

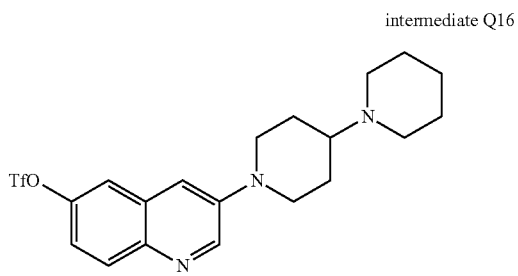 [SMILES: O=S(=O)(Oc1ccc2ncc(N3CCC(N4CCCCC4)CC3)cc2c1)C(F)(F)F]

intermediate Q16

3-(1,4'-Bipiperidin-1-yl)-6-(benzyloxy)quinoline (Q16.i) was prepared from Intermediate B using the same procedure as described for Q10.i by using the equivalent amount of 1,4'-Bipiperidin (7.1) instead of 1-methyl-1,4-diazepane (1.1). LCMS (method N): [M+H]$^+$=402, $t_R$=1.83 min.

3-(1,4'-Bipiperidin-1'-yl)quinolin-6-ol (Q16.ii) was prepared from Q16.i using the same procedure as described for Q10.ii. LCMS (method N): [M+H]$^+$=312, $t_R$=0.89 min.

3-(1,4'-Bipiperidin-1'-yl)quinolin-6-yl trifluoromethanesulfonate (intermediate Q16) was prepared from Q16.ii using the same procedure as described for intermediate Q10. LCMS (method N): [M+H]$^+$=444, $t_R$=1.94 min.

Intermediate Q17

3-(4-Cyclohexylpiperazin-1-yl)quinolin-6-yl trifluoromethanesulfonate

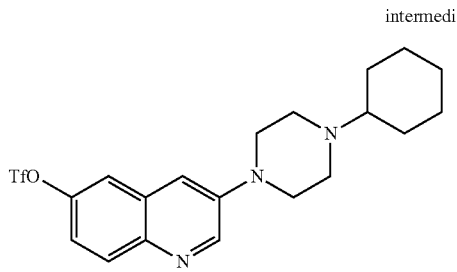

intermediate Q17

6-(Benzyloxy)-3-(4-cyclohexylpiperazin-1-yl)quinoline (Q17.i) was prepared from Intermediate B using the same procedure as described for Q10.i by using the equivalent amount of 1-cyclohexylpiperazin (8.1) instead of 1-methyl-1,4-diazepane (1.1). LCMS (method N): [M+H]$^+$=402, $t_R$=1.94 min.

3-(4-Cyclohexylpiperazin-1-yl)quinolin-6-ol (Q17.ii) was prepared from Q17.i using the same procedure as described for Q10.ii. LCMS (method N): [M+H]$^+$=312, $t_R$=1.25 min.

3-(4-Cyclohexylpiperazin-1-yl)quinolin-6-yl trifluoromethanesulfonate (intermediate Q17) was prepared from Q17.ii using the same procedure as described for intermediate Q10. LCMS (method N): [M+H]$^+$=444, $t_R$=1.97 min.

Intermediate Q18

3-(4-(Pyrrolidin-1-yl)piperidin-1-yl)quinolin-6-yl trifluoromethanesulfonate

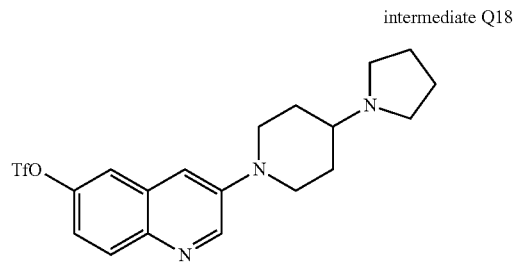 [SMILES: O=S(=O)(Oc1ccc2ncc(N3CCC(N4CCCC4)CC3)cc2c1)C(F)(F)F]

intermediate Q18

6-(Benzyloxy)-3-(4-(pyrrolidin-1-yl)piperidin-1-yl) quinoline (Q18.i) was prepared from Intermediate B using the same procedure as described for Q10.i by using the equivalent amount of 4-(pyrrolidin-1-yl)piperidin (9.1) instead of 1-methyl-1,4-diazepane (1.1). LCMS (method N): [M+H]$^+$=388, $t_R$=1.86 min.

3-(4-(Pyrrolidin-1-yl)piperidin-1-yl)quinolin-6-ol (Q18.ii) was prepared from Q18.i using the same procedure as described for Q10.ii. LCMS (method N): [M+H]$^+$=298, $t_R$=0.37 min.

3-(4-(Pyrrolidin-1-yl)piperidin-1-yl)quinolin-6-yl trifluoromethanesulfonate (intermediate Q18) was prepared from Q18.ii using the same procedure as described for intermediate Q10. LCMS (method N): [M+H]$^+$=430, $t_R$=1.83 min.

Intermediate Q19

3-(4-Phenylpiperazin-1-yl)quinolin-6-yl trifluoromethanesulfonate

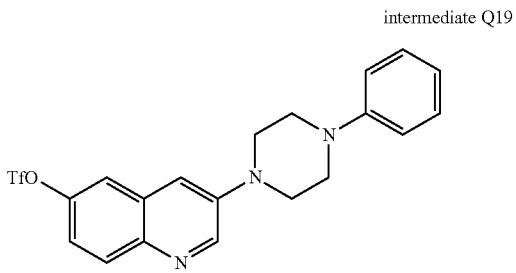 [SMILES: O=S(=O)(Oc1ccc2ncc(N3CCN(c4ccccc4)CC3)cc2c1)C(F)(F)F]

intermediate Q19

6-(Benzyloxy)-3-(4-phenylpiperazin-1-yl)quinoline (Q19.i) was prepared from Intermediate B using the same procedure as described for Q10.i by using the equivalent amount of 1-phenyl-piperazine (10.1) instead of 1-methyl-1,4-diazepane (1.1). LCMS (method N): [M+H]$^+$=396, $t_R$=2.88 min.

3-(4-Phenylpiperazin-1-yl)quinolin-6-ol (Q19.ii) was prepared from Q19.i using the same procedure as described for Q10.ii. LCMS (method N): [M+H]$^+$=306, $t_R$=2.09 min.

3-(4-Phenylpiperazin-1-yl)quinolin-6-yl trifluoromethanesulfonate (intermediate Q19) was prepared from Q19.ii using the same procedure as described for intermediate Q10. LCMS (method N): [M+H]$^+$=438, $t_R$=2.90 min.

Intermediate Q20

3-(2-Methylmorpholino)quinolin-6-yl trifluoromethanesulfonate

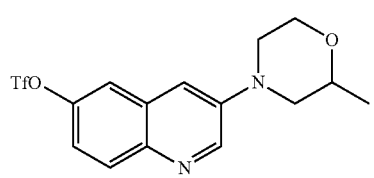
intermediate Q20

4-(6-(Benzyloxy)quinolin-3-yl)-2-methylmorpholine (Q20.i) was prepared from Intermediate B using the same procedure as described for Q10.i by using the equivalent amount of 2-methylmorpholine (11.1) instead of 1-methyl-1,4-diazepane (1.1). LCMS (method N): [M+H]$^+$=335, $t_R$=2.59 min.

3-(2-Methylmorpholino)quinolin-6-ol (Q20.ii) was prepared from Q20.i using the same procedure as described for Q20.ii. LCMS (method N): [M+H]$^+$=245, $t_R$=1.51 min.

3-(2-Methylmorpholino)quinolin-6-yl trifluoromethanesulfonate (intermediate Q20) was prepared from Q20.ii using the same procedure as described for intermediate Q10. LCMS (method N): [M+H]$^+$=377, $t_R$=2.65 min.

Intermediate Q21

3-(2,6-Dimethylmorpholino)quinolin-6-yl trifluoromethanesulfonate

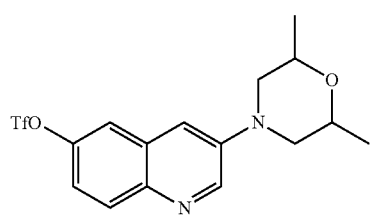
intermediate Q21

4-(6-(Benzyloxy)quinolin-3-yl)-2,6-dimethylmorpholine (Q21.i) was prepared from Intermediate B using the same procedure as described for Q10.i by using the equivalent amount of 2,6-dimethylmorpholine (12.1) instead of 1-methyl-1,4-diazepane (1.1). LCMS (method N): [M+H]$^+$=349, $t_R$=2.68 min.

3-(2,6-Dimethylmorpholino)quinolin-6-ol (Q21.ii) was prepared from Q21.i using the same procedure as described for Q10.ii. LCMS (method N): [M+H]$^+$=259, $t_R$=1.40 min.

3-(2,6-Dimethylmorpholino)quinolin-6-yl trifluoromethanesulfonate (intermediate Q21) was prepared from Q21.ii using the same procedure as described for intermediate Q10. LCMS (method N): [M+H]$^+$=391, $t_R$=2.72 min.

Intermediate Q22

(2S,6R)-tert-Butyl 2,6-dimethyl-4-(6-(trifluoromethylsulfonyloxy)quinolin-3-yl) piperazine-1-carboxylate

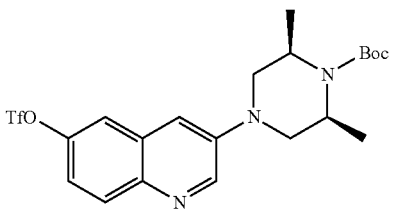
intermediate Q22 tert-Butyl 4-(6-(benzyloxy)quinolin-3-yl)-2,6-dimethylpiperazine-1-carboxylate (Q22.i) was prepared from Intermediate B using the same procedure as described for Q10.i by using the equivalent amount of (2S,6R)-tert-Butyl 2,6-dimethylpiperazine-1-carboxylate (13.1) instead of 1-methyl-1,4-diazepane (1.1). LCMS (method N): [M+H]$^+$=448, $t_R$=2.96 min.

tert-Butyl 4-(6-hydroxyquinolin-3-yl)-2,6-dimethylpiperazine-1-carboxylate (Q22.ii) was prepared from Q22.i using the same procedure as described for Q10.ii. LCMS (method N): [M+H]$^+$=358, $t_R$=1.27 min.

(2S,6R)-tert-Butyl 2,6-dimethyl-4-(6-(trifluoromethylsulfonyloxy)quinolin-3-yl) piperazine-1-carboxylate (intermediate Q22) was prepared from Q22.ii using the same procedure as described for intermediate Q10. LCMS (method N): [M+H]$^+$=490, $t_R$=2.96 min.

Intermediate Q23

3-(4-Methoxypiperidin-1-yl)quinolin-6-yl trifluoromethanesulfonate

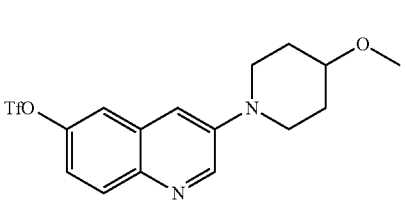
intermediate Q23

6-(Benzyloxy)-3-(4-methoxypiperidin-1-yl)quinoline (Q23.i) was prepared from Intermediate B using the same procedure as described for Q10.i by using the equivalent amount of 4-methoxypiperidin (14.1) instead of 1-methyl-1,4-diazepane (1.1). LCMS (method N): [M+H]$^+$=349, $t_R$=2.54 min.

3-(4-Methoxypiperidin-1-yl)quinolin-6-ol (Q23.ii) was prepared from Q23.i using the same procedure as described for Q10.ii. LCMS (method N): [M+H]$^+$=259, $t_R$=1.58 min.

3-(4-Methoxypiperidin-1-yl)quinolin-6-yl trifluoromethanesulfonate (intermediate Q23) was prepared from Q23.ii using the same procedure as described for intermediate Q10. LCMS (method N): [M+H]$^+$=391, $t_R$=2.66 min.

Intermediate Q24

(S)-tert-Butyl 3-methyl-4-(6-(trifluoromethylsulfonyloxy)quinolin-3-yl)piperazine-1-carboxylate

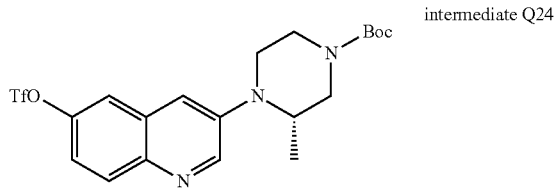 [SMILES: C[C@H]1CN(C(=O)OC(C)(C)C)CCN1c1cnc2ccc(OS(=O)(=O)C(F)(F)F)cc2c1]

(S)-tert-Butyl 4-(6-(benzyloxy)quinolin-3-yl)-3-methylpiperazine-1-carboxylate (Q24.i) was prepared from Intermediate B using the same procedure as described for Q10.i by using the equivalent amount of (S)-tert-Butyl 3-methylpiperazine-1-carboxylate (15.1) instead of 1-methyl-1,4-diazepane (1.1). LCMS (method N): [M+H]$^+$=434, $t_R$=2.81 min.

(S)-tert-Butyl 4-(6-hydroxyquinolin-3-yl)-3-methylpiperazine-1-carboxylate (Q24.ii) was prepared from Q24.i using the same procedure as described for Q10.ii. LCMS (method N): [M+H]$^+$=344, $t_R$=1.28 min.

(S)-tert-Butyl 3-methyl-4-(6-(trifluoromethylsulfonyloxy)quinolin-3-yl)piperazine-1-carboxylate (intermediate Q24) was prepared from Q24.ii using the same procedure as described for intermediate Q10. LCMS (method N): [M+H]$^+$= 476, $t_R$=2.79 min.

Intermediate Q25

Trifluoro-methanesulfonic acid 3-(8-oxa-2-aza-spiro[4.5]dec-2-yl)-quinolin-6-yl ester

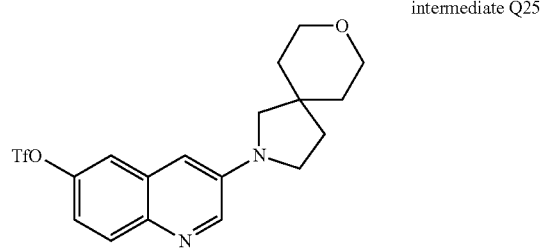 [SMILES: O=S(=O)(Oc1ccc2ncc(N3CCC4(CCOCC4)C3)cc2c1)C(F)(F)F]

6-Benzyloxy-3-(8-oxa-2-aza-spiro[4.5]dec-2-yl)-quinoline (Q25.i) was prepared from Intermediate B using the same procedure as described for Q10.i by using the equivalent amount of 8-oxa-2-aza-spiro[4.5]decan (16.1) instead of 1-methyl-1,4-diazepane (1.1). LCMS (method A): [M+H]$^+$= 375, $t_R$=2.47 min.

3-(8-Oxa-2-aza-spiro[4.5]dec-2-yl)-quinolin-6-ol (Q25.ii) was prepared from Q25.i using the same procedure as described for Q10.ii. LCMS (method A): [M+H]$^+$=285, $t_R$=4.90 min.

Trifluoro-methanesulfonic acid 3-(8-oxa-2-aza-spiro[4.5]dec-2-yl)-quinolin-6-yl ester (intermediate Q25) was prepared from Q25.ii using the same procedure as described for intermediate Q10. LCMS (method A): [M+H]$^+$=417, $t_R$=2.73 min.

Intermediate Q26

Trifluoro-methanesulfonic acid 3-(tetrahydro-furan-3-ylamino)-quinolin-6-yl ester

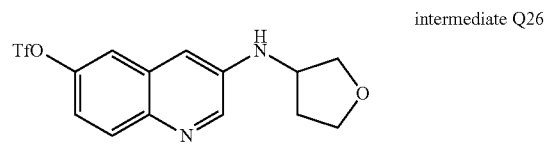 [SMILES: O=S(=O)(Oc1ccc2ncc(NC3CCOC3)cc2c1)C(F)(F)F]

(6-Benzyloxy-quinolin-3-yl)-(tetrahydro-furan-3-yl)-amine (Q26.i) was prepared from Intermediate B using the same procedure as described for Q10.i by using the equivalent amount of 3-Amino-tetrahydro-furan (17.1) instead of 1-methyl-1,4-diazepane (1.1). LCMS (method A): [M+H]$^+$=321, $t_R$=2.38 min.

3-(Tetrahydro-furan-3-ylamino)-quinolin-6-ol (Q26.ii) was prepared from Q26.i using the same procedure as described for Q10.ii. LCMS (method A): [M+H]$^+$=231, $t_R$=1.58 min.

Trifluoro-methanesulfonic acid 3-(tetrahydro-furan-3-ylamino)-quinolin-6-yl ester (intermediate Q26) was prepared from Q26.ii using the same procedure as described for intermediate Q10. LCMS (method A): [M+H]$^+$=363, $t_R$=2.54 min.

Intermediate Q27

3-(4-((tert-butyldimethylsilyl)oxy)piperidin-1-yl)quinolin-6-yl trifluoromethanesulfonate

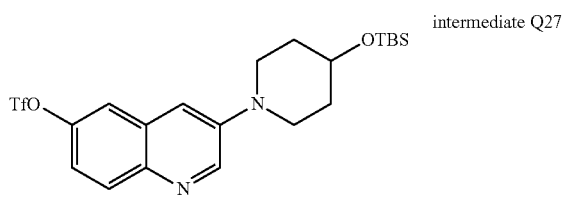 [SMILES: CC(C)(C)[Si](C)(C)OC1CCN(c2cnc3ccc(OS(=O)(=O)C(F)(F)F)cc3c2)CC1]

6-(benzyloxy)-3-(4-((tert-butyldimethylsilyl)oxy)piperidin-1-yl)quinoline (Q27.i) was prepared from Intermediate B using the same procedure as described for Q10.i by using the equivalent amount of 1-((tert-butyldimethylsilyl)oxy)piperidin (18.1) instead of 1-methyl-1,4-diazepane (1.1). LCMS (method M): [M+H]$^+$=449, $t_R$=2.46 min.

3-(4-((tert-butyldimethylsilyl)oxy)piperidin-1-yl)quinolin-6-ol (Q27.ii) was prepared from Q27.i using the same procedure as described for Q10.ii. LCMS (method N): [M+H]$^+$=359, $t_R$=2.81 min.

3-(4-((tert-butyldimethylsilyl)oxy)piperidin-1-yl)quinolin-6-yl trifluoromethanesulfonate (intermediate Q27) was prepared from Q27.ii using the same procedure as described for intermediate Q10. $^1$H-NMR (400 MHz, CDCl$_3$) δ ppm 8.68 (s, 1H), 7.89 (d, 1H), 7.21 (d, 1H), 7.11 (dd, 1H), 7.01 (s, 1H), 3.91~3.98 (m, 1H), 3.49-3.59 (m, 2H), 3.12-3.20 (m, 2H), 1.88-1.98 (m, 2H), 1.68-1.78 (m, 2H), 0.92 (s, 9H), 0.10 (s, 6H).

Intermediate Q28

3-(2-(tert-butyldimethylsilyloxy)ethylamino)quinolin-6-yltrifluoromethanesulfonate

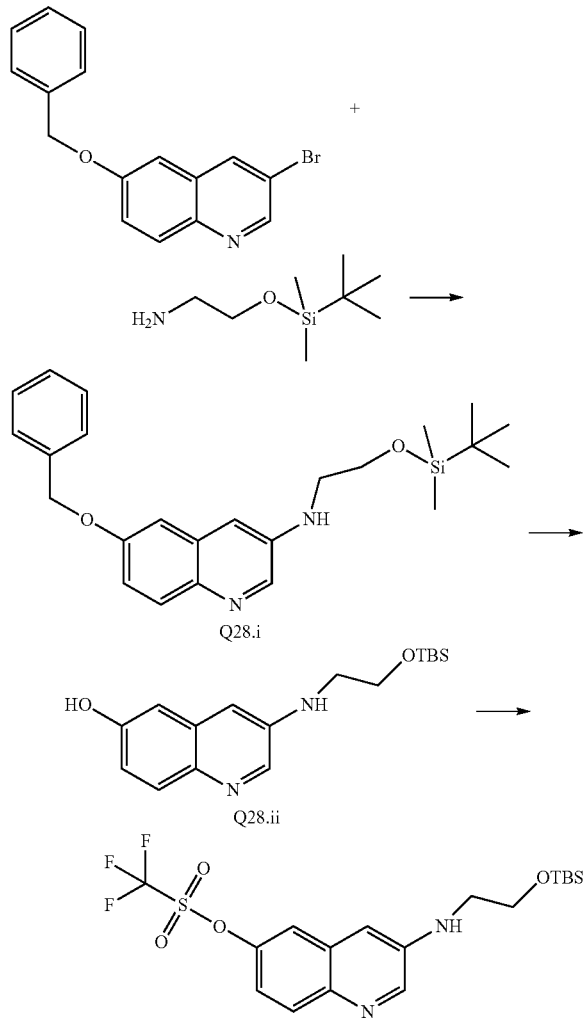

6-(benzyloxy)-N-(2-(tert-butyldimethylsilyloxy)ethyl)quinolin-3-amine (Q28.i)

To a suspension of Intermediate B (4.0 g, 12.73 mmol) in toluene (90 ml), 2-(tert-butyl-dimethyl-silanyloxy)-ethylamine (6.70 g, 38.2 mmol), KO$^t$Bu (0.714 g, 6.37 mmol), xantphos (1.473 g, 2.55 mmol) and Pd$_2$(dba)$_3$ (0.291 g, 0.318 mmol) were added under N$_2$ atmosphere. The reaction was stirred at 100° C. for 8 h. After being cooled to rt, the mixture was concentrated under reduced pressure. The residue was then dissolved in 200 ml of EtOAc, washed with water (30 ml) and brine (30 ml). The organic phase was dried over Na$_2$SO$_4$, then filtered and concentrated to afford the crude product, which was purified by silica gel chromatography (DCM/ MeOH=30/1) to afford the title compound as brown oil (3.6 g, 40.1% yield). LCMS (method B): [M+H]$^+$=409, t$_R$=3.21 min.

3-(2-(tert-buty ldimethylsilyloxy)ethylamino)quinolin-6-ol (Q28.ii)

To a solution of Q28.i (4.0 g, 9.79 mmol) in MeOH (200 ml), 10% palladium on carbon (1.042 g, 0.979 mmol) was added. After being stirred under H$_2$ atmosphere at 25° C. for 3 h, the reaction mixture was filtered through celite and concentrated under reduced pressure to afford the title compound as pale yellow oil (2.5 g, 39.3% yield). The crude product was used without further purification. LCMS (method B): [M+H]$^+$=319, t$_R$=2.42 min.

3-(2-(tert-buty ldimethylsilyloxy)ethylamino)quinolin-6-yl trifluoromethanesulfonate (Intermediate Q28)

To a solution of Q28.ii (2.3 g, 7.22 mmol) in DCM (200 ml) was added pyridine (1.168 ml, 14.44 mmol). The mixture was cooled to 0° C., and trifluoromethanesulfonic anhydride (3.06 g, 10.83 mmol) was then added in dropwise. The reaction was allowed to warm to rt and stirred for 2 h. The reaction solvent was removed under reduced pressure and the residue was dissolved in DCM (50 ml), washed with water (10 ml) and brine (10 ml). The organic phase was then dried over anhydrous Na$_2$SO$_4$, filtered and concentrated to give the crude product, which was purified by silica gel chromatography (DCM/MeOH=30/1) to afford the title compound as brown oil (1.5 g, 17.06% yield). LCMS (method B): [M+H]$^+$=450, t$_R$=3.33 min.

Intermediate Q29

3-(tert-butoxycarbonylamino)quinolin-6-yl trifluoromethanesulfonate

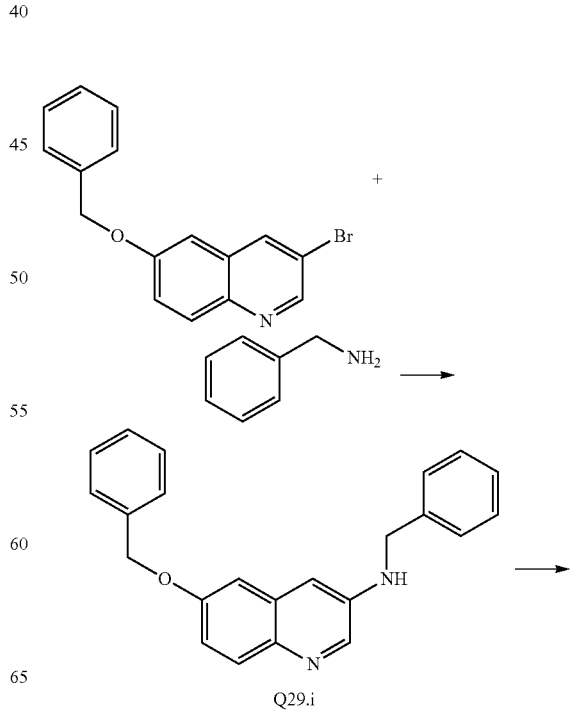

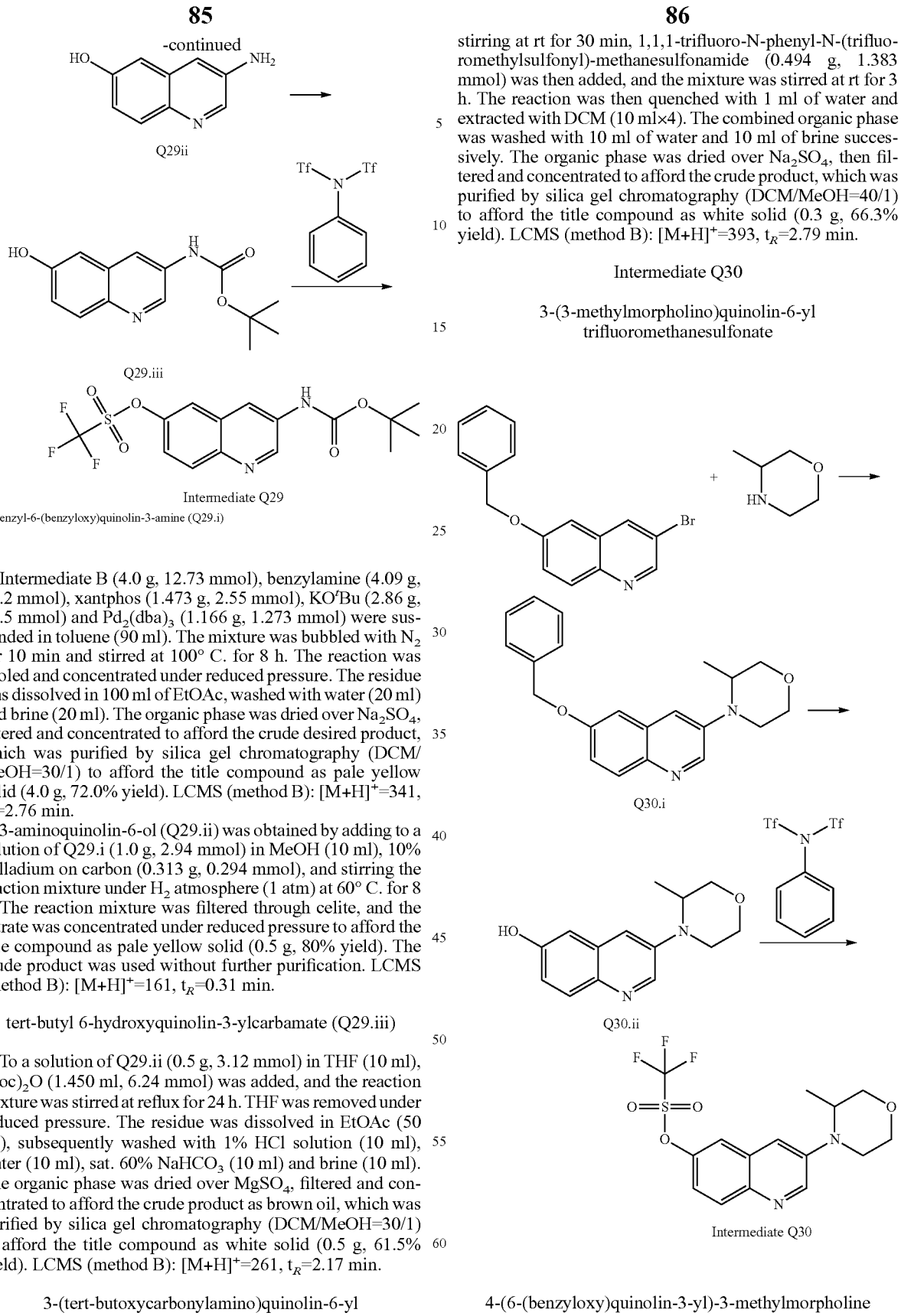

stirring at rt for 30 min, 1,1,1-trifluoro-N-phenyl-N-(trifluoromethylsulfonyl)-methanesulfonamide (0.494 g, 1.383 mmol) was then added, and the mixture was stirred at rt for 3 h. The reaction was then quenched with 1 ml of water and extracted with DCM (10 ml×4). The combined organic phase was washed with 10 ml of water and 10 ml of brine successively. The organic phase was dried over $Na_2SO_4$, then filtered and concentrated to afford the crude product, which was purified by silica gel chromatography (DCM/MeOH=40/1) to afford the title compound as white solid (0.3 g, 66.3% yield). LCMS (method B): $[M+H]^+=393$, $t_R=2.79$ min.

Intermediate Q30

3-(3-methylmorpholino)quinolin-6-yl trifluoromethanesulfonate

N-benzyl-6-(benzyloxy)quinolin-3-amine (Q29.i)

Intermediate B (4.0 g, 12.73 mmol), benzylamine (4.09 g, 38.2 mmol), xantphos (1.473 g, 2.55 mmol), $KO^tBu$ (2.86 g, 25.5 mmol) and $Pd_2(dba)_3$ (1.166 g, 1.273 mmol) were suspended in toluene (90 ml). The mixture was bubbled with $N_2$ for 10 min and stirred at 100° C. for 8 h. The reaction was cooled and concentrated under reduced pressure. The residue was dissolved in 100 ml of EtOAc, washed with water (20 ml) and brine (20 ml). The organic phase was dried over $Na_2SO_4$, filtered and concentrated to afford the crude desired product, which was purified by silica gel chromatography (DCM/MeOH=30/1) to afford the title compound as pale yellow solid (4.0 g, 72.0% yield). LCMS (method B): $[M+H]^+=341$, $t_R=2.76$ min.

3-aminoquinolin-6-ol (Q29.ii) was obtained by adding to a solution of Q29.i (1.0 g, 2.94 mmol) in MeOH (10 ml), 10% Palladium on carbon (0.313 g, 0.294 mmol), and stirring the reaction mixture under $H_2$ atmosphere (1 atm) at 60° C. for 8 h. The reaction mixture was filtered through celite, and the filtrate was concentrated under reduced pressure to afford the title compound as pale yellow solid (0.5 g, 80% yield). The crude product was used without further purification. LCMS (method B): $[M+H]^+=161$, $t_R=0.31$ min.

tert-butyl 6-hydroxyquinolin-3-ylcarbamate (Q29.iii)

To a solution of Q29.ii (0.5 g, 3.12 mmol) in THF (10 ml), $(Boc)_2O$ (1.450 ml, 6.24 mmol) was added, and the reaction mixture was stirred at reflux for 24 h. THF was removed under reduced pressure. The residue was dissolved in EtOAc (50 ml), subsequently washed with 1% HCl solution (10 ml), water (10 ml), sat. 60% $NaHCO_3$ (10 ml) and brine (10 ml). The organic phase was dried over $MgSO_4$, filtered and concentrated to afford the crude product as brown oil, which was purified by silica gel chromatography (DCM/MeOH=30/1) to afford the title compound as white solid (0.5 g, 61.5% yield). LCMS (method B): $[M+H]^+=261$, $t_R=2.17$ min.

3-(tert-butoxycarbonylamino)quinolin-6-yl trifluoromethanesulfonate (Intermediate Q29)

To a solution of Q29.iii (0.3 g, 1.153 mmol) in THF (10 ml), NaH (60%, 0.055 g, 2.305 mmol) was added. After 4-(6-(benzyloxy)quinolin-3-yl)-3-methylmorpholine (Q30.i)

A mixture of Intermediate B (1.0 g, 3.18 mmol), 3-methylmorpholine (0.966 g, 9.55 mmol), $Pd_2(dba)_3$ (0.291 g, 0.318 mmol), xantphos (0.368 g, 0.637 mmol) and KO'Bu (0.714 g, 6.37 mmol) in toluene (30 ml) was bubbled with argon for 10 min. The reaction was stirred at 100° C. for 8 h, cooled and concentrated under reduced pressure. The residue was dissolved in 50 ml of EtOAc, washed with water and brine. The organic phase was dried over Na₂SO₄, filtered and concentrated. The residue was purified by silica gel chromatography (DCM/MeOH=30/1) to afford the title compound as pale yellow solid (800 mg, 60.9% yield). LCMS (method B): [M+H]⁺=335, $t_R$=2.53 min.

3-(3-methylmorpholino)quinolin-6-ol (Q30.ii)

To a solution of Q30.i (800 mg, 2.392 mmol) in methanol (200 ml) was added 10% Palladium on carbon (255 mg, 0.239 mmol), and the reaction mixture was stirred under H₂ atmosphere (1 atm) at rt for 3 h. The Pd/C was filtered off over celite and the filtrate was concentrated to afford the title compound (600 mg, 73.9% yield) as pale yellow solid. The crude product was used without further purification. LCMS (method B): [M+H]⁺=245, $t_R$=1.42 min.

3-(3-methylmorpholino)quinolin-6-yl trifluoromethanesulfonate (Intermediate Q30)

To a solution of Q30.ii (200 mg, 0.819 mmol) in THF (10 ml), was added NaH (60%, 65.5 mg, 1.637 mmol). After stirred at rt for 30 min, 1,1,1-trifluoro-N-phenyl-N-(trifluoromethylsulfonyl)-methanesulfonamide (585 mg, 1.637 mmol) was added, and the mixture was stirred at rt for 3 h. Water was added (1 mL) and the mixture was extracted with DCM (10 ml×4), the combined organic phase was washed with water, brine, dried over Na₂SO₄, filtered and concentrated to afford the crude product. The crude product was purified by silica gel chromatography (DCM/MeOH=40/1) to afford the title compound as brown oil (100 mg, 32.5% yield). LCMS (method B): [M+H]⁺=377, $t_R$=2.62 min.

Intermediate Q31

3-(2,2,6,6-tetramethylpiperidin-4-ylamino)quinolin-6-yl trifluoromethanesulfonate

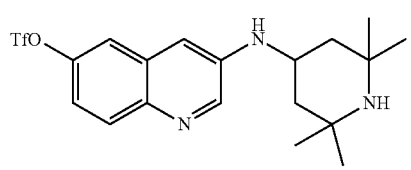

Intermediate Q31

The title compound was prepared starting from Intermediate B using the same procedure as described for intermediate Q30. LCMS (method B): [M+H]⁺=432, $t_R$=2.03 min.

Intermediate Q32

3-(1-methyl-1H-pyrazol-4-yl)quinolin-6-yl trifluoromethanesulfonate

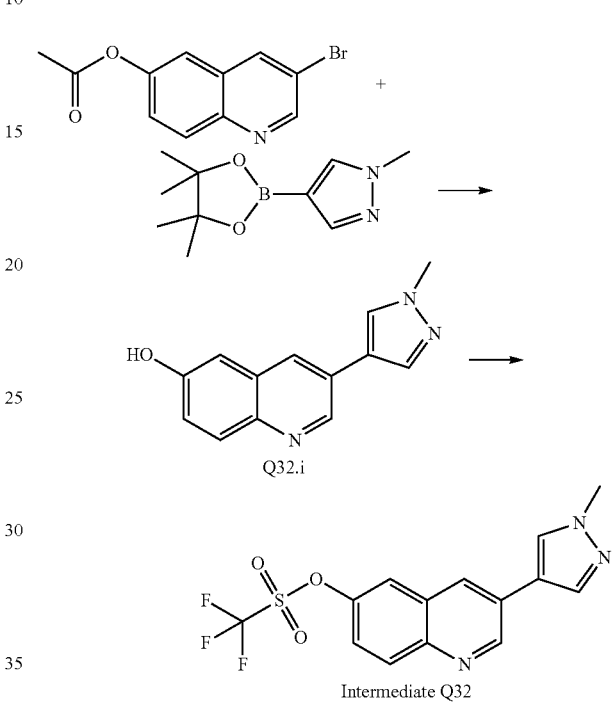

Intermediate Q32

3-(1-methyl-1H-pyrazol-4-yl)quinolin-6-ol (Q32.i)

A mixture of Intermediate A (1.8 g, 6.76 mmol), 1-methyl-4-(4,4,5,5-tetramethyl-1,3,2-dioxaborolan-2-yl)-1H-pyrazole (1.548 g, 7.44 mmol), Na₂CO₃ (2.151 g, 20.29 mmol) and Pd(PPh₃)₄ (0.782 g, 0.676 mmol) in DMF (10 ml) was bubbled with argon for 10 min. Then the mixture was heated at 90° C. for 5 h. After being cooled to rt, the mixture was diluted with EtOAc (40 ml), washed with water and brine, dried over Na₂SO₄, filtered and concentrated. The residue was recrystallized from EtOAc to afford the title compound as pale gray solid (1.1 g, 65% yield). ¹H-NMR (400 MHz, DMSO-d₆) δ ppm 9.97 (s, 1H), 8.91 (s, 1H), 8.33 (s, 1H), 8.23 (d, 2H), 8.00 (s, 1H), 7.80 (d, 1H), 7.22 (dd, 1H), 7.00 (d, 1H), 3.90 (s, 3H). LCMS (method B): [M+H]⁺=226, $t_R$=1.41 min.

3-(1-methyl-1H-pyrazol-4-yl)quinolin-6-yl trifluoromethanesulfonate (Intermediate Q32)

Q32.i (0.9 g, 4.00 mmol) was dissolved in pyridine (8 ml). The solution was cooled to 0° C. and trifluoromethanesulfonic anhydride (1.353 g, 4.79 mmol) was added. The reaction was allowed to warm up to rt and stirred at rt for 10 h. The reaction was then quenched with saturated NaHCO₃ and extracted with DCM (20 ml×3). The combined organic phase was washed with water, brine, dried over Na₂SO₄ and concentrated. The residue was recrystallized from EtOAc to afford the title compound as gray solid. ¹H-NMR (400 MHz, DMSO-d$_6$) δ ppm 9.30 (s, 1H), 8.61 (s, 1H), 8.42 (s, 1H), 8.17 (d, 1H), 8.10 (t, 2H), 7.76 (dd, 1H), 3.92 (s, 3H). LCMS (method B): [M+H]+=358, t$_R$=2.43 min.

Intermediate Q33

3-morpholinoquinolin-6-yl trifluoromethanesulfonate intermediate A

Q33.i

Intermediate Q33

3-Morpholin-4-ylquinolin-6-ol (Q33.i)

A mixture of Intermediate A (0.8 g, 3.01 mmol), morpholine (1.048 g, 12.03 mmol), Pd$_2$(dba)$_3$ (0.275 g, 0.301 mmol), xantphos (0.305 g, 0.602 mmol) and KO$^t$Bu (0.337 g, 3.01 mmol) in toluene (15 ml) was bubbled with N$_2$ for 15 min and then was heated at 100° C. for 5 h under MW radiation. The mixture was quenched with saturated aqueous NaHCO$_3$ solution. The aqueous phase was extracted with DCM/IPA (10 ml, v/v=3/1) for 3 times. The combined extract was dried over anhydrous MgSO$_4$. Filtered and concentrated, the residue was purified by silica gel chromatography to afford the title compound (0.31 g, 40.3% yield). LCMS (method B): [M+H]$^+$=231, t$_R$=1.1 min.

3-morpholin-4-ylquinolin-6-yl trifluoromethanesulfonate (Intermediate Q33)

To a solution of Q33.i (300 mg, 1.303 mmol) in pyridine (5 ml) was added Tf$_2$O (441 mg, 1.563 mmol) at 0° C. The mixture was then stirred at rt for 20 h. The reaction was quenched with 60% NaHCO$_3$ aqueous solution and the aqueous phase was extracted with DCM (20 ml×3). The combined extract was washed with water, dried over anhydrous MgSO$_4$, filtered and concentrated to afford the title compound as brown solid (0.22 g, 37.3% yield), which was used directly in the next step. LCMS (method B): [M+H]$^+$=363, t$_R$=2.49 min.

Alternatively, Intermediate Q33 can by prepared according to the procedure described for Intermediates Q10 and Q28 starting from Intermediate B, via 6-benzyloxy-3-morpholin-4-yl-quinol (Q33.ii)

Q33.ii

Intermediate Q34

Trifluoro-methanesulfonic acid 3-(1-methyl-piperidin-4-ylamino)-quinolin-6-yl ester intermediate Q34

6-Benzyloxy-quinolin-3-yl-(1-methyl-piperidin-4-yl)-amine (Q34.i) was prepared from Intermediate B and 4-amino-1-methylpiperidine using the same procedure as described for Q10.i. LCMS (method O): [M+H]$^+$=248, t$_R$=1.38 min.

3-(1-Methyl-piperidin-4-ylamino)-quinolin-6-ol (Q34.ii) was prepared from Q34.i using the same procedure as described for Q10.ii. LCMS (method O): [M+H]$^+$=258, t$_R$=0.92 min.

3-(4-(tert-Butoxycarbonylamino)piperidin-1-yl)quinolin-6-yl trifluoromethanesulfonate (intermediate Q34) was prepared from Q34.ii using the same procedure as described for intermediate Q10. LCMS (method O): [M+H]$^+$=390, t$_R$=1.35 min. $^1$H NMR (400 MHz, MeOH-d$_4$) δ ppm 8.49 (d, 1H), 7.92 (d, 1H), 7.69 (d, 1 h), 7.31 (dd, 1H), 7.27 (d, 1H), 3.62 (m, 1H), 3.28 (m, 2H), 2.86 (m, 2H), 2.65 (s, 3H), 2.26 (m, 2H), 1.75 (m, 2H).

Intermediate Q35

3-(morpholinomethyl)quinolin-6-yl trifluoromethanesulfonate

Q35.i

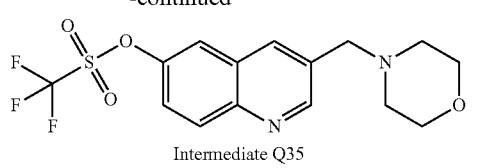

Intermediate Q35

3-(morpholinomethyl)quinolin-6-ol (Q35.i)

A mixture of Cs$_2$CO$_3$ (4.75 g, 14.49 mmol), Intermediate A (1.285 g, 4.83 mmol) and trifluoroborate salts (1 g, 4.83 mmol) in THF (15 ml) was bubbled with N$_2$ for 10 min. Then Pd(OAc)$_2$ (0.033 g, 0.145 mmol) was added. The mixture was stirred at 80° C. for 20 h. The mixture was diluted with water, the organic phase was separated and the aqueous phase was concentrated and dried on vacuum to afford the title compound as yellow solid The solid was used in the next step without further purification (440 mg, 33.6% yield). LCMS (method B): [M+H]$^+$=245, t$_R$=0.44 min.

3-(morpholinomethyl)quinolin-6-yl trifluoromethanesulfonate (Intermediate Q35)

To a solution of 3-(morpholinomethyl)quinolin-6-ol (400 mg, 1.637 mmol) in pyridine (5 ml) was added trifluoromethanesulfonic anhydride (462 mg, 1.637 mmol) and the mixture was stirred at rt for 8 h. The reaction was quenched with saturated aqueous NaHCO$_3$ solution. The aqueous phase was extracted with DCM for 3 times The extract was washed with water and brine. The organic phase was dried over MgSO$_4$, filtered and concentrated. The residue was purified by silica gel chromatography to afford the title compound as yellow oil (110 mg, 16.1% yield). LCMS (method B): [M+H]$^+$=377, t$_R$=1.78 min.

Intermediate Q36

3-(oxetan-3-ylamino)quinolin-6-yl trifluoromethanesulfonate

Intermediate Q36

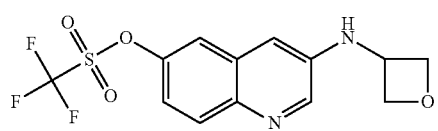

The title compound was prepared from Intermediate B and 3-aminooxetane using the same procedure as described for intermediate Q30. LCMS (method B): [M+H]$^+$=349, t$_R$=2.50 min.

SYNTHESES OF EXAMPLES

The following section describes the synthesis of examples in detail. The characterizing data for these compounds as well as for other examples synthesized by similar methods are given in the table below.

Example 1

Synthesis Method 1A tert-butyl 1-(6-(6-(1-methyl-1H-pyrazol-4-yl)-[1,2,4]triazolo[4,3-a]pyridin-3-ylthio)quinolin-3-yl)pyrrolidin-3-ylcarbamate

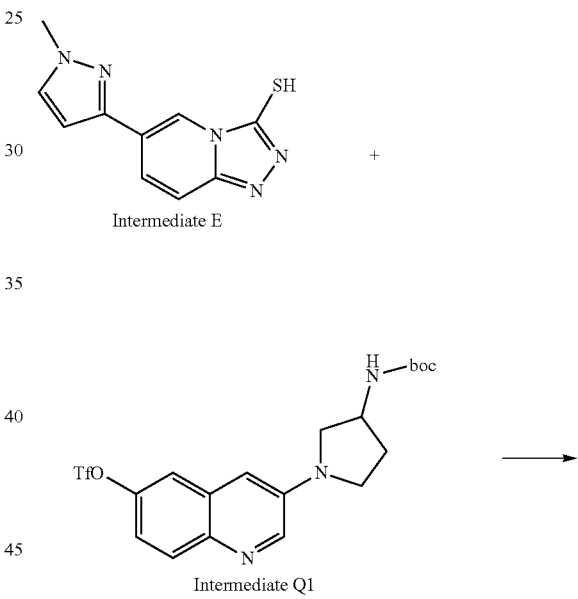

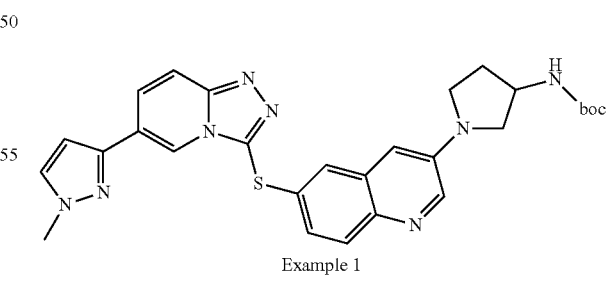

Example 1

A mixture of Intermediate E (10 mg, 0.043 mmol), Intermediate Q1 (20 mg, 0.043 mmol), Pd$_2$(dba)$_3$ (1.94 mg, 2.17 µmol), Xantphos (2.51 mg, 4.33 µmol) and DIPEA (0.015 mL, 0.087 mmol) in DMF (0.5 mL) was bubbled with Argon for 20 min. The result mixture was heated at 100° C. overnight, then cooled to rt, filtrated and the filtrate was concentrated under reduced pressure. The residue was purified by prep-HPLC to give the title compound as yellow solid (15 mg, yield 57%). [Method 1A]

Example 2

Synthesis Method 1B 1-(6-(6-(1-methyl-1H-pyrazol-4-yl)-[1,2,4]triazolo[4,3-a]pyridin-3-ylthio)quinolin-3-yl)pyrrolidin-3-amine

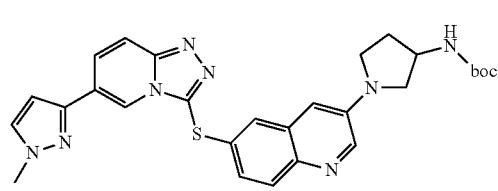

Example 1

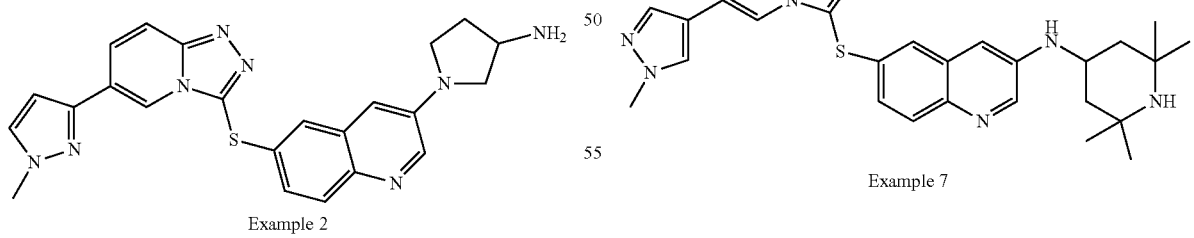

Example 2

To a solution of Example 1 (14 mg, 0.026 mmol) in DCM (2.0 mL) was added TFA (0.5 mL) dropwise under ice-bath. The mixture was stirred at rt for 2 hours, then based with saturated NaHCO₃. The result solution was concentrated under reduced pressure. The residue was purified by prep-HPLC to give the title compound as yellow solid (9 mg, yield 71%). [Method 1B]

Example 7

Method 2

6-(8-fluoro-6-(1-methyl-1H-pyrazol-4-yl)-[1,2,4]triazolo[4,3-a]pyridin-3-ylthio)-N-(2,2,6,6-tetramethylpiperidin-4-yl)quinolin-3-amine

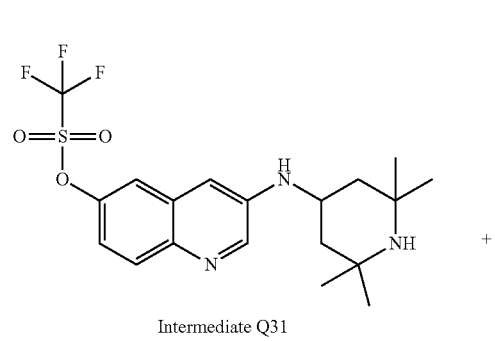

Intermediate Q31

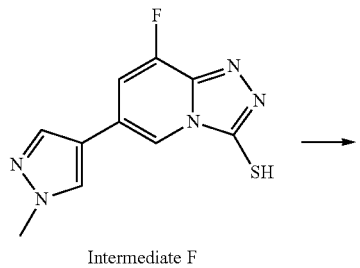

Intermediate F

Example 7

A mixture of Intermediate Q31 (100 mg, 0.232 mmol), Intermediate F (57.8 mg, 0.232 mmol), Pd₂(dba)₃ (21.22 mg, 0.023 mmol), xantphos (26.8 mg, 0.046 mmol) and DIPEA (0.081 ml, 0.464 mmol) in DMF (5 ml) was bubbled with Argon gas for 10 min, then the reaction tube was sealed and heated at 100° C. for 1 h under MW radiation. The solvent was removed under reduced pressure. The residue was purified by prep-HPLC to afford the title compound as pale yellow solid (60 mg, 48.8% yield). [Method 2]

Example 16

Reference Compound

6-[6-(1-Methyl-1H-pyrazol-4-yl)-[1,2,4]triazolo[4,3-a]pyridin-3-ylsulfanyl]-3-(pyrrolidin-3-yloxy)-quinoline

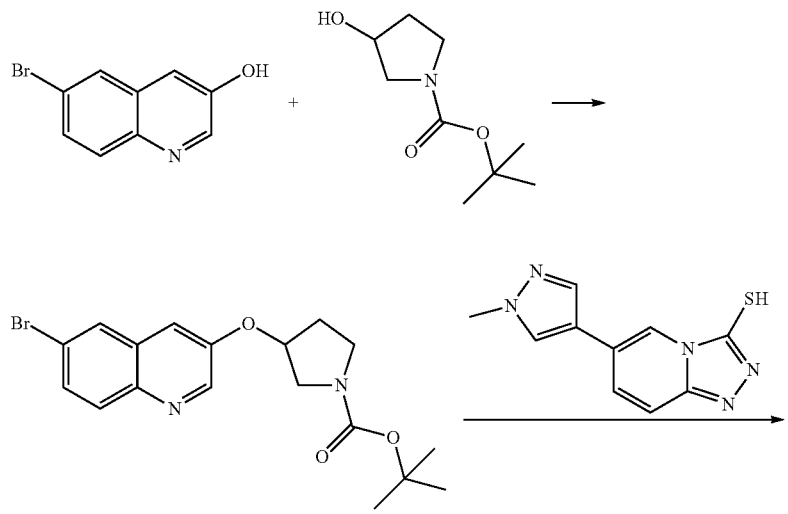

16.1

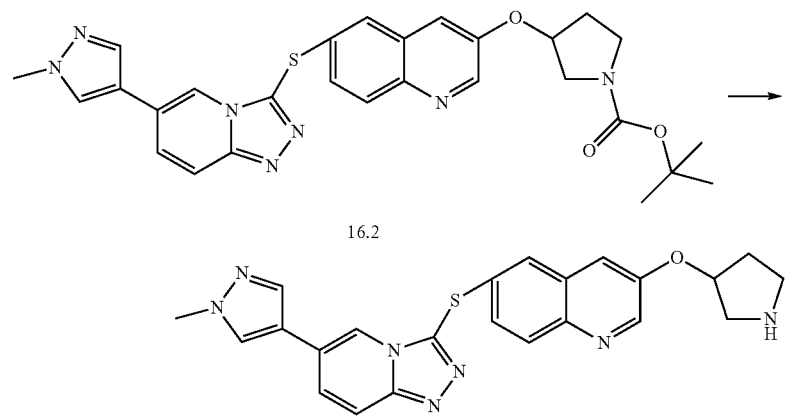

16.2

Example 16 tert-butyl 3-(6-bromoquinolin-3-yloxy)pyrrolidine-1-carboxylate (16.1)

To a solution of 6-bromoquinolin-3-ol (500 mg, 2.232 mmol), tert-butyl 3-hydroxypyrrolidine-1-carboxylate (418 mg, 2.232 mmol) and triphosphine (875 mg, 3.35 mmol) in THF (10 ml) was added DEAD (0.424 ml, 2.68 mmol) at 0° C. Then the mixture was stirred at 50° C. for 6 h under $N_2$. The mixture was diluted with ether and filtered. The filtrate was concentrated. The residue was purified by silica gel chromatography eluted with Hex/EA (from 100% to 95%) to afford the title compound (650 mg, 67% yield) as brown gel.

3-{6-[6-(1-Methyl-1H-pyrazol-4-yl)-[1,2,4]triazolo[4,3-a]pyridin-3-ylsulfanyl]-quinolin-3-yloxy}-pyrrolidine-1-carboxylic acid tert-butyl ester (16.2) was synthesized using the same procedure as example 1 (method 1A). (68 mg, 41% yield). $^1$H-NMR (400 MHz, DMSO-$d_6$) δ ppm 8.98 (s, 1H), 8.54 (s, 1H), 8.31 (s, 1H), 7.97 (m, 3H), 7.81 (d, 1H), 7.53 (s, 1H), 7.16 (d, 1H), 7.07 (s, 1H), 5.47 (m, 1H), 3.83 (s, 3H), 3.55 (m, 1H), 3.14 (m, 3H), 2.20 (m, 2H), 1.34 (s, 9H). LCMS (method B): [M+H]$^+$=544, $t_R$=2.20 min.

6-[6-(1-Methyl-1H-pyrazol-4-yl)-[1,2,4]triazolo[4,3-a]pyridin-3-ylsulfanyl]-3-(pyrrolidin-3-yloxy)-quinoline (example 16) was obtained by stirring a solution of 16.2 (40 mg, 0.074 mmol) in MeOH (contains 10% HCl) at rt for about 2 h. The solvent was removed and the residue was purified by prep-HPLC to give white solid (20 mg, 61% yield) as the title compound. $^1$H-NMR (400 MHz, DMSO-$d_6$) δ ppm 8.96 (s, 1H), 8.55 (s, 1H), 8.31 (s, 1H), 7.99 (m, 2H), 7.93 (d, 1H), 7.82 (d, 1H), 7.55 (s, 1H), 7.13 (d, 1H), 7.00 (s, 1H), 5.31 (m, 1H), 3.83 (s, 3H), 3.06 (m, 1H), 2.90 (m, 2H), 2.83 (m, 2H), 2.02 (m, 1H), 1.75 (m, 1H). LCMS (method B): [M+H]+= 444, t$_R$=1.69 min.

Example 28

Method 1C 6-(6-(1-methyl-1H-pyrazol-4-yl)-[1,2,4]triazolo[4,3-a]pyridin-3-ylthio)-3-(4-(2,2,2-trifluoroethyl)piperazin-1-yl)quinoline

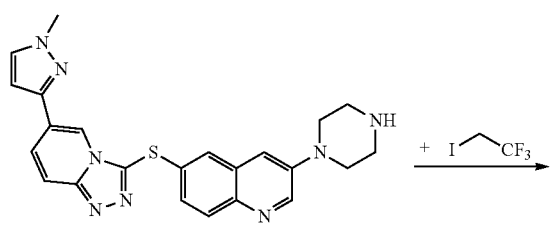

Example 27

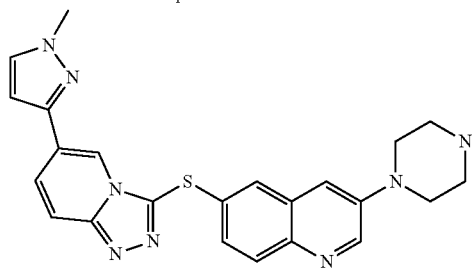

Example 28

A suspension of 6-(6-(1-methyl-1H-pyrazol-4-yl)-[1,2,4]triazolo[4,3-a]pyridin-3-ylthio)-3-(piperazin-1-yl)quinoline (Example 27—see in Table below) (12 mg, 0.027 mmol), 1,1,1-trifluoro-2-iodoethane (56.9 mg, 0.271 mmol) and DIPEA (17.5 mg, 0.136 mmol) in DMF (1 mL) was sealed in a microwave vial and heated at 120° C. for 6 hours. The solvent was removed and the residue was purified by prep-HPLC to give the title compound as yellow solid (3 mg, yield 20%). [Method 1C]

Example 29

Method 1D 2-(4-(6-(6-(1-Methyl-1H-pyrazol-4-yl)-[1,2,4]triazolo[4,3-a]pyridin-3-ylthio)quinolin-3-yl)-1,4-diazepan-1-yl)ethanol

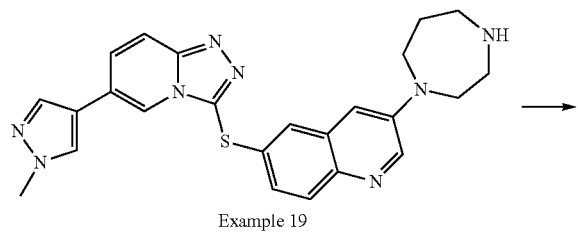

Example 19

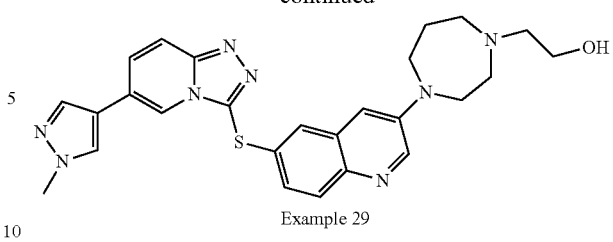

Example 29

A mixture of 3-(1,4-Diazepan-1-yl)-6-(6-(1-methyl-1H-pyrazol-4-yl)-[1,2,4]triazolo[4,3-a]pyridin-3-ylthio)quinoline (Example 19—see in Table below) (15 mg, 0.033 mmol), 2-bromoethanol (12.33 mg, 0.099 mmol) and K$_2$CO$_3$ (9.08 mg, 0.066 mmol) in DMF (0.5 ml) was stirred at rt for 24 hr. The mixture was purified by prep-HPLC to give the title compound (6 mg, yield 36%). [Method 1D]

Example 49

1-(6-((6-(1-methyl-1H-pyrazol-4-yl)-[1,2,4]triazolo[4,3-a]pyridin-3-yl)thio)quinolin-3-yl)piperidin-4-ol

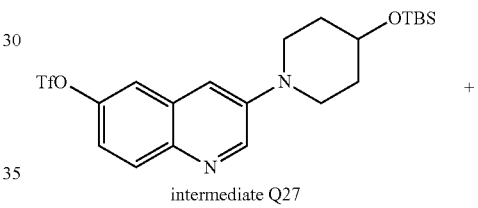

intermediate Q27

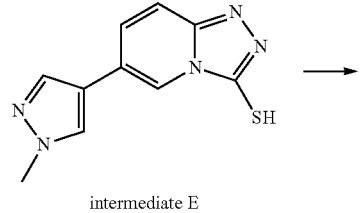

intermediate E

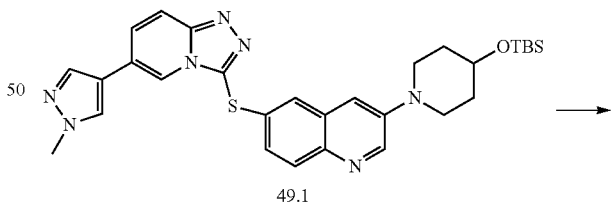

49.1

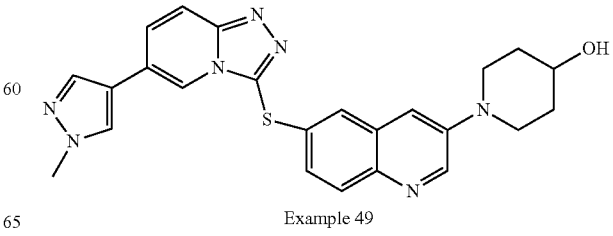

Example 49

3-(4-((tert-butyldimethylsilyl)oxy)piperidin-1-yl)-6-((6-(1-methyl-1H-pyrazol-4-yl)-[1,2,4]triazolo[4,3-a]pyridin-3-yl)thio)quinoline (49.1)

The title compound was prepared using the same procedure as described in the synthesis of example 1 starting from Intermediate Q27 and Intermediate E. LCMS (method B): [M+H]$^+$=571, $t_R$=3.20.

1-(6-((6-(1-methyl-1H-pyrazol-4-yl)-[1,2,4]triazolo[4,3-a]pyridin-3-yl)thio)quinolin-3-yl)piperidin-4-ol (Example 49) (Method 1E)

To a solution of (49.1) (48.5 mg, 0.085 mmol) in MeOH (2 mL) was added HCl solution in MeOH (1M) (5 mL, 5.00 mmol). The reaction mixture was stirred at rt for 1 h, quenched with saturated NaHCO$_3$ solution and extracted with extracted with CH$_2$Cl$_2$. The combined organic layers were dried over anhydrous Na$_2$SO$_4$, concentrated, purified via biotage by flash chromatography on silica gel using a gradient of 0-10% MeOH/CH$_2$Cl$_2$ to give the title compound (38 mg, 0.083 mmol, 98% yield). [Method 1E]

Example 53

Method 3)

2-(6-(6-(1-methyl-1H-pyrazol-4-yl)-[1,2,4]triazolo[4,3-a]pyridin-3-ylthio)quinolin-3-ylamino)ethanol N-(2-(tert-butyldimethylsilyloxy)ethyl)-6-(6-(1-methyl-1H-pyrazol-4-yl)-[1,2,4]triazolo[4,3-a]pyridin-3-ylthio)quinolin-3-amine (53.1)

A mixture of Intermediate Q28 (0.2 g, 0.444 mmol), Intermediate E (0.103 g, 0.444 mmol), xantphos (0.051 g, 0.089 mmol), Pd$_2$(dba)$_3$ (0.041 g, 0.044 mmol) and DIPEA (0.155 ml, 0.888 mmol) in DMF (10 ml) was bubbled with Ar gas for 10 min and then the reaction mixture was stirred under MW radiation at 110° C. for 1 h. The solvent was removed under reduced pressure. The residue was purified by silica gel chromatography (DCM/MeOH=40/1) to afford the title compound as brown oil (0.1 g, 42.4% yield). LCMS (method B): [M+H]$^+$=532, $t_R$=2.74 min.

2-(6-(6-(1-methyl-1H-pyrazol-4-yl)-[1,2,4]triazolo[4,3-a]pyridin-3-ylthio)quinolin-3-ylamino)ethanol (Example 53)

To a solution of (53.1) (100 mg, 0.188 mmol) in THF (10 ml), TBAF (98 mg, 0.376 mmol) was added. The reaction mixture was stirred at rt for 3 h. The solvent was then removed under reduced pressure. The residue was dissolved in 30 ml of DCM, washed with water (10 ml×3) and brine (10 ml) successively. The organic phase was dried over Na$_2$SO$_4$, then filtered and concentrated. The residue was purified by silica

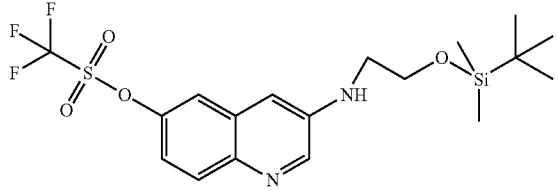

Intermediate 28

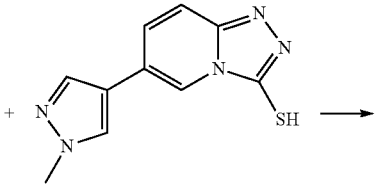

Intermediate E

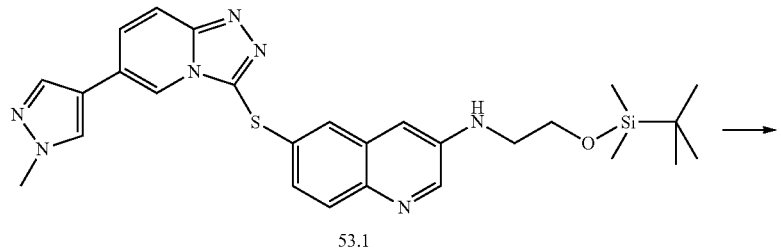

53.1

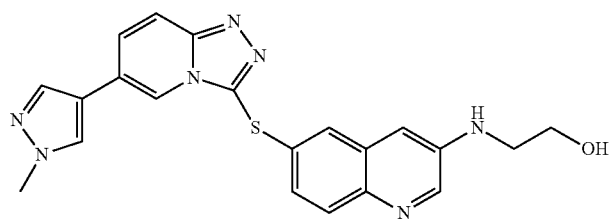

Example 53 gel chromatography (DCM/MeOH=10/1) to afford the title compound as pale yellow solid (22 mg, 28% yield). [Method 3]

Example 55

Method 4

6-(8-fluoro-6-(1-methyl-1H-pyrazol-4-yl)-[1,2,4]triazolo[4,3-a]pyridin-3-ylthio)quinolin-3-amine hydrochloride

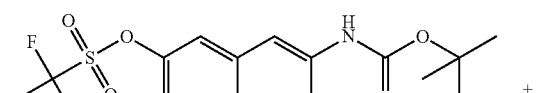

Intermediate Q29

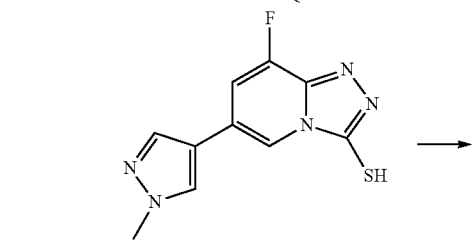

Intermediate F

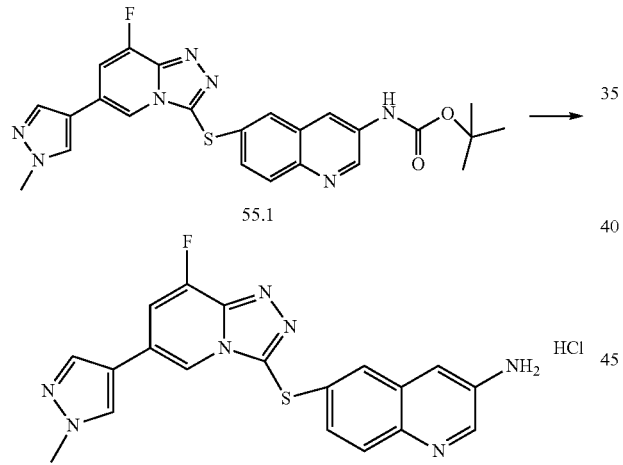

Tert-butyl 6-(8-fluoro-6-(1-methyl-1H-pyrazol-4-yl)-[1,2,4]triazolo[4,3-a]pyridin-3-ylthio)quinolin-3-ylcarbamate (55.1)

A mixture of Intermediate Q29 (0.2 g, 0.510 mmol), Intermediate F (0.127 g, 0.510 mmol), Pd$_2$(dba)$_3$ (0.047 g, 0.051 mmol), xantphos (0.059 g, 0.102 mmol) and DIPEA (0.178 ml, 1.019 mmol) in DMF (10 ml) was bubbled with Ar gas for 10 min, and the reaction tube was sealed and heated at 110° C. for 1 h under MW radiation. The solvent was removed under reduced pressure. The residue was purified by silica gel chromatography (DCM/MeOH=40/1) to afford the title product as brown oil (0.12 g, 47.9% yield). LCMS (method B): [M+H]$^+$=492, t$_R$=2.52 min.

6-(8-fluoro-6-(1-methyl-1H-pyrazol-4-yl)-[1,2,4]triazolo[4,3-a]pyridin-3-ylthio)quinolin-3-amine hydrochloride (Example 55)

(55.1) (0.12 g, 0.244 mmol) was dissolved in HCl solution (4 M in MeOH, 20 ml, 0.08 mol), and the reaction mixture was stirred at rt for 2 h. The solvent was removed under reduced pressure to afford the title product as yellow solid (60 mg, 62.8% yield). [Method 4]

Example 57

Method 5

4-(6-(8-fluoro-6-(1H-pyrazol-4-yl)-[1,2,4]triazolo[4,3-a]pyridin-3-ylthio)quinolin-3-yl)morpholine

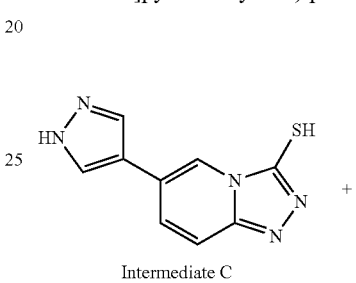

Intermediate C

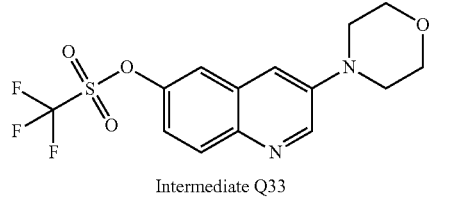

Intermediate Q33

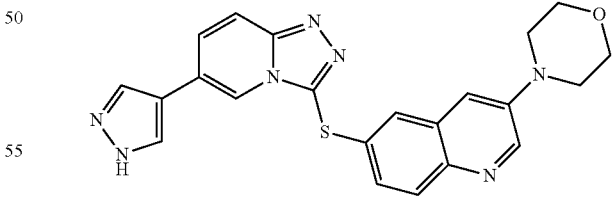

Example 57

A mixture of Intermediate C (100 mg, 0.460 mmol), Intermediate Q33 (167 mg, 0.460 mmol), xantphos (53.3 mg, 0.092 mmol), Pd$_2$(dba)$_3$ (42.2 mg, 0.046 mmol), DIPEA (0.161 ml, 0.921 mmol) in DMF (10 ml) was bubbled with Argon gas for 10 min, then the reaction tube was sealed and heated at 110° C. for 1 h under MW radiation. The solvent was removed under reduced pressure. The residue was purified by silica gel chromatography (DCM/MeOH=40/1) to afford the title compound as yellow solid (45 mg, 23% yield). [Method 5]

Example 59

Method 6

3-methyl-4-(6-(6-(1-methyl-1H-pyrazol-4-yl)-[1,2,4]triazolo[4,3-a]pyridin-3-ylthio)quinolin-3-yl)-morpholine

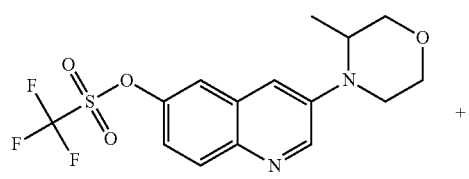

Intermediate Q30

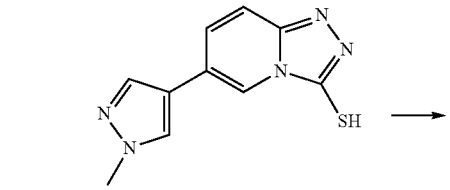

Intermediate E

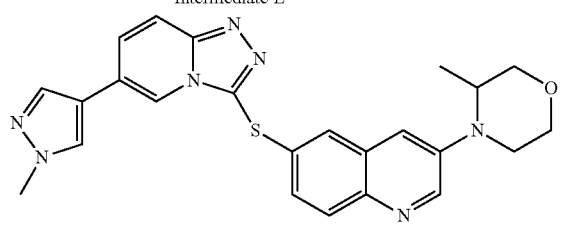

Example 59

A mixture of Intermediate Q30 (100 mg, 0.266 mmol), Intermediate E (61.5 mg, 0.266 mmol), xantphos (30.7 mg, 0.053 mmol), Pd$_2$(dba)$_3$ (24.33 mg, 0.027 mmol) and DIPEA (0.093 ml, 0.531 mmol) in DMF (5 ml) was bubbled with Ar gas for 10 min, then the reaction tube was sealed and heated at 110° C. for 1 h under MW radiation. The solvent was removed under reduced pressure. The residue was purified by silica gel chromatography (DCM/MeOH=40/1) and then was repurified by prep-HPLC to afford the title compound as white solid (40 mg, 32.9% yield). [Method 6]

Example 63

Reference Example 6-(6-(1-methyl-1H-pyrazol-4-yl)-[1,2,4]triazolo[4,3-a]pyridin-3-ylthio)quinoline

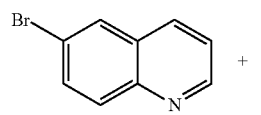

Intermediate E

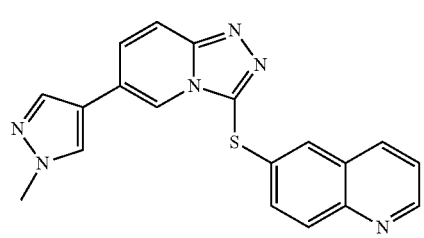

Example 63

A mixture of 6-bromoquinoline (72.0 mg, 0.346 mmol), Intermediate E (80 mg, 0.346 mmol), Pd$_2$(dba)$_3$ (31.7 mg, 0.035 mmol), xantphos (40.0 mg, 0.069 mmol) and DIPEA (0.242 ml, 1.384 mmol) in DMF (10 ml) was bubbled with N$_2$ for 15 min. The reaction was stirred at 100° C. for 2 h under MW radiation. The mixture was concentrated and the residue obtained was purified by silica gel chromatography eluted with DCM/MeOH (from 100% to 90%) to afford the title compound as yellow solid (63 mg, 45.7% yield). $^1$H-NMR (400 MHz, DMSO-d$_6$) δ ppm 8.65 (d, 1H), 8.59 (s, 1H), 8.28 (m, 2H), 7.98 (m, 3H), 7.89 (s, 1H), 7.81 (d, 1H), 7.59 (d, 1H), 7.50 (m, 1H), 3.84 (s, 3H). LCMS (method B): [M+H]$^+$=359, t$_R$=2.0 min.

Example 65

Reference Example 6-(8-fluoro-6-(1-methyl-1H-pyrazol-4-yl)-[1,2,4]triazolo[4,3-a]pyridin-3-ylthio)quinoline

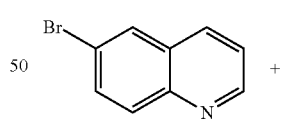

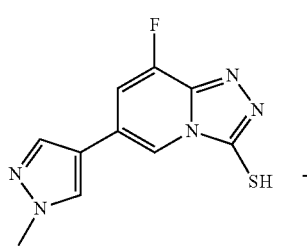

Intermediate F

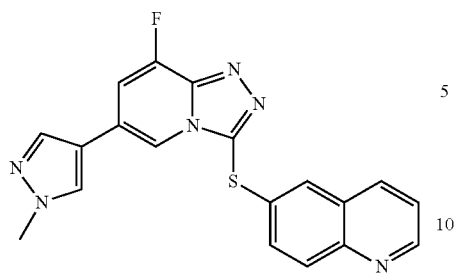

Example 65

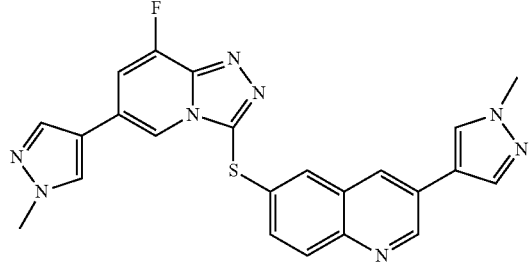

Example 66

A mixture of Intermediate F (40 mg, 0.160 mmol), 6-bromoquinoline (33.4 mg, 0.160 mmol), xantphos (18.57 mg, 0.032 mmol), Pd$_2$(dba)$_3$ (14.69 mg, 0.016 mmol) and DIPEA (0.111 ml, 0.642 mmol) in DMF (5 ml) was bubbled with N$_2$ for 15 min and then was heated to 120° C. for 5 h under MW radiation. The solvent was removed under reduced pressure. The residue was purified with by silica gel chromatography eluted with DCM/MeOH (from 100% to 90%) to afford the title compound as a brownish solid (20 mg, 29.8% yield). $^1$H-NMR (400 MHz, DMSO-d$_6$) δ ppm 8.87 (s, 1H), 8.50 (s, 1H), 8.35 (s, 1H), 8.29 (d, 1H), 8.04 (m, 1H), 7.98 (d, 1H), 7.91 (d, 1H), 7.85 (d, 1H), 7.65 (d, 1H), 7.53 (m, 1H), 3.84 (s, 3H). LCMS (method B): [M+H]$^+$=377, t$_R$=1.95 min.

Example 66

Reference Example 6-(8-fluoro-6-(1-methyl-1H-pyrazol-4-yl)-[1,2,4]triazolo[4,3-a]pyridin-3-ylthio)-3-(1-methyl-1H-pyrazol-4-yl)quinoline

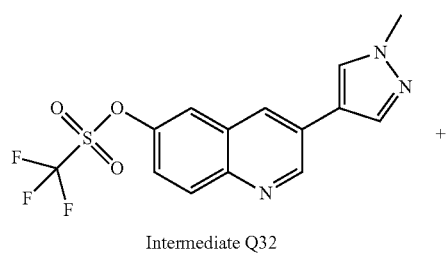

Intermediate Q32

+

Intermediate F

A mixture of Intermediate F (30 mg, 0.120 mmol), Intermediate Q32 (43.0 mg, 0.120 mmol), Pd$_2$(dba)$_3$ (11.01 mg, 0.012 mmol), xantphos (13.93 mg, 0.024 mmol) and DIPEA (0.084 ml, 0.481 mmol) in DMF (0.5 ml) was bubbled with N$_2$ for 15 min. The mixture was heated at 105° C. for 5 h under MW radiation. The solvent was removed under reduced pressure. The residue was purified by silica gel chromatography eluted with DCM/MeOH (from 100% to 90%) to afford the title compound as a white solid (20 mg, 32.8% yield). $^1$H-NMR (400 MHz, DMSO-d$_6$) δ ppm 9.14 (s, 1H), 9.50 (s, 1H), 8.34 (s, 3H), 8.03 (d, 2H), 7.94 (s, 1H), 7.85 (d, 1H), 7.69 (s, 1H), 7.58 (d, 1H), 3.90 (s, 3H), 3.83 (s, 3H). LCMS (method B): [M+H]$^+$=457, t$_R$=2.10 min.

Example 67

Method 8

3-(4,4-Difluoro-piperidin-1-yl)-6-[8-fluoro-6-(1-methyl-1H-pyrazol-4-yl)[1,2,4]triazolo[4,3-a]pyridin-3-ylsulfanyl]-quinoline

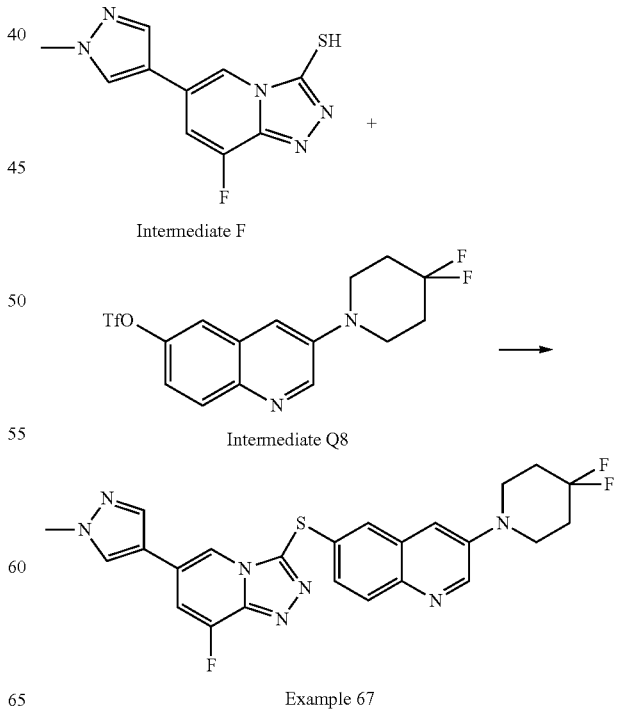

A mixture of Intermediate F (62.9 mg, 0.252 mmol), Intermediate Q8 (100 mg, 0.252 mmol), Pd₂(dba)₃ (23.10 mg, 0.025 mmol), xantphos (29.2 mg, 0.050 mmol) and DIPEA (0.132 ml, 0.757 mmol) in DMF (3 ml) was bubbled with argon for 10 min. Then the mixture was heated to 100° C. under microwave radiation for 45 min. The solvent was removed and the residue was purified by prep-HPLC to give white solid (35 mg, 28% yield). [Method 8]

Example 69

Method 9

4-(6-(6-(1-methyl-1H-pyrazol-4-yl)-[1,2,4]triazolo[4,3-a]pyridin-3-ylthio)quinolin-3-yl)morpholine

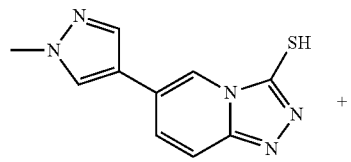

Intermediate E

+

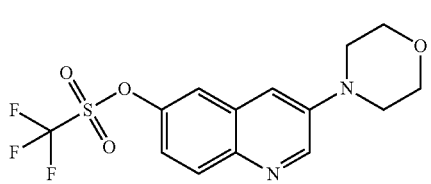

Intermediate Q33

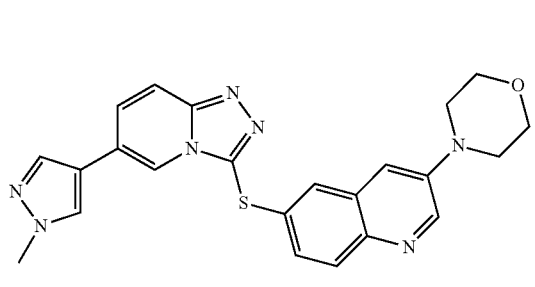

Example 69

A mixture of Intermediate E (1.27 g, 5.52 mmol), Intermediate Q33 (2 g, 5.52 mmol), Pd₂(dba)₃ (505 mg, 0.55 mmol), xantphos (639 mg, 1.10 mmol) and DIPEA (2.41 ml, 13.8 mmol) in DMF (20 ml) was bubbled with N₂ for 15 min and then was heated at 100° C. for 8 h. The solvent was removed under reduced pressure. The residue was purified by silica gel chromatography eluted with MeOH in DCM (from 0 to 10%) to afford the title compound as a yellow solid (1.35 g, 55% yield). [Method 9]

Example 73

Reference Compound 2-(4-(3-(3-(1-methyl-1H-pyrazol-4-yl)quinolin-6-ylthio)-[1,2,4]triazolo[4,3-a]pyridin-6-yl)-1H-pyrazol-1-yl)ethanol

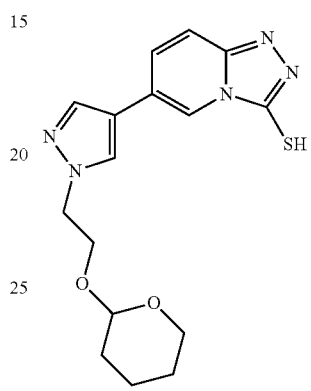

Intermediate G

+

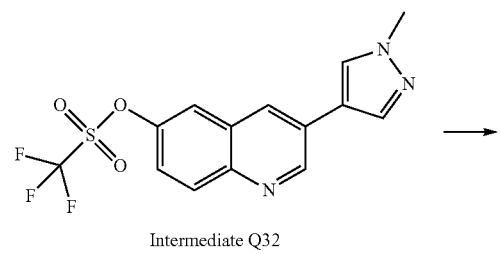

Intermediate Q32

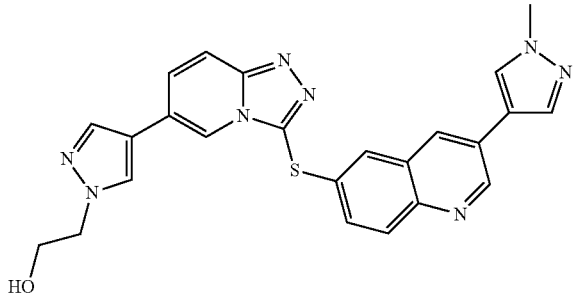

Example 73

The title compound was prepared using the same procedure as described in the synthesis of example 2. ¹H-NMR (400 MHz, DMSO-d₆) δ ppm 9.50 (d, 1H), 9.20 (s, 1H), 9.10 (s, 1H), 8.91 (s, 1H), 8.37 (m, 3H), 8.12 (m, 5H), 4.34 (m, 2H), 4.0 (s, 3H), 3.94 (t, 2H). LCMS (method B): [M+H]⁺=469, $t_R$=2.0 min.

Example 76

Method 10 According to Scheme 2)

1-(3-((3-(4-hydroxypiperidin-1-yl)quinolin-6-yl)thio)-[1,2,4]triazolo[4,3-a]pyridin-6-yl)-ethanone O-(2-hydroxyethyl)oxime 6-((6-Bromo-[1,2,4]triazolo[4,3-a]pyridin-3-yl)thio)-3-(4-((tert-butyldimethylsilyl)oxy) piperidin-1-yl) quinoline (76.1)

To a solution of Intermediate I (500 mg, 2.173 mmol) and Intermediate Q27 (1066 mg, 2.173 mmol) in DMF (8 ml) was added xantphos (251 mg, 0.435 mmol), Pd$_2$(dba)$_3$ (199 mg, 0.217 mmol) and DIEA (1.139 ml, 6.52 mmol), and the tube

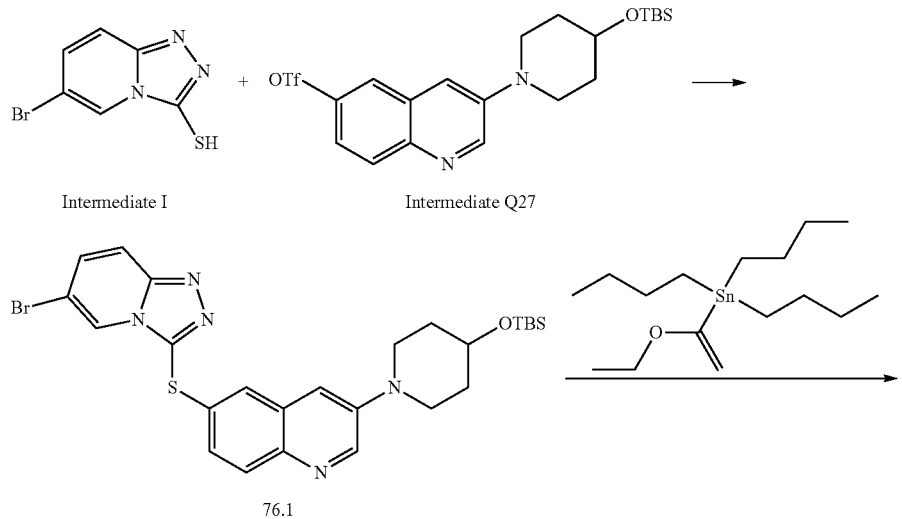

Intermediate I      Intermediate Q27

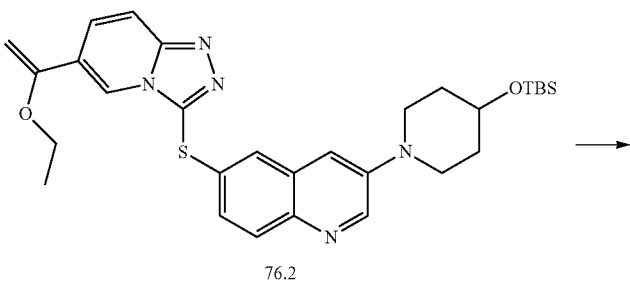

76.1

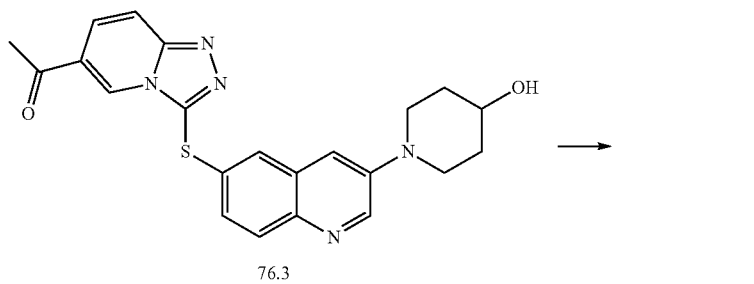

76.2

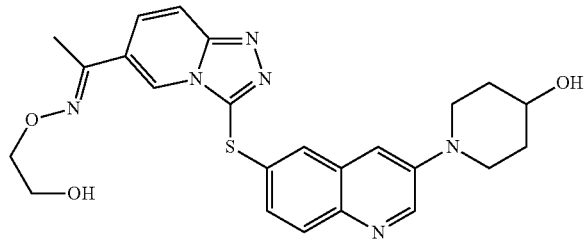

76.3

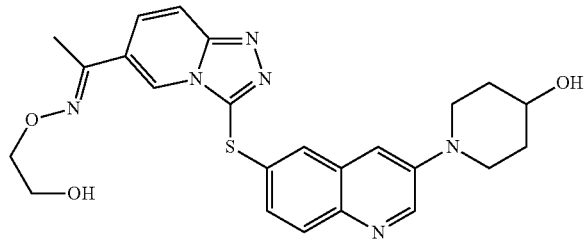

Example 76 was bubbled with Argon gas for several minutes, and the tube was sealed and heated to 100° C. for 5 hr. The reaction was monitored by TLC. The solvent was removed under reduced pressure and the residue was purified by flash chromatography and eluented with DCM/MeOH (40:1~20:1) to give desired product (76.1) as yellow powder (438 mg, yield 33.6%). $^1$H-NMR (400 MHz, CDCl$_3$) δ ppm 8.75 (s, 1H), 8.34 (s, 1H), 7.92 (d, 1H), 7.77 (d, 1H), 7.54 (s, 1H), 7.36-7.42 (m, 2H), 7.18 (s, 1H), 3.96-3.98 (m, 1H), 3.49-3.35 (m, 2H), 3.17-3.23 (m, 2H), 1.88-1.94 (m, 2H), 1.69-1.75 (m, 2H), 0.92 (s, 9H), 0.09 (s, 6H).

3-(4-((Tert-butyldimethylsilyl)oxy)piperidin-1-yl)-6-((6-(1-ethoxyvinyl)-[1,2,4]triazolo[4,3-a]pyridin-3-yl)thio)quinoline (76.2)

The solution of (76.1) (100 mg, 0.175 mmol) and PdCl$_2$(PPh$_3$)$_2$ (12.30 mg, 0.018 mmol) in 1,4-Dioxane (2 ml) was bubbled with Argon for 5 mins, Tin reagent (95 mg, 0.263 mmol) was added by injection and the mixture was bubbled with Argon for another 5 mins, and the tube was sealed and heated to 120° C. for 3 hr. Monitored the reaction by TLC. The solvent was evaporated and the residue was purified by flash chromatography and eluented with DCM/MeOH (40:1~20:1) to give pure desired product (76.2) as orange oil (90 mg, yield 90%). $^1$H-NMR (400 MHz, CDCl$_3$) δ ppm 8.73 (s, 1H), 8.41 (s, 1H), 7.97 (d, 1H), 7.78 (d, 1H), 7.57 (s, 2H), 7.42-7.49 (m, 2H), 7.21 (s, 1H), 4.68 (s, 1H), 4.36 (s, 1H), 3.88-3.98 (m, 3H), 3.48-3.53 (m, 2H), 3.18-3.23 (m, 2H), 1.88-1.91 (m, 2H), 1.66-1.74 (m, 2H), 1.38 (t, 3H), 0.91 (s, 9H), 0.09 (s, 6H).

1-(3-((3-(4-Hydroxypiperidin-1-yl)quinolin-6-yl)thio)-[1,2,4]triazolo[4,3-a]pyridin-6-yl)ethanone (76.3)

To the solution of (76.2) (90 mg, 0.160 mmol) in THF (2 ml) was added about 2 N HCl (1 mL) at rt and the mixture was continue stirred for 30 mins, Checked the reaction by LCMS and TLC. The reaction solution was neutralized with sat-.NaHCO$_3$ aqueous until the pH to 8~9 and extracted with DCM for three times, the combined organic layers were washed with brine, dried over Na$_2$SO$_4$, filtered and concentrated to give crude product which was purified by flash chromatography and eluented with DCM/MeOH (40:1~20:1) to obtained pure desired product (76.3) as yellow solid (42 mg, yield 62.5%). $^1$H-NMR (400 MHz, MeOH-d$_4$) δ ppm 8.95 (s, 1H), 8.72 (s, 1H), 7.98 (d, 1H), 7.87 (d, 1H), 7.80 (d, 1H), 7.75 (s, 1H), 7.39-7.43 (m, 2H), 3.78-3.84 (m, 1H), 3.68-3.74 (m, 2H), 3.02-3.08 (m, 2H), 2.57 (s, 3H), 1.98-2.01 (m, 2H), 1.62-1.71 (m, 2H). LCMS (method A): [M+H]$^+$= 420.1, t$_R$=2.013 min.

(E)-1-(3-((3-(4-Hydroxypiperidin-1-yl)quinolin-6-yl)thio)-[1,2,4]triazolo[4,3-a]pyridin-6-yl)ethanone O-(2-hydroxyethyl)oxime (Example 76)

To the solution of (76.3) (30 mg, 0.072 mmol) and 2-(aminooxy)ethanol (6.06 mg, 0.079 mmol) in MeOH (3 ml) was added a drop of 2 N HCl, sealed the tube and stirred at 50° C. for overnight. The solvent was evaporated under reduced pressure to give crude desired product as orange oil which was purified by chromatography and eluent with DCM/MeOH (30:1-20:1) to obtained pure desired product as yellow solid (25 mg, 69.4%).

Example 77

Method 11 According to Scheme 2

(E)-1-(3-((3-morpholinoquinolin-6-yl)thio)-[1,2,4]triazolo[4,3-a]pyridin-6-yl)ethanone oxime

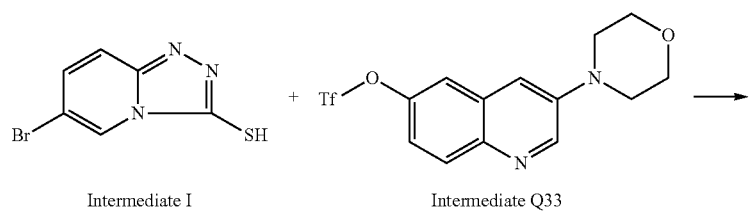

Intermediate I        Intermediate Q33

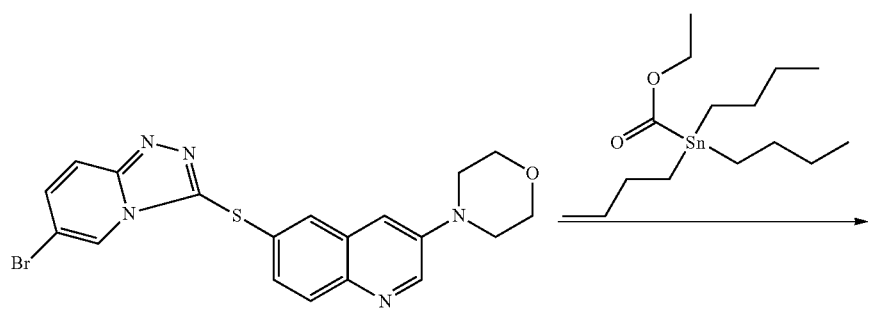

77.1

-continued

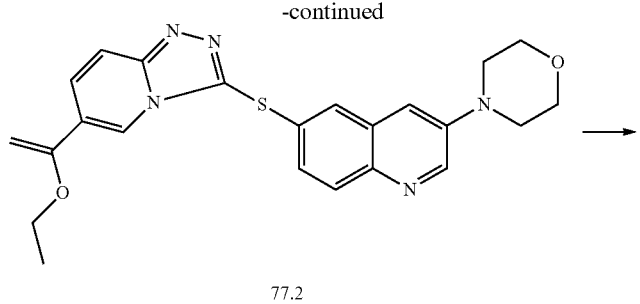

77.2

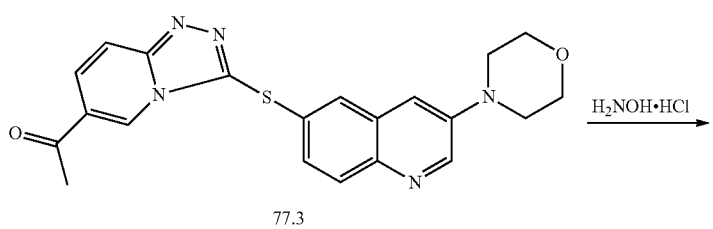

77.3

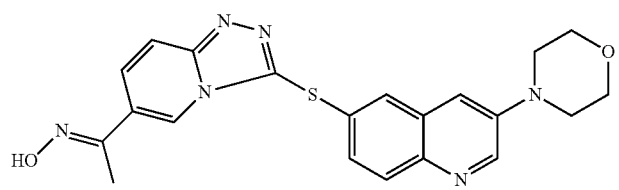

Example 77

4-(6-((6-bromo-[1,2,4]triazolo[4,3-a]pyridin-3-yl)thio)quinolin-3-yl)morpholine (77.1)

A microwave tube was charged with Intermediate I (127 mg, 0.552 mmol), Intermediate Q33 (200 mg, 0.552 mmol), Pd$_2$(dba)$_3$ (50.5 mg, 0.055 mmol), Xantphos (35.1 mg, 0.061 mmol) and DIPEA (143 mg, 1.104 mmol), followed by addition of DMF (8 ml), after which the reaction was bubbled by N2 for 5 min, sealed and irritated by microwave at 110° C. for 45 min. The reaction was evaporated to dryness and the residue was purified by flash chromatography (CombiFlash, ISCO, eluent MeOH/DCM from 0 to 15%) to afford the title compound (110 mg, yield 45.1%). LCMS (method A): [M+H]$^+$=441.5, t$_R$=2.34 min. $^1$H NMR (400 MHz, CDCl$_3$) δ ppm 3.29 (br. s., 4H) 3.92 (br. s., 4H) 7.24 (br. s., 1H) 7.43 (t, 2H) 7.59 (s, 1H) 7.79 (d, 1H) 7.98 (d, 1H) 8.36 (s, 1H) 8.77 (br. s., 1H)

4-(6-((6-(1-ethoxyvinyl)-[1,2,4]triazolo[4,3-a]pyridin-3-yl)thio)quinolin-3-yl)morpholine (77.2)

The solution of (77.1) (110 mg, 0.249 mmol) and PdCl$_2$(PPh$_3$)$_2$ (17.45 mg, 0.025 mmol) in 1,4-dioxane (4 ml) was bubbled by N$_2$ for 5 min. Tributyl(1-ethoxyvinyl)stannane (135 mg, 0.373 mmol) was added. The reaction tube was flushed by N2 for 5 min again and sealed. The sealed-tube was stirred at 120° C. for 2 h. The reaction was evaporated to dryness and the residue was directly used in the next step. LCMS (method A): [M+H]$^+$=433.6, t$_R$=2.54 min.

1-(3-((3-morpholinoquinolin-6-yl)thio)-[1,2,4]triazolo[4,3-a]pyridin-6-yl)ethanone (77.3)

The crude (77.2) was dissolved in THF (20 ml) and 1 ml of HCl (2N) was added. The mixture was stirred at rt for 10 min. The mixture was neutralized by saturated aqueous NaHCO$_3$ and evaporated to dryness. The residue was purified by column chromatography (CombiFlash-ISCO, eluent DCM/MeOH from 20/1 to 8/1 for 40 min gradiently) to afford the title compound (40 mg, yield 39.8% over 2 steps). LCMS (method A): [M+H]$^+$=405.6, t$_R$=2.08 min. $^1$H NMR (400 MHz, CDCl$_3$) δ ppm 2.57 (s., 3H) 3.17-3.34 (t, 4H) 3.82-4.00 (t, 4H) 7.15 (d, 1H) 7.46 (d, 1H) 7.64 (s, 1H) 7.88 (s, 2H) 7.93 (d, 1H) 8.76 (d, 1H) 8.78 (s, 1H)

(E)-1-(3-((3-morpholinoquinolin-6-yl)thio)-[1,2,4]triazolo[4,3-a]pyridin-6-yl)ethanone oxime (Example 77)

To a solution of (77.3) (10 mg, 0.025 mmol) and hydroxylamine hydrochloride (6.86 mg, 0.099 mmol) in EtOH (5 ml) was added 0.01 ml of HCl (2 N) and the mixture was stirred in a sealed tube at 80° C. overnight. The mixture was evaporated to dryness and dissolved in H$_2$O again, which was neutralized Example 78

Method 12

(E)-1-(3-((3-morpholinoquinolin-6-yl)thio)-[1,2,4]triazolo[4,3-a]pyridin-6-yl)ethanone O-(2-hydroxyethyl)oxime

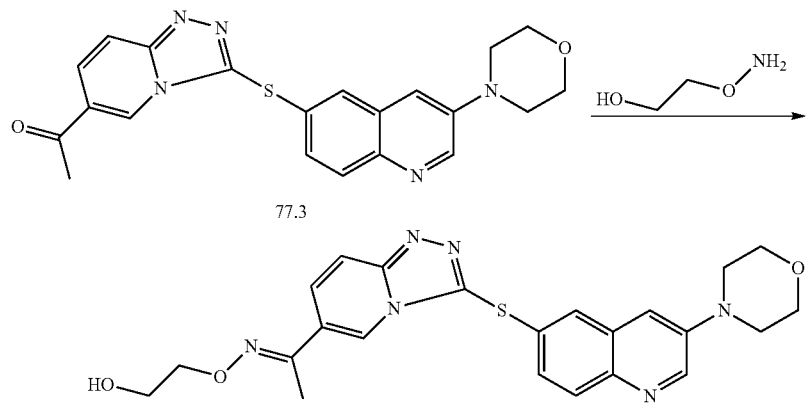

Example 78

To a solution of 1-(3-((3-morpholinoquinolin-6-yl)thio)-[1,2,4]triazolo[4,3-a]pyridin-6-yl)ethanone (77.3) (15 mg, 0.037 mmol) and 2-(aminooxy)ethanol (5.7 mg, 0.074 mmol) in EtOH (5 ml) was added 2 drops of HCl (2 N) and the mixture was stirred in a sealed tube at 80° C. overnight. The mixture was evaporated to dryness and the residue was triturated in H₂O. The resulted precipitate was filtered quickly and dried to afford the title compound as HCl salt (11.1 mg, yield 55.8%).

Example 79

Method 13 According to Scheme 2

(E)-1-(3-(3-(morpholinomethyl)quinolin-6-ylthio)-[1,2,4]triazolo[4,3-a]pyridin-6-yl)ethanone oxime

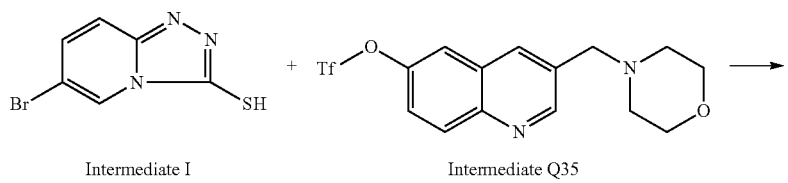

Intermediate I      Intermediate Q35

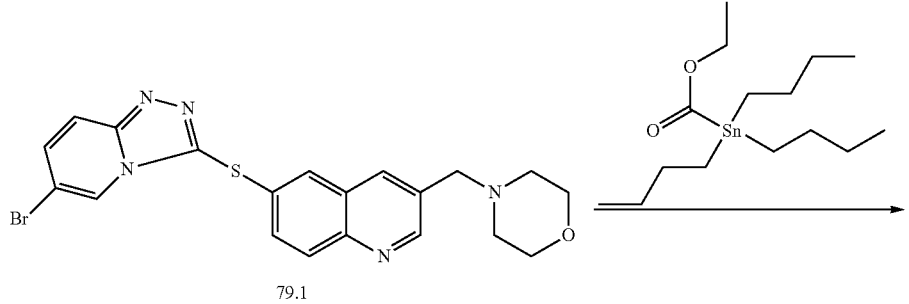

79.1

-continued

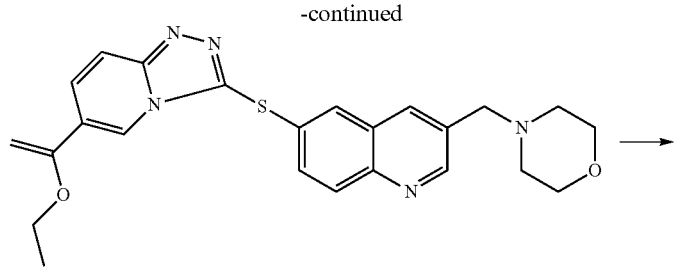

79.2

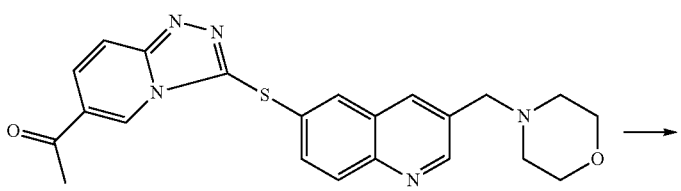

79.3

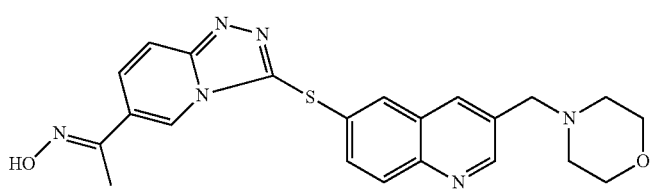

Example 79

4-((6-((6-bromo-[1,2,4]triazolo[4,3-a]pyridin-3-yl)thio)quinolin-3-yl)methyl)-morpholine (79.1) (Method 13A)

A microwave tube was charged with Intermediate I (200 mg, 0.869 mmol), Intermediate Q35 (327 mg, 0.869 mmol), Pd$_2$(dba)$_3$ (80 mg, 0.087 mmol), Xantphos (55.3 mg, 0.096 mmol) and DIPEA (225 mg, 1.738 mmol), followed by addition of DMF (6 ml), after which the reaction was bubbled by N$_2$ for 5 min, sealed and stirred at 80° C. for 2 h. The reaction was evaporated to dryness and the residue was purified by flash chromatography (CombiFlash, ISCO, eluent MeOH/DCM from 0 to 15%) to afford the title compound (167 mg, yield 42.1%). LCMS (method A): [M+H]$^+$=458.1, t$_R$=1.59 min.

4-((6-((6-(1-ethoxyvinyl)-[1,2,4]triazolo[4,3-a]pyridin-3-yl)thio)quinolin-3-yl)methyl)morpholine (79.2) (Method 13B)

The solution of (79.1) (140 mg, 0.307 mmol) and PdCl$_2$(PPh$_3$)$_2$ (32.3 mg, 0.046 mmol) in 1,4-dioxane (6 ml) was bubbled by N$_2$ for 5 min. Tributyl(1-ethoxyvinyl)stannane (222 mg, 0.614 mmol) was added. The reaction tube was flushed (not bubbled) by N$_2$ for 5 min again and sealed. The sealed-tube was stirred at 120° C. for 2 h. The reaction was evaporated to dryness and the residue was purified by flash chromatography (CombiFlash, ISCO, eluent MeOH/DCM from 0 to 15%) to afford the title compound (62.8 mg, yield 45.7%). LCMS (method A): [M+H]$^+$=448.1, t$_R$=3.09 min.

1-(3-((3-(morpholinomethyl)quinolin-6-yl)thio)-[1,2,4]triazolo[4,3-a]pyridin-6-yl)ethanone hydrochloride (79.3) (Method 13C)

(79.2) (62.8 mg, 0.140 mmol) was dissolved in THF (10 ml) and 0.5 ml of HCl (2N) was added. The mixture was stirred at rt for 10 min. A precipitate appeared. 5 ml of MeOH was added and the solution became clean. The mixture was stirred for another 10 min. LCMS showed the starting material was consumed completely and about 20% di-methyl ketal side-product seems to be formed. The mixture was evaporated to dryness, which was used in next step directly. LCMS (method A): [M+H]$^+$=420.0, t$_R$=2.12 min.

(E)-1-(3-(3-(morpholinomethyl)quinolin-6-ylthio)-[1,2,4]triazolo[4,3-a]pyridin-6-yl)ethanone oxime (Example 79) (Method 13D)

To a solution of (79.3) (23 mg, 0.047 mmol) and hydroxylamine hydrochloride (6.49 mg, 0.093 mmol) in EtOH (5 ml) was added 2 drops of HCl (2 N) by a 1-ml syringe to reach pH about 5 and the mixture was stirred in a sealed tube at 80° C. overnight. The mixture was evaporated to dryness and dissolved in H2O again, which was neutralized immediately by NaHCO$_3$ until pH reached about 9. The resulted precipitate was filtered quickly. The filtrate was extracted by DCM/MeOH (10/1, 2×). The combined organic layers were washed by water again, dried over Na$_2$SO$_4$, filtered and evaporated to afford target the title compound (16.24 mg, yield 80%).

Example 80

Method 14

(E)-1-(3-((3-(morpholinomethyl)quinolin-6-yl)thio)-[1,2,4]triazolo[4,3-a]pyridin-6-yl)ethanone O-(2-hydroxyethyl)oxime (Example 80)

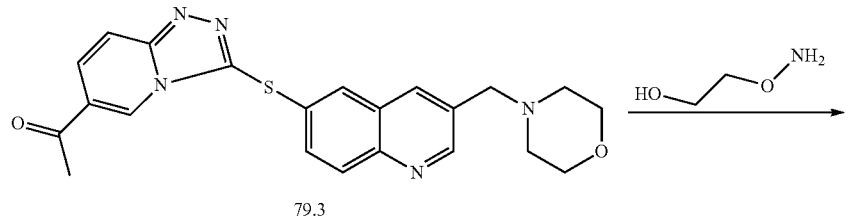

79.3

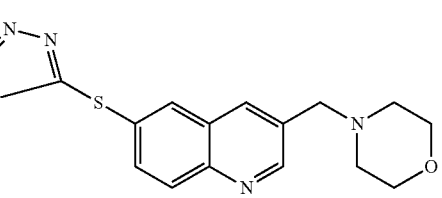

Example 80

To a solution of 1-(3-(3-(morpholinomethyl)quinolin-6-ylthio)-[1,2,4]triazolo[4,3-a]pyridin-6-yl)ethanone hydrochloride (79.3) (23 mg, 0.047 mmol) and 2-(aminooxy)ethanol (10.80 mg, 0.140 mmol) in MeOH (5 ml) was added 2 drops of HCl (2 N) by a 1-ml syringe to reach pH about 3 and the mixture was stirred in a sealed tube at 85° C. for 3 h. The mixture was evaporated to dryness and the residue was dissolved in water. The solution was neutralized by adding solid NaHCO$_3$ until pH reached 9, then extracted by DCM (3×). The combined organic layers were washed by water again, dried over Na$_2$SO$_4$, filtered and evaporated. The residue was purified by preparative base HPLC (gradient eluent NB from 20/80 to 95/5. mobile phase A: NH$_4$OH/CH$_3$CN 0.04%; mobile phase B: NH$_4$OH/H$_2$O 0.04%). The desired fractions were collected, evaporated by BUCHI under 30 mbar at 35° C. to remove CH$_3$CN. The remained solution was lyophilized to afford the title compound (12.2 mg, yield 54.2%).

Example 81

Method 15 According to Scheme 2

(S,E)-1-(3-(3-(3-(dimethylamino)pyrrolidin-1-yl)quinolin-6-ylthio)-[1,2,4]triazolo[4,3-a]pyridin-6-yl)ethanone O-2-hydroxyethyl oxime hydrochloride

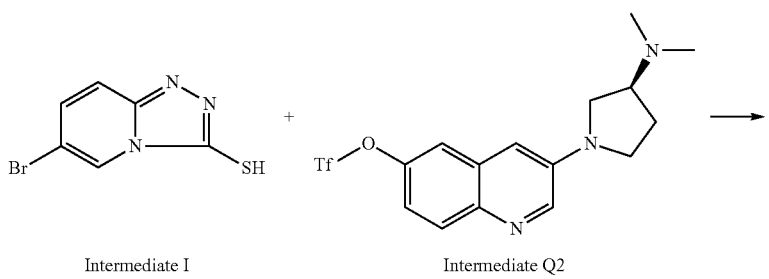

Intermediate I   Intermediate Q2

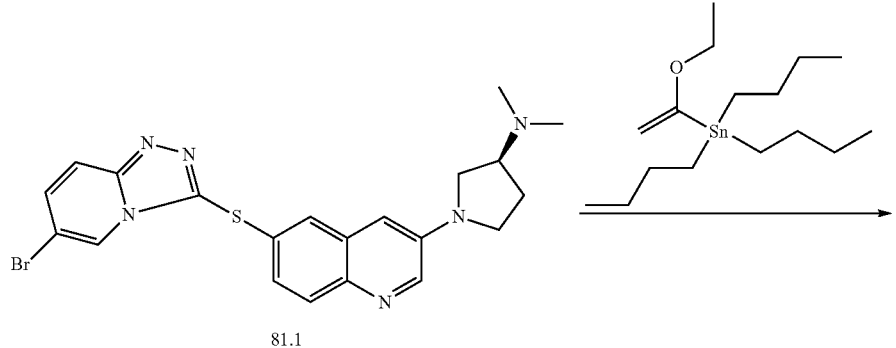

81.1

81.2

(S)-1-(6-((6-bromo-[1,2,4]triazolo[4,3-a]pyridin-3-yl)thio)quinolin-3-yl)-N,N-dimethylpyrroli-din-3-amine (81.1)

The title compound was prepared using the same procedure as described for 79.1 (method 13A). LCMS (method A): [M+H]$^+$=469.0, $t_R$=1.64 min.

(S)-1-(6-(6-(1-ethoxyvinyl)-[1,2,4]triazolo[4,3-a]pyridin-3-ylthio)quinolin-3-yl)-N,N-dimethylpyrroli-din-3-amine (81.2)

The solution of (81.1) (256.5 mg, 0.546 mmol) and PdCl$_2$(PPh$_3$)$_2$ (38.4 mg, 0.055 mmol) in DMF (10 ml) was bubbled by N$_2$ for 5 min. Tributyl(1-ethoxyvinyl)stannane (296 mg, 0.820 mmol) was added. The reaction tube was flushed by N$_2$ for 5 min again and sealed. The sealed-tube was stirred at 85° C. for 16 h. The mixture was evaporated to dryness and the residue was purified by flash chromatography (CombiFlash, ISCO, eluent MeOH/DCM from 0 to 10%) to afford the title compound (35 mg, yield 13.91%). LCMS (method A): [M+H]$^+$=461.2, $t_R$=1.96 min.

(S)-1-(3-(3-(3-(dimethylamino)pyrrolidin-1-yl)quinolin-6-ylthio)-[1,2,4]triazolo[4,3-a]pyridin-6-yl)ethanone hydrochloride (81.3)

(81.2) (35 mg, 0.076 mmol) was dissolved in THF (5 ml) and 0.1 ml of HCl (2N) was added. The mixture was stirred at rt for 30 min. The mixture was evaporated to dryness, which was used in next step directly. LCMS (method A): [M+H]$^+$=433.2, $t_R$=1.51 min.

(S,E)-1-(3-(3-(3-(dimethylamino)pyrrolidin-1-yl)quinolin-6-ylthio)-[1,2,4]triazolo[4,3-a]pyridin-6-yl)ethanone O-2-hydroxyethyl oxime hydrochloride (Example 81)

To a solution of (81.3) (12 mg, 0.026 mmol) and 2-(aminooxy)ethanol (9.86 mg, 0.128 mmol) in MeOH (5 ml) was added 2 drops of HCl (2 N) by a 1-ml syringe to reach pH about 3 and the mixture was stirred in a sealed tube at 85° C. for 16 h. The mixture was evaporated to dryness and the residue was purified by preparative acid HPLC (gradient eluent NB from 20/80 to 95/5. mobile phase A: TFA/CH$_3$CN 0.05%; mobile phase B: TFA/H$_2$O 0.05%). The desired fractions were collected, evaporated by BUCHI under 30 mbar at 35° C. to remove CH$_3$CN. The remained solution was lyophilized to afford title compound (11.5 mg, yield 85%).

Example 82

Method 16

(S,E)-1-(3-(3-(3-(dimethylamino)pyrrolidin-1-yl)quinolin-6-ylthio)-[1,2,4]triazolo[4,3-a]pyridin-6-yl)ethanone oxime hydrochloride To a solution of (81.3) (12 mg, 0.026 mmol) and hydroxylamine hydrochloride (7.11 mg, 0.102 mmol) in MeOH (3 ml) was added 2 drops of HCl (2N) by a 1-ml syringe to reach pH about 3 and the mixture was stirred in a sealed tube at 85° C. for 3 h. The mixture was evaporated to dryness and the residue was purified by preparative acid HPLC (gradient eluent NB from 20/80 to 95/5. mobile phase A: TFA/CH$_3$CN 0.05%; mobile phase B: TFA/H$_2$O 0.05%). The desired fractions

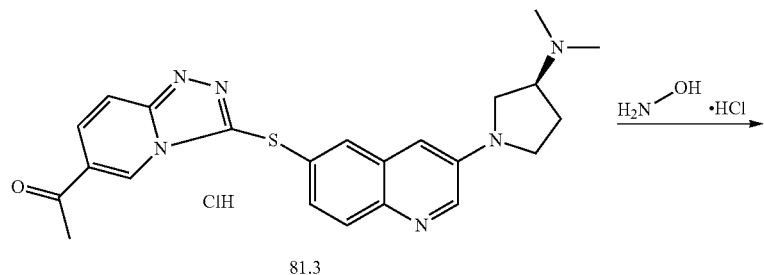

81.3

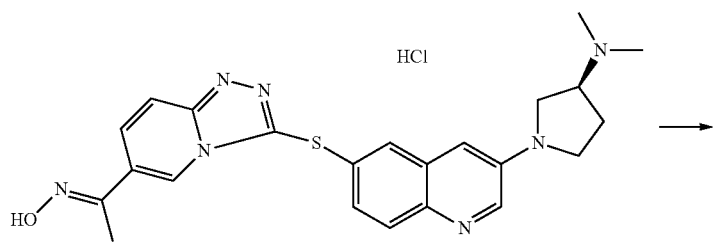

Example 82

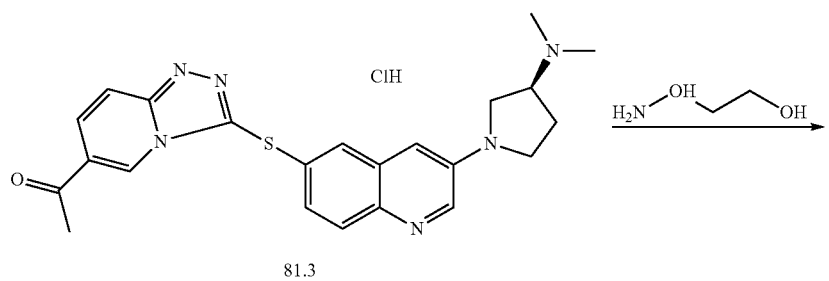

81.3

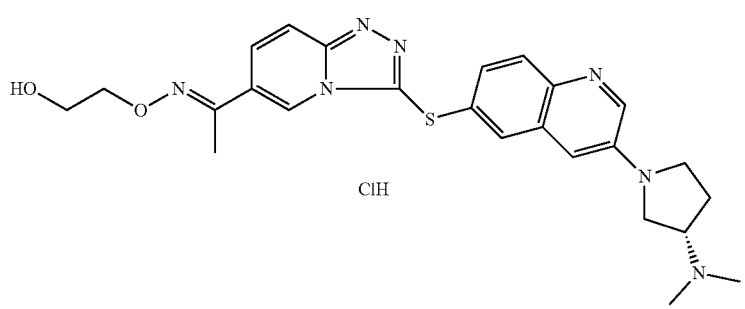

Example 81 were collected, evaporated by BUCHI under 30 mbar at 40° C. to remove CH₃CN. The remained solution was lyophilized to afford the title compound (8.1 mg, yield 65.4%).

Example 83

Method 17 According to Scheme 2

(E)-1-(3-(3-(tetrahydro-2H-pyran-4-ylamino)quinolin-6-ylthio)-[1,2,4]triazolo[4,3-a]pyridin-6-yl)ethanone O-2-hydroxyethyl oxime hydrochloride 6-(6-bromo-[1,2,4]triazolo[4,3-a]pyridin-3-ylthio)-N-(tetrahydro-2H-pyran-4-yl)quinolin-3-amine (83.1)

A microwave tube was charged with Intermediate I (200 mg, 0.869 mmol), Intermediate Q9 (327 mg, 0.869 mmol), Pd₂(dba)₃ (80 mg, 0.087 mmol), Xantphos (55.3 mg, 0.096 mmol) and DIPEA (225 mg, 1.738 mmol), followed by addition of DMF (5 ml), after which the reaction was bubbled by N₂ for 5 min, sealed and stirred at 80° C. for 16 h. The reaction was evaporated to dryness and the residue was purified by flash chromatography (CombiFlash, ISCO, eluent MeOH/

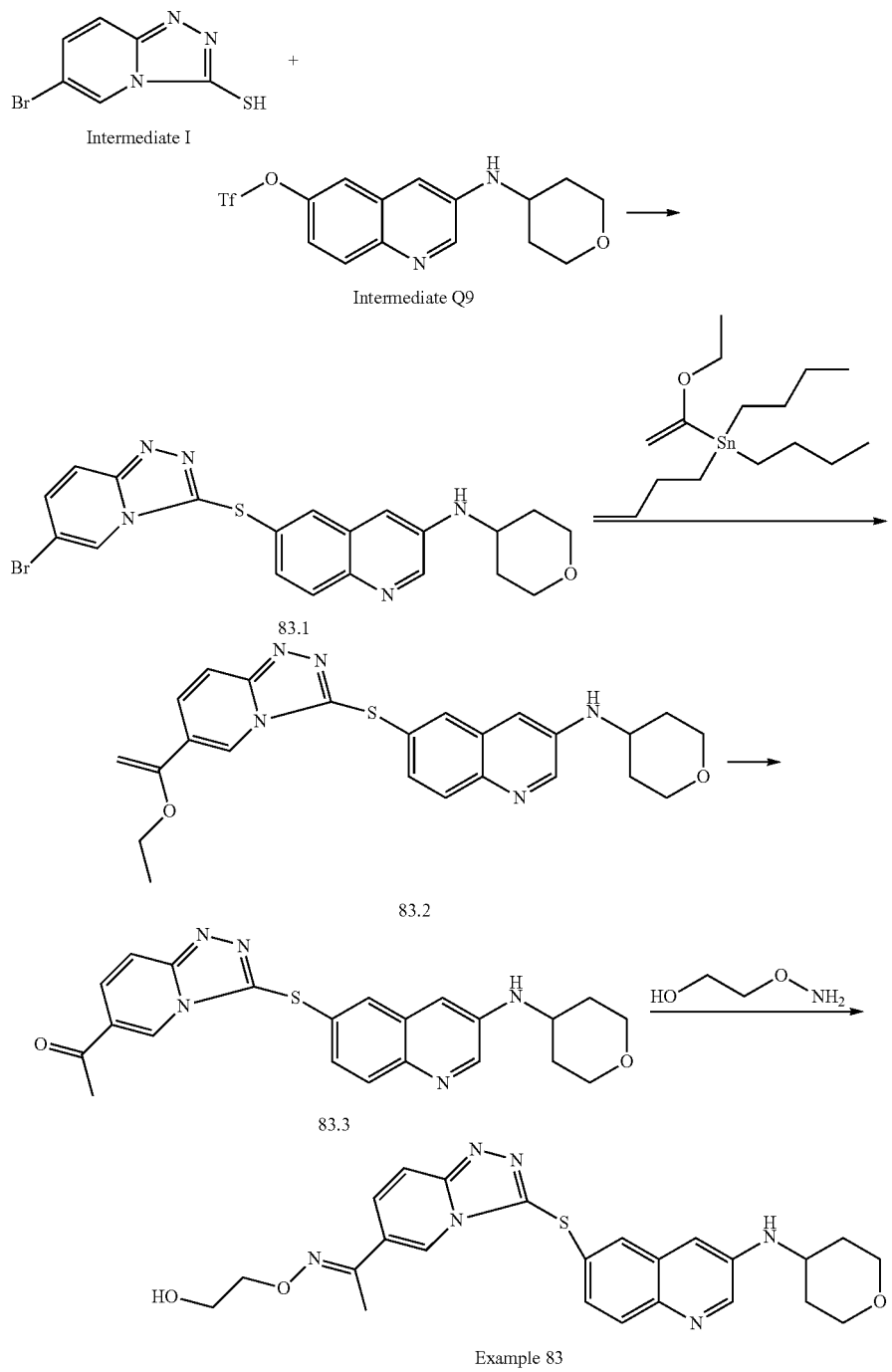

DCM from 0 to 15%) to afford the title compound (150 mg, yield 37.8%). LCMS (method A): [M+H]$^+$=456.0, $t_R$=2.33 min.

7-((6-(1-ethoxyvinyl)-[1,2,4]triazolo[4,3-a]pyridin-3-yl)thio)-N-(tetrahydro-2H-pyran-4-yl)quinolin-3-amine (83.2)

The title compound was prepared using the same procedure as described in the synthesis of 79.2 (method 13B). LCMS (method A): [M+H]$^+$=448.2, $t_R$=2.55 min.

1-(3-(3-(tetrahydro-2H-pyran-4-ylamino)quinolin-6-ylthio)-[1,2,4]triazolo[4,3-a]pyridin-6-yl)ethanone hydrochloride (83.3)

The title compound was prepared using the same procedure as described in the synthesis of 81.3 (method 15C). LCMS (method A): [M+H]$^+$=420.1, $t_R$=2.10 min.

(E)-1-(3-(3-(tetrahydro-2H-pyran-4-ylamino)quinolin-6-ylthio)-[1,2,4]triazolo[4,3-a]pyridin-6-yl)ethanone O-2-hydroxyethyl oxime hydrochloride (Example 83)

The title compound was prepared using the same procedure as described in the synthesis of Example 81 (method 15D).

Example 85

Method 18 According to Scheme 2

(S,E)-1-{3-[3-(3-dimethylamino-pyrrolidin-1-yl)-quinolin-6-ylthio]-8-fluoro-[1,2,4]triazolo[4,3-a]pyridin-6-yl}-ethanone O-(2-hydroxy-ethyl)-oxime hydrochloride

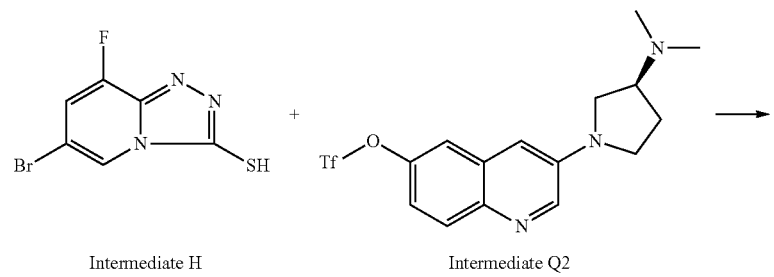

Intermediate H    Intermediate Q2

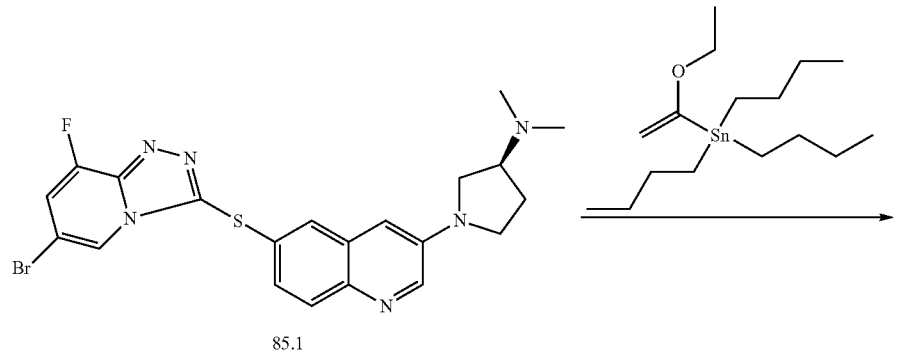

85.1

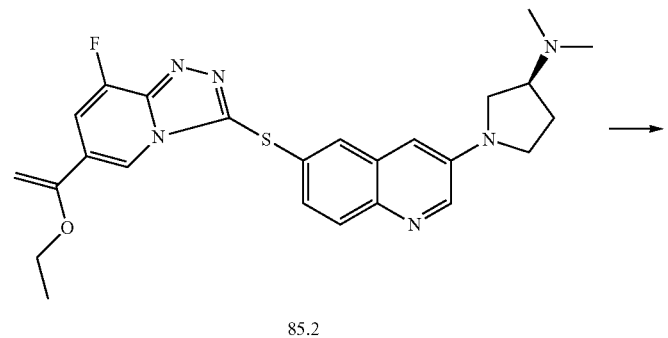

85.2

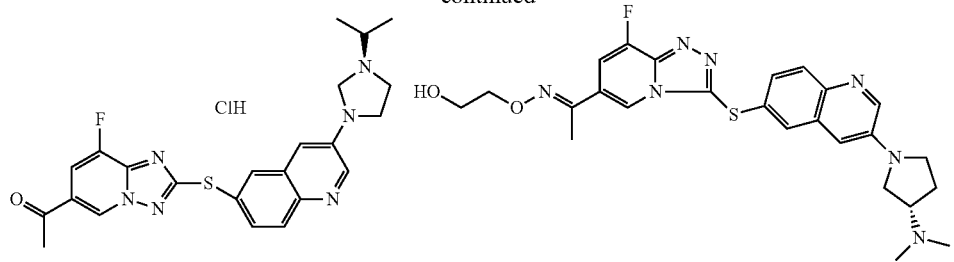

Example 85

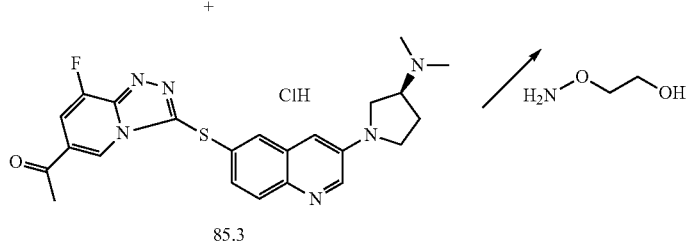

(S)-1-(6-(6-bromo-8-fluoro-[1,2,4]triazolo[4,3-a]pyridin-3-ylthio)quinolin-3-yl)-N,N-dimethylpyrrolidin-3-amine (85.1)

A microwave tube was charged with Intermediate H (600 mg, 2.419 mmol), Intermediate Q2 (314 mg, 0.806 mmol), Pd$_2$(dba)$_3$ (148 mg, 0.161 mmol), (9,9-dimethyl-9H-xanthene-4,5-diyl)bis(diphenylphosphine) (103 mg, 0.177 mmol) and DIPEA (417 mg, 3.23 mmol), followed by addition of DMF (20 ml), after which the reaction was bubbled by N2 for 5 min, sealed and irritated by microwave at 100° C. for 40 min. Then another 0.2 eq. of Pd$_2$(dba)$_3$ and another 0.22 eq. of Xantphos was added. The mixture was irritated by microwave at 100° C. for another 40 min and then stirred at 100° C. for 5 h. The mixture was evaporated to dryness and the residue was purified by flash chromatography (CombiFlash, ISCO, eluent MeOH/DCM from 0 to 10%) to afford the title compound (185 mg, 66.4% pure, yield 31.3%). LCMS (method A): [M+H]$^+$=486.8, $t_R$=2.30 min.

(S)-1-(6-(6-(1-ethoxyvinyl)-8-fluoro-[1,2,4]triazolo[4,3-a]pyridin-3-ylthio)quinolin-3-yl)-N,N-dimethylpyrrolidin-3-amine (85.2)

The solution of (85.1) (175 mg, 0.359 mmol) and PdCl$_2$(PPh$_3$)$_2$ (37.8 mg, 0.054 mmol) in DMF (10 ml) was bubbled by N2 for 5 min. tributyl(1-ethoxyvinyl)stannane (195 mg, 0.539 mmol) was added. The reaction tube was flushed by N$_2$ for 5 min again and sealed. The sealed-tube was stirred at 90° C. for 2 h. Then the reaction was continued at 110° C. for 16 h. The mixture was evaporated to dryness and the residue was purified by column chromatography (CombiFlash, ISCO, eluent MeOH/DCM from 0 to 10%) to afford the target product (40 mg, 30% pure, yield 6.98%). LCMS (method A): [M+H]$^+$=479.1, $t_R$=1.92 min.

(S)-1-(3-(3-(3-(dimethylamino)pyrrolidin-1-yl)quinolin-6-ylthio)-8-fluoro-[1,2,4]triazolo[4,3-a]pyridin-6-yl)ethanone hydrochloride (85.3) and (S)-1-(2-((3-(3-(dimethylamino)pyrroli-din-1-yl)quinolin-6-yl)thio)-8-fluoro-[1,2,4]triazolo[1,5-a]pyridin-6-yl)ethanone (85.4)

To a solution of (85.2) (40 mg, 0.025 mmol, 30% pure) in THF (10 ml) was added 2 drops of HCl (2 N) and the mixture was stirred for 5 min. The mixture was evaporated to dryness and the residue was purified by preparative HPLC (gradient eluent: NB from 20/80 to 95/5, A=CH3CN with 0.05% TFA, B=H2O with 0.05% TFA) to afford the title compounds as HCl salt.

(S)-1-(3-(3-(3-(dimethylamino)pyrrolidin-1-yl)quinolin-6-ylthio)-8-fluoro-[1,2,4]triazolo[4,3-a]pyridin-6-yl)ethanone hydrochloride (85.3, 4 mg, yield 32.8%). LCMS (method A): [M+H]$^+$=451.1, $t_R$=1.46 min. $^1$H NMR (400 MHz, DEUTERIUM OXIDE) δ ppm 2.32-2.46 (m, 1H) 2.61 (s, 3H) 2.67 (m, 1H) 2.97 (s, 6H) 3.49-3.63 (m, 1H) 3.67-3.84 (m, 2H) 3.90-4.02 (m, 1H) 4.09-4.27 (m, 1H) 7.59 (d, 1H) 7.72-7.83 (m, 2H) 7.87-7.97 (m, 2H) 8.61 (s, 1H) 8.89 (s, 1H).

(S)-1-(2-((3-(3-(dimethylamino)pyrrolidin-1-yl)quinolin-6-yl)thio)-8-fluoro-[1,2,4]triazolo-[1,5-a]pyridin-6-yl)ethanone (85.4, 4 mg, yield 32.8%). LCMS (method A): [M+H]$^+$=451.1, $t_R$=1.77 min. $^1$H NMR (400 MHz, DEUTERIUM OXIDE) δ ppm 2.28-2.47 (m, 1H) 2.61-2.74 (m, 1H) 2.84 (s, 3H) 2.98 (s, 6H) 3.47-3.62 (m, 1H) 3.67-3.81 (m, 2H) 3.95 (t, 1H) 4.14-4.24 (m, 1H) 7.52 (d, 1H) 7.60 (d, 1H) 7.76 (br. s., 1H) 7.85 (s, 1H) 7.94 (d, 1H) 8.58 (br. s., 1H) 9.26 (s, 1H).

(S,E)-1-{3-[3-(3-dimethylamino-pyrrolidin-1-yl)-quinolin-6-ylthio]-8-fluoro-[1,2,4]triazolo[4,3-a]pyridin-6-yl}-ethanone O-(2-hydroxy-ethyl)-oxime hydrochloride (Example 85)

The title compound was prepared from (85.3) using the same procedure as described in the synthesis of Example 81 (method 15D).

Example 86

Method 19

(E)-1-(3-(3-(4-methylpiperazin-1-yl)quinolin-6-ylthio)-[1,2,4]triazolo[4,3-a]pyridin-6-yl)ethanone O-2-hydroxyethyl oxime

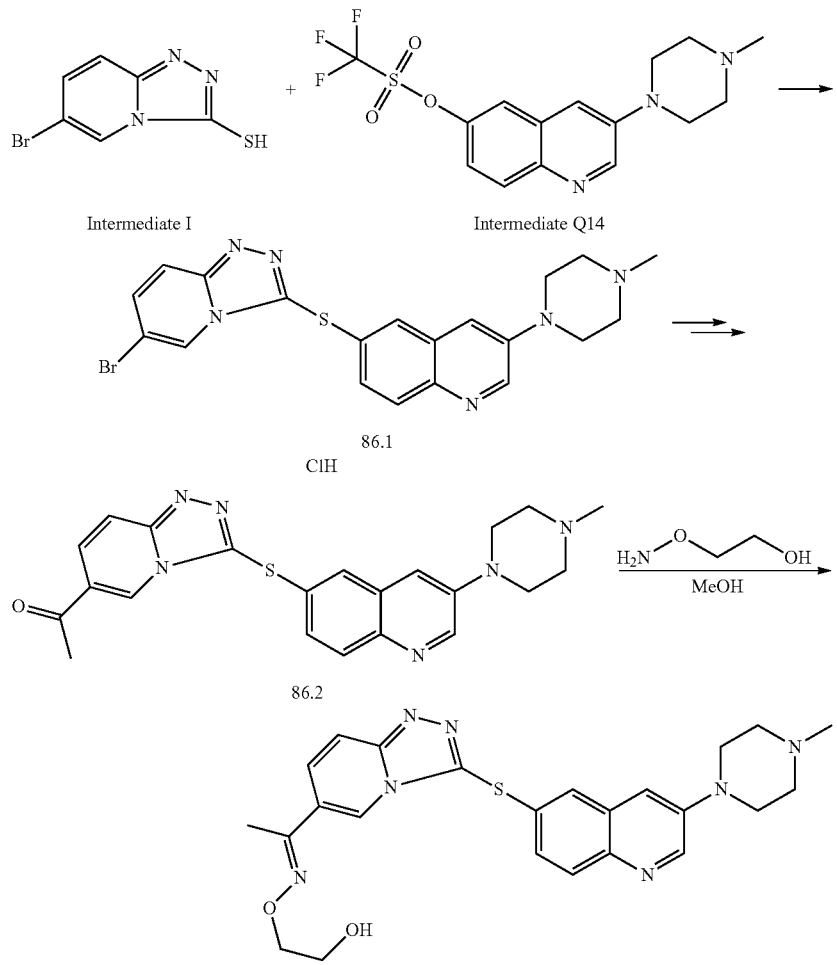

Example 86

6-(6-bromo-[1,2,4]triazolo[4,3-a]pyridin-3-ylthio)-3-(4-methylpiperazin-1-yl)quinoline (86.1)

A solution of Intermediate I (138 mg, 0.599 mmol), Intermediate Q14 (150 mg, 0.4 mmol), Pd$_2$(dba)$_3$ (36.6 mg, 0.04 mmol), xantphos (46.2 mg, 0.08 mmol) and DIPEA (0.14 ml, 0.799 mmol) in DMF (6 ml) was bubbled by N$_2$ for 10 min, and then heated at 100° C. for 4 hours in oil bath. The reaction mixture was quenched with water and extracted with EtOAc for three times. The combined extract was washed with brine and dried over anhydrous Na$_2$SO$_4$. Solvent was evaporated and the residue was purified by silica gel chromatography to afford the title compound (0.08 g, 44% yield). LCMS (method A): [M+H]$^+$=455/457, t$_R$=1.7 min.

1-(3-(3-(4-methylpiperazin-1-yl)quinolin-6-ylthio)-[1,2,4]triazolo[4,3-a]pyridin-6-yl)ethanone (86.2)

A solution of (86.1) (80 mg, 0.176 mmol) and PdCl$_2$(PPh$_3$)$_2$ (12.3 mg, 0.018 mmol) in dioxane (6 ml) was bubbled by N$_2$ for 10 min, then tributyl(1-ethoxyvinyl)stannane (127 mg, 0.351 mmol) was added and the solution was heated at 110° C. under N$_2$ for 3 hours in oil bath. The reaction mixture was quenched with KF solution and extracted with EtOAc for three times. The combined extract was washed with brine and dried over anhydrous Na$_2$SO$_4$. Solvent was evaporated and the crude was dissolved in MeOH (10 ml). Drops of 3N HCl solution were added and the solution was then stirred at rt for 4 hours. Solvent was evaporated and the residue was purified on flash chromatography (gradient eluent: MeOH/DCM from 0-10%) to afford the title compound as yellow solid (0.16 g, >100%, contains some impurities). LCMS (method A): [M+H]$^+$=419.2, t$_R$=1.45 min.

(E)-1-(3-(3-(4-methylpiperazin-1-yl)quinolin-6-ylthio)-[1,2,4]triazolo[4,3-a]pyridin-6-yl)ethanone O-2-hydroxyethyl oxime (Example 86)

A solution of (86.2) (120 mg, 0.287 mmol) and 2-(aminooxy)ethanol (44.2 mg, 0.573 mmol) in MeOH (10 ml) was added drops of HCl (3 N) to reach pH about 5 and then stirred at rt for overnight. Solvent was evaporated and the residue was purified by preparative base HPLC (gradient eluent NB from 20/80 to 95/5. mobile phase A: NH$_4$OH/CH$_3$CN 0.05%; mobile phase B: NH$_4$OH/H$_2$O 0.05%) to afford the title compound (20 mg, yield 15%).

The following table provides structural formula and names and characterizing data of the compounds of the invention described above and of further compounds synthesized according to the methods described.

| Ex. | Structure Name | LCMS (method) NMR | Method | Starting Material |
|---|---|---|---|---|
| 1 | tert-butyl 1-(6-(6-(1-methyl-1H-pyrazol-4-yl)-[1,2,4]triazolo[4,3-a]pyridin-3-ylthio)quinolin-3-yl)pyrrolidin-3-ylcarbamate | LCMS (method N): [M + H]$^+$ = 543, t$_R$ = 2.40 min. $^1$H-NMR (400 MHz, CDCl$_3$) δ ppm 8.40 (s, 1H), 8.15 (s, 1H), 7.82 (m, 2H), 7.64 (s, 1H), 7.59 (s, 1H), 7.45 (d, 1H), 7.40 (s, 1H), 7.26 (s, 1H), 7.21 (d, 1H), 6.70 (s, 1H), 4.90 (broad, 1H), 4.38 (broad, 1H), 3.92 (s, 3H), 3.67~3.63 (m, 1H), 3.53~3.47 (m, 1H), 3.43~3.37 (m, 1H), 3.26~3.24 (m, 1H), 2.35~2.27 (m, 1H), 2.02~2.00 (broad, 1H), 1.44 (s, 9H). | 1A | Intermediates E + Q1 |
| 2 | 1-(6-(6-(1-methyl-1H-pyrazol-4-yl)-[1,2,4]triazolo[4,3-a]pyridin-3-ylthio)quinolin-3-yl)pyrrolidin-3-amine | LCMS (method N): [M + H]$^+$ = 443, t$_R$ = 1.65 min. $^1$H-NMR (400 MHz, MeOH-d$_4$) δ ppm 8.47 (s, 1H), 8.37 (s, 1H), 8.03 (s, 1H), 7.86~7.82 (m, 2H), 7.78~7.71 (m, 2H), 7.57 (s, 1H), 7.21 (d, 1H), 6.95 (s, 1H), 3.89 (s, 3H), 3.67 (broad, 1H), 3.59~3.54 (m, 2H), 3.42~3.36 (m, 1H), 3.13~3.10 (m, 1H), 2.26~2.21 (m, 1H), 1.93~1.85 (broad, 1H). | 1B | Ex 1 |
| 3 | (S)-N,N-dimethyl-1-(6-(6-(1-methyl-1H-pyrazol-3-yl)-[1,2,4]triazolo[4,3-a]pyridin-3-ylthio)quinolin-3-yl)pyrrolidin-3-amine | LCMS (method N): [M + H]$^+$ = 471, t$_R$ = 1.63 min. $^1$H-NMR (400 MHz, MeOH-d$_4$) δ ppm 8.38 (s, 1H), 8.25 (s, 1H), 7.98 (s, 1H), 7.78~7.75 (m, 2H), 7.67~7.62 (m, 2H), 7.44 (s, 1H), 7.13 (d, 1H), 6.78 (s, 1H), 3.85 (s, 3H), 3.51~3.47 (m, 1H), 3.43~3.39 (m, 1H), 3.27~3.23 (m, 1H), 3.13~3.08 (m, 1H), 2.86~2.82 (m, 1H), 2.29 (s, 6H), 2.25~2.20 (m, 1H), 1.90~1.82 (m, 1H). | 1A | Intermediates E + Q2 |
| 4 | (S)-tert-butyl 3-(6-(6-(1-methyl-1H-pyrazol-4-yl)-[1,2,4]triazolo[4,3-a]pyridin-3-ylthio)quinolin-3-ylamino)pyrrolidine-1-carboxylate | LCMS (method N): [M + H]$^+$ = 543, t$_R$ = 2.48 min. $^1$H-NMR (400 MHz, MeOH-d$_4$) δ ppm 8.44 (s, 1H), 8.31 (d, 1H), 8.00 (s, 1H), 7.83~7.80 (m, 2H), 7.74~7.67 (m, 2H), 7.54 (s, 1H), 7.21 (d, 1H), 6.97 (s, 1H), 4.02 (broad, 1H), 3.88 (s, 3H), 3.66~3.62 (m, 1H), 3.48~3.44 (m, 2H), 3.28~3.24 (m, 1H), 2.20~2.19 (m, 1H), 1.92~1.91 (m, 1H), 1.42 (d, 9H). | 1A | Intermediates E + Q3 |

-continued

| Ex. | Structure Name | LCMS (method) NMR | Method | Starting Material |
|---|---|---|---|---|
| 5 | 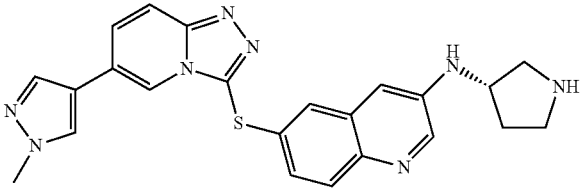<br>(S)-6-(6-(1-methyl-1H-pyrazol-4-yl)-[1,2,4]triazolo[4,3-a]pyridin-3-ylthio)-N-(pyrrolidin-3-yl)quinolin-3-amine | LCMS (method N): [M + H]⁺ = 443, $t_R$ = 1.64 min. ¹H-NMR (400 MHz, MeOH-d₄) δ ppm 8.43 (s, 1H), 8.30 (s, 1H), 7.99 (s, 1H), 7.82~7.79 (m, 2H), 7.72~7.63 (m, 2H), 7.53 (s, 1H), 7.21~7.14 (m, 1H), 6.92 (s, 1H), 3.95 (broad, 1H), 3.87 (s, 3H), 3.69~3.45 (m, 1H), 3.21~3.17 (m, 1H), 3.14~3.09 (m, 1H), 3.00~2.99 (m, 1H), 2.87~2.84 (m, 1H), 2.23~2.16 (m, 1H), 1.93~1.77 (m, 1H). | 1B | Ex 4 |
| 6 | 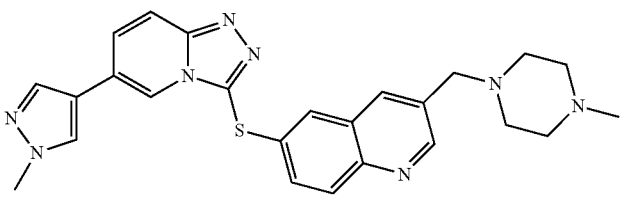<br>6-(6-(1-methyl-1H-pyrazol-4-yl)-[1,2,4]triazolo[4,3-a]pyridin-3-ylthio)-3-((4-methylpiperazin-1-yl)methyl)quinoline | LCMS (method N): [M + H]⁺ = 471, $t_R$ = 1.59 min. ¹H-NMR (400 MHz, MeOH-d₄) δ ppm 8.76 (s, 1H), 8.48 (s, 1H), 8.07 (s, 1H), 8.03 (s, 1H), 7.89 (d, 1H), 7.83~7.81 (m, 3H), 7.74 (d, 1H), 7.58 (d, 1H), 3.90 (s, 3H), 3.64 (s, 2H), 2.48 (broad, 8H), 2.23 (s, 3H). | 1A | Intermediates E + Q4 |
| 7 | 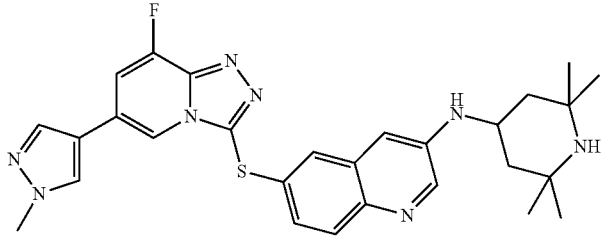<br>6-(8-fluoro-6-(1-methyl-1H-pyrazol-4-yl)-[1,2,4]triazolo[4,3-a]pyridin-3-ylthio)-N-(2,2,6,6-tetramethylpiperidin-4-yl)quinolin-3-amine | LCMS (method B): [M + H]⁺ = 531, $t_R$ = 1.81 min. ¹H-NMR (400 MHz, DMSO-d₆) δ ppm 8.45 (s, 1H), 8.40 (s, 1H), 8.32 (s, 1H), 8.03 (s, 1H), 7.80 (d, 1H), 7.72 (s, 1H), 7.68 (d, 1H), 7.16 (d, 1H), 6.94 (s, 1H), 6.15 (d, 1H), 3.84 (s, 3H), 3.72 (d, 1H), 1.84 (d, 2H), 1.22 (s, 7H), 1.04 (m, 8H). | 2 | Intermediates F + Q31 |
| 8 | 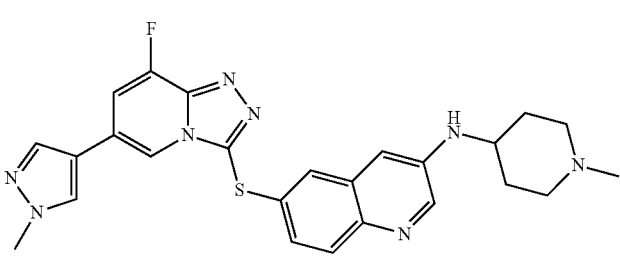<br>{6-[8-Fluoro-6-(6-(1-methyl-1H-pyrazol-4-yl)-[1,2,4]triazolo[4,3-a]pyridin-3-ylsulfanyl]-quinolin-3-yl}-(1-methyl-piperidin-4-yl)-amine | LCMS (method B): [M + H]⁺ = 489, $t_R$ =1.85 min. ¹H-NMR (400 MHz, DMSO-d₆) δ ppm 8.44 (s, 1H), 8.40 (s, 1H), 8.33 (s, 1H), 8.01 (s, 1H), 7.81 (d, 1H), 7.68 (d, 1H), 7.55 (s, 1H), 7.18 (d, 1H), 6.94 (s, 1H), 6.26 (d, 1H), 3.84 (s, 3H), 3.28 (m, 1H), 2.70 (m, 2H), 2.16 (s, 3H), 2.01 (m, 2H), 1.89 (m, 2H), 1.41 (m, 2H). | 2 | Intermediates F + Q34 |

-continued

| Ex. | Structure Name | LCMS (method) NMR | Method | Starting Material |
|---|---|---|---|---|
| 9 | 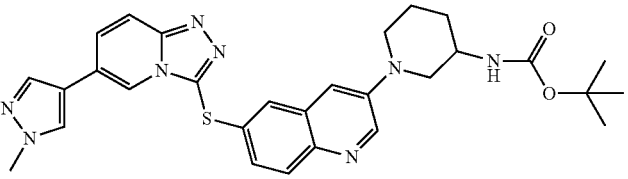tert-butyl 1-(6-(6-(1-methyl-1H-pyrazol-4-yl)-[1,2,4]triazolo[4,3-a]pyridin-3-ylthio)quinolin-3-yl)piperidin-3-ylcarbamate | LCMS (method N): [M + H]⁺ = 458, $t_R$ = 2.48 min. ¹H-NMR (400 MHz, CDCl₃) δ ppm 8.71 (s, 1H), 8.19 (s, 1H), 7.90~7.86 (m, 2H), 7.67 (m, 1H), 7.58 (m, 1H), 7.49~7.46 (m, 2H), 7.38 (d, 1H), 7.16 (s, 1H), 4.79 (broad, 1H), 3.94 (s, 3H), 3.86 (broad, 1H), 3.52~3.50 (m, 1H), 3.27 (broad, 1H), 3.13 (broad, 1H), 3.01-2.97 (m, 1H), 1.89~1.87 (m, 2H), 1.76~1.74 (m, 1H), 1.57~1.55 (m, 2H), 1.45 (s, 9H). | 1A | Intermediates E + Q5 |
| 10 | 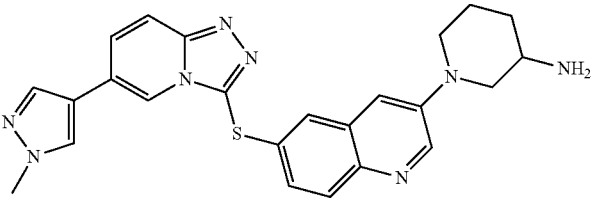1-(6-(6-(1-methyl-1H-pyrazol-4-yl)-[1,2,4]triazolo[4,3-a]pyridin-3-ylthio)quinolin-3-yl)piperidin-3-amine | LCMS (method N): [M + H]⁺ = 457, $t_R$=1.68 min. ¹H-NMR (400 MHz, CDCl₃) δ ppm 8.70 (s, 1H), 8.19 (s, 1H), 7.87~7.83 (m, 2H), 7.66 (s, 1H), 7.58 (s, 1H), 7.47~7.45 (m, 2H), 7.34 (dd, 1H), 7.12 (d, 1H), 3.93 (s, 3H), 3.64~3.61 (m, 1H), 3.50~3.47 (m, 1H), 3.09~3.05 (m, 1H), 2.92~2.86 (m, 1H), 2.76~2.71 (m, 1H), 2.10~1.96 (m, 3H), 1.91~1.86 (m, 1H), 1.73~1.69 (m, 1H), 1.37~1.32 (m, 1H) | 1B | Ex 9 |
| 11 | 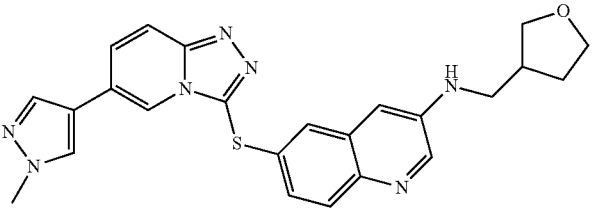6-(6-(1-methyl-1H-pyrazol-4-yl)-[1,2,4]triazolo[4,3-a]pyridin-3-ylthio)-N-((tetrahydrofuran-3-yl)methyl)quinolin-3-amine | LCMS (method N): [M + H]⁺ = 458, $t_R$ = 2.16 min. ¹H-NMR (400 MHz, CDCl₃) δ ppm 8.41 (s, 1H), 8.29 (d, 1H), 7.98 (s, 1H), 7.81~7.78 (m, 2H), 7.70 (dd, 1H), 7.65 (d, 1H), 7.52 (d, 1H), 7.16 (dd, 1H), 6.90 (d, 1H), 3.88~3.81 (m, 5H), 3.74~3.68 (m, 1H), 3.56~3.53 (m, 1H), 3.06 (d, 2H), 2.59~2.54 (m, 1H), 2.12~2.04 (m, 1H), 1.70~1.64 (m, 1H) | 1A | Intermediates E + Q6 |
| 12 | 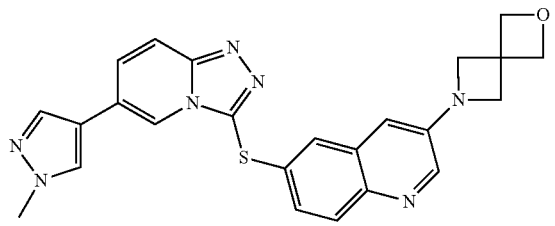6-(6-(6-(1-methyl-1H-pyrazol-4-yl)-[1,2,4]triazolo[4,3-a]pyridin-3-ylthio)quinolin-3-yl)-2-oxa-6-azaspiro[3.3]heptane | LCMS (method N): [M + H]⁺ = 456, $t_R$ = 2.28 min. ¹H-NMR (400 MHz, CDCl₃) δ ppm 8.48 (s, 1H), 8.23 (d, 1H), 8.04 (s, 1H), 7.87 (d, 1H), 7.82~7.77 (m, 3H), 7.60 (d, 1H), 7.30 (dd, 1H), 6.98 (d, 1H), 4.84 (s, 4H), 4.17 (s, 4H), 3.90 (s, 3H) | 1A | Intermediates E + Q7 |

-continued

| Ex. | Structure Name | LCMS (method) NMR | Method | Starting Material |
|---|---|---|---|---|
| 13 | 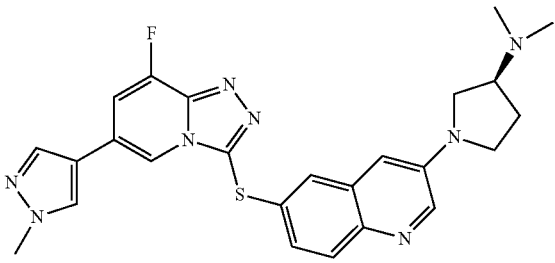<br>(S)-1-(6-(8-fluoro-6-(1-methyl-1H-pyrazol-4-yl)-[1,2,4]triazolo[4,3-a]pyridin-3-ylthio)quinolin-3-yl)-N,N-dimethylpyrrolidin-3-amine | LCMS (method N): $[M + H]^+ = 489$, $t_R = 1.62$ min. $^1$H-NMR (400 MHz, MeOH-d$_4$) δ ppm 8.39 (d, 1H), 8.33 (s, 1H), 8.03 (s, 1H), 7.82 (s, 1H), 7.74 (d, 1H), 7.60 (s, 1H), 7.59 (d, 1H), 7.25 (dd, 1H), 6.99 (d, 1H), 3.88 (s, 3H), 3.64~3.53 (m, 2H), 3.41~3.35 (m, 1H), 3.23~3.19 (m, 1H), 2.97~2.93 (m, 1H), 2.33 (s, 6H), 2.33~2.27 (m, 1H), 1.95~1.90 (m, 1H) | 1A | Intermediates F + Q2 |
| 14 | 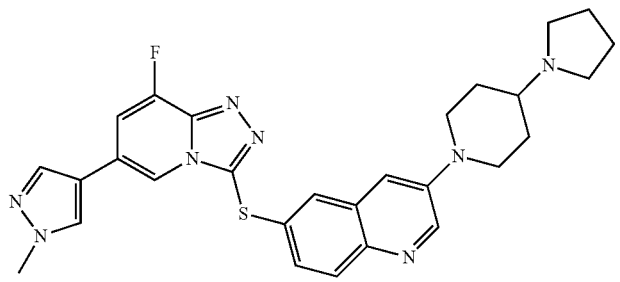<br>6-(8-fluoro-6-(1-methyl-1H-pyrazol-4-yl)-[1,2,4]triazolo[4,3-a]pyridin-3-ylthio)-3-(4-(pyrrolidin-1-yl)piperidin-1-yl)quinoline | LCMS (method N): $[M + H]^+ = 529$, $t_R = 1.67$ min. $^1$H-NMR (400 MHz, MeOH-d$_4$) δ ppm 8.70 (s, 1H), 8.36 (s, 1H), 8.05 (s, 1H), 7.84 (s, 1H), 7.80 (d, 1H), 7.68 (s, 1H), 7.62 (d, 1H), 7.41~7.38 (m, 2H), 3.89~3.85 (m, 5H), 2.82 (t, 2H), 2.66 (s, 4H), 2.27 (broad, 1H), 2.08~2.05 (m, 2H), 1.81 (s, 4H), 1.67~1.62 (m, 2H) | 1A | Intermediates F + Q18 |
| 15 | 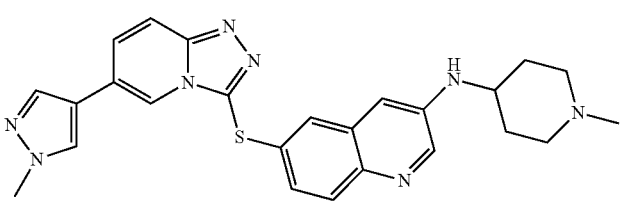<br>(1-Methyl-piperidin-4-yl)-{6-[6-(1-methyl-1H-pyrazol-4-yl)-[1,2,4]triazolo[4,3-a]pyridin-3-ylsulfanyl]-quinolin-3-yl}-amine | LCMS (method B): $[M + H]^+ = 471$, $t_R = 1.68$ min. $^1$H-NMR (400 MHz, DMSO-d$_6$) δ ppm 8.53 (s, 1H), 8.39 (d, 1H), 8.30 (s, 1H), 7.98 (s, 1H), 7.96 (d, 1H), 7.78 (dd, 1H), 7.67 (d, 1H), 7.52 (d, 1H), 7.14 (d, 1H), 6.94 (d, 1H), 6.25 (d, 1H), 3.85 (s, 3H), 3.22 (m, 1H), 2.70 (m, 2H), 2.16 (s, 3H), 2.01 (m, 2H), 1.88 (m, 2H), 1.44 (m, 2H). | 2 | Intermediates E + Q34 |
| 17 | 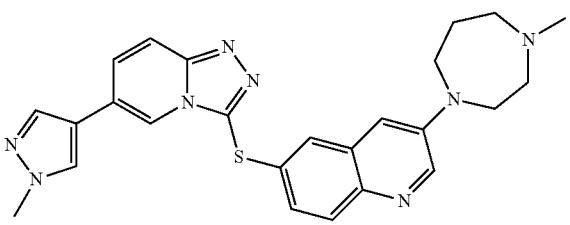<br>3-(4-Methyl-1,4-diazepan-1-yl)-6-(6-(1-methyl-1H-pyrazol-4-yl)-[1,2,4]triazolo[4,3-a]pyridin-3-ylthio)quinoline | LCMS (method N): $[M + H]^+ = 471$, $t_R = 2.29$ min. $^1$H-NMR (400 MHz, MeOH-d$_4$) δ ppm 2.00-2.06 (m, 2H) 2.35 (s, 3H) 2.53-2.63 (m, 2H) 2.75 (m, 2H) 3.51-3.59 (m, 2H) 3.61-3.70 (m, 2H) 3.90 (s, 3H) 7.15 (s, 1H) 7.25 (d, 1H) 7.58 (s, 1H) 7.69-7.81 (m, 2H) 7.81-7.90 (m, 2H) 8.05 (s, 1H) 8.49 (d, 1H) 8.54 (d, 1H). | 1A | Intermediates E + Q10 |

| Ex. | Structure Name | LCMS (method) NMR | Method | Starting Material |
|---|---|---|---|---|
| 18 | tert-Butyl 4-(6-(6-(1-methyl-1H-pyrazol-4-yl)-[1,2,4]triazolo[4,3-a]pyridin-3-ylthio)quinolin-3-yl)-1,4-diazepane-1-carboxylate | LCMS (method O): [M + H]$^+$ = 557, $t_R$ = 3.69 min $^1$H-NMR (400 MHz, MeOH-$d_4$) δ ppm 0.94 (s, 5H) 1.15 (s, 4H) 1.83-1.98 (m, 2H) 3.36 (m, 2H) 3.58-3.72 (m, 4H) 3.72-3.82 (m, 2H) 3.91 (s, 3H) 7.22 (s, 1H) 7.25-7.36 (m, 1H) 7.58 (s, 1H) 7.70-7.83 (m, 2H) 7.83-7.92 (m, 2H) 8.07 (s, 1H) 8.49 (d, 1H) 8.57 (s, 1H). | 1A | Intermediates E + Q11 |
| 19 | 3-(1,4-Diazepan-1-yl)-6-(6-(1-methyl-1H-pyrazol-4-yl)-[1,2,4]triazolo[4,3-a]pyridin-3-ylthio)quinoline | LCMS (method N): [M + H]$^+$ = 457, $t_R$ = 1.64 min $^1$H-NMR (400 MHz, CDCl$_3$) δ ppm 1.85-1.99 (m, 2H) 2.80 (t, 2H) 3.05 (t, 2H) 3.60 (t, 2H) 3.65 (t, 2H) 3.93 (s, 3H) 6.84-6.92 (m, 1H) 7.24 (d, 1H) 7.41 (s, 1H) 7.46 (d, 1H) 7.60 (s, 1H) 7.67 (s, 1H) 7.79 (d, 1H) 7.85 (d, 1H) 8.19 (s, 1H) 8.58 (d, 1H). | 1B | Ex 18 |
| 20 | tert-Butyl 1-(6-(6-(1-methyl-1H-pyrazol-4-yl)-[1,2,4]triazolo[4,3-a]pyridin-3-ylthio)quinolin-3-yl)piperidin-4-ylcarbamate | LCMS (method N): [M + H]$^+$ = 557, $t_R$ = 2.47 min $^1$H-NMR (400 MHz, CDCl$_3$) δ ppm 1.47 (s, 9H) 1.57-1.61 (m, 2H) 2.10 (d, 2H) 2.96 (t, 2H) 3.72 (d, 2H) 3.96 (s, 3H) 4.51 (m, 1) 7.17 (s, 1H) 7.39 (d, 1H) 7.49 (d, 1H) 7.60 (s, 1H) 7.66 (s, 1H) 7.89 (t, 1H) 8.20 (s, 1H) | 1A | Intermediates E + Q12 |
| 21 | 1-(6-(6-(1-Methyl-1H-pyrazol-4-yl)-[1,2,4]triazolo[4,3-a]pyridin-3-ylthio)quinolin-3-yl)piperidin-4-amine | LCMS (method N): [M + H]$^+$ = 457, $t_R$ = 1.54 min $^1$H-NMR (400 MHz, MeOH-$d_4$) δ ppm 1.73-1.81 (m, 2H) 2.12 (d, 2H) 2.88 (t, 2H) 3.32-3.35 (m, 1H) 3.85 (d, 2H) 3.88 (s, 3H) 7.27-7.41 (m, 2H) 7.58 (s, 1H) 7.68-7.75 (m, 2H) 7.78-7.82 (m, 2H) 8.01 (s, 1H) 8.41 (s, 1H) 8.63 (s, 1H) | 1B | Ex 20 |

| Ex. | Structure Name | LCMS (method) NMR | Method | Starting Material |
|---|---|---|---|---|
| 22 | 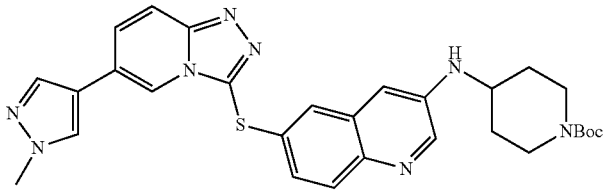<br>ter-Butyl 4-(6-(6-(1-methyl-1H-pyrazol-4-yl)-[1,2,4]triazolo[4,3-a]pyridin-3-ylthio)quinolin-3-ylamino)piperidine-1-carboxylate | LCMS (method O):<br>$[M + H]^+ = 557$, $t_R = 2.52$ min<br>$^1$H NMR (400 MHz, MeOH-d$_4$)<br>δ ppm 1.33-1.45 (m, 2H) 1.48 (s, 9 H) 2.06 (d, 2H) 2.98 (t, 2H) 3.47 (m, 1H) 3.95 (s, 3H) 4.00-4.17 (m, 2H) 6.83 (s, 1H) 7.31 (d, 1H) 7.45 (s, 1H) 7.47 (d, 1H) 7.59 (s, 1H) 7.67 (s, 1H) 7.86 (t, 2H) 8.20 (s, 1H) 8.37 (s, 1H) | 1A | Intermediates E + Q13 |
| 23 | 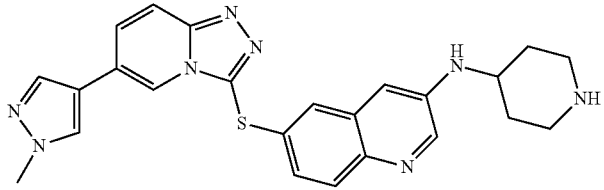<br>6-(6-(1-Methyl-1H-pyrazol-4-yl)-[1,2,4]triazolo[4,3-a]pyridin-3-ylthio)-N-(piperidin-4-yl)quinolin-3-amine | LCMS (method O):<br>$[M + H]^+ = 457$, $t_R = 2.33$ min<br>$^1$H NMR (400 MHz, MeOH-d$_4$)<br>δ ppm 1.65-1.84 (m, 2H) 2.23 (d, 2H) 3.18 (t, 2H) 3.48 (d, 2H) 3.62 (m, 1H) 3.85 (s, 3H) 7.04 (s, 1H) 7.14 (d, 1H) 7.42 (s, 1H) 7.63 (m, 2H) 7.75 (m., 2H) 7.97 (s, 1H) 8.32 (s, 1H) 8.36 (br. s., 1H) | 1B | Ex 22 |
| 24 | 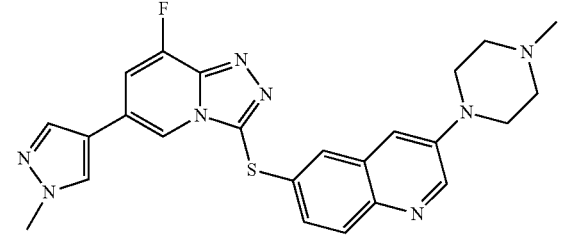<br>6-[8-Fluoro-6-(1-methyl-1H-pyrazol-4-yl)-[1,2,4]triazolo[4,3-a]pyridin-3-ylsulfanyl]-3-(4-methyl-piperazin-1-yl)-quinoline | LCMS (method B):<br>$[M + H]^+ = 475$, $t_R = 1.63$ min<br>$^1$H-NMR (400 MHz, DMSO-d$_6$)<br>δ ppm 8.81 (s, 1H), 8.47 (s, 1H), 8.35 (s, 1H), 8.03 (s, 1H), 7.83 (d, 1H), 7.79 (d, 1H), 7.54 (s, 1H), 7.39 (s, 1H), 7.35 (d, 1H), 3.83 (s, 3H), 3.25 (t, 4H), 2.49 (t, 4H), 2.21 (s, 3H) | 2 | Intermediates F + Q14 |
| 25 | 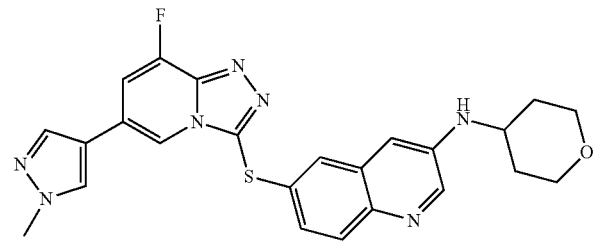<br>{6-[8-Fluoro-6-(1-methyl-1H-pyrazol-4-yl)-[1,2,4]triazolo[4,3-a]pyridin-3-ylsulfanyl]-quinolin-3-yl}-(tetrahydro-pyran-4-yl)-amine | LCMS (method B):<br>$[M + H]^+ = 476$, $t_R = 2.21$ min<br>$^1$H-NMR (400 MHz, DMSO-d$_6$)<br>δ ppm 8.46 (s, 1H), 3.39 (d, 1H), 8.34 (s, 1H), 8.03 (s, 1H), 7.83 (d, 1H), 7.69 (d, 1H), 7.50 (s, 1H), 7.19 (d, 1H), 6.99 (s, 1H), 6.36 (d, 1H), 3.84 (m, 2H), 3.83 (s, 3H), 3.46 (m, 1H), 3.42 (m, 2H), 1.88 (m, 2H), 1.37 (m, 2H) | 2 | Intermediates F + Q9 |

| Ex. | Structure Name | LCMS (method) NMR | Method | Starting Material |
|---|---|---|---|---|
| 26 | 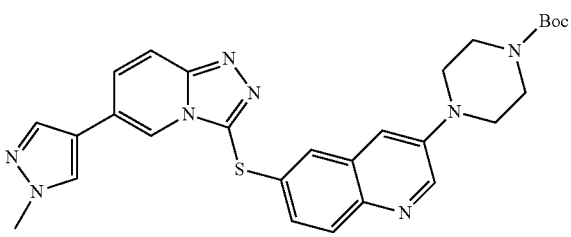<br>tert-Butyl 4-(6-(6-(1-methyl-1H-pyrazol-4-yl)-[1,2,4]triazolo[4,3-a]pyridin-3-ylthio)quinolin-3-yl)piperazine-1-carboxylate | LCMS (method N): $[M + H]^+ = 543$, $t_R = 2.51$ min. $^1$H NMR (400 MHz, CDCl$_3$) δ ppm 1.50 (s, 9 H) 3.26 (br, 4H) 3.64 (br, 4H) 3.96 (s, 3H) 7.25 (s, 1H) 7.41-7.57 (m, 3H) 7.61 (s, 1H) 7.69 (s, 1H) 7.90 (d, 1H) 8.02-8.08 (m., 1H) 8.21 (s, 1H) 8.72 (s, 1H) | 1A | Intermediates E + Q15 |
| 27 | 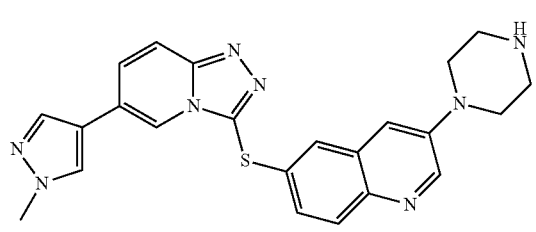<br>6-(6-(1-Methyl-1H-pyrazol-4-yl)-[1,2,4]triazolo[4,3-a]pyridin-3-ylthio)-3-(piperazin-1-yl)quinoline | LCMS (method N): $[M + H]^+ = 443$, $t_R = 1.62$ min $^1$H NMR (400 MHz, MeOH-d$_4$) δ ppm 2.97-3.02 (m., 4H) 3.20-3.25 (m 4H) 3.87 (s, 3H) 7.22-7.34 (m, 2H) 7.56 (s, 1H) 7.67-7.71 (m, 2H) 7.73-7.85 (m, 2H) 7.99 (s, 1H) 8.41 (s, 1H) 8.61 (s., 1H) | 1B | Ex 26 |
| 28 | 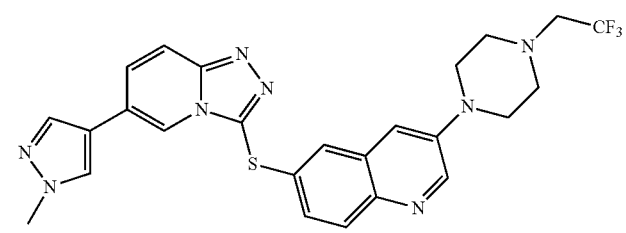<br>6-(6-(1-methyl-1H-pyrazol-4-yl)-[1,2,4]triazolo[4,3-a]pyridin-3-ylthio)-3-(4-(2,2,2-trifluoroethyl)piperazin-1-yl)quinoline | LCMS (method N): $[M + H]^+ = 525$, $t_R = 2.42$ min. $^1$H-NMR (400 MHz, CDCl$_3$) δ ppm 8.72 (d, 1H), 8.20 (s, 1H), 7.89~7.86 (m, 2H), 7.68 (s, 1H), 7.59 (s, 1H), 7.51~7.46 (m, 1H), 7.39 (dd, 1H), 7.12 (d, 1H), 3.95 (s, 3H), 3.30 (t, 4H), 3.06 (q, 2H), 2.88 (t, 4H) | 1C | Ex 27 |
| 29 | 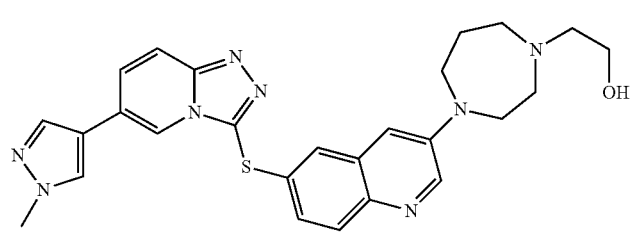<br>2-(4-(6-(6-(1-Methyl-1H-pyrazol-4-yl)-[1,2,4]triazolo[4,3-a]pyridin-3-ylthio)quinolin-3-yl)-1,4-diazepan-1-yl)ethanol | LCMS (method N): $[M + H]^+ = 501$, $t_R = 1.35$ min $^1$H NMR (400 MHz, MeOH-d$_4$) δ ppm 1.88-2.03 (m, 2H) 2.62-2.67 (m, 4H) 2.83-3.03 (m, 2H) 3.47-3.70 (m, 6H) 7.12 (d, 1H) 7.23 (d, 1H) 7.58 (s, 1H) 7.67-7.78 (m, 2H) 7.78-7.88 (m, 2H) 8.02 (s, 1H) 8.46 (s, 1H) 8.52 (s, 1H) | 1D | Ex 19 |

-continued

| Ex. | Structure Name | LCMS (method) NMR | Method | Starting Material |
|---|---|---|---|---|
| 30 | 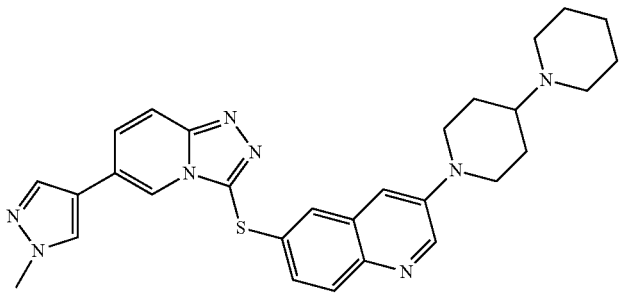<br>3-(1,4'-Bipiperidin-1'-yl)-6-(6-(1-methyl-1H-pyrazol-4-yl)-[1,2,4]triazolo[4,3-a]pyridin-3-ylthio)-quinoline | LCMS (method O): [M + H]$^+$ = 525, $t_R$ = 1.00 min<br>$^1$H NMR (400 MHz, CDCl$_3$) δ ppm 0.83-0.90 (m, 1H) 1.24-1.28 (m, 2H) 1.46-1.50 (m, 2H) 1.57-1.86 (m, 7H) 1.91-2.11 (m, 2H) 2.58-2.65 (m, 5H) 2.78-2.82 (m, 2H) 3.74-3.88 (m, 2H) 3.93 (s, 3H) 7.10 (s, 1H) 7.30-7.41 (m, 1H) 7.45-7.47 (m., 2H) 7.59 (s, 1H) 7.66 (s, 1H) 7.83-7.87 (m, 2H) 8.19 (s, 1H) 8.71 (s, 1H) | 1A | Intermediates E + Q16 |
| 31 | 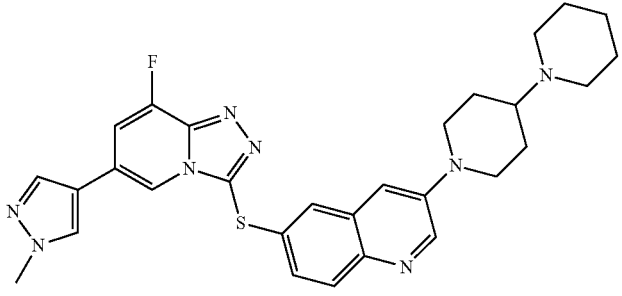<br>3-(1,4'-Bipiperidin-1'-yl)-6-(8-fluoro-6-(1-methyl-1H-pyrazol-4-yl)-[1,2,4]triazolo[4,3-a]pyridin-3-ylthio)quinoline | LCMS (method O): [M + H]$^+$ = 543, $t_R$ = 1.72 min<br>$^1$H NMR (400 MHz, CDCl$_3$) δ ppm 1.36- 1.47 (m, 2H) 1.55-1.59 (m, 4H) 1.61-1.76 (m, 2H) 1.93 (d, 2H) 2.38-2.44 (m, 1H) 2.49-2.53 (m, 4H) 2.78 (t, 2H) 3.80 (d, 2H) 3.91 (s, 3H) 7.08 (s, 1H) 7.12 (d, 1H) 7.31 (d, 1H) 7.47 (s, 1H) 7.60-7.64 (m, 2H) 7.81 (d, 1H) 8.01 (s, 1H) 8.69 (s, 1H),. | 1A | Intermediates F + Q16 |
| 32 | 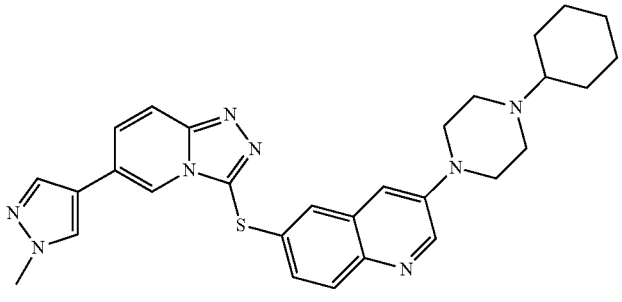<br>3-(4-Cyclohexylpiperazin-1-yl)-6-(6-(1-methyl-1H-pyrazol-4-yl)-[1,2,4]triazolo[4,3-a]pyridin-3-ylthio)quinoline | LCMS (method N): [M + H]$^+$ = 525, $t_R$ = 1.75 min<br>$^1$H NMR (400 MHz, MeOH-d$_4$) δ ppm 1.12-1.38 (m, 5H) 1.67 (d, 1H) 1.82 (d, 2H) 1.95 (d, 2H) 2.31-2.35 (m, 1H) 2.74-2.84 (m, 4H) 3.34-3.38 (m, 4H) 3.91 (s, 3H) 7.32-7.44 (m, 2H) 7.69 (d, 1H) 7.74-7.91 (m, 4H) 8.02 (s, 1H) 8.48 (s, 1H) 8.71 (d, 1H) | 1A | Intermediates E + Q17 |

| Ex. | Structure Name | LCMS (method) NMR | Method | Starting Material |
|---|---|---|---|---|
| 33 | 6-(6-(1-Methyl-1H-pyrazol-4-yl)-[1,2,4]triazolo[4,3-a]pyridin-3-ylthio)-3-(4-(pyrrolidin-1-yl)piperidin-1-yl)quinoline | LCMS (method N): [M + H]⁺ = 511, $t_R$ = 1.67 min ¹H NMR (400 MHz, MeOH-d₄) δ ppm 1.55-1.70 (m, 2H) 1.82-1.86 (m, 4H) 2.06 (d, 2H) 2.33 (t, 1H) 2.70-2.74 (m, 4H) 2.80 (t, 2H) 3.84 (d, 2H) 3.88 (s, 3H) 7.35-7.37 (m, 2H) 7.64 (s, 1H) 7.76-7.78 (m, 2H) 7.81-7.89 (m, 2H) 8.04 (s, 1H) 8.49 (s, 1H) 8.68 (s, 1H) | 1A | Intermediates E + Q9 |
| 34 | 6-(6-(1-Methyl-1H-pyrazol-4-yl)-[1,2,4]triazolo[4,3-a]pyridin-3-ylthio)-3-(4-phenylpiperazin-1-yl)quinoline | LCMS (method N): [M + H]⁺ = 519, $t_R$ = 2.39 min ¹H NMR (400 MHz, CDCl₃) δ ppm 3.35-3.46 (m, 8 H) 3.94 (s, 3H) 6.89-7.01 (m, 3H) 7.18 (d, 1H) 7.26-7.33 (m, 2H) 7.39 (dd, 1H) 7.45-7.54 (m, 2H) 7.60 (s, 1H) 7.68 (s, 1H) 7.88 (t, 2H) 8.21 (s, 1H) 8.78 (d, 1H) | 1A | Intermediates E + Q19 |
| 35 | 2-Methyl-4-(6-(6-(1-methyl-1H-pyrazol-4-yl)-[1,2,4]triazolo[4,3-a]pyridin-3-ylthio)quinolin-3-yl)morpholine | LCMS (method N): [M + H]⁺ = 458, $t_R$ = 2.28 min ¹H NMR (400 MHz, CDCl₃) δ ppm 1.22 (d, 3H) 2.51 (t, 1H) 2.85 (td, 1H) 3.46 (t, 2H) 3.67-3.81 (m, 2H) 3.89 (s, 3H) 3.98 (dd, 1H) 7.04 (d, 1H) 7.25-7.33 (m, 1H) 7.38-7.47 (m, 2H) 7.61 (s, 1H) 7.62 (s, 1H) 7.78 (d, 1H) 7.80 (d, 1H) 8.16 (s, 1H) 8.65 (d, 1H) | 1A | Intermediates E + Q20 |
| 35A | (S)-2-Methyl-4-(6-(6-(1-methyl-1H-pyrazol-4-yl)-[1,2,4]triazolo[4,3-a]pyridin-3-ylthio)quinolin-3-yl)morpholine | obtained by chiral separation of Ex 35 | | |

| Ex. | Structure Name | LCMS (method) NMR | Method | Starting Material |
|---|---|---|---|---|
| 35B | (R)-2-Methyl-4-(6-(6-(1-methyl-1H-pyrazol-4-yl)-[1,2,4]triazolo[4,3-a]pyridin-3-ylthio)quinolin-3-yl)morpholine | obtained by chiral separation of Ex 35 | | |
| 36 | 4-(6-(8-Fluoro-6-(1-methyl-1H-pyrazol-4-yl)-[1,2,4]triazolo[4,3-a]pyridin-3-ylthio)quinolin-3-yl)-2-methylmorpholine | LCMS (method N): $[M + H]^+ = 476$, $t_R = 2.31$ min $^1$H NMR (400 MHz, CDCl$_3$) δ ppm 1.23 (d, 3H) 2.53 (t, 1H) 2.87 (td, 1H) 3.48 (t, 2H) 3.68-3.84 (m, 2H) 3.91 (s, 3H) 4.00 (dd, 1H) 7.07 (d, 1H) 7.12 (d, 1H) 7.30 (dd, 1H) 7.48 (d, 1H) 7.61 (s, 1H) 7.64 (s, 1H) 7.80 (d, 1H) 8.01 (s, 1H) 8.66 (d, 1H) | 1A | Intermediates F + Q20 |
| 37 | 2,6-Dimethyl-4-(6-(6-(1-methyl-1H-pyrazol-4-yl)-[1,2,4]triazolo[4,3-a]pyridin-3-ylthio)quinolin-3-yl)morpholine | LCMS (method N): $[M + H]^+ = 472$, $t_R = 2.39$ min. $^1$H NMR (400 MHz, CDCl$_3$) δ ppm 1.26-1.30 (m, 6H) 2.50 (t, 2H) 3.53 (d, 2H) 3.77-3.90 (m, 2H) 3.95 (s, 3H) 7.10 (d, 1H) 7.38 (dd, 1H) 7.44-7.51 (m, 2H) 7.61 (s, 1H) 7.68 (s, 1H) 7.86 (d, 1H) 7.89 (d, 1H) 8.20 (s, 1H) 8.71 (d, 1H) | 1A | Intermediates E + Q21 |
| 38 | 4-(6-(8-Fluoro-6-(1-methyl-1H-pyrazol-4-yl)-[1,2,4]triazolo[4,3-a]pyridin-3-ylthio)quinolin-3-yl)-2,6-dimethylmorpholine | LCMS (method N): $[M + H]^+ = 490$, $t_R = 2.42$ min $^1$H NMR (400 MHz, CDCl$_3$) δ ppm 1.28-1.32 (m, 6H) 2.52 (t, 2H) 3.55 (d, 2H) 3.85 (br, 2H) 3.95 (s, 3H) 7.04-7.22 (m, 2H) 7.40 (d, 1H) 7.50 (s, 1H) 7.60 (s, 1H) 7.66 (s, 1H) 7.90 (d, 1H) 8.04 (S, 1H) 8.73 (s, 1H) | 1A | Intermediates F + Q21 |

-continued

| Ex. | Structure Name | LCMS (method) NMR | Method | Starting Material |
|---|---|---|---|---|
| 39 | 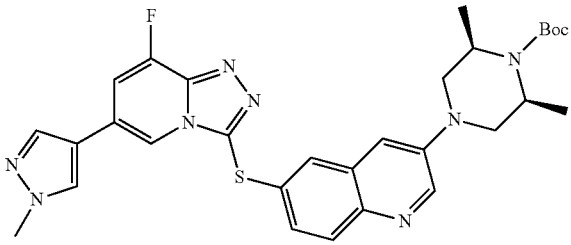<br>(2S,6R)-tert-Butyl 4-(6-(8-fluoro-6-(1-methyl-1H-pyrazol-4-yl)-[1,2,4]triazolo[4,3-a]pyridin-3-ylthio)quinolin-3-yl)-2,6-dimethylpiperazine-1-carboxylate | LCMS (method N): [M + H]⁺ = 589, $t_R$ = 2.63 min. ¹H NMR (400 MHz, CDCl₃) δ ppm 1.37 (d, 6H) 1.50 (s, 9 H) 3.06 (d, 2H) 3.51 (d, 2H) 3.96 (s, 3H) 4.31-4.35 (m, 2H) 7.19 (d, 1H) 7.25-7.29 (m, 3H), 7.56 (d, 1H) 7.61 (s, 1H) 7.68 (s, 1H) 8.05 (s, 1H) 8.70 (d, 1H) | 1A | Intermediates F + Q22 |
| 40 | 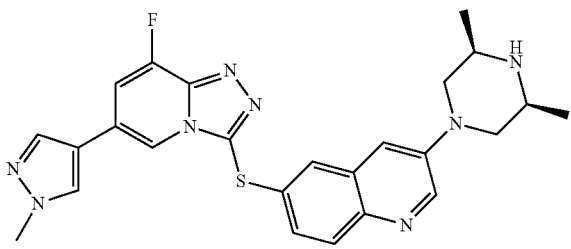<br>3-((3S,5R)-3,5-Dimethylpiperazin-1-yl)-6-(8-fluoro-6-(1-methyl-1H-pyrazol-4-yl)-[1,2,4]triazolo[4,3-a]pyridin-3-ylthio)quinoline | LCMS (method N): [M + H]⁺ = 489, $t_R$ = 1.71 min ¹H NMR (400 MHz, MeOH-d₄) δ ppm 1.12 (d, 6H) 2.28 (t, 2H) 2.87-2.99 (m, 2H) 3.60 (d, 2H) 3.86 (s, 3H) 7.17-7.31 (m, 2H) 7.46 (d, 1H) 7.55 (s, 1H) 7.66 (d, 1H) 7.79 (s, 1H) 7.99 (s, 1H) 8.26 (s, 1H) 8.55-8.62 (m, 1H) | 1B | Ex 39 |
| 41 | 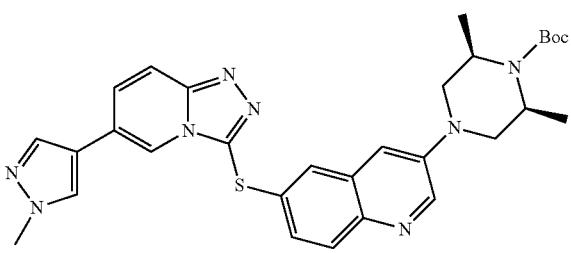<br>(2S,6R)-tert-Butyl 2,6-dimethyl-4-(6-(6-(1-methyl-1H-pyrazol-4-yl)-[1,2,4]triazolo[4,3-a]pyridin-3-ylthio)quinolin-3-yl)piperazine-1-carboxylate | LCMS (method N): [M + H]⁺ = 571 , $t_R$ = 2.64 min ¹H NMR (400 MHz, CDCl₃) δ ppm 1.37 (d, 6H) 1.51 (s, 9 H) 3.02 (d, 2H) 3.49 (d, 2H) 3.96 (s, 3H) 4.30-4.34 (m, 2H) 7.21 (s, 1H) 7.40-7.56 (m, 3H) 7.60 (s, 1H) 7.69 (s, 1H) 7.89 (d, 1H) 7.98 (d, 1H) 8.21 (s, 1H) 8.70 (s, 1H) | 1A | Intermediates E + Q22 |
| 42 | 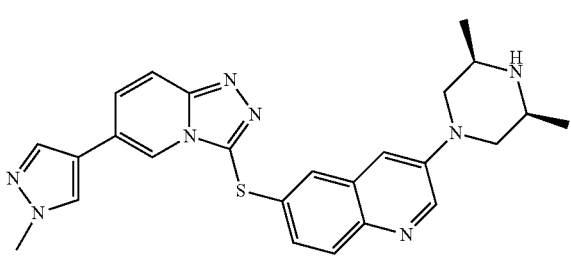<br>3-((3S,5R)-3,5-Dimethylpiperazin-1-yl)-6-(6-(1-methyl-1H-pyrazol-4-yl)-[1,2,4]triazolo[4,3-a]pyridin-3-ylthio)quinoline | LCMS (method N): [M + H]⁺ = 471, $t_R$ = 1.69 min ¹H NMR (400 MHz, MeOH-d₄) δ ppm 1.12 (d, 6H) 2.27 (t, 2H) 2.90-2.94 (m, 2H) 3.54-3.65 (m, 2H) 3.85 (s, 3H) 7.18-7.29 (m, 2H) 7.54 (d, 1H) 7.60-7.71 (m, 2H) 7.71-7.83 (m, 2H) 7.96 (s, 1H) 8.38 (s, 1H) 8.60 (d, 1H) | 1B | Ex 41 |

-continued

| Ex. | Structure Name | LCMS (method) NMR | Method | Starting Material |
|---|---|---|---|---|
| 43 | 3-(4-Methoxypiperidin-1-yl)-6-(6-(1-methyl-1H-pyrazol-4-yl)-[1,2,4]triazolo[4,3-a]pyridin-3-ylthio)quinoline | LCMS (method B): [M + H]⁺ = 472, $t_R$ = 5.49 min ¹H NMR (400 MHz, CDCl₃) δ ppm 1.56-1.76 (m, 2H) 1.91-1.95 (m., 2H) 2.99 (t, 2H) 3.23-3.55 (m, 5H) 3.86 (s, 3H) 7.03 (s, 1H) 7.24 (d, 1H) 7.33-7.47 (m, 2H) 7.60 (br, 2H) 7.74 (s, 1H) 7.76 (s, 1H) 8.13 (s, 1H) 8.63 (s, 1H) | 1A | Intermediates E + Q23 |
| 44 | 6-(8-Fluoro-6-(1-methyl-1H-pyrazol-4-yl)-[1,2,4]triazolo[4,3-a]pyridin-3-ylthio)-3-(4-methoxypiperidin-1-yl)quinoline | LCMS (method N): [M + H]⁺ = 490, $t_R$ = 2.31 min ¹H NMR (400 MHz, CDCl₃) δ ppm 1.67-1.82 (m, 2H) 1.96-2.09 (m, 2H) 2.99-3.15 (m, 2H) 3.38 (s, 3H) 3.41-3.47 (m, 1H) 3.50-3.62 (m, 2H) 3.94 (s, 3H) 7.06-7.21 (m, 2H) 7.35 (d, 1H) 7.50 (s, 1H) 7.60 (s, 1H) 7.64 (s, 1H) 7.85 (d, 1H) 8.03 (s, 1H) 8.78 (d, 1H) | 1A | Intermediates F + Q23 |
| 45 | (S)-tert-Butyl 4-(6-(8-fluoro-6-(1-methyl-1H-pyrazol-4-yl)-[1,2,4]triazolo[4,3-a]pyridin-3-ylthio)quinolin-3-yl)-3-methylpiperazine-1-carboxylate | LCMS (method N): [M + H]⁺ = 575, $t_R$ = 2.54 min ¹H NMR (400 MHz, CDCl₃) δ ppm 1.07 (d, 3H) 1.50 (s, 9 H) 3.19 (d, 2H) 3.28 (br, 2H) 3.95 (s, 3H) 4.01-4.10 (m, 1H) 7.10-7.20 (m, 2H) 7.41 (dd, 1H) 7.55 (d, 1H) 7.59 (s, 1H) 7.66 (s, 1H) 7.93 (d, 1H) 8.02-8.09 (m, 1H), 8.72 (d, 1H) | 1A | Intermediates F + Q24 |
| 46 | (S)-6-(8-Fluoro-6-(1-methyl-1H-pyrazol-4-yl)-[1,2,4]triazolo[4,3-a]pyridin-3-ylthio)-3-(2-methylpiperazin-1-yl)quinoline | LCMS (method N): [M + H]⁺ = 475, $t_R$ = 2.79 min ¹H NMR (400 MHz, CDCl₃) δ ppm 1.12 (d, 3H) 2.86-3.03 (m, 2H) 3.07-3.29 (m, 4H) 3.94 (s, 3H) 4.01 (dt, 1H) 7.09 (d, 1H) 7.12-7.18 (m, 1H) 7.36 (dd, 1H) 7.53 (d, 1H) 7.59 (s, 1H) 7.65 (s, 1H) 7.87 (d, 1H) 8.04 (s, 1H) 8.72 (d, 1H) | 1B | Ex 45 |

| Ex. | Structure Name | LCMS (method) NMR | Method | Starting Material |
|---|---|---|---|---|
| 47 | 2-(6-((6-(1-methyl-1H-pyrazol-4-yl)-[1,2,4]triazolo[4,3-a]pyridin-3-yl)thio)quinolin-3-yl)-8-oxa-2-azaspiro[4.5]decane | LCMS (method A): [M + H]$^+$ = 498, t$_R$ = 2.33 min $^1$H-NMR (400 MHz, CDCl$_3$) δ ppm 8.47 (s, 1H), 8.20 (s, 1H), 7.87 (d, 2H), 7.66 (s, 1H), 7.59 (s, 1H), 7.47 (m, 2H), 7.26 (m, 1H), 6.78 (m, 1H), 3.95 (s, 3H), 3.76 (m, 2H), 3.70 (m, 2H), 3.49 (m, 2H), 3.30 (m, 2H), 2.00 (m, 2H), 1.67 (m, 4H) | 1A | Intermediates E + Q25 |
| 48 | 2-(6-(8-fluoro-6-(1-methyl-1H-pyrazol-4-yl)-[1,2,4]triazolo[4,3-a]pyridin-3-ylthio)quinolin-3-yl)-8-oxa-2-azaspiro[4.5]decane | LCMS (method A): [M + H]$^+$ = 516, t$_R$ = 2.37 min $^1$H-NMR (400 MHz, CDCl$_3$) δ ppm 8.47 (d, 1H), 8.03 (s, 1H), 7.89 (d, 1H), 7.64 (s, 1H), 7.60 (s, 1H), 7.50 (m, 1H), 7.29 (m, 1H), 7.14 (m, 1H), 6.80 (m, 1H), 3.95 (s, 3H), 3.76 (m, 2H), 3.70 (m, 2H), 3.50 (m, 2H), 3.30 (m, 2H), 2.00 (m, 2H), 1.67 (m, 4H) | 1A | Intermediates F + Q25 |
| 49 | 1-(6-((6-(1-methyl-1H-pyrazol-4-yl)-[1,2,4]triazolo[4,3-a]pyridin-3-yl)thio)quinolin-3-yl)piperidin-4-ol | LCMS (method A): [M+H]$^+$ = 458, t$_R$ = 2.07 min $^1$H-NMR (400 MHz, CDCl$_3$) δ ppm 9.75 (d, 1H), 8.20 (s, 1H), 7.89 (m, 2H), 7.66 (s, 1H), 7.60 (s, 1H), 7.53 (d, 1H), 7.49 (dd, 1H), 7.40 (dd, 2H), 5.31 (s, 1H), 3.95 (s, 3H), 3.94 (m, 1H), 3.65 (m, 2H), 3.07 (m, 2H), 2.07 (m, 2H), 1.73 (m, 2H) | 1A & 1E | Intermediates E + Q27 |
| 50 | 1-(6-((8-fluoro-6-(1-methyl-1H-pyrazol-4-yl)-[1,2,4]triazolo[4,3-a]pyridin-3-yl)thio)quinolin-3-yl)piperidin-4-ol | LCMS (method A): [M + H]$^+$ = 476, t$_R$ = 2.10 min $^1$H-NMR (400 MHz, MeOH-d$_4$) δ ppm 9.04 (s, 1H), 8.49 (s, 1H), 8.23 (s, 1H), 8.18 (s, 1H), 8.0 (d, 1H), 7.95 (s, 1H), 7.78 (d, 1H), 7.71 (d, 2H), 3.93 (s, 3H), 3.89 (m, 3H), 3.28 (m, 2H), 2.0 (m, 2H), 1.66 (m, 2H) | 1A & 1E | Intermediates F + Q27 |

| Ex. | Structure Name | LCMS (method) NMR | Method | Starting Material |
|---|---|---|---|---|
| 51 | 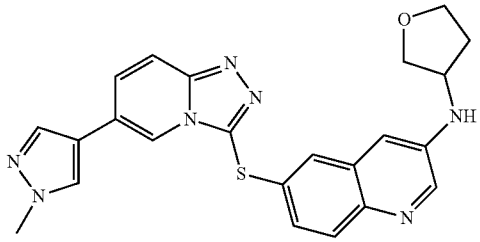<br>6-[6-(1-Methyl-1H-pyrazol-3-yl)-[1,2,4]triazolo[4,3-a]pyridin-3-ylsulfanyl]-quinolin-3-yl}-(tetrahydro-furan-3-yl)-amine | LCMS (method A):<br>[M + H]⁺ = 444, $t_R$ = 2.11 min<br>¹H-NMR (400 MHz, CDCl₃) δ ppm 8.35 (s, 1H), 8.21 (s, 1H), 7.88 (m, 2H), 7.68 (s, 1H), 7.59 (s, 1H), 7.49 (m, 2H), 7.32 (d, 1H), 6.81 (s, 1H), 4.24 (m, 1H), 4.16 (m, 1H), 3.95 (s, 3H), 3.85 (m, 1H), 3.73 (m, 1H), 2.35 (m, 1H), 1.90 (m, 1H), 1.55 (m, 1H), 1.45 (m, 1H) | 1A | Intermediates E + Q26 |
| 52 | 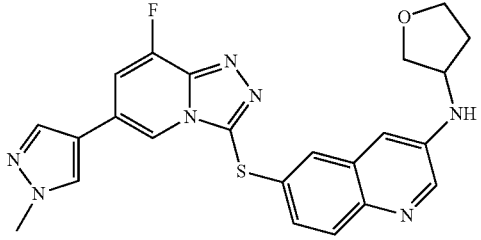<br>{6-[8-Fluoro-6-(1-methyl-1H-pyrazol-3-yl)-[1,2,4]triazolo[4,3-a]pyridin-3-ylsulfanyl]-quinolin-3-yl}-(tetrahydro-furan-3-yl)-amine | LCMS (method A):<br>[M + H]⁺ = 462, $t_R$ = 2.16 min<br>¹H-NMR (400 MHz, CDCl₃) δ ppm 8.61 (s, 1H), 8.05 (s, 1H), 8.00 (d, 1H), 7.67 (s, 1H), 7.60 (s, 1H), 7.52 (s, 1H), 7.38 (d, 1H), 7.18 (d, 1H), 6.93 (s, 1H), 4.15 (m, 1H), 4.06 (m, 1H), 3.95 (s, 3H), 3.93 (m, 1H), 3.78 (m, 1H), 2.35 (m, 1H), 1.95 (m, 1H), 1.55 (m, 1H), 1.45 (m, 1H). | 1A | Intermediates F + Q26 |
| 53 | 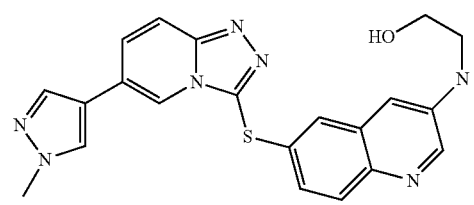<br>2-(6-(6-(1-methyl-1H-pyrazol-4-yl)-[1,2,4]triazolo[4,3-a]pyridin-3-ylthio)quinolin-3-ylamino)ethanol | LCMS (method B):<br>[M + H]⁺ = 418, $t_R$ = 1.95 min<br>¹H-NMR (400 MHz, DMSO-d₆) δ ppm 8.54 (s, 1H), 8.44 (s, 1H), 8.30 (s, 1H), 7.97 (d, 2H), 7.77 (d, 1H), 7.68 (t, 1H), 7.51 (s, 1H), 7.13 (d, 1H), 6.92 (s, 1H), 6.35 (s, 1H), 4.71 (t, 1H), 3.84 (s, 3H), 3.57 (d, 2H), 3.13 (d, 2H) | 3 | Intermediates E + Q28 |
| 54 | 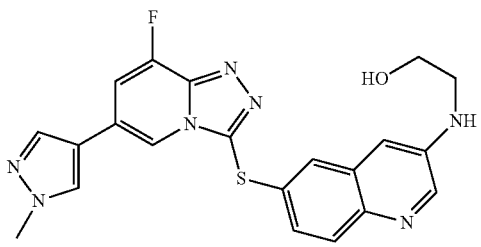<br>2-(6-(8-fluoro-6-(1-methyl-1H-pyrazol-4-yl)-[1,2,4]triazolo[4,3-a]pyridin-3-ylthio)quinolin-3-ylamino)ethanol | LCMS (method B):<br>[M + H]⁺ = 432, $t_R$ = 3.03 min<br>¹H-NMR (400 MHz, DMSO-d₆) δ ppm 8.45 (t, 2H), 8.34 (d, 1H), 8.02 (d, 1H), 7.81 (dd, 1H), 7.70 (dd, 1H), 7.52 (s, 1H), 7.18 (dd, 1H), 6.92 (s, 1H), 6.37 (s, 1H), 4.73 (d, 1H), 3.85 (s, 3H), 3.58 (t, 2H), 3.13 (d, 2H) | 3 | Intermediates F + Q28 |

| Ex. | Structure Name | LCMS (method) NMR | Method | Starting Material |
|---|---|---|---|---|
| 55 | 6-(8-fluoro-6-(1-methyl-1H-pyrazol-4-yl)-[1,2,4]triazolo[4,3-a]pyridin-3-ylthio)quinolin-3-amine hydrochloride | LCMS (method B): [M + H]+= 392, t$_R$ = 1.89 min $^1$H-NMR (400 MHz, DMSO-d$_6$) δ ppm 8.63 (s, 1H), 8.47 (s, 1H), 8.36 (s, 1H), 8.0 (d, 2H), 7.85 (d, 1H), 7.75 (d, 2H), 7.46 (d, 1H), 3.8 (s, 3H) | 4 | Intermediates F + Q29 |
| 56 | 6-(6-(1-methyl-1H-pyrazol-4-yl)-[1,2,4]triazolo[4,3-a]pyridin-3-ylthio)quinolin-3-amine hydrochloride | LCMS (method B): [M + H]$^+$ = 374, t$_R$ = 1.85 min $^1$H-NMR (400 MHz, DMSO-d$_6$) δ ppm 9.80 (d, 2H), 8.64 (d, 2H), 8.37 (d, 1H), 8.05 (t, 3H), 7.90 (d, 1H), 7.84 (d, 1H), 7.79 (d, 1H), 7.74 (t, 1H), 3.8 (s, 3H). | 4 | Intermediates E + Q29 |
| 57 | 4-(6-(6-(1H-pyrazol-4-yl)-[1,2,4]triazolo[4,3-a]pyridin-3-ylthio)quinolin-3-yl)morpholine | LCMS (method B): [M + H]$^+$ = 430, t$_R$ = 2.10 min $^1$H-NMR (400 MHz, DMSO-d$_6$) δ ppm 13.08 (s, 1H), 8.81 (s, 1H), 8.59 (s, 1H), 8.37 (s, 1H), 8.05 (s, 1H), 7.98 (d, 1H), 7.84 (dd, 2H), 7.59 (s, 1H), 7.42 (s, 1H), 7.34 (d, 1H), 3.75 (t, 4H), 3.23 (t, 4H) | 5 | Intermediates C + Q33 |
| 58 | 4-(6-(8-fluoro-6-(1H-pyrazol-4-yl)-[1,2,4]triazolo[4,3-a]pyridin-3-ylthio)quinolin-3-yl)morpholine | LCMS (method B): [M + H]$^+$ = 448, t$_R$ = 2.14 min $^1$H-NMR (400 MHz, DMSO-d$_6$) δ ppm 13.11 (s, 1H), 8.81 (s, 1H), 8.50 (s, 1H), 8.40 (s, 1H), 8.0 (s, 1H), 7.89 (d, 2H), 7.60 (s, 1H), 7.40 (m, 2H), 3.75 (t, 4H), 3.23 (t, 4H) | 5 | Intermediates D + Q33 |
| 59 | 3-methyl-4-(6-(6-(1-methyl-1H-pyrazol-4-yl)-[1,2,4]triazolo[4,3-a]pyridin-3-ylthio)quinolin-3-yl)morpholine | LCMS (method B): [M + H]$^+$ = 458, t$_R$ = 2.22 min $^1$H-NMR (400 MHz, DMSO-d$_6$) δ ppm 8.78 (d, 1H), 8.50 (s, 1H), 8.32 (s, 1H), 7.99 (t, 2H), 7.80 (dd, 2H), 7.55 (d, 1H), 7.35 (d, 1H), 7.29 (t, 1H), 4.12 (m, 1H), 3.93 (d, 1H), 3.83 (s, 3H), 3.71 (dd, 2H), 3.56 (dd, 1H), 3.27 (s, 1H), 3.05 (m, 1H), 1.01 (s, 3H) | 6 | Intermediates E + Q30 |

| Ex. | Structure Name | LCMS (method) NMR | Method | Starting Material |
|---|---|---|---|---|
| 60 | 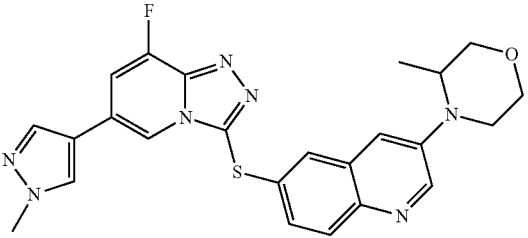<br>4-(6-(8-fluoro-6-(1-methyl-1H-pyrazol-4-yl)-[1,2,4]triazolo[4,3-a]pyridin-3-ylthio)quinolin-3-yl)-3-methylmorpholine | LCMS (method B): [M + H]$^+$ = 476, $t_R$ = 2.26 min<br>$^1$H-NMR (400 MHz, DMSO-d$_6$) δ ppm 8.78 (d, 1H), 8.47 (s, 1H), 8.34 (s, 1H), 8.03 (s, 1H), 7.80 (dd, 2H), 7.56 (d, 1H), 7.35 (dd, 2H), 4.11 (m, 1H), 3.91 (d, 1H), 3.90 (s, 3H), 3.71 (dd, 2H), 3.57 (t, 1H), 3.27 (d, 1H), 3.05 (t, 1H), 1.01 (s, 3H) | 6 | Intermediates F + Q30 |
| 61 | 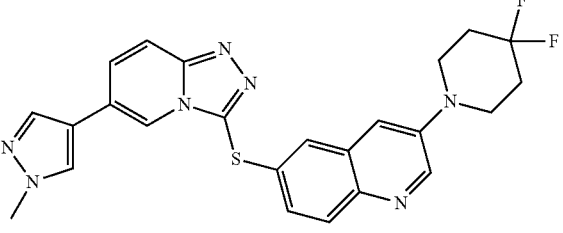<br>3-(4,4-Difluoro-piperidin-1-yl)-6-[6-(1-methyl-1H-pyrazol-4-yl)-[1,2,4]triazolo[4,3-a]pyridin-3-ylsulfanyl]-quinoline | LCMS (method B): [M + H]$^+$ = 478, $t_R$ = 2.45 min<br>$^1$H-NMR (400 MHz, DMSO-d$_6$) δ ppm 8.84 (d, 1H), 8.55 (s, 1H), 8.31 (s, 1H), 7.99 (d, 1H), 7.98 (s, 1H), 7.80 (m, 2H), 7.55 (d, 1H), 7.52 (d, 1H), 7.34 (dd, 1H), 3.84 (s, 3H), 3.45 (t, 4H), 2.08 (m, 4H) | 2 | Intermediates E + Q8 |
| 62 | 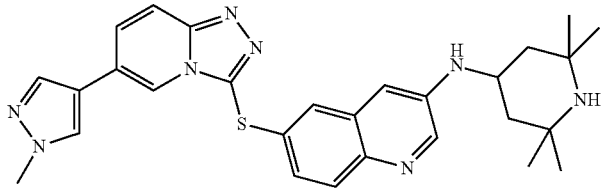<br>6-(6-(1-methyl-1H-pyrazol-4-yl)-[1,2,4]triazolo[4,3-a]pyridin-3-ylthio)-N-(2,2,6,6-tetramethyl piperidin-4-yl)quinolin-3-amine | LCMS (method B): [M + H]$^+$ = 513, $t_R$ = 1.80 min<br>$^1$H-NMR (400 MHz, DMSO-d$_6$) δ ppm 8.55 (d, 1H), 8.40 (s, 1H), 8.30 (s, 1H), 7.97 (d, 2H), 7.78 (d, 1H), 7.68 (d, 2H), 7.11 (d, 1H), 6.93 (d, 1H), 6.15 (d, 1H), 3.84 (s, 3H), 3.72 (d, 1H), 1.84 (d, 2H), 1.22 (m, 7H), 1.04 (m, 8H) | 2 | Intermediates F + Q31 |
| 64 | 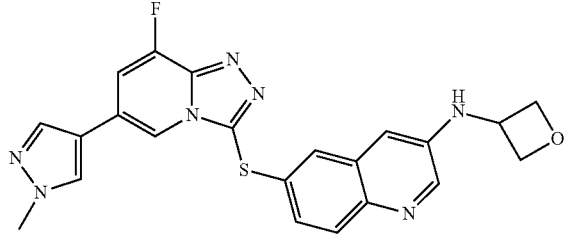<br>6-(8-fluoro-6-(1-methyl-1H-pyrazol-4-yl)-[1,2,4]triazolo[4,3-a]pyridin-3-ylthio)-N-(oxetan-3-yl)quinolin-3-amine | LCMS (method B): [M + H]$^+$ = 448, $t_R$ = 2.07 min<br>$^1$H-NMR (400 MHz, DMSO-d$_6$) δ ppm 8.45 (t, 2H), 8.33 (s, 1H), 8.01 (s, 1H), 7.82 (d, 1H), 7.74 (d, 1H), 7.53 (d, 1H), 7.24 (dd, 1H), 7.13 (d, 1H), 6.79 (d, 1H), 4.89 (t, 2H), 4.57 (m, 1H), 4.42 (t, 2H), 3.84 (s, 3H) | 2 | Intermediates F + Q36 |

| Ex. | Structure Name | LCMS (method) NMR | Method | Starting Material |
|---|---|---|---|---|
| 67 | 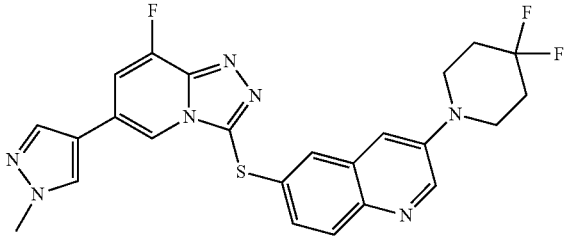<br>3-(4,4-Difluoro-piperidin-1-yl)-6-[8-fluoro-6-(1-methyl-1H-pyrazol-4-yl)[1,2,4]triazolo[4,3-a]pyridin-3-ylsulfanyl]-quinoline | LCMS (method B): $[M + H]^+ = 496$, $t_R = 2.48$ min<br>$^1$H-NMR (400 MHz, DMSO-$d_6$)<br>δ ppm 8.84 (d, 1H), 8.46 (d, 1H), 8.33 (s, 1H), 8.80 (s, 1H), 7.82 (d, 1H), 7.80 (s, 1H), 7.56 (d, 1H), 7.51 (d, 1H), 7.38 (dd, 1H), 3.84 (s, 3H), 3.45 (t, 4H), 2.08 (m, 4H) | 8 | Intermediates F + Q8 |
| 68 | 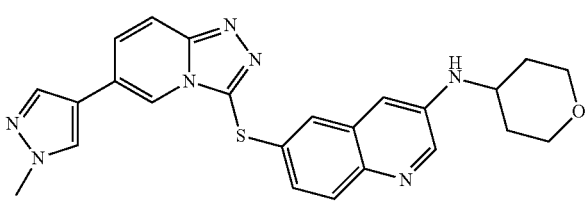<br>{6-[6-(1-Methyl-1H-pyrazol-4-yl)-[1,2,4]triazolo[4,3-a]pyridin-3-ylsulfanyl]-quinolin-3-yl}-(tetrahydro-pyran-4-yl)-amine | LCMS (method B): $[M + H]^+ = 458$, $t_R = 2.20$ min<br>$^1$H-NMR (400 MHz, DMSO-$d_6$)<br>δ ppm 8.54 (s, 1H), 8.39 (s, 1H), 8.31 (s, 1H), 7.98 (s, 1H), 7.97 (d, 1H), 7.80 (s, 1H), 7.78 (d, 1H), 7.48 (s, 1H), 7.15 (d, 1H), 6.99 (s, 1H), 6.34 (d, 1H), 3.87 (m, 2H), 3.84 (s, 3H), 3.49 (m, 1H), 3.48 (m, 2H), 1.90 (m, 2H), 1.37 (m, 2H) | 2 | Intermediates E + Q9 |
| 69 | 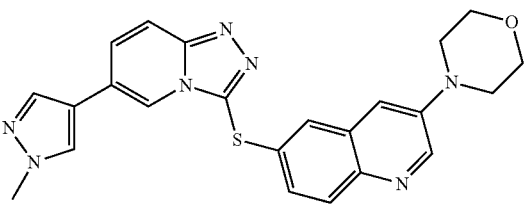<br>4-(6-(6-(1-methyl-1H-pyrazol-4-yl)-[1,2,4]triazolo[4,3-a]pyridin-3-ylthio)quinolin-3-yl)morpholine | LCMS (method B): $[M + H]^+ = 444$, $t_R = 2.09$ min<br>$^1$H-NMR (400 MHz, DMSO-$d_6$)<br>δ ppm 8.81 (s, 1H), 8.55 (s, 1H), 8.30 (s, 1H), 7.99 (d, 2H), 7.80 (dd, 2H), 7.57 (s, 1H), 7.41 (d, 1H), 7.32 (dd, 1H), 3.83 (s, 3H), 3.75 (t, 4H), 3.22 (t, 4H) | 9 | Intermediates E + Q33 |
| 70 | 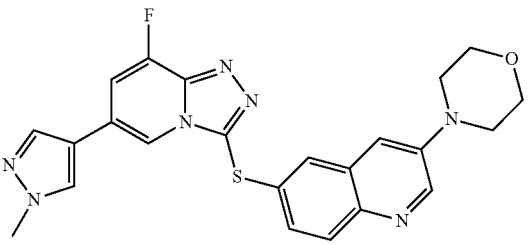<br>4-(6-(8-fluoro-6-(1-methyl-1H-pyrazol-4-yl)-[1,2,4]triazolo[4,3-a]pyridin-3-ylthio)quinolin-3-yl)morpholine | LCMS (method B): $[M + H]^+ = 462$, $t_R = 2.11$ min<br>$^1$H-NMR (400 MHz, DMSO-$d_6$)<br>δ ppm 8.82 (s, 1H), 8.46 (s, 1H), 8.33 (s, 1H), 8.02 (s, 1H), 7.83 (d, 2H), 7.58 (s, 1H), 7.42 (s, 1H), 7.39 (d, 1H), 3.84 (s, 3H), 3.75 (t, 4H), 3.38 (t, 4H) | 9 | Intermediates F + Q33 |

-continued

| Ex. | Structure Name | LCMS (method) NMR | Method | Starting Material |
|---|---|---|---|---|
| 71 | 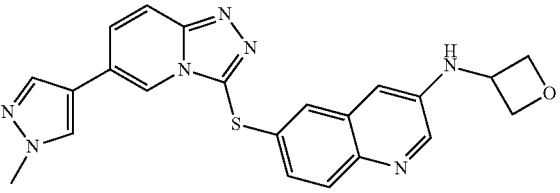  6-(6-(1-methyl-1H-pyrazol-4-yl)-[1,2,4]triazolo[4,3-a]pyridin-3-ylthio)-N-(oxetan-3-yl)quinolin-3-amine | LCMS (method B): $[M + H]^+ = 430$, $t_R = 2.04$ min $^1$H-NMR (400 MHz, DMSO-$d_6$) δ ppm 8.54 (s, 1H), 8.42 (d, 1H), 8.30 (s, 1H), 7.98 (t, 2H), 7.77 (dd, 1H), 7.73 (dd, 1H), 7.50 (s, 1H), 7.20 (dd, 1H), 7.10 (d, 1H), 6.79 (d, 1H), 4.87 (t, 2H), 4.58 (m, 1H), 4.42 (t, 2H), 3.84 (s, 3H). | 2 | Intermediates E + Q36 |
| 72 | 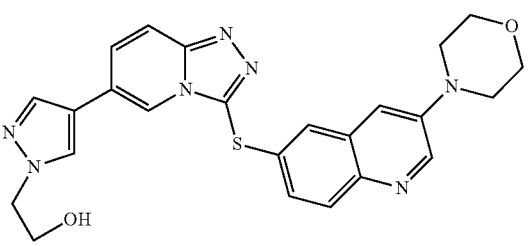  2-(4-(3-(3-morpholinoquinolin-6-ylthio)-[1,2,4]triazolo[4,3-a]pyridin-6-yl)-1H-pyrazol-1-yl)ethanol | LCMS (method B): $[M + H]^+ = 374$, $t_R = 1.99$ min $^1$H-NMR (400 MHz, DMSO-$d_6$) δ ppm 9.02 (s, 1H), 8.70 (s, 1H), 8.27 (d, 2H), 8.0 (m, 5H), 7.76 (d, 1H), 4.26 (s, 2H), 3.89 (s, 6H), 3.44 (s, 4H) | 2 | Intermediates G + Q33 |
| 74 | 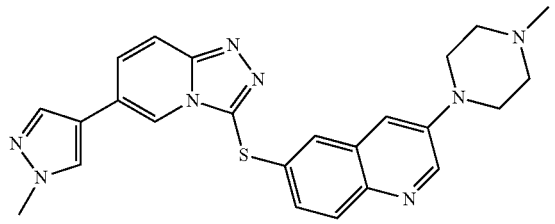  3-(4-Methyl-piperazin-1-yl)-6-[6-(1-methyl-1H-pyrazol-4-yl)-[1,2,4]triazolo[4,3-a]pyridin-3-ylsulfanyl]-quinoline | LCMS (method B): $[M + H]^+ = 457$, $t_R = 1.63$ min $^1$H-NMR (400 MHz, DMSO-$d_6$) δ ppm 8.80 (s, 1H), 8.55 (s, 1H), 8.31 (s, 1H), 7.99 (d, 1H), 7.98 (s, 1H), 7.80 (dd, 2H), 7.55 (s, 1H), 7.39 (s, 1H), 7.30 (d, 1H), 3.84 (s, 3H), 3.25 (t, 4H), 2.45 (t, 4H), 2.21 (s, 3H). | 2 | Intermediates E + Q14 |
| 75 | 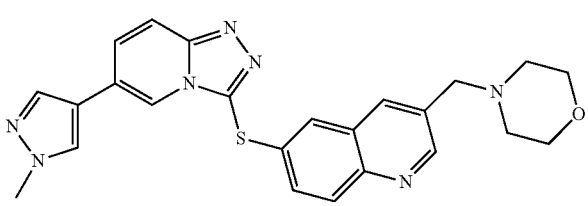  4-((6-(6-(1-methyl-1H-pyrazol-4-yl)-[1,2,4]triazolo[4,3-a]pyridin-3-ylthio)quinolin-3-yl)methyl)-morpholine | LCMS (method B): $[M + H]^+ = 458$, $t_R = 1.31$ min $^1$H-NMR (400 MHz, DMSO-$d_6$) δ ppm 8.82 (s, 1H), 8.59 (d, 1H), 8.32 (s, 1H), 8.17 (s, 1H), 7.96 (m, 3H), 7.83 (m, 2H), 7.58 (d, 1H), 3.83 (s, 3H), 3.74 (s, 2H), 3.73 (s, 6H), 3.12 (s, 2H). | 2 | Intermediates E + Q35 |

| Ex. | Structure Name | LCMS (method) NMR | Method | Starting Material |
|---|---|---|---|---|
| 76 | (E)-1-(3-((3-(4-hydroxypiperidin-1-yl)quinolin-6-yl)thio)-[1,2,4]triazolo[4,3-a]pyridin-6-yl)-ethanone O-(2-hydroxyethyl) oxime | LCMS (method A): [M + H]⁺ = 479.1, $t_R$ = 2.122 min. ¹H-NMR (400 MHz, MeOH-d₄) δ ppm 8.69 (s, 1H), 8.38 (s, 1H), 7.98 (d, 1H), 7.75-7.78 (m, 2H), 7.67 (s, 1H), 7.38 (s, 1H), 7.32 (d, 1H), 4.22-4.24 (m, 2H), 3.78-3.82 (m, 3H), 3.65-3.77 (m, 2H), 2.98-3.05 (m, 2H), 2.15 (s, 3H), 1.95-2.00 (m, 2H), 1.63-1.69 (m, 2H). | 10 (4 steps) | Intermediates I + Q27 |
| 77 | (E)-1-(3-((3-morpholinoquinolin-6-yl)thio)-[1,2,4]triazolo[4,3-a]pyridin-6-yl)ethanone oxime | LCMS (method A): [M + H]⁺ = 421.1, $t_R$ = 2.18 min. ¹H NMR (400 MHz, DMSO-d₆) δ ppm 2.11 (s, 3H) 3.25 (br. s., 4H) 3.66-3.87 (m, 4H) 7.34 (d, 1H) 7.43 (br. s., 1H) 7.61 (s, 1H) 7.82 (d, 1H) 7.84-8.01 (m, 2H) 8.39 (s, 1H) 8.83 (s, 1H) 11.60 (s, 1H) | 11 (4 steps) | Intermediates I + Q33 |
| 78 | (E)-1-(3-((3-morpholinoquinolin-6-yl)thio)-[1,2,4]triazolo[4,3-a]pyridin-6-yl)ethanone O-(2-hydroxyethyl oxime | LCMS (method A): [M + H]⁺ = 465.2, $t_R$ = 2.21 min. ¹H NMR (400 MHz, MeOH-d₄) δ ppm 2.24 (s, 3H) 3.43 (br. s., 4H) 3.82 (br. s., 2H) 3.88 (br. s., 4H) 4.28 (br. s., 2H) 7.69 (d, 1H) 7.86 (br. s., 1H) 7.90 (d, 1H) 7.99 (d, 1H) 8.04-8.20 (m, 2H) 8.52 (s, 1H) 9.02 (br. s., 1H) | 12 | Intermediate 77.3 |
| 79 | (E)-1-(3-(3-(morpholinomethyl)quinolin-6-ylthio)-[1,2,4]triazolo[4,3-a]pyridin-6-yl)ethanone oxime | LCMS (method A): [M + H]⁺ = 435.1, $t_R$ = 1.54 min. ¹H NMR (400 MHz, MeOH-d₄) δ ppm 2.14 (s, 3H) 2.48 (br. s., 4H) 3.69 (m, 6H) 7.65 (d, 1H) 7.81 (d, 1H) 7.89 (s, 1H) 7.97 (d, 1H) 8.04 (d, 1H) 8.16 (s, 1H) 8.43 (s, 1H) 8.84 (s, 1H) | 13 (4 steps) | Intermediates I + Q35 |

-continued

| Ex. | Structure Name | LCMS (method) NMR | Method | Starting Material |
|---|---|---|---|---|
| 80 | 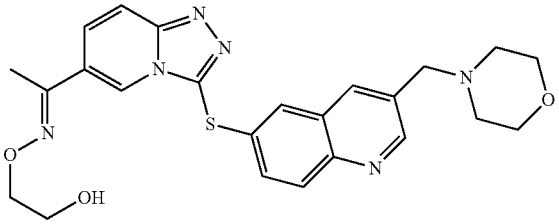<br>(E)-1-(3-((3-(morpholinomethyl)quinolin-6-yl)thio)-[1,2,4]triazolo[4,3-a]pyridin-6-yl)ethanone O-(2-hydroxyethyl) oxime | LCMS (method A): [M + H]$^+$ = 479.1, $t_R$ = 1.60 min. $^1$H NMR (400 MHz, CDCl$_3$) δ ppm 2.20 (s, 3H) 2.34-2.61 (br. s., 4H) 3.56-3.80 (m, 6H) 3.86-3.98 (m, 2H) 4.26-4.39 (m, 2H) 7.62 (dd, 1H) 7.73 (s, 1H) 7.76-7.88 (m, 2H) 7.94 (br. s., 1H) 8.03 (d, 1H) 8.29 (s, 1H) 8.88 (s, 1H) | 14 | Intermediate 79.3 |
| 81 | 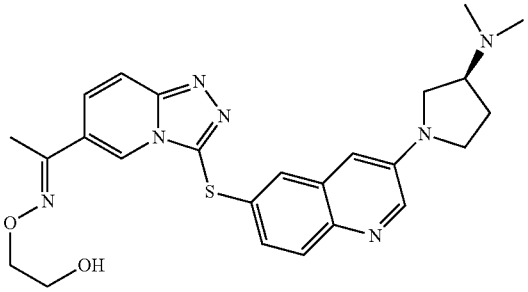<br>(S,E)-1-(3-(3-(3-(dimethylamino)pyrrolidin-1-yl)quinolin-6-ylthio)-[1,2,4]triazolo[4,3-a]pyridin-6-yl)ethanone O-2-hydroxyethyl oxime | LCMS (method A): [M + H]$^+$ = 492.2, $t_R$ = 1.64 min. $^1$H NMR (400 MHz, MeOH-d$_4$) δ ppm 2.20 (s, 3H) 2.30-2.44 (m, 1H) 2.57-2.72 (m, 1H) 3.01 (s, 6H) 3.46-3.60 (m, 1H) 3.67-3.84 (m, 4H) 3.90 (dd, 1H) 4.13 (quin, 1H) 4.21-4.30 (m, 2H) 7.41 (d, 1H) 7.43-7.54 (m, 1H) 7.69 (d, 1H) 7.89 (d, 1H) 7.86 (d, 1H) 8.03-8.11 (m, 1H) 8.46 (s, 1H) 8.60 (d, 1H) | 15 (4 steps) | Intermediates I + Q2 |
| 82 | 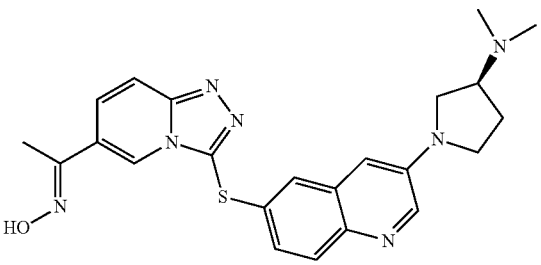<br>(S,E)-1-(3-(3-(3-(dimethylamino)pyrrolidin-1-yl)quinolin-6-ylthio)-[1,2,4]triazolo[4,3-a]pyridin-6-yl)ethanone oxime | LCMS (method A): [M + H]$^+$ = 448.0, $t_R$ = 2.24 min. $^1$H NMR (400 MHz, MeOH-d$_4$) δ ppm 2.16 (s, 3H) 2.28-2.48 (m, 1H) 2.56-2.75 (m, 1H) 3.01 (s, 6H) 3.47-3.61 (m, 1H) 3.68-3.84 (m, 2H) 3.91 (dd, 1H) 4.13 (quin, 1H) 7.42-7.57 (m, 2H) 7.67 (d, 1H) 7.78-7.95 (m, 2H) 8.09 (dd, 1H) 8.43 (s, 1H) 8.62 (d, 1H). | 16 | Intermediate 81.3 |
| 83 | 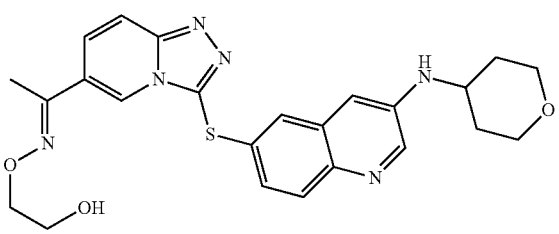<br>(E)-1-(3-(3-(tetrahydro-2H-pyran-4-ylamino)quinolin-6-ylthio)-[1,2,4]triazolo[4,3-a]pyridin-6-yl)ethanone O-2-hydroxyethyl oxime | LCMS (method A): [M + H]$^+$ = 479.2, $t_R$ = 2.21 min. $^1$H NMR (400 MHz, MeOH-d$_4$) δ ppm 1.50-1.60 (m, 2H) 2.03 (d, 2H) 2.05 (s, 3H) 3.55 (t, 2H) 3.58-3.68 (m, 2H) 3.81 (t, 1H) 3.97-4.00 (m, 2H) 4.27 (t, 2H) 7.48 (dd, 1H) 7.63 (d, 1H) 7.70 (d, 1H) 7.85-7.89 (m, 2H) 8.09 (dd, 1H) 8.49-8.52 (m, 2H) | 17 (4 steps) | Intermediates I + Q2 |

| Ex. | Structure Name | LCMS (method) NMR | Method | Starting Material |
|---|---|---|---|---|
| 84 | 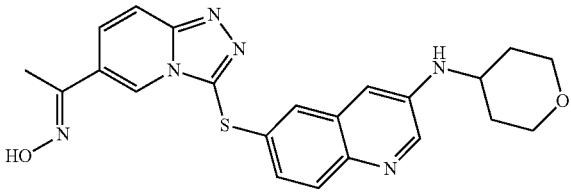<br>(E)-1-(3-(3-(tetrahydro-2H-pyran-4-ylamino)quinolin-6-ylthio)-[1,2,4]triazolo[4,3-a]pyridin-6-yl)ethanone oxime | LCMS (method A): [M + H]$^+$ = 435.0, $t_R$ = 3.30 min. $^1$H NMR (400 MHz, MeOH-d$_4$) δ ppm 1.46-1.64 (m, 2H) 2.03 (d, 2H) 2.18 (s, 3H) 3.52-3.61 (m, 2H) 3.61-3.72 (m, 1H) 3.99 (dt, 2H) 7.48 (dd, 1H) 7.63 (d, 1H) 7.69 (d, 1H) 7.82-7.86 (m, 1H) 7.86-7.92 (m, 1H) 8.10 (dd, 1H) 8.46 (s, 1H) 8.51 (d, 1H) | 16 | Intermediate 83.3 |
| 85 | 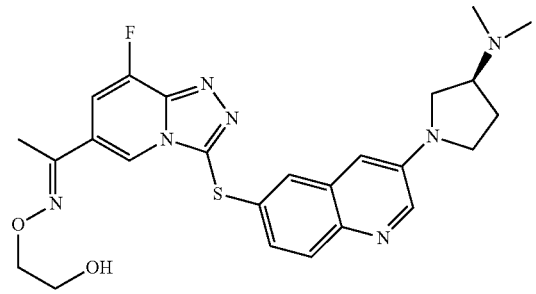<br>(S,E)-1-{3-[3-(3-dimethylamino-pyrrolidin-1-yl)-quinolin-6-ylthio]-8-fluoro-[1,2,4]triazolo[4,3-a]pyridin-6-yl}-ethanone O-(2-hydroxy-ethyl)-oxime | LCMS (method A): [M + H]$^+$ = 510.1, $t_R$= 1.73 min. $^1$H NMR (400 MHz, MeOH-d$_4$) δ ppm 2.15-2.30 (m, 3 H) 2.30-2.45 (m, 1 H) 2.57-2.72 (m, 1 H) 3.01 (s, 6 H) 3.48-3.59 (m, 2 H) 3.69-3.78 (m, 1H) 3.78-3.85 (m, 3 H) 3.90 (dd, J = 10.79, 7.53 Hz, 1 H) 4.13 (quin, J = 7.15 Hz, 1 H) 4.21-4.36 (m, 2 H) 7.41 (d, J = 2.76 Hz, 1 H) 7.49 (dd, J = 8.78, 2.01 Hz, 1 H) 7.74 (d, J = 2.01 Hz, 1 H) 7.81 (dd, J = 11.80, 1.00 Hz, 1 H) 7.90 (d, J = 8.78 Hz, 1 H) 8.32 (d, J = 1.00 Hz, 1 H) 8.61 (d, J = 2.76 Hz, 1 H) | 18 (4 steps) | Intermediates H + Q2 |
| 86 | 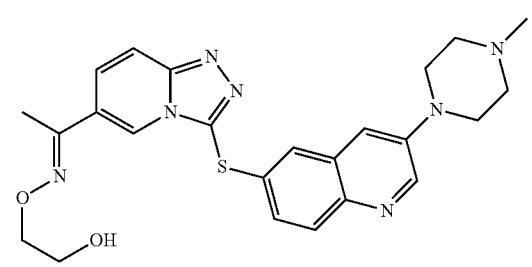<br>(E)-1-(3-(3-(4-methylpiperazin-1-yl)quinolin-6-ylthio)-[1,2,4]triazolo[4,3-a]pyridin-6-yl)ethanone O-2-hydroxyethyl oxime | LCMS (method A): [M + H]$^+$ = 478.0, $t_R$ = 1.74 min. $^1$H NMR (400 MHz, MeOH-d$_4$) δ ppm 2.18 (s, 3H) 2.37 (s, 3H) 2.65 (m, 4H) 3..36 (m, 4H) 3.79 (t, 2H) 4.25 (t, 2H) 7.41 (dd, 1H) 7.46 (d, 1H) 7.74 (d, 1H) 7.83 (m, 2H) 8.03 (d, 1H) 8.43 (s, 1H) 8.75 (d, 1H) | 19 (3 steps) | Intermediates I + Q14 |

Comparative Examples

The following compounds were used for comparative purposes, and synthesized according to the procedures described in the cited reference:

Comparator No. 1: 6-{Difluoro-[6-(1-methyl-1H-pyrazol-4-yl)-[1,2,4]triazolo[4,3-b]pyridazin-3-yl]-methyl}-quinoline (JNJ-38877605)

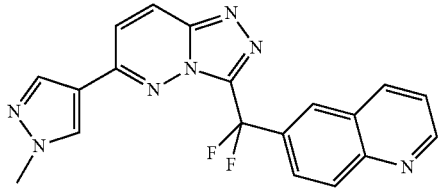 [SMILES: Cn1cc(-c2ccc3nnc(C(F)(F)c4ccc5ncccc5c4)n3n2)cn1]

6-{Difluoro-[6-(1-methyl-1H-pyrazol-4-yl)-[1,2,4]triazolo[4,3-b]pyridazin-3-yl]-methyl}-quinoline was disclosed as Example 61 in WO 2007/075567.

Comparator No. 2: 1-{3-[3-(4-Methyl-piperazin-1-yl)-quinolin-6-ylmethyl]-[1,2,4]triazolo[4,3-b]pyridazin-6-yl}-ethanone O-(2-hydroxy-ethyl)-oxime

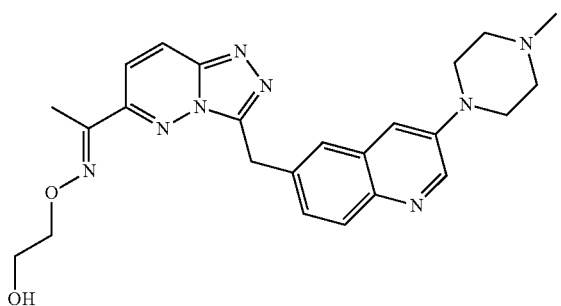 [SMILES: C/C(=N\OCCO)c1ccc2nnc(Cc3ccc4ncc(N5CCN(C)CC5)cc4c3)n2n1]

1-{3-[3-(4-Methyl-piperazin-1-yl)-quinolin-6-ylmethyl]-[1,2,4]triazolo[4,3-b]pyridazin-6-yl}-ethanone O-(2-hydroxy-ethyl)-oxime was disclosed as Example 63 in WO 2011/020861.

Comparator No. 3: 2-[4-(3-Quinolin-6-ylmethyl-3H-[1,2,3]triazolo[4,5-b]pyrazin-5-yl)-pyrazol-1-yl]-ethanol (PF-04217903)

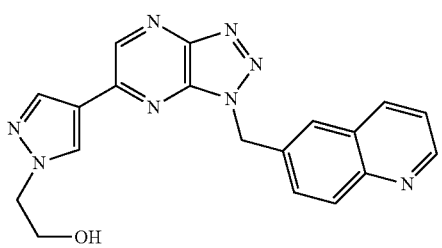 [SMILES: OCCn1cc(-c2cnc3nnn(Cc4ccc5ncccc5c4)c3n2)cn1]

2-[4-(3-Quinolin-6-ylmethyl-3H-[1,2,3]triazolo[4,5-b]pyrazin-5-yl)-pyrazol-1-yl]-ethanol was disclosed as Example 209 in WO 2007/132308 and in WO 2009/068955

Comparator No. 4: 6-[6-(1-Methyl-1H-pyrazol-4-yl)-[1,2,4]triazolo[4,3-b]pyridazin-3-ylsulfanyl]-quinoline (SGX523)

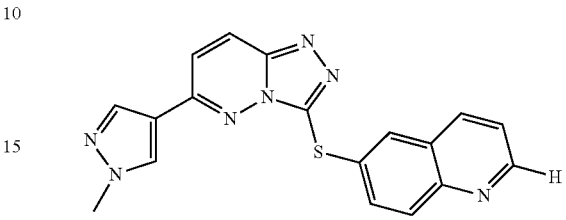

6-[6-(1-Methyl-1H-pyrazol-4-yl)-[1,2,4]triazolo[4,3-b]pyridazin-3-ylsulfanyl]-quinoline was disclosed as Example 4 in WO 2008/051808.

The activity of a compound according to the present invention can be assessed by the following in vitro & in vivo methods.

1. C-Met Enzyme Assay (EPK c-Met Profiling Assay)

A number of compounds of the present invention were assayed in an antibody based kinase phosphorylation assay as follows.

The EPK kinase assay for c-Met receptor tyrosine kinase was developed, using the purified recombinant GST-fusion protein, containing the cytoplasmic domain of the enzyme. GST-c-MET (969-1390) was purified by affinity chromatography.

The kinase assay is based on the LanthaScreen™ technology. LanthaScreen™ is the detection of Time-Resolved Fluorescence Resonance Energy Transfer (TR-FRET) using lanthanide chelates to measure interactions between various binding partners. In a TR-FRET kinase assay, a long-lifetime lanthanide donor species is conjugated to an antibody that specifically binds to a phosphorylated product of a kinase reaction that is labeled with a suitable acceptor fluorophore. This antibody-mediated interaction brings the lanthanide donor and the acceptor into proximity such that resonance energy transfer can take place, resulting in a detectable increase in the FRET signal.

The kinase reactions were performed in 384 well microtiter plates in a total reaction volume of 10.05 µL. The assay plates were prepared with 0.05 µL per well of test compound in the appropriate test concentration, as described under "preparation of compound dilutions". The reactions were started by combining 5 µL of ATP solution with 5 µL of enzyme-substrate mix (consisting of kinase and substrate). The final concentrations in the kinase reactions were 25 mM Tris/HCl, 1 mM DTT, 0.025% Tween20, 10 µM sodium orthovanadate, 0.25% BSA, 0.5% DMSO, 10 mM MgCl$_2$, 3 mM MnCl$_2$, 2 µM ATP, 50 nM Fluorescein-PolyEAY, and 0.3 nM enzyme. The reactions were incubated for 60 minutes at room temperature and stopped by adding 5 µL of stop buffer (50 mM EDTA, 0.04% NP40, 20 mM Tris/HCl). Subsequently 5 µL of detection mix (50 mM Tris/HCl, 2 mM DTT, 0.05% Tween20, 20 µM sodium orthovanadate, 1% BSA, 1 nM Tb-PY20 antibody) were added to the stopped reactions. After 45 minutes incubation in dark at room temperature, the plates were measured in a Perkinelmer Envision fluorescence reader. The effect of compound on the enzymatic activity was in all assays obtained from the linear progress curves and determined from one reading (end point measurement).

Results are summarized in the Table 1-A below. "Active" compounds of the invention have an $IC_{50}$ in this enzyme assay of less than 500 nM, preferably less than 100 nM, more preferably less than 50 nM and most preferably less than 10 nM.

As it can be seen, each of the exemplified compounds of the invention has an $IC_{50}$ value in this enzyme assay below 500 nM. The preferred compounds of the invention each have an $IC_{50}$ value in this enzyme assay below 100 nM, and the most preferred compounds have $IC_{50}$ values in this enzyme assay below 10 nM.

Results for some further compounds as described herein are summarized in the Table 1-B below.

For comparison, results for reference examples and for comparator compounds are summarized below in Table 1-C.

TABLE 1-A c-Met Inhibitory activity of compounds of the invention

| Example No. | c-Met Biochem $IC_{50}$ [nM] | Example No. | c-Met Biochem $IC_{50}$ [nM] |
|---|---|---|---|
| 1 | 9 | 40 | 1 |
| 2 | 5 | 41 | 15 |
| 3 | 2 | 42 | 4 |
| 6 | 8 | 43 | 2 |
| 9 | 7 | 44 | 1 |
| 10 | 3 | 45 | 399 |
| 12 | 4 | 46 | 18 |
| 13 | 1 | 47 | 5 |
| 14 | 2 | 48 | 5 |
| 17 | 3 | 49 | 3 |
| 18 | 48 | 50 | 4 |
| 19 | 8 | 57 | 2 |
| 20 | 15 | 58 | 3 |
| 21 | 2 | 59 | 3 |
| 24 | 2 | 60 | 4 |
| 26 | 69 | 61 | 4 |
| 27 | 3 | 67 | 1 |
| 28 | 78 | 69 | 3 |
| 29 | 4 | 70 | 3 |
| 30 | 2 | 72 | 12 |
| 31 | 3 | 74 | 4 |
| 32 | 12 | 75 | 24 |
| 33 | 4 | 76 | 7 |
| 34 | 45 | 77 | 5 |
| 35 | 4 | 78 | 2 |
| 35A | 5 | 79 | 83 |
| 35B | 4 | 80 | 33 |
| 36 | 4 | 81 | 6 |
| 37 | 2 | 82 | 6 |
| 38 | 2 | 85 | 15 |
| 39 | 23 | 86 | 10 |

TABLE 1-B c-Met Inhibitory activity of selected further compounds of the invention

| Example No. | c-Met Biochem $IC_{50}$ [nM] | Example No. | c-Met Biochem $IC_{50}$ [nM] |
|---|---|---|---|
| 4 | 11 | 53 | 1 |
| 5 | 6 | 54 | 8 |
| 7 | 3 | 55 | 1.3 |
| 8 | 1 | 56 | 13 |
| 11 | 4 | 62 | 6 |
| 15 | 4 | 64 | 8 |
| 22 | 19 | 68 | 5 |
| 23 | 11 | 71 | 6 |

TABLE 1-B-continued c-Met Inhibitory activity of selected further compounds of the invention

| Example No. | c-Met Biochem $IC_{50}$ [nM] | Example No. | c-Met Biochem $IC_{50}$ [nM] |
|---|---|---|---|
| 25 | 4 | 83 | 8 |
| 51 | 4 | 84 | 8 |
| 52 | 2 | | |

TABLE 1-C c-Met Inhibitory activity of reference and comparator compounds

| Compound No. | c-Met Biochem $IC_{50}$ [nM] |
|---|---|
| Reference Example No. 16 | 312 |
| Reference Example No. 63 | 3 |
| Reference Example No. 65 | 18 |
| Reference Example No. 66 | 3 |
| Reference Example No. 73 | 5 |
| Comparator No. 1 (JNJ-38877605) | 3 |
| Comparator No. 2 | 6 |
| Comparator No. 3 (PF-04217903) | 4 |
| Comparator No. 4 (SGX523) | <10 |

2. GTL16 Cell Viability Assay:

GTL16 cell line is derived from a gastric cancer patient. GTL16 expresses high level of c-Met receptor tyrosine kinase due to the gene amplification. The growth of GTL16 is highly dependent on c-Met kinase activity; hence it is used as a cell-based assay to monitor the cellular activity of the c-Met kinase inhibitors.

GTL16 cells were seeded in DMEM medium with 10% FBS and 1% Pene. & Strep. at 5000 cells/well/90 µL in 96 well plate and incubated overnight for attachment at 37° C. in 5% $CO_2$ incubator. 10-fold serials dilutions of compounds were added to the cell as 10 µL/well. The final assay volume was 100 µl/well. The assay plates were incubated at 37° C. in 5% $CO_2$ incubator for 24 hours. The viability of cells was measured using the CellTiter Glo (Cat#G7573 Promega) according to the protocol suggested by the vender. Briefly, the plates were cooled at room temperature for 10 mins and 100 µl of CellTiter Glo reagent was added into each well. Plates were shaken for 10 mins. The chemiluminescent light unit was read in Envision from Perkin Elmer. All the tests were run at triplicates. The $IC_{50}$ was calculated using Spotfire software.

Results are summarized in the Table 2-A below. "Active" compounds of the invention have an $IC_{50}$ in this enzyme assay of less than 1500 nM, preferably less than 1000 nM, preferably less than 500 nM, more preferably less than 100 nM, more preferably less than 20 nM and most preferably less than 10 nM.

Each of the exemplified compounds has an $IC_{50}$ value in this enzyme assay below 1500 nM. The preferred compounds of the invention each have an $IC_{50}$ value in this enzyme assay below 500 nM, more preferred compounds have $IC_{50}$ values in this enzyme assay below 100 nM and the most preferred compounds have $IC_{50}$ values in this enzyme assay below 10 nM.

Results for some further compounds as described herein are summarized in the Table 2-B below.

For comparison, results for reference examples and for comparator compounds are summarized below in Table 2-C.

TABLE 2-A c-Met inhibitory activity of selected compounds of the invention

| Example No. | GTL-16 Proliferation $IC_{50}$ [nM] | Example No. | GTL-16 Proliferation $IC_{50}$ [nM] |
|---|---|---|---|
| 1 | 2 | 39 | 9 |
| 2 | 6 | 40 | 1 |
| 3 | 1 | 41 | 6 |
| 6 | 27 | 42 | 0.6 |
| 9 | 3 | 43 | 0.3 |
| 10 | 21 | 44 | 0.8 |
| 12 | 0.6 | 47 | 3 |
| 13 | 0.4 | 48 | 1 |
| 14 | 2 | 49 | 4 |
| 17 | 3 | 50 | 1 |
| 18 | 105 | 57 | 10 |
| 19 | 35 | 58 | 8 |
| 20 | 1 | 59 | 11 |
| 21 | 36 | 60 | 11 |
| 24 | 0.9 | 61 | 2 |
| 26 | 10 | 67 | 0.3 |
| 27 | 4 | 69 | 3 |
| 28 | 2 | 70 | 1 |
| 29 | 40 | 72 | 86 |
| 30 | 2 | 74 | 2 |
| 31 | 0.4 | 75 | 10 |
| 32 | 4 | 76 | 54 |
| 33 | 4 | 77 | 8 |
| 34 | 1 | 78 | 3 |
| 35 | 0.4 | 79 | 1138 |
| 35A | 1 | 80 | 125 |
| 35B | 4 | 81 | 4 |
| 36 | 0.9 | 82 | 4 |
| 37 | 0.9 | 85 | 23 |
| 38 | 3 | 86 | 51 |

TABLE 2-B c-Met inhibitory activity of selected further compounds of the invention

| Example No. | GTL-16 Proliferation $IC_{50}$ [nM] | Example No. | GTL-16 Proliferation $IC_{50}$ [nM] |
|---|---|---|---|
| 4 | 1 | 53 | 17 |
| 5 | 385 | 54 | 14 |
| 7 | 24 | 55 | 1 |
| 8 | 1 | 56 | 33 |
| 11 | 2 | 62 | 73 |
| 15 | 2 | 64 | 5 |
| 22 | 2 | 68 | 3 |
| 23 | 289 | 71 | 35 |
| 25 | 8 | 83 | 1 |
| 51 | 9 | 84 | 3 |
| 52 | 2 | | |

TABLE 2-C c-Met Inhibitory activity of reference and comparator compounds

| Compound No. | GTL-16 Proliferation $IC_{50}$ [nM] |
|---|---|
| Reference Example No. 16 | 1182 |
| Reference Example No. 63 | 8 |
| Reference Example No. 65 | 10 |
| Reference Example No. 66 | 3 |
| Comparator No. 1 (JNJ-38877605) | <10 |
| Comparator No. 3 (PF-04217903) | <10 |

3. hPDE3 Assay

Phosphodiesterase-3 (PDE3) is one of a family of phosphodiesterases responsible for the regulation of cyclic nucleotide second messengers. Human PDE3 has high affinity for both cAMP and cGMP and is distributed in a wide range of tissues and cell types. Inhibitors of hPDE3 are potentially useful as inotropic/vasodilator, antithrombotic and anti-inflammatory agents (Komas et al. 1996). Agents that inhibit PDE3 were originally investigated for the treatment of heart failure but have unwanted arrhythmic side effects (Dart R. C., Medical Toxicology, Edition 3, page 708; Lippincott 2004).

PDE3 assays to measure the inhibitory potential of compounds at this enzyme are well known to the person skilled in the art. For example, cAMP and cGMP levels can be measured by the use of the tritium containing compounds $^3$HcAMP and $^3$HcGMP as described in [Hansen, R. S., and Beavo, J. A., PNAS 1982; 79: 2788-92]. To screen a compound pool comprised of a large number of compounds, the microtiter plate-based scintillation proximity assay (SPA) as described in [Bardelle, C. et al. (1999) Anal. Biochem. 275: 148-155] can be applied. Alternatively, the phosphodiesterase activity of the recombinant protein can be assayed using a commercially available SPA kit (Amersham Pharmacia). Such an assay for PDE3 was e.g. described within Kima et al (2004) Bioorganic & Medicinal Chemistry Letters, Vol 14(9): 2099-2103. An alternative PDE3 assay for measuring the PDE3 inhibitory potential of c-Met inhibitors was disclosed in WO 2010/138673.

A possible isolation method for human PDE3 from human platelets is disclosed within Ito et al (1996) Cell Signal. 1996 December; 8(8):575-81.

Here, compounds of formula I were screened for their ability to inhibit human PDE3 in the assay based on Amersham Pharmacia Biotech's Phosphodiesterase (PDE) [$^3$H]-adenosine 3',5' cyclic phosphate ([$^3$H]cAMP) Scintillation Proximity Assay (SPA). The assay is based on the hydrolysis of [$^3$H]cAMP, by human platelet PDE3, to [$^3$H]5'-adenoside monophosphate (5'-AMP). The [$^3$H]5'-AMP is specifically captured by yttrium silicate SPA beads in the presence of zinc sulphate. When [$^3$H]5'-AMP binds to the beads, β-particles are emitted and excite, by their proximity, the fluorophore in the beads and hence produce light. Free [$^3$H]cAMP in turn does not activate the scintillant, since the unbound radioactivity is released too distant from the scintillant, and hence does not produce light.

Materials
  Optiplate and TopSeal-S (Can berra Packard)
  Human platelet PDE3 (partially purified from human platelets)—a titration curve of human platelet PDE3 activity was performed to optimise the concentration of hPDE3 required in the assay.
  Yttrium silicate SPA beads and [$^3$H]cAMP (Amersham)
  Tris-Base, magnesium chloride, ethylenediaminetetraacetic acid (di-sodium salt), bovine serum albumin BSA and cAMP (Sigma)

Solutions and Buffers:
  Assay buffer: 7.56 g Tris-Base was dissolved in approximately 800 mL distilled water and the pH adjusted to 7.5 with 1 M hydrochloric acid. 10.3 mL 1 M magnesium chloride and 4.25 mL 0.5 M EDTA were added. The solution was made to 1 L with distilled water and stored at 4° C. On day of use 18 mL of the above solution was removed and 2 mL 5 mg/ml BSA were added thereto.
  Enzyme buffer: 10 mM Tris-HCl at pH 7.5, 1 mM EDTA
  Yttrium silicate SPA beads: 1 vial was reconstituted in 28 mL distilled water and stored at 4° C.

Assay

The assay was performed in a final volume of 100 μL per well of an Optiplate (Canberra Packard). A 10 μL aliquot of the test compound dissolved in DMSO/distilled water was placed in a well of an Optiplate plate, followed by the addition of 80 μL 'Assay mix' (5.5 μL [$^3$H]cAMP and 88 μL "cold" cAMP were diluted to 8.8 mL using assay buffer). The reaction was started by adding 10 µL hPDE3 (50 µL stock hPDE3 solution was diluted 50 fold to 2.5 mL using enzyme buffer). The plate was incubated at room temperature for 30 min, the reaction was then terminated by the addition of 50 µL Yttrium silicate SPA beads (pre-warmed to room temperature) to all wells. The plate incubated at room temperature for at least 15 min. The plate was sealed using TopSeal-S according to the manufacturer's instructions and counted using a Packard TopCount, each well being counted for 1 min. $IC_{50}$ values were determined using non-linear regression.

Results of some exemplary compounds are summarized in the Table 3-A below. Compounds of the invention have preferably high $IC_{50}$ values in this enzyme assay, preferably more than 5 µM, more preferably more than 10 µM and most preferably more than 30 µM. As it can be seen, each of the exemplified compounds has an $IC_{50}$ value in this enzyme assay above 10 µM. Results for some further compounds as described herein are summarized in the Table 3-B below.

For comparison, results for reference examples and for comparator compounds are summarized below in Table 3-C. As it can be seen from the data comparator compounds with different core structures show significantly lower PDE3 $IC_{50}$ values.

TABLE 3-A

PDE3 Inhibitory activity of selected compounds of the invention

| Example No. | hPDE3 $IC_{50}$ [µM] | Example No. | hPDE3 $IC_{50}$ [µM] |
| --- | --- | --- | --- |
| 3 | 14 | 57 | 10 |
| 6 | 30 | 58 | 13 |
| 10 | 17 | 59 | 6 |
| 13 | 24 | 61 | 12 |
| 21 | 30 | 69 | >30 |
| 27 | 17 | 70 | >30 |
| 30 | 25 | 74 | 18 |
| 31 | 30 | 76 | 14 |
| 32 | 26 | 77 | 12 |
| 34 | 30 | 78 | 28 |
| 35A | 16 | 79 | >30 |
| 42 | 29 | 80 | 30 |
| 43 | 20 | 82 | 11 |
| 46 | 30 | 85 | 30 |
| 47 | 12 | 86 | 27 |
| 50 | 30 | | |

TABLE 3-B

PDE3 Inhibitory activity of selected further compounds of the invention

| Example No. | hPDE3 $IC_{50}$ [µM] |
| --- | --- |
| 8 | 30 |
| 15 | 30 |
| 22 | 15 |
| 23 | 30 |
| 51 | 7 |
| 53 | 14 |
| 54 | 13 |
| 55 | >30 |
| 56 | 17 |
| 62 | 18 |
| 68 | 10 |
| 83 | 20 |
| 84 | 6 |

TABLE 3-C

PDE3 Inhibitory activity of reference and comparator compounds

| Compound No. | c-Met Biochem $IC_{50}$ [nM] |
| --- | --- |
| Reference Example No. 63 | 15 |
| Reference Example No. 66 | >30 |
| Reference Example No. 73 | 7 |
| Comparator No. 1 (JNJ-38877605) | 4 |
| Comparator No. 2 | 4 |
| Comparator No. 3 (PF-04217903) | 7 |
| Comparator No. 4 (SGX523) | 3 |

4. Metabolic Stability in Monkey Liver Cytosol Fractions

The compounds of the invention were analysed with regard to their metabolic stability in view of the recent publication of apparent species dependent toxicity reported for 6-(6-(1-methyl-1H-pyrazol-4-yl)-[1,2,4]triazolo[4,3-b]pyridazin-3-ylthio)quinoline (SGX523), a c-MET inhibitor that entered clinical development for the treatment of solid tumors [Diamond et al (2010) DRUG METABOLISM AND DISPOSITION, Vol. 38, No. 8, 1277-1285]. Patients treated with SGX523 exhibited compromised renal function presumably resulting from crystal deposits in renal tubules. Metabolite profiling of SGX523 indicated that metabolite [6-(6-(1-methyl-1H-pyrazol-4-yl)-[1,2,4]triazolo[4,3-b]pyridazin-3-ylthio)quinolin-2(1H)-one (M11)] was generated by monkey and human liver S-9, and to a lesser extent by rat S-9, whereas M11 was absent in dog S-9 incubations. It was shown that aldehyde oxidase (AO) was responsible for the generation of the 2-quinolinone-SGX523 metabolite which is markedly less-soluble than SGX523 itself. It was concluded that this metabolite is likely involved in the observed obstructive nephropathy reported in clinical studies, and that there is a need to conduct thorough metabolic evaluations early in drug development to select the most relevant nonclinical species for toxicological evaluation.

The metabolic stability of the compounds of the invention with regard to human aldehyde oxidase (AO) was analysed by using monkey liver cytosol which also has a high level of AO and is most comparable to the human situation [Pryde et al (2010) "Aldehyde Oxidase: An Enzyme of Emerging Importance in Drug Discovery" J. Med. Chem. 53, 8441-8460].

Incubation Protocol

Test compound was dissolved in DMSO to 10 mM, diluted to 10 µM with 0.6% ACN in $H_2O$ (1000-fold). The 10-µM solution was further diluted in to 2 µM with $H_2O$. In a 400-uL reaction system, the final concentration for test compound and cytosol is 1 µM and 2 mg/ml, respectively. Monkey liver cytosol is pooled monkey liver cytosol (male cyno), 20 mg/ml [from iPhase Pharma Service (Beijing, China) Catalogue#6CMCC1, Lot#6MCMCC001]. The volumes added to the reaction mixture were as follows:

| Reagent | Final concentration | Stock | 400 uL |
| --- | --- | --- | --- |
| Potassium Phosphate buffer (pH 7.4) | 50 mM | 500 mM | 40 uL |
| Monkey liver cytosol | 2 mg/ml | 20 mg/ml | 40 uL |
| Test compound | 1 µM | 2 µM | 200 uL |
| $H_2O$ | | | 120 uL |

There was a 10 min preincubation at 37° C., and then the reactions are initiated by addition of test compound. At specific reaction time points (30, 60 and 120 minutes), reaction aliquots (25 µL) are removed and reactions are terminated by addition of acetonitrile (100 µL) containing internal standard (125 ng/ml JNJ-38877605). For time 0 point, the cytosol fraction was first terminated by the addition of acetonitrile, followed by the addition of substrate. All the samples were centrifuged at ~3400×g at 4° C. for 10 min. The supernatants were diluted 1:1 (v/v) in $H_2O$ and analyzed by LC-MS/MS.

In Vitro Clearance Calculation

Each microsomal elimination rate, $k_{mic}$, is based on a 4-point elimination curve tested in singlet. LC-MS/MS raw data for a reaction plate is returned as integrated analyte peak areas for the TA and IS. These values may be converted to analyte: IS peak area ratios to standardize data comparisons. The reaction time point (eg. 0, 30, 60, 120 min) is plotted versus the natural logarithm of percent TA remaining relative to 0 minutes (based on relative peak area ratio). The slope of this clearance plot, $k_{mic}$, is used to calculate the in vitro half-life, $$t_{1/2} = \frac{0.693}{-k_{mic}}.$$

In order to focus on linear reaction kinetics, whenever possible, data points representing <10% TA remaining are generally excluded from the definition of the clearance plot slope. The reaction $t_{1/2}$ is the core experimental value used for calculating in vitro intrinsic clearance value, $CL_{int}$ (μL/min/mg microsomal protein), $$CL_{int} = \frac{0.693}{t_{1/2}} \cdot \frac{V}{M}.$$

Here, V is the incubation volume (μL), and M is the microsomal protein content in the incubation (mg).

Results

Results of some exemplary compounds are summarized in the Table 4-A below. Compounds of the invention have preferably a high in vitro half-life $t_{1/2}$ in this assay, preferably a $t_{1/2}$ of more than 250 min, more preferably more than 500 min and more than 1000 min, and most preferably more than 5000 min or even higher.

As it can be seen, each of the exemplified compounds demonstrates good metabolic stability in this assay. Preferred compounds of the invention are metabolically stable, and/or produce metabolites that do not have undesirable effects in the body. For example the metabolites formed do not interfere, or have limited interference, with normal renal function.

Results for some further compounds as described herein are summarized in the Table 4-B below.

For comparison, results for reference examples and for comparator compounds are summarized below in Table 4-C.

As it can be seen from the table especially compounds with no substituent in the 3-position of the quinoline ring show low metabolic stability in this assay.

TABLE 4-A

Metabolic stability of selected compounds of the invention

| Example No. | $t_{1/2}$ [min] | Example No. | $t_{1/2}$ [min] |
|---|---|---|---|
| 2 | 1879 | 59 | 642 |
| 3 | 447 | 61 | 838 |
| 6 | 19143 | 69 | 19143 |
| 10 | 3093 | 70 | 3656 |
| 13 | 350 | 72 | 1141 |
| 17 | 606 | 74 | 4527 |

TABLE 4-A-continued

Metabolic stability of selected compounds of the invention

| Example No. | $t_{1/2}$ [min] | Example No. | $t_{1/2}$ [min] |
|---|---|---|---|
| 21 | 500 | 75 | 34931 |
| 27 | 7002 | 76 | 1698 |
| 29 | 608 | 77 | 9999 |
| 33 | 891 | 78 | 2334 |
| 37 | 653 | 80 | 6352 |
| 40 | 11628 | 82 | 2019 |
| 43 | 882 | 85 | 917 |
| 47 | 540 | 86 | 3544 |
| 50 | 1856 | | |

TABLE 4-B

Metabolic stability of further selected compounds of the invention

| Example No. | $t_{1/2}$ [min] | Example No. | $t_{1/2}$ [min] |
|---|---|---|---|
| 5 | 1347 | 51 | 5 |
| 7 | 351 | 52 | 6 |
| 8 | 1106 | 62 | 8404 |
| 11 | 144 | 64 | 3 |
| 15 | 414 | 68 | 271 |
| 23 | 1498 | 83 | 228 |
| 25 | 185 | 84 | 207 |

TABLE 4-C

Metabolic stability of reference and comparator compounds

| Compound No. | $t_{1/2}$ [min] |
|---|---|
| Reference Example No. 66 | 407 |
| Comparator No. 2 | 542 |
| Comparator No. 4 (SGX523) | 284 |

Furthermore, certain preferred compounds of the invention have good exposure in vivo, and/or have a favourable solubility profile. Assays to measure bioavailability, pharmacokinetic profiles and solubility are well known in the art.

Certain preferred compounds of the invention produce metabolites in vivo which themselves have a favourable solubility profile, thereby avoiding or limiting undesirable effects in vivo.

Those skilled in the art will recognize, or be able to ascertain using no more than routine experimentation, many equivalents to the specific embodiments and methods described herein. Such equivalents are intended to be encompassed by the scope of the following claims.

We claim:
1. A compound of formula (I)

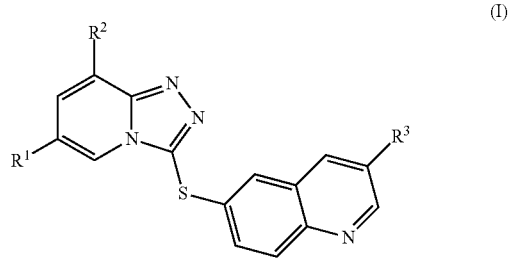

wherein
R$^1$ is selected from
  (i) pyrazolyl, optionally substituted by (C$_1$-C$_4$)alkyl, said (C$_1$-C$_4$)alkyl being optionally substituted by one OH group, and
  (ii) —CR$^9$=N—O—R$^{10}$, wherein
    R$^9$ is hydrogen or (C$_1$-C$_4$)alkyl; and,
    R$^{10}$ is hydrogen or (C$_1$-C$_4$)alkyl, said (C$_1$-C$_4$)alkyl being optionally substituted by one OH group;
R$^2$ is selected from hydrogen and halo; and
R$^3$ is —(C$_0$-C$_2$)alkyl-heterocyclyl$^1$,
wherein heterocyclyl$^1$ is a 4, 5, 6, 7 or 8 membered saturated or partially unsaturated N-heterocyclic ring which is attached via the N-atom and optionally comprises additional 1 or 2 ring heteroatoms independently selected from N, O and S in a position or positions other than adjacent to the linking N atom, wherein the total number of ring S-atoms does not exceed 1, and the total number of ring O-atoms does not exceed 1,
wherein the N-heterocyclic ring is optionally substituted
  (i) by one, two or three substituents independently selected from —OH, halo, —CONH$_2$, —CONH(C$_1$-C$_4$)alkyl, —CON((C$_1$-C$_4$)alkyl)$_2$, —COO(C$_1$-C$_4$)alkyl, —NH$_2$, —NH—COO(C$_1$-C$_4$)alkyl, —NH(C$_1$-C$_3$)alkyl, —N((C$_1$-C$_3$)alkyl)$_2$, —O(C$_1$-C$_4$)alkyl, heterocyclyl$^2$, —(C$_3$-C$_8$)cycloalkyl, phenyl and (C$_1$-C$_4$)alkyl, said (C$_1$-C$_4$)alkyl being optionally substituted by one, two or three substituents independently selected from OH and halo;
    wherein heterocyclyl$^2$ is a 5 or 6-membered saturated or partially unsaturated monocyclic group comprising 1 or 2 ring heteroatoms independently selected from N and O, wherein the total number of ring O atoms does not exceed 1, and which is optionally substituted by one or two substituents independently selected from OH and (C$_1$-C$_4$)alkyl; or
  (ii) by two groups which are attached to the same carbon atom and are combined into a cyclic 4, 5, 6, or 7 membered saturated or partially unsaturated ring system optionally comprising 1 or 2 ring heteroatoms independently selected from N, O and S, wherein the total number of ring S atoms does not exceed 1, which cyclic ring system is optionally substituted by —OH or (C$_1$-C$_4$)alkyl;
and wherein the substituted N-heterocyclic ring is optionally substituted by one or two additional (C$_1$-C$_4$)alkyl groups;
or a pharmaceutically acceptable salt thereof.

2. A compound or pharmaceutically acceptable salt thereof according to claim 1, wherein R$^3$ is selected from
  (i) optionally substituted —(C$_1$-C$_2$)alkyl-heterocyclyl$^1$, under the proviso that R$^1$ is optionally substituted pyrazole, and
  (ii) optionally substituted heterocyclyl$^1$.

3. A compound or pharmaceutically acceptable salt thereof according to claim 1, wherein R$^1$ is pyrazolyl, optionally substituted by (C$_1$-C$_4$)alkyl, said (C$_1$-C$_4$)alkyl being optionally substituted by one OH group.

4. A compound or pharmaceutically acceptable salt thereof according to claim 1, wherein R$^1$ is —CR$^9$=N—O—R$^{10}$, wherein
  R$^9$ is hydrogen or (C$_1$-C$_4$)alkyl; and,
  R$^{10}$ is hydrogen or (C$_1$-C$_4$)alkyl, said (C$_1$-C$_4$)alkyl being optionally substituted by one OH group; and
R$^3$ is optionally substituted heterocyclyl$^1$.

5. A compound or pharmaceutically acceptable salt thereof according to claim 4, wherein R$^1$ is —CR$^9$=N—O—R$^{10}$, wherein
  R$^9$ is (C$_1$-C$_2$)alkyl; and,
  R$^{10}$ is hydrogen or (C$_1$-C$_2$)alkyl, said (C$_1$-C$_2$)alkyl being optionally substituted by one OH group.

6. A compound or pharmaceutically acceptable salt thereof according to claim 2, wherein R$^3$ is -methyl-heterocyclyl$^1$, wherein heterocyclyl$^1$ is a 5 or 6 membered saturated N-heterocyclic ring which is attached via the N-atom and optionally comprises one additional ring heteroatom selected from N and O in a position other than adjacent to the linking N atom, wherein any additional ring N-atom is substituted with an (C$_1$-C$_4$)alkyl group.

7. A compound or pharmaceutically acceptable salt thereof according to claim 1, wherein R$^3$ is heterocyclyl$^1$, wherein heterocyclyl$^1$ is a 4, 5, 6, or 7 membered saturated N-heterocyclic ring which is attached via the N-atom and optionally comprises one additional ring heteroatom independently selected from N and O in a position other than adjacent to the linking N atom, wherein the N-heterocyclic ring is optionally substituted
  (i) at one or two ring C-atoms by overall one or two substituents independently selected from —OH, halo, —NH$_2$, —NH—COO(C$_1$-C$_4$)alkyl, —NH(C$_1$-C$_3$)alkyl, —N((C$_1$-C$_3$)alkyl)$_2$, —O(C$_1$-C$_4$)alkyl, heterocyclyl$^2$, and (C$_1$-C$_4$)alkyl;
    wherein heterocyclyl$^2$ is a 5 or 6-membered saturated N-heterocyclic$^2$ ring which is attached via the N-atom;
  (ii) at the optionally present additional ring N-atom by one substituent selected from —COO(C$_1$-C$_4$)alkyl, —(C$_5$-C$_6$)cycloalkyl, phenyl and (C$_1$-C$_4$)alkyl, said (C$_1$-C$_4$)alkyl being optionally substituted by one, two or three substituents independently selected from OH and halo; or
  (iii) by two groups which are attached to the same carbon atom and are combined into a cyclic 4, 5, or 6 membered saturated ring system comprising 1 ring O-atom.

8. A compound or pharmaceutically acceptable salt thereof according to claim 7, wherein R$^3$ is heterocyclyl$^1$, wherein heterocyclyl$^1$ is a 4, 5, 6, or 7 membered saturated N-heterocyclic ring which is attached via the N-atom and optionally comprises one additional ring heteroatom independently selected from N and O in a position other than adjacent to the linking N atom, wherein the N-heterocyclic ring is optionally substituted
  (i) at one or two ring C-atoms by overall one or two substituents independently selected from —OH, halo, —NH$_2$, —NH(C$_1$-C$_3$)alkyl, —N((C$_1$-C$_3$)alkyl)$_2$, —O(C$_1$-C$_4$)alkyl, heterocyclyl$^2$, and (C$_1$-C$_4$)alkyl;
    wherein heterocyclyl$^2$ is a 5 or 6-membered saturated N-heterocyclic$^2$ ring which is attached via the N-atom;
  (ii) at the optionally present additional ring N-atom by one substituent selected from —(C$_5$-C$_6$)cycloalkyl, phenyl and (C$_1$-C$_2$)alkyl, said (C$_1$-C$_2$)alkyl being optionally substituted by one, two or three substituents independently selected from OH and halo; or
  (iii) by two groups which are attached to the same carbon atom and are combined into a cyclic 4 or 6 membered saturated ring system comprising 1 ring O-atom.

9. A compound or pharmaceutically acceptable salt thereof according to claim 1, wherein
R$^1$ is selected from 1-methyl-1H-pyrazol-4-yl, 1-yl-ethanone oxime, and 1-yl ethanone O-(2-hydroxyethyl)-oxime,
R$^2$ is hydrogen or fluoro,
R$^3$ is heterocyclyl$^1$, wherein heterocyclyl$^1$ is selected from a) a 4, 5 or 6 membered saturated N-heterocyclic ring attached via the N-atom and substituted
   (i) at one or two ring C-atom or atoms by overall one or two substituents selected from —OH, fluoro, —NH$_2$, —N(methyl)$_2$, methoxy, piperidin-1-yl, pyrrolidin-1-yl, and methyl; or
   (ii) by two groups which are attached to the same carbon atom and are combined into a cyclic 4 or 6 membered saturated ring system comprising 1 ring O-atom;
b) a 6 membered saturated N-heterocyclic ring attached via the N-atom and comprising one ring O-atom in a position other than adjacent to the linking N atom, wherein the N-heterocyclic ring is optionally substituted by one or two methyl groups; and
c) a 6 or 7 membered saturated N-heterocyclic ring attached via the N-atom and comprising one additional ring N-atom in a position other than adjacent to the linking N atom, wherein the N-heterocyclic ring is optionally substituted
   (i) at the additional ring N-atom a substituent selected from cyclohexyl, phenyl and (C$_1$-C$_2$)alkyl, said (C$_1$-C$_2$)alkyl being optionally substituted by one, two or three substituents independently selected from OH and halo; or
   (ii) at one or two ring C-atoms by one or two methyl groups.

10. A compound or pharmaceutically acceptable salt thereof according to claim 1, wherein
R$^1$ is selected from 1-methyl-1H-pyrazol-4-yl, 1-yl-ethanone oxime, and 1-yl ethanone O-(2-hydroxyethyl)-oxime,
R$^2$ is hydrogen or fluoro,
R$^3$ is heterocyclyl$^1$, wherein heterocyclyl$^1$ is selected from piperazin-1-yl, morpholin-4-yl, 4-methoxypiperidin-1-yl, 4-hydroxypiperidin-1-yl, 3,5-dimethylpiperazin-1-yl, 3-N,N-dimethylaminopyrrolidin-1-yl, 3-amino-piperidin-1-yl, 3-amino-pyrrolidin-1-yl and 4-methyl-piperazin-1-yl.

11. A compound or pharmaceutically acceptable salt thereof according to claim 10, wherein
R$^1$ is selected from 1-methyl-1H-pyrazol-4-yl,
R$^2$ is hydrogen or fluoro, and
R$^3$ is heterocyclyl$^1$, wherein heterocyclyl$^1$ is selected from piperazin-1-yl, morpholin-4-yl, 4-methoxypiperidin-1-yl, 4-hydroxypiperidin-1-yl, 3,5-dimethylpiperazin-1-yl, and 4-methyl-piperazin-1-yl.

12. A compound or pharmaceutically acceptable salt thereof according to claim 1, wherein R$^2$ is selected from hydrogen and fluoro, preferably hydrogen.

13. A compound or pharmaceutically acceptable salt thereof according to claim 1, wherein the compound is selected from
No. 2 1-(6-(6-(1-Methyl-1H-pyrazol-4-yl)-[1,2,4]triazolo[4,3-a]pyridin-3-ylthio)quinolin-3-yl)pyrrolidin-3-amine
No. 3 (S)—N,N-Dimethyl-1-(6-(6-(1-methyl-1H-pyrazol-3-yl)-[1,2,4]triazolo[4,3-a]pyridin-3-ylthio)quinolin-3-yl)pyrrolidin-3-amine
No. 6 6-(6-(1-Methyl-1H-pyrazol-4-yl)-[1,2,4]triazolo[4,3-a]pyridin-3-ylthio)-3-((4-methylpiperazin-1-yl)methyl)quinoline
No. 10 1-(6-(6-(1-Methyl-1H-pyrazol-4-yl)-[1,2,4]triazolo[4,3-a]pyridin-3-ylthio)quinolin-3-yl)piperidin-3-amine
No. 12 6-(6-(1-Methyl-1H-pyrazol-4-yl)-[1,2,4]triazolo[4,3-a]pyridin-3-ylthio)quinolin-3-yl)-2-oxa-6-azaspiro[3.3]heptane
No. 13 (S)-1-(6-(8-Fluoro-6-(1-methyl-1H-pyrazol-4-yl)-[1,2,4]triazolo[4,3-a]pyridin-3-ylthio)quinolin-3-yl)-N,N-dimethylpyrrolidin-3-amine
No. 14 6-(8-Fluoro-6-(1-methyl-1H-pyrazol-4-yl)-[1,2,4]triazolo[4,3-a]pyridin-3-ylthio)-3-(4-(pyrrolidin-1-yl)piperidin-1-yl)quinoline
No. 17 3-(4-Methyl-1,4-diazepan-1-yl)-6-(6-(1-methyl-1H-pyrazol-4-yl)-[1,2,4]triazolo[4,3-a]pyridin-3-ylthio)quinoline
No. 19 3-(1,4-Diazepan-1-yl)-6-(6-(1-methyl-1H-pyrazol-4-yl)-[1,2,4]triazolo[4,3-a]pyridin-3-ylthio)quinoline
No. 21 1-(6-(6-(1-Methyl-1H-pyrazol-4-yl)-[1,2,4]triazolo[4,3-a]pyridin-3-ylthio)quinolin-3-yl)piperidin-4-amine
No. 24 6-[8-Fluoro-6-(1-methyl-1H-pyrazol-4-yl)-[1,2,4]triazolo[4,3-a]pyridin-3-ylsulfanyl]-3-(4-methyl-piperazin-1-yl)-quinoline
No. 27 6-(6-(1-Methyl-1H-pyrazol-4-yl)-[1,2,4]triazolo[4,3-a]pyridin-3-ylthio)-3-(piperazin-1-yl)quinoline
No. 28 6-(6-(1-Methyl-1H-pyrazol-4-yl)-[1,2,4]triazolo[4,3-a]pyridin-3-ylthio)-3-(4-(2,2,2-trifluoroethyl)piperazin-1-yl)quinoline
No. 29 2-(4-(6-(6-(1-Methyl-1H-pyrazol-4-yl)-[1,2,4]triazolo[4,3-a]pyridin-3-ylthio)quinolin-3-yl)-1,4-diazepan-1-yl)ethanol
No. 30 3-(1,4'-Bipiperidin-1'-yl)-6-(6-(1-methyl-1H-pyrazol-4-yl)-[1,2,4]triazolo[4,3-a]pyridin-3-ylthio)quinoline
No. 31 3-(1,4'-Bipiperidin-1'-yl)-6-(8-fluoro-6-(1-methyl-1H-pyrazol-4-yl)-[1,2,4]triazolo[4,3-a]pyridin-3-ylthio)quinoline
No. 32 3-(4-Cyclohexylpiperazin-1-yl)-6-(6-(1-methyl-1H-pyrazol-4-yl)-[1,2,4]triazolo[4,3-a]pyridin-3-ylthio)quinoline
No. 33 6-(6-(1-Methyl-1H-pyrazol-4-yl)-[1,2,4]triazolo[4,3-a]pyridin-3-ylthio)-3-(4-(pyrrolidin-1-yl)piperidin-1-yl)quinoline
No. 34 6-(6-(1-Methyl-1H-pyrazol-4-yl)-[1,2,4]triazolo[4,3-a]pyridin-3-ylthio)-3-(4-phenylpiperazin-1-yl)quinoline
No. 35 2-Methyl-4-(6-(6-(1-methyl-1H-pyrazol-4-yl)-[1,2,4]triazolo[4,3-a]pyridin-3-ylthio)quinolin-3-yl)morpholine
No. 35A (S)-2-Methyl-4-(6-(6-(1-methyl-1H-pyrazol-4-yl)-[1,2,4]triazolo[4,3-a]pyridin-3-ylthio)quinolin-3-yl)morpholine
No. 35B (R)-2-Methyl-4-(6-(6-(1-methyl-1H-pyrazol-4-yl)-[1,2,4]triazolo[4,3-a]pyridin-3-ylthio)quinolin-3-yl)morpholine
No. 36 4-(6-(8-Fluoro-6-(1-methyl-1H-pyrazol-4-yl)-[1,2,4]triazolo[4,3-a]pyridin-3-ylthio)quinolin-3-yl)-2-methylmorpholine
No. 37 2,6-Dimethyl-4-(6-(6-(1-methyl-1H-pyrazol-4-yl)-[1,2,4]triazolo[4,3-a]pyridin-3-ylthio)quinolin-3-yl)morpholine
No. 38 4-(6-(8-Fluoro-6-(1-methyl-1H-pyrazol-4-yl)-[1,2,4]triazolo[4,3-a]pyridin-3-ylthio) quinolin-3-yl)-2,6-dimethylmorpholine
No. 40 3-((3S,5R)-3,5-Dimethylpiperazin-1-yl)-6-(8-fluoro-6-(1-methyl-1H-pyrazol-4-yl)-[1,2,4]triazolo[4,3-a]pyridin-3-ylthio)quinoline
No. 42 3-((3S,5R)-3,5-Dimethylpiperazin-1-yl)-6-(6-(1-methyl-1H-pyrazol-4-yl)-[1,2,4]triazolo[4,3-a]pyridin-3-ylthio)quinoline No. 43 3-(4-Methoxypiperidin-1-yl)-6-(6-(1-methyl-1H-pyrazol-4-yl)-[1,2,4]triazolo[4,3-a]pyridin-3-ylthio)quinoline No. 44 6-(8-Fluoro-6-(1-methyl-1H-pyrazol-4-yl)-[1,2,4]triazolo[4,3-a]pyridin-3-ylthio)-3-(4-methoxypiperidin-1-yl)quinoline No. 46 (S)-6-(8-Fluoro-6-(1-methyl-1H-pyrazol-4-yl)-[1,2,4]triazolo[4,3-a]pyridin-3-ylthio)-3-(2-methylpiperazin-1-yl)quinoline No. 47 2-(6-((6-(1-Methyl-1H-pyrazol-4-yl)-[1,2,4]triazolo[4,3-a]pyridin-3-yl)thio)quinolin-3-yl)-8-oxa-2-azaspiro[4.5]decane No. 48 2-(6-(8-Fluoro-6-(1-methyl-1H-pyrazol-4-yl)-[1,2,4]triazolo[4,3-a]pyridin-3-ylthio)quinolin-3-yl)-8-oxa-2-azaspiro[4.5]decane No. 49 1-(6-((6-(1-Methyl-1H-pyrazol-4-yl)-[1,2,4]triazolo[4,3-a]pyridin-3-yl)thio)quinolin-3-yl)piperidin-4-ol No. 50 1-(6-((8-Fluoro-6-(1-methyl-1H-pyrazol-4-yl)-[1,2,4]triazolo[4,3-a]pyridin-3-yl)thio)quinolin-3-yl)piperidin-4-ol No. 57 4-(6-(6-(1H-pyrazol-4-yl)-[1,2,4]triazolo[4,3-a]pyridin-3-ylthio)quinolin-3-yl)morpholine No. 58 4-(6-(8-Fluoro-6-(1H-pyrazol-4-yl)-[1,2,4]triazolo[4,3-a]pyridin-3-ylthio)quinolin-3-yl)morpholine No. 59 3-Methyl-4-(6-(6-(1-methyl-1H-pyrazol-4-yl)-[1,2,4]triazolo[4,3-a]pyridin-3-ylthio)quinolin-3-yl)-morpholine No. 60 4-(6-(8-Fluoro-6-(1-methyl-1H-pyrazol-4-yl)-[1,2,4]triazolo[4,3-a]pyridin-3-ylthio)quinolin-3-yl)-3-methylmorpholine No. 61 3-(4,4-Difluoro-piperidin-1-yl)-6-[6-(1-methyl-1H-pyrazol-4-yl)-[1,2,4]triazolo[4,3-a]pyridin-3-ylsulfanyl]-quinoline No. 67 3-(4,4-Difluoro-piperidin-1-yl)-6-[8-fluoro-6-(1-methyl-1H-pyrazol-4-yl)[1,2,4]triazolo[4,3-a]pyridin-3-ylsulfanyl]-quinoline No. 69 4-(6-(6-(1-Methyl-1H-pyrazol-4-yl)-[1,2,4]triazolo[4,3-a]pyridin-3-ylthio)quinolin-3-yl)morpholine No. 70 4-(6-(8-Fluoro-6-(1-methyl-1H-pyrazol-4-yl)-[1,2,4]triazolo[4,3-a]pyridin-3-ylthio)quinolin-3-yl)morpholine No. 72 2-(4-(3-(3-Morpholin-4-yl-quinolin-6-ylthio)-[1,2,4]triazolo[4,3-a]pyridin-6-yl)-1H-pyrazol-1-yl)ethanol No. 74 3-(4-Methyl-piperazin-1-yl)-6-[6-(1-methyl-1H-pyrazol-4-yl)-[1,2,4]triazolo[4,3-a]pyridin-3-ylsulfanyl]-quinoline No. 75 4-((6-(6-(1-Methyl-1H-pyrazol-4-yl)-[1,2,4]triazolo[4,3-a]pyridin-3-ylthio)quinolin-3-yl)methyl)-morpholine No. 76 (E)-1-(3-((3-(4-Hydroxypiperidin-1-yl)quinolin-6-yl)thio)-[1,2,4]triazolo[4,3-a]pyridin-6-yl)-ethanone O-(2-hydroxyethyl)oxime No. 77 (E)-1-(3-((3-Morpholin-4-yl-quinolin-6-yl)thio)-[1,2,4]triazolo[4,3-a]pyridin-6-yl)ethanone oxime No. 78 (E)-1-(3-((3-Morpholin-4-yl-quinolin-6-yl)thio)-[1,2,4]triazolo[4,3-a]pyridin-6-yl)ethanone O-(2-hydroxyethyl)oxime No. 81 (S,E)-1-(3-(3-(3-(Dimethylamino)pyrrolidin-1-yl)quinolin-6-ylthio)-[1,2,4]triazolo[4,3-a]pyridin-6-yl)ethanone O-2-hydroxyethyl oxime No. 82 (S,E)-1-(3-(3-(3-(Dimethylamino)pyrrolidin-1-yl)quinolin-6-ylthio)-[1,2,4]triazolo[4,3-a]pyridin-6-yl)ethanone oxime No. 85 (S,E)-1-{3-[3-(3-Dimethylamino-pyrrolidin-1-yl)-quinolin-6-ylthio]-8-fluoro-[1,2,4]triazolo[4,3-a]pyridin-6-yl)ethanone O-(2-hydroxy-ethyl)-oxime, and No. 86 (S,E)-1-(3-(3-(4-Methylpiperazin-1-yl)quinolin-6-ylthio)-[1,2,4]triazolo[4,3-a]pyridin-6-yl)ethanone O-2-hydroxyethyl oxime.

14. A compound or pharmaceutically acceptable salt thereof, wherein the compound is selected from No. 8 {6-[8-Fluoro-6-(1-methyl-1H-pyrazol-4-yl)-[1,2,4]triazolo[4,3-a]pyridin-3-ylsulfanyl]-quinolin-3-yl}-(1-methyl-piperidin-4-yl)-amine, and No. 15 (1-Methyl-piperidin-4-yl)-{6-[6-(1-methyl-1H-pyrazol-4-yl)-[1,2,4]triazolo[4,3-a]pyridin-3-ylsulfanyl]-quinolin-3-yl}-amine.

15. A pharmaceutical composition comprising a therapeutically effective amount of a compound or a pharmaceutically acceptable salt thereof according to claim 1, and one or more pharmaceutically acceptable carriers.

* * * * *